US012077558B2

(12) United States Patent
Schmidt et al.

(10) Patent No.: US 12,077,558 B2
(45) Date of Patent: Sep. 3, 2024

(54) PHOSPHORUS (V)-BASED REAGENTS, PROCESSES FOR THE PREPARATION THEREOF, AND THEIR USE IN MAKING STEREO-DEFINED ORGANOPHOSPHORUS (V) COMPOUNDS

(71) Applicants: Bristol-Myers Squibb Company, Princeton, NJ (US); The Scripps Research Institute, La Jolla, CA (US)

(72) Inventors: Michael Anthony Schmidt, Cranbury, NJ (US); Bin Zheng, Kendall Park, NJ (US); Kyle Knouse, New Oxford, PA (US); Justine deGruyter, College Station, TX (US); Martin D. Eastgate, Titusville, NJ (US); Phil Baran, San Diego, CA (US); William R. Ewing, Yardley, PA (US); Richard E. Olson, Cambridge, MA (US); Ivar M. McDonald, Woodstock, CT (US)

(73) Assignees: Bristol-Myers Squibb Company, Princeton, NJ (US); The Scripps Research Institute, La Jolla, CA (US)

( * ) Notice: Subject to any disclaimer, the term of this patent is extended or adjusted under 35 U.S.C. 154(b) by 0 days.

(21) Appl. No.: 18/167,772

(22) Filed: Feb. 10, 2023

(65) Prior Publication Data
US 2023/0242569 A1 Aug. 3, 2023

Related U.S. Application Data

(62) Division of application No. 16/382,692, filed on Apr. 12, 2019, now Pat. No. 11,613,554.

(60) Provisional application No. 62/729,314, filed on Sep. 10, 2018, provisional application No. 62/697,896, filed on Jul. 13, 2018, provisional application No. 62/668,098, filed on May 7, 2018, provisional application No. 62/657,551, filed on Apr. 13, 2018.

(51) Int. Cl.
*C07H 21/00* (2006.01)
*C07H 19/11* (2006.01)
*C07H 19/213* (2006.01)

(52) U.S. Cl.
CPC .................... *C07H 21/00* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Thomas, Jr. et al. | |
| 4,415,732 A | 11/1983 | Caruthers et al. | |
| 4,458,066 A | 7/1984 | Caruthers et al. | |
| 4,500,707 A | 2/1985 | Caruthers et al. | |
| 4,668,777 A | 5/1987 | Caruthers et al. | |
| 4,725,677 A | 2/1988 | Koester et al. | |
| 4,973,679 A | 11/1990 | Caruthers et al. | |
| 5,132,418 A | 7/1992 | Caruthers et al. | |
| RE34,069 E | 9/1992 | Koster et al. | |
| 5,670,633 A | 9/1997 | Cook et al. | |
| 6,166,197 A | 12/2000 | Cook et al. | |
| 6,242,589 B1 * | 6/2001 | Cook ............... C07H 21/00 536/25.31 |
| 2016/0237427 A1 | 8/2016 | Olson et al. | |

FOREIGN PATENT DOCUMENTS

| | | |
|---|---|---|
| DE | 3520386 A1 | 12/1986 |
| JP | 2006248949 A | 9/2009 |
| WO | WO-9637504 A1 | 11/1996 |
| WO | WO-9938878 A1 | 8/1999 |
| WO | WO-0004034 A2 | 1/2000 |
| WO | WO-03095665 A2 | 11/2003 |
| WO | WO-2007031091 A2 | 3/2007 |
| WO | WO-2007134181 A2 | 11/2007 |
| WO | WO-2008150729 A2 | 12/2008 |
| WO | WO-2008154401 A2 | 12/2008 |
| WO | WO-2009006478 A2 | 1/2009 |
| WO | WO-2009067647 A1 | 5/2009 |
| WO | WO-2009100320 A2 | 8/2009 |
| WO | WO-2009124295 A2 | 10/2009 |
| WO | WO-2010036698 A1 | 4/2010 |
| WO | WO-2011017521 A2 | 2/2011 |
| WO | WO-2011085102 A1 | 7/2011 |
| WO | WO-2011115818 A1 | 9/2011 |
| WO | WO-2015164693 A1 | 10/2015 |
| WO | WO-2016079181 A1 | 5/2016 |
| WO | WO-2019023459 A1 | 1/2019 |
| WO | WO-2019046498 A1 | 3/2019 |

OTHER PUBLICATIONS

Alul, R.H., et al., "Oxalyl-CPG: A Labile Support for Synthesis of Sensitive Oligonucleotide Derivatives," Nucleic Acids Research 19(7):1527-1532, Oxford University Press, England (Apr. 1991).
Christensen, U.B. and Pedersen, E.B., "Intercalating Nucleic Acids Containing Insertions of 1-o-(1-pyrenylmethyl)glycerol: Stabilisation of dsDNA and Discrimination of DNA over RNA," Nucleic Acids Research 30(22):4918-4925, Oxford University Press, England (Nov. 2002).
Cook, P.D, "Medicinal Chemistry of Antisense Oligonucleotides—future Opportunities," Anti-Cancer Drug Design, 6(6):585-607 (Dec. 1991).
Delgado, C., et al., "The Uses and Properties of PEG-Linked Proteins," Critical Reviews in Therapeutic Drug Carrier Systems 9(3-4):249-304, CRC Press, Inc., United States (1992).
Englisch, U., et al., "Chemically Modified Oligonucleotides as Probes and Inhibitors," Angewandte Chemie, International Edition in English 30(6):613-629, Wiley Library, United States (1991).

(Continued)

*Primary Examiner* — Traviss C McIntosh, III
(74) *Attorney, Agent, or Firm* — Sterne, Kessler, Goldstein & Fox P.L.L.C.

(57) ABSTRACT

The present invention relates to novel phosphorous (V) (P(V)) reagents, methods for preparing thereof, and methods for preparing organophosphorous (V) compounds by using the novel reagents.

20 Claims, 2 Drawing Sheets

(56) References Cited

OTHER PUBLICATIONS

Feldman, A.W and Romesberg, F.E, "Expansion of the Genetic Alphabet: A Chemist's Approach to Synthetic Biology," Accounts of Chemical Research, 51(2):394-403, American Chemical Society, United States (Feb. 2018).
Gao, R., et al., "Identification of Specific Nonbridging Phosphate Oxygens Important for DNA Cleavage by Human Topoisomerase I," Biochemistry, 43(20):6167-6181, American Chemical Society, United States (May 2004).
Huang, H., et al., "Structure of (5'S)-8,5'-Cyclo-2'-Deoxyguanosine in DNA," Journal of the American Chemical Society, 133(50):20357-20368, American Chemical Society, United States (Dec. 2011).
Hutter, D., et al., "Labeled Nucleoside Triphosphates With Reversibly Terminating Aminoalkoxyl Groups," Nucleosides, Nucleotides & Nucleic Acids, 29(11):879-895, Taylor & Francis, United States (Nov. 2010).
Krishnakumar, K.S and Strazewski, P, "Synthesis of a Deoxyxylopuromycin Analogue," Synlett, 2010(7):1055-1058 (2010).
Kroschwitz, J.I Ed., Concise Encyclopedia of Polymer Science and Engineering, John Wiley & Sons, 1990, pp. 858-859.
Lesnikowski, Z.J., et al., "Carboranyl Oligonucleotides. 3. Biochemical Properties of Oligonucleotides Containing 5-(O-carboranyl-1-yl)-2'-deoxyuridine," Biochemistry, 35(18):5741-5746, American Chemical Society, United States (May 1996).
Li, F and Mahato, R.I, "Bioconjugate Therapeutics: Current Progress and Future Perspective," Molecular Pharmaceutics, 14(5):1321-1324, American Chemical Society, United States (May 2017).
Ma, Z., et al., "Asymmetric dipolar cycloaddition reactions: a practical, convergent synthesis of chiral pyrrolidines," Tetrahedron, Asymmetry 8(6):883-887, Elsevier, Netherlands (1997).
Nagaya, Y., et al., "Practical and Reliable Synthesis of 1,2-Dideoxy-d-Ribofuranose and its Application in RNAi Studies," Nucleosides, Nucleotides & Nucleic Acids, 35(2):64-75, Taylor & Francis, United States (2016).
Ouchi, T., et al., "Synthesis and Antitumor Activity of Poly(Ethylene Glycol)s Linked to 5-fluorouracil via a Urethane or Urea Bond," Drug Design and Discovery, 9(1):93-105, Harwood Academic Publishers, Switzerland (Feb. 1992).
Pallan, P.S and Egli, M, "Selenium Modification of Nucleic Acids: Preparation of Oligonucleotides With Incorporated 2'-seme-uridine for Crystallographic Phasing of Nucleic Acid Structures," Nature Protocols, 2(3):647-651, Nature Publishing Group, England (Mar. 2007).
Pallan, P.S and Egli, M, "Selenium Modification of Nucleic Acids: Preparation of Phosphoroselenoate Derivatives for Crystallographic Phasing of Nucleic Acid Structures," Nature Protocols, 2(3):640-646, Nature Publishing Group, England (Mar. 2007).
Ravasio,N and Rossi, M, "Selective Hydrogenations Promoted by Copper Catalysts. 1. Chemoselectivity, Regioselectivity, and Stereoselectivity in the Hydrogenation of 3-substituted Steroids," The Journal of Organic Chemistry, 56 (13):4329-4333, American Chemical Society (Jun. 1991).
Schinazi, R.F and Lesnikowski, Z.J, "Boron Containing Oligonucleotides," Nucleosides Nucleotides, 17(1-3):635-647, M. Dekker, United States (Jan.-Mar. 1998).
Uehara, S., et al., "Solid-phase Synthesis of P-Boronated Oligonucleotides by the H-Boranophosphonate Method," The Journal of Organic Chemistry, 79(8):3465-3472, American Chemical Society, United States (Apr. 2014).
Wnuk, S.F., et al., "The Beta-fluorine Effect. Electronic Versus Steric Effects in Radical Deoxygenations of Fluorine-containing Pentofuranose Nucleosides," The Journal of Organic Chemistry, 67(25):8794-8797, American Chemical Society, United States (Dec. 2002).
Wright, P., et al., "Large Scale Synthesis of Oligonucleotides via Phosphoramidite Nucleosides and a High-loaded Polystyrene Support," Tetrahedron Letters 34(21):3373-3376, Elsevier, Netherlands (1993).

Zhang, Y., et al., "A Semi-synthetic Organism That Stores and Retrieves Increased Genetic Information," Nature, 551(7682):644-647, Nature Publishing Group, England (Nov. 2017).
Comel, A., New Synthetic Way for the Preparation of 1,3,2-Oxathiaphospholane or 1,3,2-Oxathiaphosphorinane 2-Sulfide Derivatives, Phosphorous, Sulfur, Silicon, and the related elements 89:25-9, Gordon and Breach Science Publishers SA, United States (1994).
Miao, Z., "Studies on Synthesis and Intramolecular Catalyzed Hydrolysis of Thiophosphoramidate Derivatives of Nucleoside," Chinese J of Chem 20:1434-1438, National Natural Science Foundation of China, China (2002).
Kaczynski, T., "Stereoselective P-Cyclisation and Diastereoisomeric Purification of 5-Phenyl-3-(pyridin-2-y1)-1,3,2-oxazaphospholidine Formed from a Thermolabile Protecting Group," Eur J. Org. Chem 14: 2522-7, Wiley-VCH Verlag GmbH & Co, Germany (2016).
Mara, C. et al., "Synthesis and evaluation of phenoxyoxazaphospholidine, phenoxyoxazaphosphinane, and benzodioxaphosphininamine sulfides and related compounds as potential anti-malarial agents," Biororganic & Medicinal Chemistry 23:3580-3583, Elsevier (2013).
Blaszczyk, J., et al., "Geometry and Conformation of Crystalline Forms of p-Naphthoxy-Substituted 2-Thio-1,3,2-oxathiaphospholanes and 2-Thio-1,3,2-dithiaphospholanes," Heteroatom Chemistry 5(5/6):519-27, VCH Publishers, Germany (1994).
Comel, A., et al., "Synthesis of 1,3,2-Oxathiaphospholane-2-Sulfide Derivatives," Phosphorous, Sulfur, Silicon, and the related elements 70:229-33, Gordon and Breach Science Publishers SA, United States (1994).
Nuretdinova, O.N., et al., "Reactions of Some 2-Oxo-1,3,2-Oxathiaphospholanes and 2-Oxo-1,3,2-Phosphorinanes With Phosphorus Pentachloride," Bulletin of the Russian Academy of Sciences Division of Chemical Science 41(11):2121-2123, Plenum Publishing, United States (1993).
Oka, N., et al., "Stereocontrolled synthesis of oligonucleotide analogs containing chiral internucleotidic phosphorus atoms," Chem Soc Rev 40:5829-43, Royal Society of Chemistry (2011).
Iwamoto, N., et al., "Stereocontrolled solid-phase Synthesis of Oligonucleoside H-Phosphonates by an Oxazaphospholidine Approach," Angew Chem Int Ed 48:496-99, Wiley VCH, Germany (2009).
Wada, T., et al., "Stereoselective synthesis of dinucleoside boranophosphates by an oxazaphopholidine method," Bioorganic & Medicinal Chem Letters 16:3111-4, Elsevier, Netherlands (2006).
Oka, N. et al., "Diastereocontrolled Synthesis of Dinucleoside Phosphorothioates Using a Novel Class of Activators, Dialkyl(cyanomethyl)ammonium Tetrafluoroboratas," J Am. Chem Soc. 124:4962-3, American Chemical Society (2002).
Oka, N. et al., "An Oxazaphospholidine Approach for the Stereocontrolled Synthesis of Oligonucleoside Phosphorothioates," J. Am. Chem Soc. 125:8307-17, American Chemical Society (2003).
Oka, N., et al., "Solid-Phase Synthesis of Stereoregular Oligodeoxyribonucleoside Phosphorothioates Using Bicyclic Oxazaphospholidine Derivatives as Monomer Units," J. Am. Chem Soc. 130:16031-7, American Chemical Society (2008).
Nukaga, Y., et al., "Stereocontrolled Solid-Phase Synthesis of PO/PS Chimeric Oligodeoxyribonucleotides on an Automated Synthesizer using an Oxazaphospholidine-Phosphoramidite Method," J. Org. Chem. Author's Manuscript (2016).
Oka, N., "Stereocontrolled Synthesis of Oligoribonucleoside Phosphorothioates by an Oxazaphospholidine Approach," Organic Letters 11(4):967-70, American Chemical Society, United States (2009).
Guo, M., et al., "Solid-Phase Stereoselective Synthesis of 2'-O-METHYL-Oligoribonucleoside Phosphorothioates Using Nucleoside Bicyclic Oxazaphospholidines," Bioorganic & Medicinal Chemistry Letters 8:2539-2544, Elsevier, Netherlands (1998).
Wan, B., et al., "Synthesis, biophysical properties and biological activity of second generation antisense oligonucleotides containing chiral phosphorothioate linkages," Nucleic Acids Research 42(22):13456-68, Oxford University Press, England (2014).
Le Clezio; I. et al., "Diastereoselective and Regioselective Synthesis of Conformationally Restricted Thio-dioxa- and Oxo-oxathiaphosphorinane Dinucleotides Featuring Noncanonical α/β

(56) References Cited

OTHER PUBLICATIONS

Torsion Angle Combinations (α,β-CNAs)," European Journal of Organic Chemistry, 2007(12):1935-1941 (2007).
Okruszek, A. et al., "Synthesis of Oligo(Deoxyribonucleoside Phosphorodithioate)s by the Dithiaphospholane Approach," Journal of Organic Chemistry 60(21): 6998-7005, (1995).
Hoang; P., "Chimie Organique—Isomerisation catalytique des thiono-2 et seleno-2-dioxaphospholanes- I . 3 . 2 et dioxaphosphorinanes-1 . 3. 2. ( *)," Comptes Rendus Des Seances De L'academie Des Sciences, Serie C: Sciences Chimiques 272: 1145ff-1148ff, Elsevier Masson Fr (1971).
Shipov; A.E. et al., "Synthesis and physiological activity of new organophosphorus pesticides of 1,3,2-oxazaphosphorinane series," Russian Chemical Bulletin 44(11): 2147-2156 (1995).
Gerland; B.. et al.,: 11 Thio- and Seleno-Dioxaphosphorinane-Constrained Dinucleotides (D-CNA): Synthesis and Conformational Study : Thio- and Seleno-Dioxaphosphorinane-Constrained Dinucleotides (D-CNA): Synthesis and Conformational Study, European Journal of Organic Chemistry 2017(11): 1450-1464 (2017).
Bielawska; H. et al., "A novel and practical synthesis of S-(1- and 2-halogenoalkyl) sugars by reaction of carbohydrate S-(O,O-dialkyl)phosphorodithioates and monothioates with fluoride anion," Tetrahedron Let 45(11): 2473-2476, Elsevier, Amsterdam, NL, (2004).
Comel; A., "New Route to the preparation of 1,3,2 Oxathaphospholanes 2-sulfide derivatives," Phosphorus, Sulfur and Silicon and the Related Elements 77:188 Taylor & Francis Inc (1993).
Radzikowska; E. et al., "Synthesis of PS/PO-Chimeric Oligonucleotides Using Mixed Oxathiaphospholane and Phosphoramidite Chemistry," Organic & Biomolecular Chemistry 13(1): 269-276 (2015).
Wu; S., et al., "Synthesis and Insecticidal Activity of Oxazaphospholidines, Oxathiaphospholanes, and Thiazaphospholidines," Agricultural and Biological Chemistry 52(11): 2911-2917 (1988).
Cremlyn; R. et al., "Some Heterocyclic Phosphorochloridates and the Formation of Other Heterocyclic Organophosphorus Compound," Phosphorus and Sulfur and the Related Elements 7(3):247-255 (1979).
Nuretdinova; O. N. et al., "Transformations of hydroxyalkyl esters of dimethylamido -O-phenylthiophosphoric acid," Bulletin of the Academy of Sciences of the Ussr, Division of Chemical Sciences 35(12): 2556-2558 (1986).
Arbuzov; B.A. et al., "Three-Dimensional Structures of Phosphorus—Containing Heterocycles . Communication 34 . 2- Phenoxy -2-0xo - I,3,2-0xathiaphosphorinane," Bulletin of the Academy of Sciences of the USSR, Division of chemical science, (1985) pp. 520-524, Retrieved from the Internet: URL:https://link.springer.com/content/pdf/10.1007/BF00947714.pdf.
Arbuzov; B.A. et al., Reaction of diarylthio- and selenophosphoric acids with oxetanes 11 , Bulletin of the Academy of Sciences of the Ussr, Division of Chemical Sciences 32(3): 613-615 (1983).
Harrison; J.M. et al., "Use of carbohydrate derivatives for studies of phosphorus stereochemistry. Part III. Stereochemical course of nucleophilic displacements of 2-substituents in 1,3,2 -dioxaphosphorinan -2-ones and related compounds 11," Journal of the Chemical Society, Perkin Transactions (1974) pp. 1053-1057.
Barthelat; M et al., "Etude infrarouge du groupement NH dans quelques phosphoramides cycliques—II. Derives du diazaphospholane-1.3.2," Spectrochimica Acta. Part A: Molecular and Biomolecular Spectroscopy 29: 79-91 (1973).
Dietz; C. et al., "Diastereoselective ortho -Metalation of a Chiral Ferrocenylphosphonic Diamide and Its Organotin Derivatives," Organometallics 32(20): 5906-5917(2013).
STN Structure Search Results for Bonnyai; P. et al., "Preparation of oxathiaphospholane derivatives as fungicides". HU202246 B, pp. 1-11 (1991).
Rammler; D.H. et al., "Studies on Polynucleotides. XIX.1 The Specific Synthesis of C3"-C5" Inter-ribonucleotidic Linkage.2 A New Approach and its Use in the Synthesis of C3"-C5"-Linked Uridine Oligonucleotides3". Journal of the American Chemical Society 85(13): 1989-1997(1963).
Tener; G. M. et al., "Studies on Polynucleotides. II. 1 The Synthesis and Characterization of Linear and Cyclic Thymidine Oligonucleotides 2", Journal of the American Chemical Society 80(23): 6223-6230 (1958).
Sierzchala; A. et al., "Oxathiaphospholane Method of Stereocontrolled Synthesis of Diribonucleoside 3',5'-Phosphorothioates," Journal of Organic Chemistry 61(19): 6713-6716, (1996).
Knouse; K.W. et al., "Unlocking P(V): Reagents for chiral phosphorothioate synthesis", Science 361(6408):1234-1238 (2018).
International Search Report and Written Opinion for International Application No. PCT/US2019/027256, European Patent Office, Netherlands, mailed on Jun. 2, 2019, 26 pages.
Hulst, R., et al., "Formation of Diphosphates. A NMR Study on the Mechanism and Stereochemistry of Diphosphate Formation from Chiral Dioxaphosphorinanes," Journal of American Chemical Society 122(13):3135-3150, American Chemical Society, United States (Mar. 2000).
Krasowska, D, et al., "Hetrocycles with a Stereogenic Phosphorus or Sulfur Atom derived from Aminoalcohols or Aminonaphthols," Chapter 4, *Advance in Heterocyclic Chemistry* 117:179-259, Elsevier Inc., Netherlands (Jan. 2015).
Sierecki, E., et al., "Diastereoselective α-allylation of Secondary Amines," *Tetrahedron* 66(52):10002-10007, Elsevier Ltd., Netherlands (Dec. 2010).
Written Opinion of the International Preliminary Examination Authority, of International Application No. PCT/US2019/027256, European Patent Office, Netherlands, mailed on Mar. 19, 2020, 6 pages.
International Preliminary Report on Patentability, of International Application No. PCT/US2019/027256, European Patent Office, Netherlands, mailed on Jul. 1, 2020, 51 pages.
Takahashi, T., et al., "Preparation of Optically Active 1,3,2-Oxathiaphosphorinanes Using (−)- 10 Mercaptoisoborneol as a Chiral Source," Heterocycles, 30(1):353-357 (1990).
Iyer, R. P., et al., "A novel nucleoside phosphoramidite synthon derived from 1R, 2S- ephedrine," Tetrahedron: Asymmetry 6(5):1051-1054, Elsevier, Netherlands (May 1995).
Tolkmith, H., and Britton, E., "Some Heterocyclic Compounds Containing Phosphorus," Journal of Organic Chemistry 24(5):705-708, American Chemical Society, United States (May 1959).
Bodalski, R., and Quin, L.D., "Reaction of epoxides with metaphosphoric acid derivatives," Journal of Organic Chemistry 56(8):2666-2671, American Chemical Society, United States (Apr. 1991).
Kotynski, A., et al., "Analysis of Organophosphorus Compounds. 1. Application of Iodine-Azide Reaction for Detection of Thiophosphoorganic Compounds in Thin-Layer Chromatography," Journal of Chromatography A 773(2):285-290, Elsevier, Netherlands (1997).
Nuretdinova, O.N., et al., "Transformations of Hydroxyalkyl Esters of Dialykylamido-O-Alkylthiophosphoric Acids," Bulletin of the Academy of Sciences of the USSR, Division of Chemical Science 36:2190-2192, Plenum Publishing Corporation, United States (1987).

* cited by examiner

PHOSPHORUS (V)-BASED REAGENTS, PROCESSES FOR THE PREPARATION THEREOF, AND THEIR USE IN MAKING STEREO-DEFINED ORGANOPHOSPHORUS (V) COMPOUNDS

CROSS-REFERENCE TO RELATED APPLICATIONS

The present application is a divisional application of U.S. application Ser. No. 16/382,692, filed on Apr. 12, 2019, which is a national phase application of PCT Application No. PCT/US2019/027256, filed on Apr. 12, 2019, which applications claim the benefit of U.S. Provisional Application No. 62/657,551, filed on Apr. 13, 2018; U.S. Provisional Application No. 62/668,098, filed on May 7, 2018; U.S. Provisional Application No. 62/697,896, filed on Jul. 13, 2018; and U.S. Provisional Application No. 62/729,314, filed on Sep. 10, 2018.

BACKGROUND OF THE INVENTION

Field of the Invention

The present invention relates to novel phosphorous (V) (P(V)) reagents and methods for preparing enantiomerically enriched (e.g., homochiral, optically pure, or single-isomer) p-chiral organophosphorous compounds by using the novel (P(V)) reagents.

Background Art

Organophosphorous compounds have wide-ranging applications as therapeutic and diagnostic agents, pest and insects control agents, along with many other applications. Organophosphorous compounds are generally classified based on the oxidation state of the phosphorous atom: +5 (phosphorous (V)) or +3 (phosphorous (III)). Organothiophosphates (phosphorous (V) compounds containing sulfur attached to phosphorous) are a subclass of organophosphate compounds where at least one of the oxygen atoms in the phosphate is replaced by sulfur. In some situations, an asymmetry induced at phosphorous results in chiral organothiophosphate compounds, which makes this class of compounds particularly suitable in therapeutic, diagnostic, research, and other applications.

A well-known and well-utilized example of organothiophosphates are nucleic acids containing a thiophosphate, e.g., phosphorothioate, backbone. The use of poly(nucleic acids), for example oligonucleotides, containing a natural phosphodiester backbone of DNA or RNA is limited by their instability to nucleases. Phosphorothioate oligonucleotides are oligonucleotides in which one of the non-crosslinked oxygen atoms in the phosphodiester bond is replaced with a sulfur atom. Oligonucleotides containing a phosphorothioate backbone have higher nuclease resistance and cell membrane permeability compared with oligonucleotides having a phosphodiester backbone.

Because of the chiral nature of a phosphorus atom in some organothiophosphates, two kinds of stereoisomers ($R_P$- and $S_P$-isomers) can exist. Therefore, in a P-chiral thiophosphate derived oligonucleotide, thousands of diastereoisomers of compound are possible, resulting in significant issues for development of such agents. It is known that properties of oligonucleotides, including binding affinity, sequence specific binding to complementary RNA, and stability to nucleases, are affected by the configurations at the phosphorous atoms. Further, it has been suggested that homochiral isomers may have differential properties (solubility, stability, activity, pharmacokinetics, etc.). Therefore, it is highly desirable to prepare phosphorothioate oligonucleotides with specific stereochemical configurations.

P-chiral organothiophosphates find another utility in making bioconjugates, including protein- and peptide-nucleic acid conjugates. Bioconjugates are compounds prepared through the attachment of a therapeutic molecule, such as a small molecular drug or a macromolecular drug to a functional molecule, such as a lipid or a polymeric carrier, via a direct covalent bond or covalently using a chemical linker. A typical bioconjugate typically includes three basic building blocks: (1) a carrier molecule, such as a polymer, a lipid, a peptide, or a protein; (2) a therapeutic agent, including both small molecule chemicals and macromolecule drugs; and (3) a chemical linker. Bioconjugates are often used as a drug delivery strategy. Modifying therapeutic agents with carrier molecules provides several advantages, including, but not limited to, (1) optimization of physico-chemical properties, (2) enhancing disease-specific targeting, (3) reducing toxicity, and (4) controlling drug release profile. See Li, F. et al., "Bioconjugate Therapeutics: Current Progress and Future Perspective," *Mol Pharm.* 2017 May 1; 14(5): 1321-1324. For example, properties of oligonucleotides and therapeutic agent, including cell-specific delivery, target specificity, and cellular uptake efficacy, can be manipulated by conjugating the agents to be delivered to a peptide. Often times, it is desirable to use thiophosphate-based linkages. Similarly, antibody-drug conjugates (ADCs) often benefit from the presence of a single isomer thiophosphate linkage. Moreover, organothiophosphates can be used to make prodrugs, as well as novel linkers for induced protein degradation.

Yet another use of organothiophosphate-based linkages is incorporation of such linkages into cyclic dinucleotides (CDNs). CDNs are important secondary signaling molecules in bacteria and in mammalian cells. In the former case, they represent secondary messengers affecting numerous responses of the prokaryotic cell, whereas in the latter, they act as agonists of the innate immune response. New discoveries have linked these two patterns of CDN utilization as secondary messengers and have revealed unexpected influences they have on shaping human genetic variation. Recently, the use of CDNs as immune stimulating agents for the treatment of cancer has received significant attention. Incorporation of thiophosphate internucleoside linkages into a CDN confers beneficial properties to the CDN.

However, there are difficulties associated with preparing P(V) organothiophosphates and phosphodiester compounds. First, it is difficult to prepare organophosphorous compounds using phosphorous (III) chemistry. Thus, there is a need for a simple and convenient method for linking molecules together through a phosphorous (V) linkage.

Second, it is difficult to prepare organothiophosphates where the stereochemical configuration at the phosphorus atom is controlled. For example, the current approach to preparing single isomer oligonucleotides, developed by Wada (FIG. 1), uses monomeric units containing a 5'-protected nucleoside incorporated into a chiral phosphoramidite. The Wada method usually produces modest yields (41-75%) and low rates of reaction, driving the need for the use of a significant excess of the phosphoramidite. In the first step of the elongation cycle (1), the nitrogen is activated for displacement through the use of an activator, N-(cyanomethyl)-pyrrolidinium triflate, (a hygrosopic solid) and then the solid supported 5'-hydroxyl can displace. The identity of the activator is critical. The activator was designed to be acidic enough to activate the nitrogen, but non-nucleophilic enough to attack the resultant protonated phosphoramidite and scramble the stereochemistry at phosphorous. In Wada's cases, the yields (96-97%) and stereoselectivities (>99:1) of these couplings are high. In the second step (2), the P(III) compound is oxidized with (Me$_2$NC(S)—S)$_2$ (DTD), then the pyrrolidine moiety of the auxiliary is capped with trifluoroacylimidazole. The auxiliary and DMTr group are finally cleaved with dichloroacetic acid (3). While this works well on smaller fragments, when fragments get long (at least 4-10mers), the generality of the activator disappears, and a new activator must be identified through experimentation. Additionally, the complexity of the process becomes a challenge for making larger oligonucleosides.

Therefore, there remains a need for simple and selective including regio- or stereo-selective synthetic methods of making organothiophosphate or organophosphate-based molecules, including oligonucleotides, peptide-oligonucleotide conjugates, ADCs, prodrugs and CDNs.

BRIEF SUMMARY OF THE INVENTION

One aspect of the present disclosure is directed to methods of making stereo-defined organosphosphorous (V) compounds using novel chiral oxathiaphospholane sulfides, referred to herein as "Compounds of the Disclosure," featuring a tetrahedral phosphorous(V) (i.e., P(V)) center. More particularly, the methods comprise coupling Compounds of the Disclosure represented by any one of Formulae (I)-(IIIe), below, to a nucleophile, followed by a reaction with a second nucleophile, thereby making a stereo-defined organophosphorous (V) linkage between the two nucleophiles. Examples of suitable nucleophiles include, but are not limited to, water, hydroxide anions, alcohols, alkoxide anions, carboxylate anions, thiols, thiolate anions, anions of a thiocarboxylic acids, amines, and amides. To be suitable for the process of the present disclosure, Compounds of the Disclosure are oxathiaphospholane sulfide compounds that are designed to undergo a cleavage (immolation) event upon (or after) addition of a second nucleophile. Suitable steps for cleavage include, but are not limited to, a ring strain/pinacol-induced cleavage, displacement of a ring-atom followed by internal displacement (immolation) or a strategic cyclic heteroatom in situ cleavage.

Compounds of the Disclosure are represented by any one of Formulae (I)-(IIIe), wherein R$^1$, R$^2$, R$^3$, R$^4$, R$^5$, R$^6$, X$^1$, X$^2$, Y, LG, n, and m are as defined below:

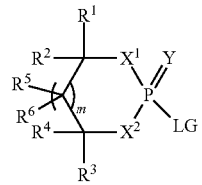

(I)

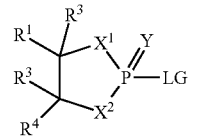

(Ia)

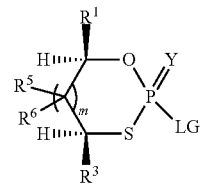

(II)

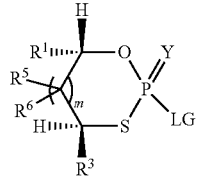

(IIa)

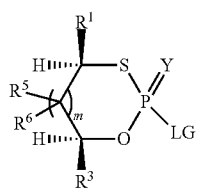

(IIb)

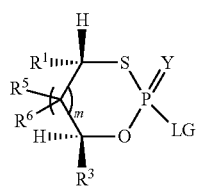

(IIc)

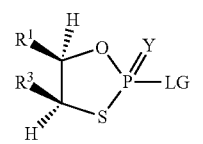

(IId)

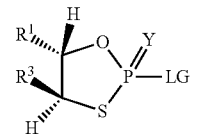

(IIe)

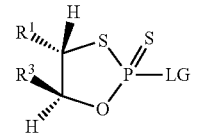

(IIf)

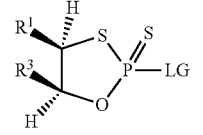

(IIg)

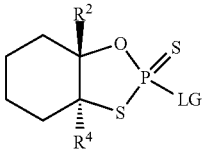

(III)

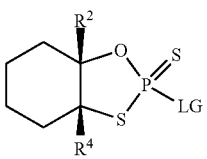
(IIIa)

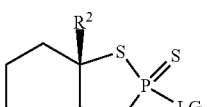
(IIIb)

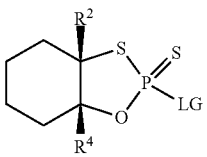
(IIIc)

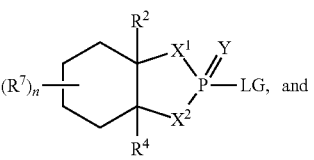
(IIId)

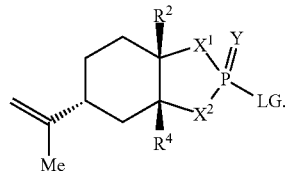
(IIIe)

Compounds of the Disclosure are useful in preparing organophosphorous (V) compounds, such as phosphate esters (e.g., phosphorothioates, phosphorodithioates, phosphodiesters) and phosphate amides. Examples of organophosphorous (V) compounds that can be prepared using Compounds of the Disclosure include, but are not limited to, achiral and chiral thiophosphates relevant to CDNs and antisense oligonucleotides, including CDNs and oligonucleotides containing phosphorothiolate internucleoside linkages, peptide-oligonucleotide conjugates, ADCs, phosphorylated natural products, phosphorylated peptides, and organic molecules containing a phosphorylation.

In another aspect, the present disclosure provides methods of making Compounds of the Disclosure, comprising reacting a dithioate salt with an epoxide or an episulfide disclosed herein. In one embodiment, an epoxide is used. A suitable epoxide is limonene oxide. In another embodiment, an episulfide is used. A suitable episulfide is thiirane.

In another aspect, the present disclosure provides methods of making Compounds of the Disclosure, comprising reacting $PCl_3$ with a mercaptoethanol or a mercaptopropanol, wherein the mercaptoethanol or mercaptopropanol is chosen from the following formulae:

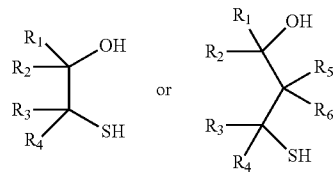

wherein $R^1$, $R^2$, $R^3$, $R^4$, $R^5$ and $R^6$ are defined below.

In another embodiment, Compounds of the Disclosure of Formulae (I)-(IIIe) can be made according to the following exemplary reaction scheme:

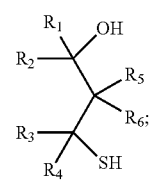

wherein $R^1$, $R^2$, $R^3$ and $R^4$ and LG are as defined below.

In another aspect, the present disclosure provides methods of making Compounds of the Disclosure, comprising reacting a $P(O)Cl_3$ with a mercaptopropanol, wherein the mercaptopropanol is represented by

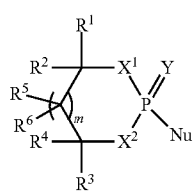

wherein $R^1$, $R^2$, $R^3$, $R^4$, $R^5$ and $R^6$ are defined below.

Also provided are compounds represented by any one of Formulae (IV)-(VIe), wherein $R^1$, $R^2$, $R^3$, $R^4$, $R^5$, $R^6$, $X^1$, $X^2$, Y, and Nu are as defined below, also collectively referred to herein as "Compounds of the Disclosure:"

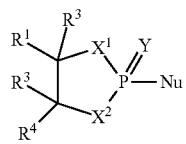
(IV)

(IVa)

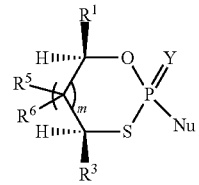
(V)

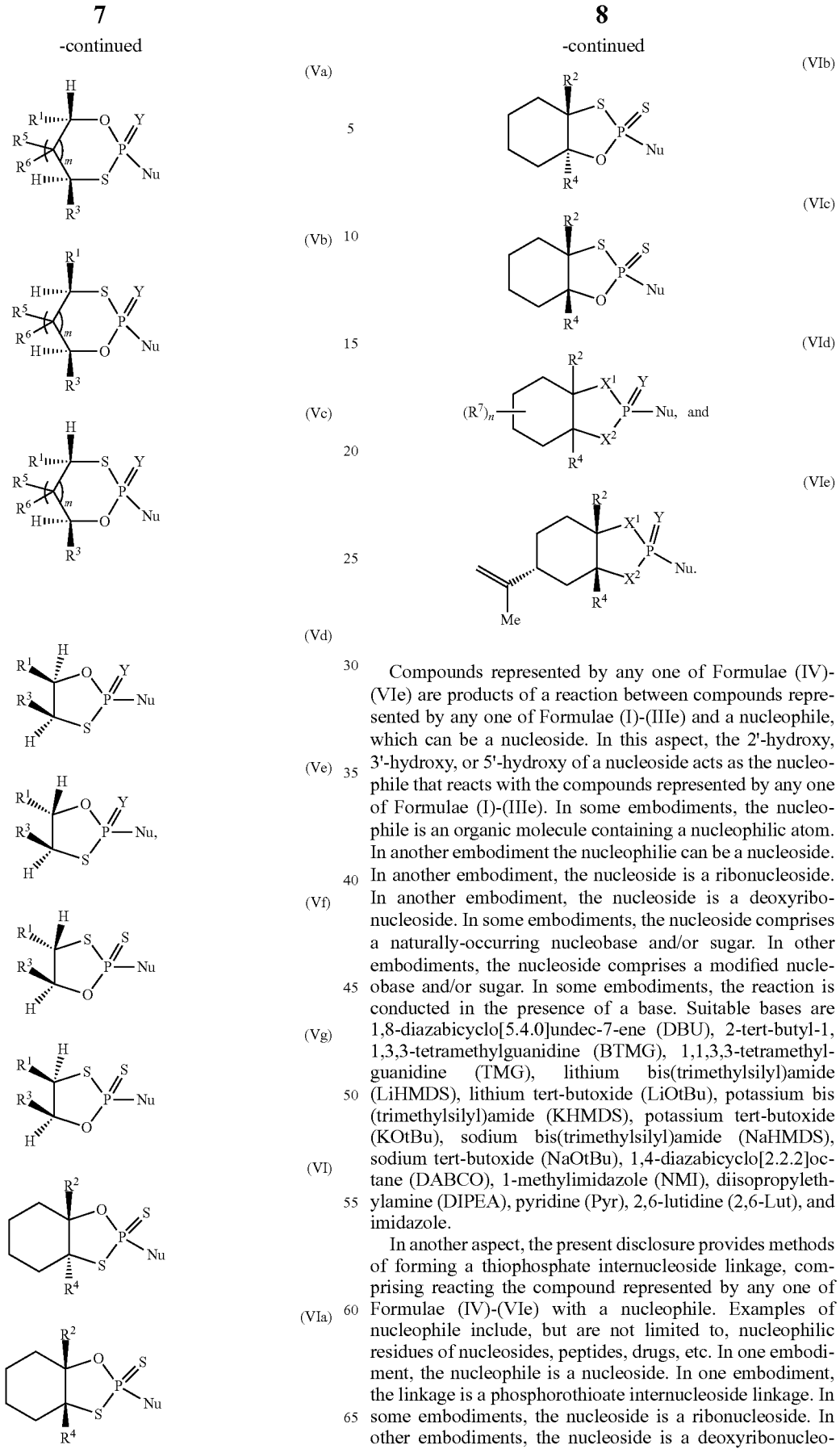

Compounds represented by any one of Formulae (IV)-(VIe) are products of a reaction between compounds represented by any one of Formulae (I)-(IIIe) and a nucleophile, which can be a nucleoside. In this aspect, the 2'-hydroxy, 3'-hydroxy, or 5'-hydroxy of a nucleoside acts as the nucleophile that reacts with the compounds represented by any one of Formulae (I)-(IIIe). In some embodiments, the nucleophile is an organic molecule containing a nucleophilic atom. In another embodiment the nucleophilie can be a nucleoside. In another embodiment, the nucleoside is a ribonucleoside. In another embodiment, the nucleoside is a deoxyribonucleoside. In some embodiments, the nucleoside comprises a naturally-occurring nucleobase and/or sugar. In other embodiments, the nucleoside comprises a modified nucleobase and/or sugar. In some embodiments, the reaction is conducted in the presence of a base. Suitable bases are 1,8-diazabicyclo[5.4.0]undec-7-ene (DBU), 2-tert-butyl-1,1,3,3-tetramethylguanidine (BTMG), 1,1,3,3-tetramethylguanidine (TMG), lithium bis(trimethylsilyl)amide (LiHMDS), lithium tert-butoxide (LiOtBu), potassium bis(trimethylsilyl)amide (KHMDS), potassium tert-butoxide (KOtBu), sodium bis(trimethylsilyl)amide (NaHMDS), sodium tert-butoxide (NaOtBu), 1,4-diazabicyclo[2.2.2]octane (DABCO), 1-methylimidazole (NMI), diisopropylethylamine (DIPEA), pyridine (Pyr), 2,6-lutidine (2,6-Lut), and imidazole.

In another aspect, the present disclosure provides methods of forming a thiophosphate internucleoside linkage, comprising reacting the compound represented by any one of Formulae (IV)-(VIe) with a nucleophile. Examples of nucleophile include, but are not limited to, nucleophilic residues of nucleosides, peptides, drugs, etc. In one embodiment, the nucleophile is a nucleoside. In one embodiment, the linkage is a phosphorothioate internucleoside linkage. In some embodiments, the nucleoside is a ribonucleoside. In other embodiments, the nucleoside is a deoxyribonucleoside. In some embodiments, the nucleoside comprises a naturally-occurring nucleobase and/or sugar. In other embodiments, the nucleoside comprises a modified nucleobase and/or sugar.

Also provided are methods of making a cyclic dinucleotide, comprising:
a) reacting any one of Compounds of the Disclosure of Formulae (I)-(IIIe) with a nucleoside in the presence of a base;
b) reacting the compound formed in step (a) with another nucleoside, thereby coupling the two nucleosides; and
c) adding any one of Compounds of the Disclosure of Formulae (I)-(IIIe). In some embodiments, the method further comprises deprotection of the nucleosides after step (b). In other embodiments, the method further comprises another deprotection step after step (c) to cyclize a precursor to form a CDN.

In some embodiments, the nucleoside is a ribonucleoside. In other embodiments, the nucleoside is a deoxyribonucleoside. In some embodiments, the nucleoside comprises a naturally-occurring nucleobase and/or sugar. In other embodiments, the nucleoside comprises a modified nucleobase and/or sugar. Suitable bases for step (a) are as described above.

In one embodiment, one or both nucleosides comprise a protecting group at the 5'-hydroxy. Useful protecting groups are disclosed below. In one embodiment, the protecting group is dimethoxytrityl (DMTr). In one embodiment, one or both nucleosides comprise a protecting group at the 3'-hydroxy. In one embodiment, the protecting group is TBS. In another embodiment, when the nucleoside is a deoxyribonucleoside, it can comprise a protecting group at the 2'-hydroxy. In one embodiment, the protecting group is TOM. In another embodiment, the protecting group is TBDPS. Yet in other embodiments, one or both nucleosides comprise a protecting group on a base. In one embodiment, the protecting group is a nucleophile protecting group. In one embodiment, the protecting group is acetyl (Ac), isobutyl (iBu), dimethylformamidyl (DMF), benzoyl (Bz), or benzyl (Bn). In another embodiment, neither nucleoside comprises a protecting group on a base.

In another aspect, the present disclosure provides methods of making an oligonucleotide, comprising:
a) reacting any one of Compounds of the Disclosure of Formulae (I)-(IIIe) with a nucleoside in the presence of a base;
b) reacting the compound formed in step (a) with another nucleoside, thereby coupling the two nucleosides;
c) adding any one of Compounds of the Disclosure of Formulae (I)-(IIIe);
d) adding another nucleoside, thereby coupling said nucleoside to the growing oligonucleotide; and
e) repeating steps (c) and (d) until the oligonucleotide comprises a desired number of nucleotides.

In some embodiments, the nucleoside is a ribonucleoside. In other embodiments, the nucleoside is a deoxyribonucleoside. In some embodiments, the nucleoside comprises a naturally-occurring nucleobase and/or sugar. In other embodiments, the nucleoside comprises a modified nucleobase and/or sugar.

In one embodiment, one, some or all nucleosides comprise a protecting group at the 5'-hydroxy. In one embodiment, the protecting group is DMTr. In one embodiment, one, some or all comprises a protecting group at the 3'-hydroxy. In one embodiment, the protecting group is tert-butyldimethylsilyl (TBS). In another embodiment, when the nucleoside is a deoxyribonucleoside, it can comprise a protecting group at the 2'-hydroxy. In one embodiment, the protecting group is TOM. In another embodiment, the protecting group is TBDPS. Yet in other embodiments, one, some or all nucleosides comprise a protecting group on a base. In one embodiment, the protecting group is Ac, iBu, DMF, Bn, or Bz. In another embodiment, none of the nucleosides comprise a protecting group on a base.

In some embodiments, the protecting group is removed after each coupling step. In one embodiment, the nucleoside in step (a) is attached to a resin at the 3'-end. In some embodiments, the method comprising cleaving the oligonucleotide from the resin.

In some embodiments, achiral phosphate or dithiophosphate, or chiral thiophosphate linkages between two nucleophilic molecules, added sequentially, can be formed. This may be used to link two molecules of interest, or in other applications, create pro-drugs, or use in pharmaceutical applications.

Additional embodiments and advantages of the disclosure will be set forth, in part, in the description that follows, and will flow from the description, or can be learned by practice of the disclosure. The embodiments and advantages of the disclosure will be realized and attained by means of the elements and combinations particularly pointed out in the appended claims.

It is to be understood that both the foregoing summary and the following detailed description are exemplary and explanatory only, and are not restrictive of the invention as claimed.

BRIEF DESCRIPTION OF THE DRAWINGS/FIGURES

DETAILED DESCRIPTION OF THE INVENTION

Compounds of the Disclosure

Figure 1:
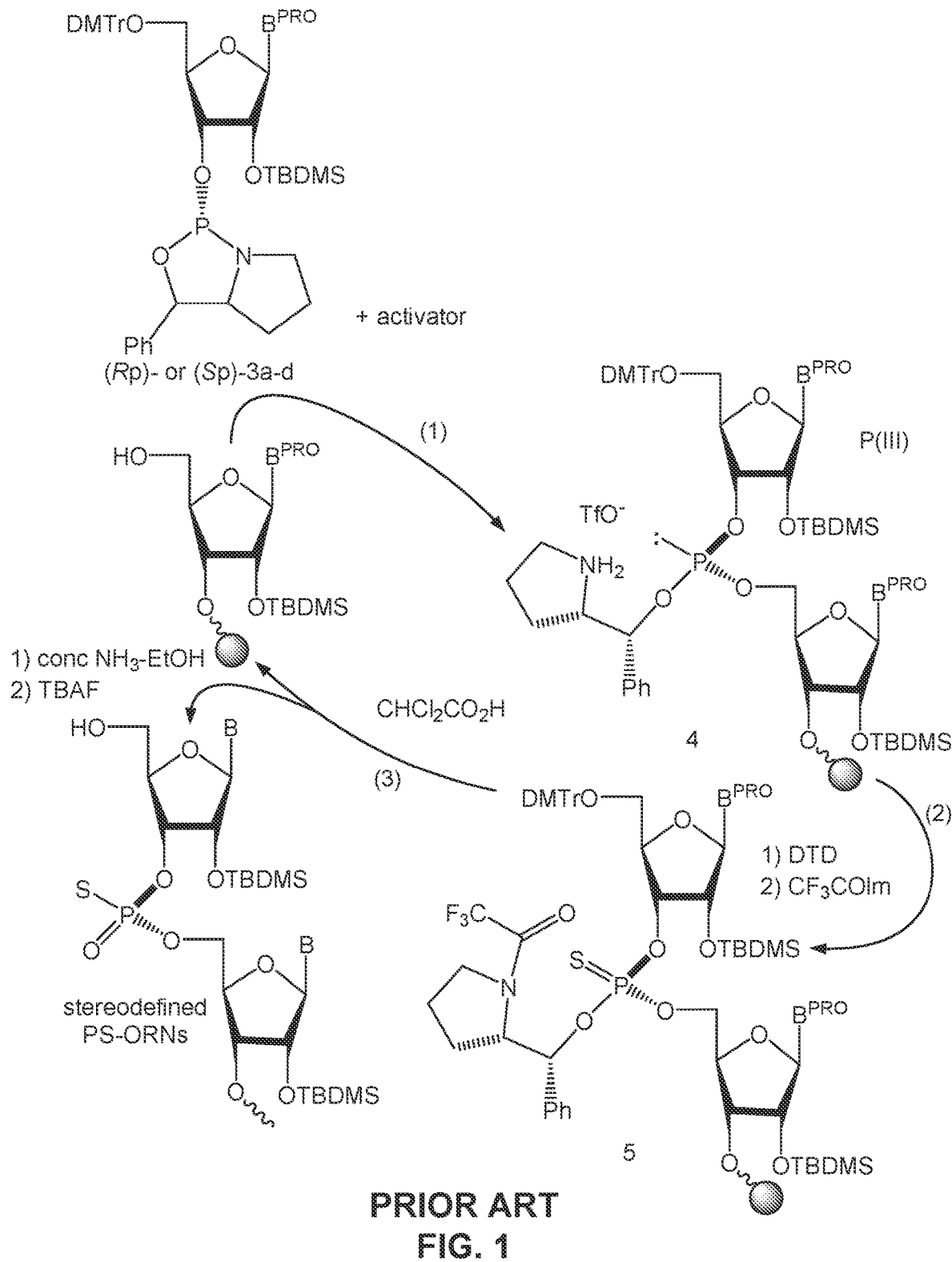
FIG. 1 is a schematic of the Wada synthesis of oligonucleotides with stereo-defined phosphorothioate linkages.

Compounds of the Disclosure are phosphorous-containing heterocycles containing phosphorous in (V) oxidation state (i.e., P(V)).

a. Phosphorous (V) Reagents

In one embodiment, Compounds of the Disclosure are compounds represented by Formula (I):

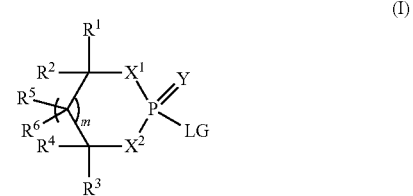

wherein
(a) $R^1$, $R^2$, $R^3$, $R^4$, $R^5$, and $R^6$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

or (b) any two of $R^1$, $R^2$, $R^3$, $R^4$, $R^5$, and $R^6$ together with the carbons to which they are attached form a $C_4$-$C_8$ cycloalkyl group, optionally substituted with one or more, the same or different, $R^a$ groups, while the remaining $R^1$, $R^2$, $R^3$, $R^4$, $R^5$, and $R^6$ are as defined above;

wherein $R^a$ is hydrogen, deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

$X^1$ and $X^2$ are independently O, S or $NR^c$; wherein $R^c$ is hydrogen or $C_1$-$C_4$ alkyl, Y is O, S or NR;

m is 0, 1 or 2, and

LG is a leaving group.

In one embodiment, the carbon bearing the $R^1$ and $R^2$ groups, the carbon bearing the $R^3$ and $R^4$ groups, or both, in the compound of formula (I) is chiral, and the compound of formula (I) is at least 90% stereochemically pure.

In another embodiment, the compounds of the present disclosure are represented by Formula (I), wherein (a) $R^1$, $R^2$, $R^3$, $R^4$, $R^5$, and $R^6$ are independently hydrogen; linear or branched $C_1$-$C_3$ alkyl; aryl; heteroaryl; or $C_3$-$C_6$ cycloalkyl;

or (b) any two of $R^1$, $R^2$, $R^3$, $R^4$, $R^5$, and $R^6$ together with the carbons to which they are attached form $C_4$-$C_6$ cycloalkyl, while the remaining $R^1$, $R^2$, $R^3$, $R^4$, $R^5$, and $R^6$ are independently hydrogen; linear or branched $C_1$-$C_3$ alkyl; aryl; heteroaryl; or $C_3$-$C_6$ cycloalkyl;

provided that either the carbon bearing the $R^1$ or $R^2$ groups, the carbon bearing the $R^3$ or $R^4$ groups, or both, is chiral;

$X^1$ and $X^2$ are independently O, S, or $NR^c$, wherein $R^c$ is hydrogen or $C_1$-$C_4$ alkyl;

Y is O, S or $NR^c$;

m is 0, 1 or 2, and

LG is a leaving group, and the compound of formula (I) is at least 90% stereochemically pure.

In one embodiment, Compounds of the Disclosure are compounds represented by Formula (Ia):

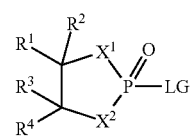

(Ia)

wherein $R^1$, $R^2$, $R^3$, $R^4$, $X^1$, $X^2$, Y, and LG are as defined above.

In some embodiments, $X^1$ is S, and $X^2$ is O. In other embodiments, $X^1$ is O, and $X^2$ is S. In other embodiments, both $X^1$ and $X^2$ are S. In some embodiments, Y is O or S. In one embodiment, Y is O. In another embodiment, Y is S. In another embodiment, Y is O or S. In one embodiment, $X^1$ is S, $X^2$ is O, and Y is O. In another embodiment, $X^1$ is S, $X^2$ is O, and Y is S. In one embodiment, $X^1$ is O, $X^2$ is S, and Y is O. In another embodiment, $X^1$ is O, $X^2$ is S, and Y is S. In one embodiment, $X^1$ is S, $X^2$ is S, and Y is S.

When both $X^1$ and $X^2$ are sulfur, Compounds of the Disclosure do not have phosphorus stereochemistry.

In another embodiment, Compounds of the Disclosure are compounds represented by Formulae (II-IIc):

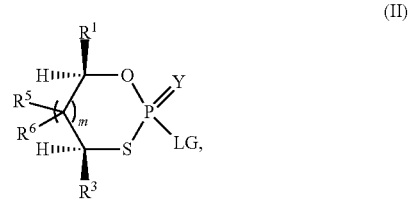

(II)

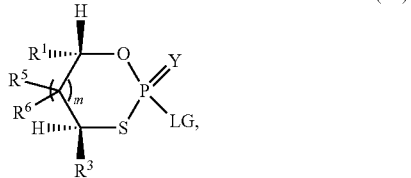

(IIa)

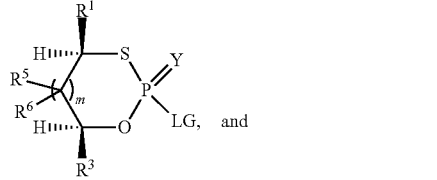

(IIb)

(IIc)

wherein (a) $R^1$, $R^3$, $R^5$ and $R^6$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

or (b) any two of $R^1$, $R^3$, $R^5$, and $R^6$ together with the carbons to which they are attached form a $C_4$-$C_8$ cycloalkyl group, optionally substituted with one or more, the same or different, $R^a$ groups, while the $R^1$, $R^3$, $R^5$ and $R^6$ are independently are as defined in (a); and $R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently, at each occurrence, the same or different, hydrogen, linear or branched $C_1$-$C_{12}$ alkyl, aryl, heteroaryl, heterocyclyl or $C_3$-$C_8$ cycloalkyl;

Y is O, S or $NR^c$, where $R^c$ is hydrogen or $C_1$-$C_4$ alkyl;

m is 0, 1 or 2, and

LG is a leaving group.

In one embodiment, the compounds of the present disclosure are represented by Formulae (II-IIc), wherein (a) $R^1$, $R^3$, $R^5$ and $R^6$ are independently hydrogen; linear or branched $C_1$-$C_3$ alkyl; $C_1$-$C_3$ alkyl substituted with halogen; CN; aryl; heteroaryl; or $C_3$-$C_6$ cycloalkyl; or (b) any two of $R^1$, $R^3$, $R^5$, and $R^6$ together with the carbons to which they are attached form $C_4$-$C_6$ cycloalkyl, while the $R^1$, $R^3$, $R^5$ and $R^6$ are independently are as defined in (a);

provided that either the carbon bearing the $R^1$ and $R^2$ groups, the carbon bearing the $R^3$ and $R^4$ groups, or both, is chiral;

Y is O, S or $NR^c$, wherein $R^c$ is hydrogen or $C_1$-$C_4$ alkyl;

m is 0, 1, or 2, and

LG is a leaving group.

In one embodiment, Compounds of the Disclosure are compounds represented by Formulae (IId-IIg):

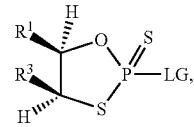
(IId)

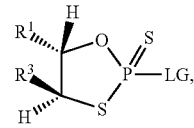
(IIe)

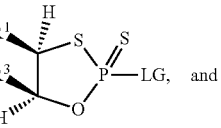
(IIf)

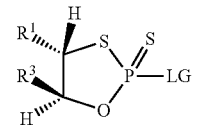
(IIg)

wherein (a) $R^1$ and $R^3$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

or (b) R and $R^3$ together with the carbons to which they are attached form a $C_4$-$C_8$ cycloalkyl group, optionally substituted with one or more, the same or different, $R^a$ groups;

$R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

provided that either the carbon bearing the $R^1$ and $R^2$ groups, the carbon bearing the $R^3$ and $R^4$ groups, or both, is chiral; and LG is a leaving group.

In yet another embodiment, Compounds of the Disclosure are compounds represented by Formulae (III-IIIc):

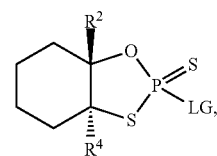
(III)

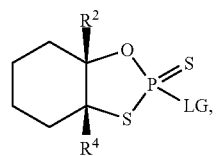
(IIIa)

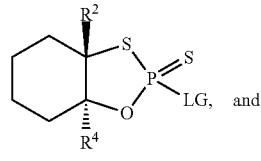
(IIIb)

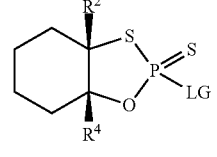
(IIIc)

wherein $R^2$ and $R^4$ are independently hydrogen or linear or branched $C_1$-$C_6$ alkyl, optionally substituted with one or more, the same or different, $R^a$ groups; and $R^a$ and LG are as defined above.

In one embodiment, Compounds of the Disclosure are compounds represented by the following Formula (IIId):

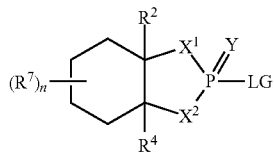

wherein
$R^2$ and $R^4$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

$R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

$R^7$ is hydrogen; $CD_3$, OH, halogen, CN, $CF_3$, linear or branched $C_1$-$C_6$ alkyl; linear or branched $C_2$-$C_6$ alkenyl, or linear or branched $C_2$-$C_6$ alkynyl;

$X^1$ and $X^2$ are independently O, S or $NR^c$, wherein $R^c$ is hydrogen or $C_1$-$C_4$ alkyl;

Y is O, S or $NR^c$;

n is 0, 1, 2, 3 or 4; and

LG is a leaving group.

In yet another embodiment, Compounds of the Disclosure are compounds represented by Formula (IIIe):

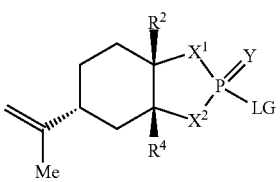

(IIIe)

wherein
$R^2$ and $R^4$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

$R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

provided that either the carbon bearing the $R^1$ and $R^2$ groups, the carbon bearing the $R^3$ and $R^4$ groups, or both, is chiral;

$X^1$ and $X^2$ are independently O, S or $NR^c$, wherein $R^c$ is hydrogen or $C_1$-$C_4$ alkyl;

Y is O, S or $NR^c$; and

LG is a leaving group.

In some embodiments, Compounds of the Disclosure can be characterized by ring strain, as represented by the following non-limiting examples:

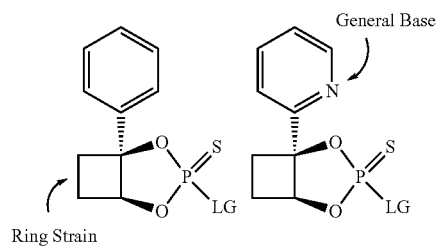

Ring Strain

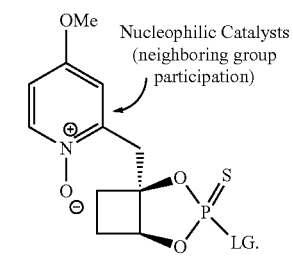

In additional embodiments, Compounds of the Disclosure comprise a strategic heteroatom (which makes the compounds amenable to in situ cleavage), as represented by the following non-limiting examples:

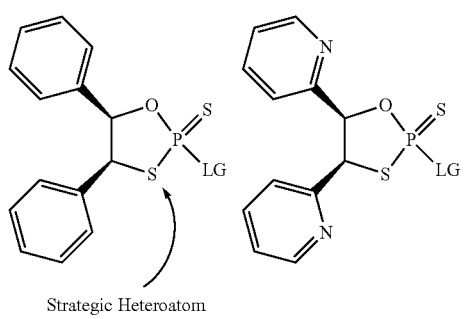

Strategic Heteroatom

-continued

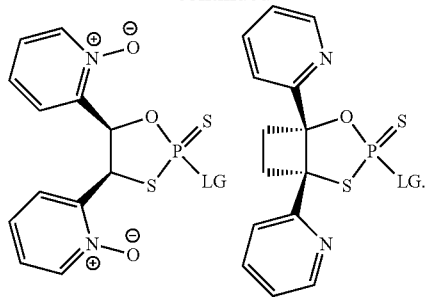

5

10

In another embodiment, Compounds of the Disclosure are any one or more of the compounds of Table 1.

TABLE 1

| Cpd. No. | Structure | Name |
|---|---|---|
| 1-1 | 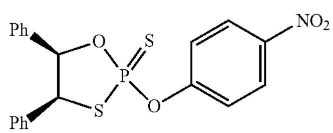 [SMILES: O=[N+]([O-])c1ccc(OP2(=S)O[C@H](c3ccccc3)[C@H](c3ccccc3)S2)cc1] | (4S,5R)-2-(4-nitrophenoxy)-4,5-diphenyl-1,3,2-oxathiaphospholane 2-sulfide |
| 1-2 | 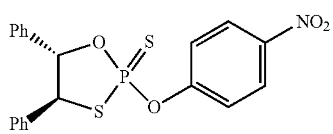 [SMILES: O=[N+]([O-])c1ccc(OP2(=S)O[C@@H](c3ccccc3)[C@H](c3ccccc3)S2)cc1] | (4S,5S)-2-(4-nitrophenoxy)-4,5-diphenyl-1,3,2-oxathiaphospholane 2-sulfide |
| 1-3 | 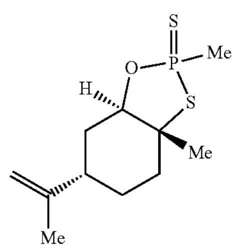 | (3aR,6S,7aR)-2,3a-dimethyl-6-(prop-1-en-2-yl)hexahydrobenzo[d][1,3,2]oxathiaphosphole 2-sulfide |
| 1-4 | 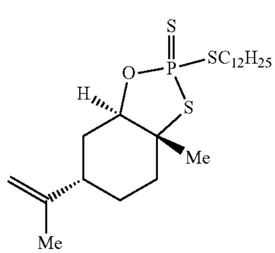 | (3aR,6S,7aR)-2-(dodecylthio)-3a-methyl-6-(prop-1-en-2-yl)hexahydrobenzo[d][1,3,2]oxathiaphosphole 2-sulfide |
| 1-5 | 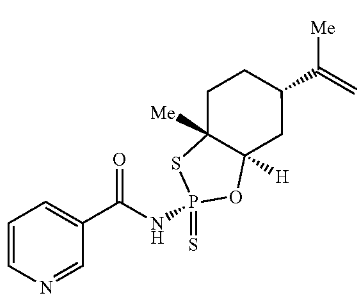 | N-((2S,3aR,6S,7aR)-3a-methyl-6-(prop-1-en-2-yl)-2-sulfidohexahydrobenzo[d][1,3,2]oxathiaphosphol-2-yl)nicotinamide |

TABLE 1-continued

| Cpd. No. | Structure | Name |
|---|---|---|
| 1-6 | 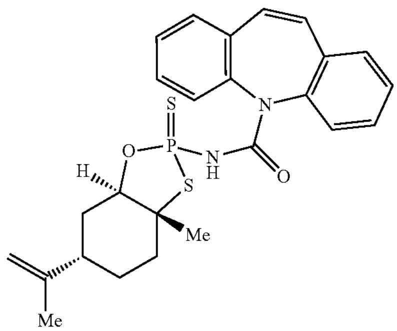 [SMILES: C=C(C)[C@H]1CC[C@@]2(C)SP(=S)(NC(=O)N3c4ccccc4C=Cc4ccccc43)O[C@@H]2C1] | N-((3aR,6S,7aR)-3a-methyl-6-(prop-1-en-2-yl)-2-sulfidohexahydrobenzo[d][1,3,2]oxathiaphosphol-2-yl)-5H-dibenzo[b,f]azepine-5-carboxamide |
| 1-7 | 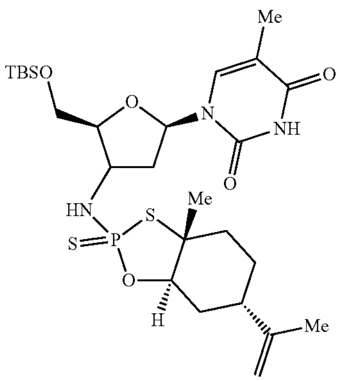 [SMILES: C=C(C)[C@H]1CC[C@@]2(C)SP(=S)(NC3C[C@H](n4cc(C)c(=O)[nH]c4=O)O[C@@H]3CO[Si](C)(C)C(C)(C)C)O[C@@H]2C1] | 1-((2R,4S,5S)-5-(((tert-butyldimethylsilyl)oxy)methyl)-4-(((3aR,6S,7aR)-3a-methyl-6-(prop-1-en-2-yl)-2-sulfidohexahydrobenzo[d][1,3,2]oxathiaphosphol 2-yl)amino)tetrahydrofuran-2-yl)-5-methylpyrimidine-2,4(1H,3H)-dione |
| 1-8 | 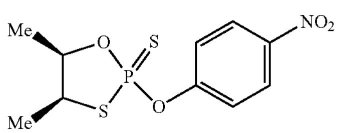 [SMILES: C[C@@H]1SP(=S)(Oc2ccc([N+](=O)[O-])cc2)O[C@@H]1C] | (4S,5R)-4,5-dimethyl-2-(4-nitrophenoxy)-1,3,2-oxathiaphospholane 2-sulfide |
| 1-9 | 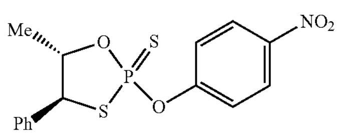 [SMILES: C[C@@H]1OP(=S)(Oc2ccc([N+](=O)[O-])cc2)S[C@H]1c1ccccc1] | (4S,5S)-4,5-dimethyl-2-(4-nitrophenoxy)-1,3,2-oxathiaphospholane 2-sulfide |
| 1-10 | 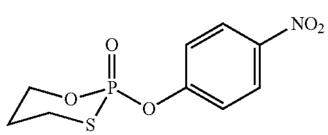 [SMILES: O=[N+]([O-])c1ccc(OP2(=O)OCCCS2)cc1] | 2-(4-nitrophenoxy)-1,3,2-oxathiaphosphinane 2-oxide |
| 1-11 | 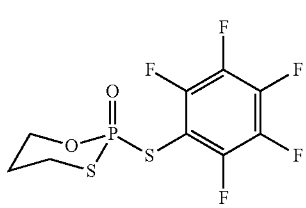 [SMILES: O=P1(Sc2c(F)c(F)c(F)c(F)c2F)OCCCS1] | 2-((perfluorophenyl)thio)-1,3,2-oxathiaphosphinane 2-oxide |
| 1-12 | 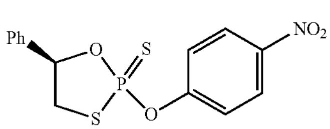 [SMILES: O=[N+]([O-])c1ccc(OP2(=S)O[C@H](c3ccccc3)CS2)cc1] | (5R)-2-(4-nitrophenoxy)-5-phenyl-1,3,2-oxathiaphospholane 2-sulfide |

TABLE 1-continued

| Cpd. No. | Structure | Name |
|---|---|---|
| 1-13 | 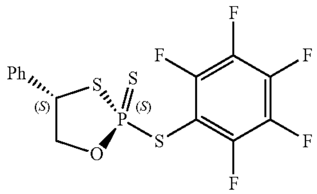 | (2S,4S)-2-((perfluorophenyl)thio)-4-phenyl-1,3,2-oxathiaphospholane 2-sulfide |
| 1-14 | 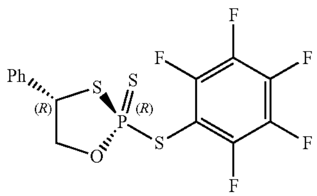 | (2R,4R)-2-((perfluorophenyl)thio)-4-phenyl-1,3,2-oxathiaphospholane 2-sulfide |
| 1-15 | 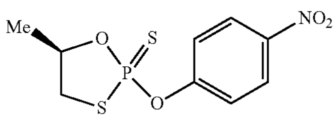 [SMILES: C[C@@H]1CSP(=S)(Oc2ccc([N+](=O)[O-])cc2)O1] | (5R)-5-methyl-2-(4-nitrophenoxy)-1,3,2-oxathiaphospholane 2-sulfide |
| 1-16 | 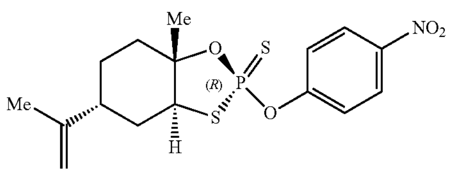 | (2R,3aS,5R,7aS)-7a-methyl-2-(4-nitrophenoxy)-5-(prop-1-en-2-yl)hexahydrobenzo[d][1,3,2]oxathiaphosphole 2-sulfide |
| 1-17 | 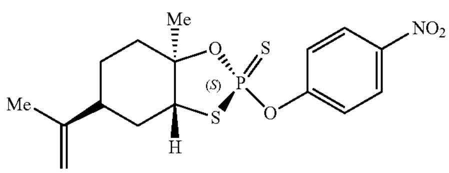 | (2S,3aR,5R,7aR)-7a-methyl-2-(4-nitrophenoxy)-5-(prop-1-en-2-yl)hexahydrobenzo[d][1,3,2]oxathiaphosphole 2-sulfide |
| 1-18 | 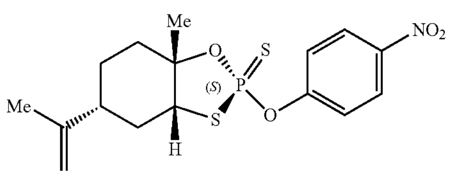 | (2S,3aS,6R,7aR)-3a-methyl-2-(4-nitrophenoxy)-6-(prop-1-en-2-yl)hexahydrobenzo[d][1,3,2]oxathiaphosphole 2-sulfide |
| 1-19 | 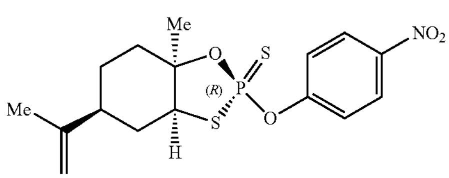 | (2R,3aR,6S,7aS)-3a-methyl-2-(4-nitrophenoxy)-6-(prop-1-en-2-yl)hexahydrobenzo[d][1,3,2]oxathiaphosphole 2-sulfide |
| 1-20 | 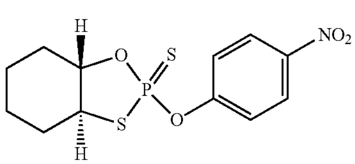 [SMILES: O=[N+]([O-])c1ccc(OP2(=S)O[C@H]3CCCC[C@@H]3S2)cc1] | (3aS,7aS)-2-(4-nitrophenoxy)hexahydrobenzo[d][1,3,2]oxathiaphosphole 2-sulfide |
| 1-21 | 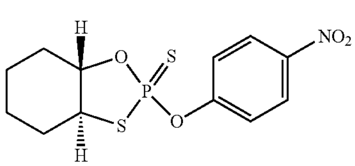 [SMILES: O=[N+]([O-])c1ccc(OP2(=S)O[C@H]3CCCC[C@@H]3S2)cc1] | (3aS,7aS)-2-(4-nitrophenoxy)hexahydrobenzo[d][1,3,2]oxathiaphosphole 2-sulfide |

TABLE 1-continued

| Cpd. No. | Name |
|---|---|
| 1-22 | (3aS,7aS)-7a-methyl-2-(4-nitrophenoxy)hexahydrobenzo[d][1,3,2]oxathiaphosphole 2-sulfide |
| 1-23 | (3aS,7aS)-3a-methyl-2-(4-nitrophenoxy)hexahydrobenzo[d][1,3,2]oxathiaphosphole 2-sulfide |
| 1-24 | (4S,5R)-5-methyl-2-(4-nitrophenoxy)-4-phenyl-1,3,2-oxathiaphospholane 2-sulfide |
| 1-25 | (4R,5S)-4-methyl-2-(4-nitrophenoxy)-5-phenyl-1,3,2-oxathiaphospholane 2-sulfide |
| 1-26 | (4S,5R)-2-(perfluorophenoxy)-4,5-diphenyl-1,3,2-oxathiaphospholane 2-sulfide |
| 1-27 | (4S,5R)-2-(naphthalen-2-ylthio)-4,5-diphenyl-1,3,2-oxathiaphospholane 2-sulfide |
| 1-28 | (4S,5R)-2-((4-nitrophenyl)thio)-4,5-diphenyl-1,3,2-oxathiaphospholane 2-sulfide |
| 1-29 | (4S,5R)-2-((4-fluorophenyl)thio)-4,5-diphenyl-1,3,2-oxathiaphospholane 2-sulfide |
| 1-30 | (4S,5R)-2-((4-fluorophenyl)thio)-4,5-diphenyl-1,3,2-oxathiaphospholane 2-sulfide |
| 1-31 | (2S,3aS,5R,7aS)-7a-methyl-2-((perfluorophenyl)thio)-5-(prop-1-en-2-yl)hexahydrobenzo[d][1,3,2]oxathiaphosphole 2-sulfide |

TABLE 1-continued

| Cpd. No. | Structure | Name |
|---|---|---|
| 1-32 | 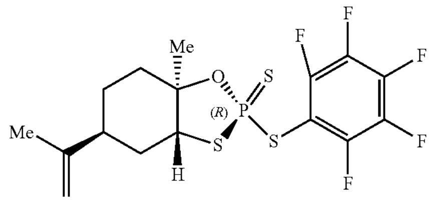 | (2R,3aR,5S,7aR)-7a-methyl-2-((perfluorophenyl)thio)-5-(prop-1-en-2-yl)hexahydrobenzo[d][1,3,2]oxathiaphosphole 2-sulfide |
| 1-33 | 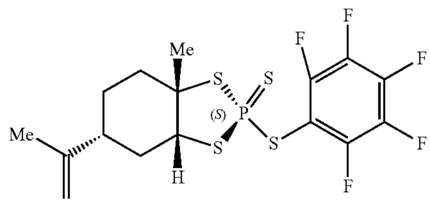 | (2S,3aS,6R,7aR)-3a-methyl-2-((perfluorophenyl)thio)-6-(prop-1-en-2-yl)hexahydrobenzo[d][1,3,2]oxathiaphosphole 2-sulfide |
| 1-34 | 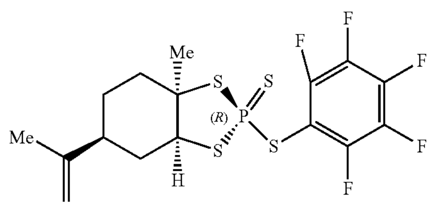 | (2R,3aR,6S,7aS)-3a-methyl-2-((perfluorophenyl)thio)-6-(prop-1-en-2-yl)hexahydrobenzo[d][1,3,2]oxathiaphosphole 2-sulfide |
| 1-35 | 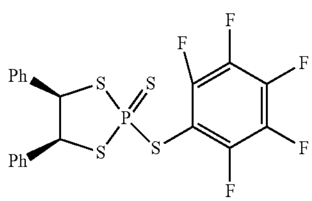 | (4S,5R)-2-((perfluorophenyl)thio)-4,5-diphenyl-1,3,2-oxathiaphospholane 2-sulfide |
| 1-36 | 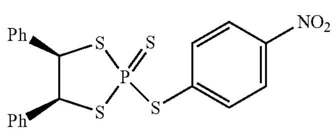 | (4S,5R)-2-(4-nitrophenoxy)-4,5-diphenyl-1,3,2-oxathiaphospholane 2-oxide |
| 1-37 | 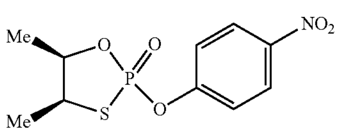 | (4S,5R)-4,5-dimethyl-2-(4-nitrophenoxy)-1,3,2-oxathiaphospholane 2-oxide |
| 1-38 | 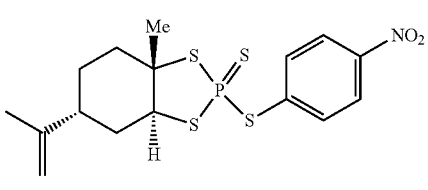 [SMILES: C=C(C)[C@@H]1CC[C@]2(C)SP(=S)(Sc3ccc([N+](=O)[O-])cc3)S[C@H]2C1] | (3aS,5R,7aS)-7a-methyl-2-(4-nitrophenoxy)-5-(prop-1-en-2-yl)hexahydrobenzo[d][1,3,2]oxathiaphosphole 2-oxide |
| 1-39 | 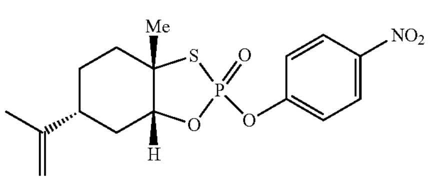 [SMILES: C=C(C)[C@@H]1CC[C@]2(C)SP(=O)(Oc3ccc([N+](=O)[O-])cc3)O[C@@H]2C1] | (3aS,6R,7aR)-3a-methyl-2-(4-nitrophenoxy)-6-(prop-1-en-2-yl)hexahydrobenzo[d][1,3,2]oxathiaphosphole 2-oxide |

TABLE 1-continued

| Cpd. No. | Structure | Name |
|---|---|---|
| 1-40 | 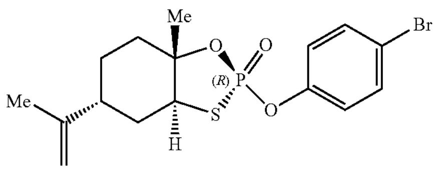 | (2R,3aS,5R,7aS)-7a-methyl-2-(4-nitrophenoxy)-5-(prop-1-en-2-yl)hexahydrobenzo[d][1,3,2]oxathiaphosphole 2-sulfide |
| 1-41 | 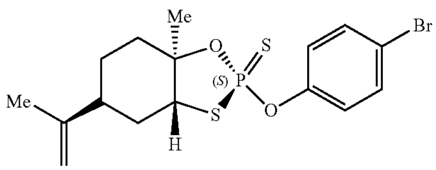 | (2S,3aR,5R,7aR)-2-(4-bromophenoxy)-7a-methyl-5-(prop-1-en-2-yl)hexahydrobenzo[d][1,3,2]oxathiaphosphole 2-sulfide |
| 1-42 | 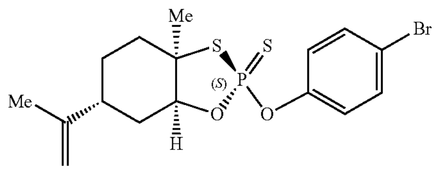 | (2S,3aS,6R,7aR)-2-(4-bromophenoxy)-3a-methyl-6-(prop-1-en-2-yl)hexahydrobenzo[d][1,3,2]oxathiaphosphole 2-sulfide |
| 1-43 | 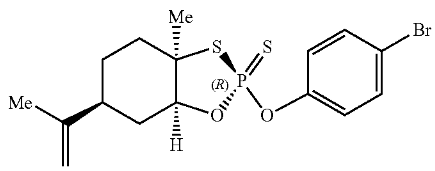 | (2R,3aR,6S,7aS)-2-(4-bromophenoxy)-3a-methyl-6-(prop-1-en-2-yl)hexahydrobenzo[d][1,3,2]oxathiaphosphole 2-sulfide |
| 1-44 | 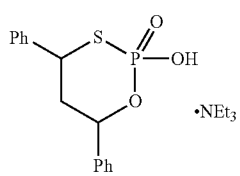 [SMILES: O=P1(O)OC(c2ccccc2)CC(c2ccccc2)S1 ; "·NEt3"] | trimethylamine salt of 2-hydroxy-4,6-diphenyl-1,3,2-oxathiaphosphinane 2-oxide |
| 1-45 | 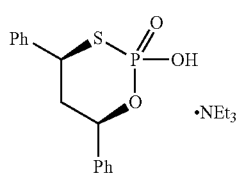 | triethylamine salt of (4S,6R)-2-hydroxy-4,6-diphenyl-1,3,2-oxathiaphosphinane 2-oxide |
| 1-46 | 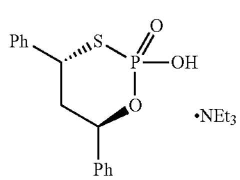 | triethylamine salt of (4R,6R)-2-hydroxy-4,6-diphenyl-1,3,2-oxathiaphosphinane 2-oxide |
| 1-47 | 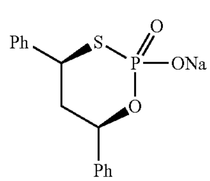 | sodium (4S,6R)-4,6-diphenyl-1,3,2-oxathiaphosphinan-2-olate 2-oxide |
| 1-48 | 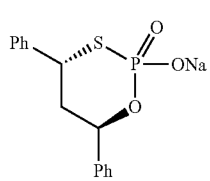 | sodium (4R,6R)-4,6-diphenyl-1,3,2-oxathiaphosphinan-2-olate 2-oxide |

TABLE 1-continued

| Cpd. No. | Structure | Name |
|---|---|---|
| 1-49 | 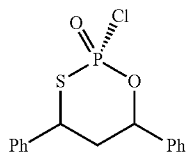 [SMILES: O=[P@@]1(Cl)OC(c2ccccc2)CC(c2ccccc2)S1] | 2-chloro-4,6-diphenyl-1,3,2-oxathiaphosphinane 2-oxide |
| 1-50 | 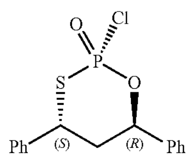 | (4S,6R)-2-chloro-4,6-diphenyl-1,3,2-oxathiaphosphinane 2-oxide |
| 1-51 | 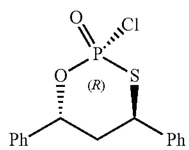 | (2R,4R,6R)-2-chloro-4,6-diphenyl-1,3,2-oxathiaphosphinane 2-oxide |
| 1-52 | 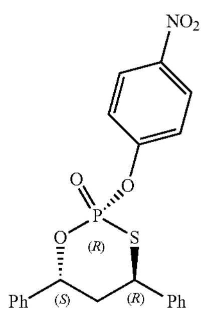 | (2R,4R,6S)-2-(4-nitrophenoxy)-4,6-diphenyl-1,3,2-oxathiaphosphinane 2-oxide |
| 1-53 | 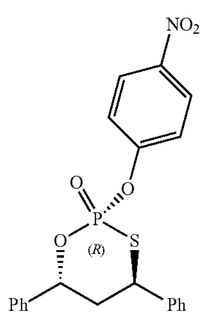 | (2R,4R,6R)-2-(4-nitrophenoxy)-4,6-diphenyl-1,3,2-oxathiaphosphinane 2-oxide |

In one embodiment, Compounds of the Disclosure are compounds selected from the group consisting of compounds 1-1 to 1-9, 1-12, and 1-15 to 1-43. In another embodiment, Compounds of the Disclosure are compounds selected from the group consisting of compounds 1-10, 1-11, 1-13, and 1-14. In another embodiment, Compounds of the Disclosure are compounds selected from the group consisting of compounds 1-44 to 1-53.

In yet another embodiment, Compounds of the Disclosure are compounds represented by Formula (Ia):

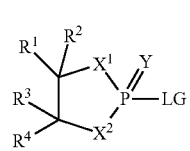

(Ia)

wherein
$R^1$, $R^2$, $R^3$, and $R^4$ are hydrogen;
$X^1$ and $X^2$ are independently O, S or $NR^c$; wherein $R^c$ is hydrogen or $C_1$-$C_4$ alkyl,
Y is O, S or $NR^c$; and
LG is a leaving group.

In another embodiment, Compounds of the Disclosure are compounds represented by Formula (Ia) above; $R^1$, $R^2$, $R^3$, and $R^4$ are hydrogen; $X^1$ and $X^2$ are S; Y is S; and LG is represented by Formula (LG1) below:

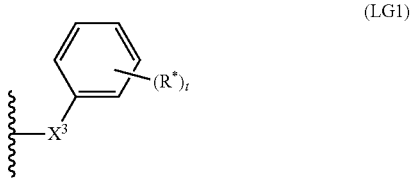

(LG1)

wherein
$X^3$ is —O—, or —S—;
R* is independently hydrogen, deuterium, —$CD_3$, $C_1$-$C_6$ alkyl, —OH, halogen, —CN, —$CF_3$, —$NO_2$, —O—$C_1$-$C_6$ alkyl, —O-aryl, —O-heteroaryl, —O—$C_3$-$C_8$ cycloalkyl, —O— heterocyclyl, —$NR^b$ $R^b$, —$COOR^b$, or —$CONR^bR^b$, where $R^a$ and $R^b$ are as defined above; and
t is 0, 1, 2, 3, 4, or 5.

In another embodiment, Compounds of the Disclosure are any one or more of the compounds of Table 2.

TABLE 2

| Cpd. No. | Structure | Name |
|---|---|---|
| 2-1 | 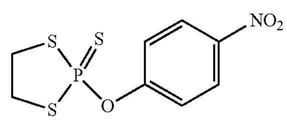 [SMILES: O=[N+]([O-])c1ccc(OP2(=S)SCCS2)cc1] | 2-(4-nitrophenoxy)-1,3,2-dithiaphospholane 2-sulfide |
| 2-2 | 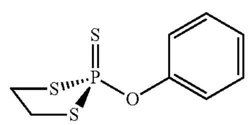 | 2-phenoxy-1,3,2-dithiaphospholane 2-sulfide |
| 2-3 | 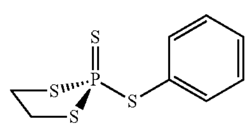 | 2-(phenylthio)-1,3,2-dithiaphospholane 2-sulfide |
| 2-4 | 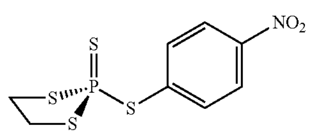 | 2-((4-nitrophenyl)thio)-1,3,2-dithiaphospholane 2-sulfide |
| 2-5 | 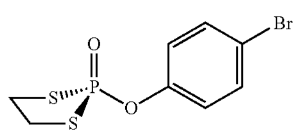 | 2-(4-bromophenoxy)-1,3,2-dithiaphospholane 2-sulfide |
| 2-6 | 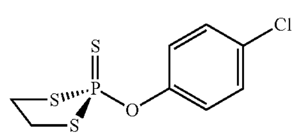 | 2-(4-chlorophenoxy)-1,3,2-dithiaphospholane 2-sulfide |

TABLE 2-continued

| Cpd. No. | Structure | Name |
|---|---|---|
| 2-7 | 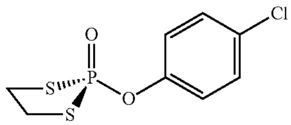 | 2-((4-chlorophenyl)thio)-1,3,2-dithiaphospholane 2-sulfide |
| 2-8 | 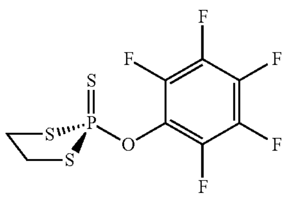 | 2-(perfluorophenoxy)-1,3,2-dithiaphospholane 2-sulfide |
| 2-9 | 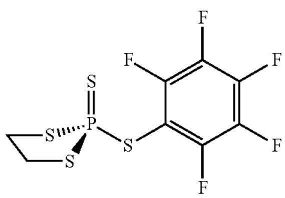 | 2-((perfluorophenyl)thio)-1,3,2-dithiaphospholane 2-sulfide |
| 2-10 | 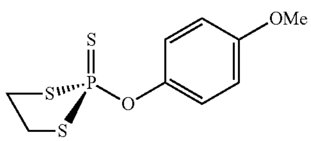 | 2-(4-methoxyphenoxy)-1,3,2-dithiaphospholane 2-sulfide |
| 2-11 | 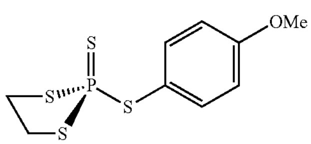 | 2-((4-methoxyphenyl)thio)-1,3,2-dithiaphospholane 2-sulfide |
| 2-12 | 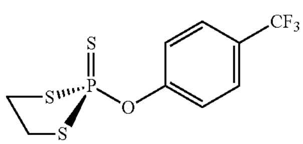 | 2-(4-(trifluoromethyl)phenoxy)-1,3,2-dithiaphospholane 2-sulfide |
| 2-13 | 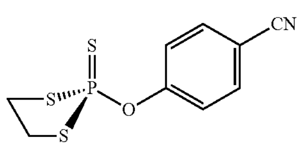 | 4-((2-sulfido-1,3,2-dithiaphospholan-2-yl)oxy)benzonitrile |
| 2-14 | 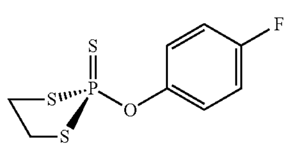 | 2-(4-fluorophenoxy)-1,3,2-dithiaphospholane 2-sulfide |
| 2-15 | 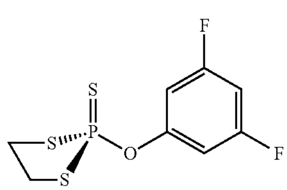 | 2-(3,5-difluorophenoxy)-1,3,2-dithiaphospholane 2-sulfide |

TABLE 2-continued

| Cpd. No. | Structure | Name |
|---|---|---|
| 2-16 | 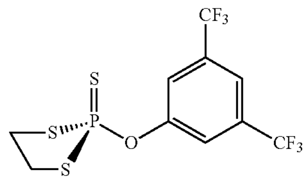 | 2-(3,5-bis(trifluoromethyl)phenoxy)-1,3,2-dithiaphospholane 2-sulfide |
| 2-17 | 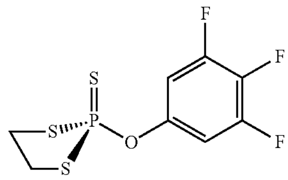 | 2-(3,4,5-trifluorophenoxy)-1,3,2-dithiaphospholane 2-sulfide |
| 2-18 | 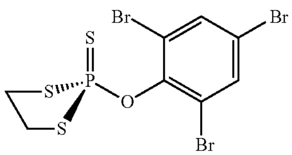 | 2-(2,4,6-tribromophenoxy)-1,3,2-dithiaphospholane 2-sulfide |
| 2-19 | 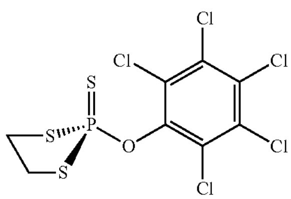 | 2-(perchlorophenoxy)-1,3,2-dithiaphospholane 2-sulfide |
| 2-20 | 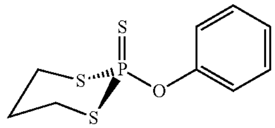 | 2-phenoxy-1,3,2-dithiaphosphinane 2-sulfide |
| 2-21 | 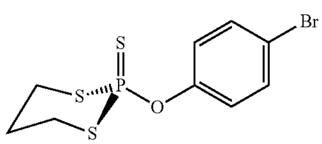 | 2-(4-bromophenoxy)-1,3,2-dithiaphosphinane 2-sulfide |

In one embodiment, Compounds of the Disclosure is compound 2-1. In another embodiment, Compounds of the Disclosure include one or more compounds selected from the group consisting of compounds 2-2 to 2-21.

The present disclosure further includes all possible stereoisomers and geometric isomers of Compounds of the Disclosure to include both racemic compounds and optically active isomers. When a Compound of the Disclosure is desired as a single enantiomer, it can be obtained either by resolution of the final product or by stereospecific synthesis from either isomerically pure starting material or use of a chiral auxiliary reagent, for example, see Z. Ma et al., Tetrahedron: Asymmetry, 8(6), pages 883-888 (1997). Resolution of the final product, an intermediate, or a starting material can be achieved by any suitable method known in the art. Additionally, in situations where tautomers of the Compounds of the Disclosure are possible, the present disclosure is intended to include all tautomeric forms of the compounds.

b. Nucleoside-Loaded Reagents

In another aspect, the present disclosure provides compounds represented by any one of Formulae (IV)-(VIe). In one embodiment, the compounds of the present disclosure are represented by Formula (IV):

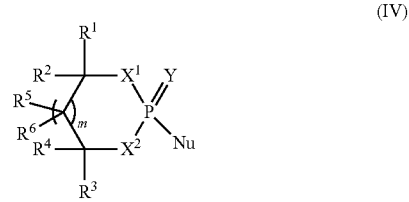

(IV)

wherein (a) $R^1$, $R^2$, $R^3$, $R^4$, $R^5$, and $R^6$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl;

optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

or (b) any two of $R^1$, $R^2$, $R^3$, $R^4$, $R^5$, and $R^6$ together with the carbons to which they are attached form a $C_4$-$C_8$ cycloalkyl group, optionally substituted with one or more, the same or different, $R^a$ groups, while the remaining $R^1$, $R^2$, $R^3$, $R^4$, $R^5$, and $R^6$ are as defined in (a);

$R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

$X^1$ and $X^2$ are independently O, S or $NR^c$; wherein $R^c$ is hydrogen or $C_1$-$C_4$ alkyl;

Y is O, S or $NR^c$;

m is 0, 1, or 2, and

Nu is a nucleoside;

provided that either the carbon bearing the $R^1$ and $R^2$ groups, the carbon bearing the $R^3$ and $R^4$ groups, or both, is chiral;

wherein the compound of formula (IV) is at least 90% stereochemically pure, with the proviso that Compound IV does not include any of the following compounds:

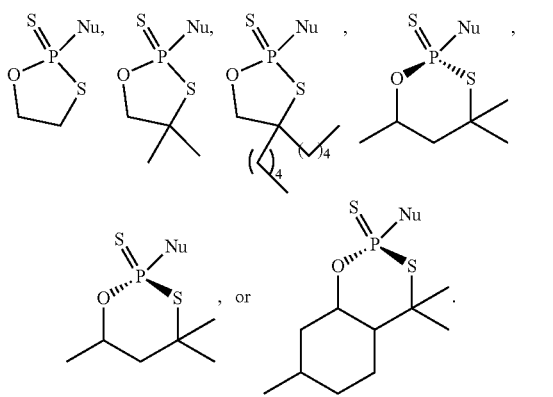

In one embodiment, the compound of the present disclosure are represented by Formula (IV), wherein (a) $R^1$, $R^2$, $R^3$, $R^4$, $R^5$, and $R^6$ are independently hydrogen; linear or branched $C_1$-$C_3$ alkyl; $C_1$-$C_3$ alkyl substituted with halogen; CN; aryl; heteroaryl; or $C_3$-$C_6$ cycloalkyl;

or (b) any two of $R^1$, $R^2$, $R^3$, $R^4$, $R^5$, and $R^6$ together with the carbons to which they are attached form $C_4$-$C_6$ cycloalkyl, while the remaining $R^1$, $R^2$, $R^3$, $R^4$, $R^5$, and $R^6$ are as defined in (a);

provided that either the carbon bearing the $R^1$ and $R^2$ groups, the carbon bearing the $R^3$ and $R^4$ groups, or both, is chiral;

$X^1$ and $X^2$ are independently O, S or $NR^c$, wherein $R^c$ is hydrogen or $C_1$-$C_4$ alkyl;

Y is O, S or NR;

m is independently 0, 1, or 2; and

Nu is a nucleoside.

In another embodiment, the compounds of the present disclosure are represented by Formula (IVa):

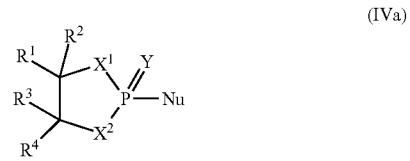

wherein $R^1$, $R^2$, $R^3$, $R^4$, $X^1$, $X^2$, Y, and Nu are as described for Formula (IV).

In another embodiment, the compounds of the present disclosure are represented by Formulae (V-Vc):

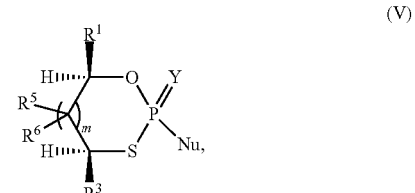

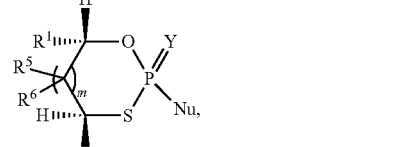

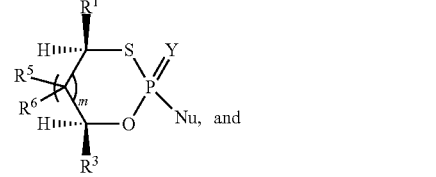

wherein (a) $R^1$, $R^3$, $R^5$ and $R^6$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups; or (b) any two of $R^1$, $R^3$, $R^5$, and $R^6$ together with the carbons to which they are attached form a $C_4$-$C_8$ cycloalkyl group, optionally substituted with one or more, the same or different, $R^a$ groups while the remaining $R^1$, $R^3$, $R^5$, and $R^6$ are as defined in (a);

$R^a$ is hydrogen; deuterium; $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

m is 0, 1, or 2;

Y is O, S or $NR^c$, wherein $R^c$ is hydrogen or $C_1$-$C_4$ alkyl; and

Nu is a nucleoside.

In one embodiment, the compounds of the present disclosure are represented by Formula (V), wherein (a) $R^1$, $R^3$, $R^5$ and $R^6$ are independently hydrogen; linear or branched $C_1$-$C_3$ alkyl; $C_1$-$C_3$ alkyl substituted with halogen; CN; aryl; heteroaryl; or $C_3$-$C_6$ cycloalkyl; or (b) any two of $R^1$, $R^3$, $R^5$, and $R^6$ together with the carbons to which they are attached form $C_4$-$C_6$ cycloalkyl, while the remaining $R^1$, $R^3$, $R^5$, and $R^6$ are as defined in (a);

provided that either the carbon bearing the $R^1$ and $R^2$ groups, the carbon bearing the $R^3$ and $R^4$ groups, or both, is chiral;

Y is O, S or $NR^c$, wherein $R^c$ is hydrogen or $C_1$-$C_4$ alkyl;

m is 0, 1, or 2, and

Nu is a nucleoside.

In another embodiment, the compounds of the present disclosure are represented by any one of Formulae (Vd-Vg):

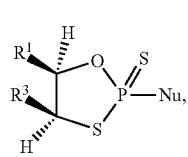
(Vd)

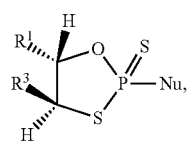
(Ve)

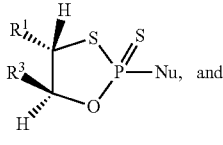
(Vf)

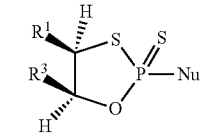
(Vg)

wherein $R^1$, $R^3$ and Nu are as described for Formulae (V-Vc).

In yet another embodiment, the compounds of the present disclosure are represented by any one of Formulae (VI-VIc):

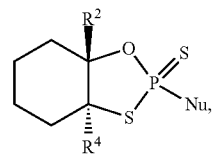
(VI)

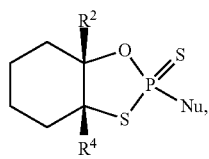
(VIa)

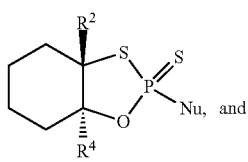
(VIb)

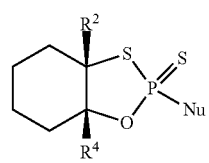
(VIc)

wherein $R^2$ and $R^4$ are independently hydrogen; linear or branched $C_1$-$C_6$ alkyl, optionally substituted with one or more, the same or different, $R^a$ groups; linear or branched $C_2$-$C_6$ alkenyl, optionally substituted with one or more, the same or different, $R^a$ groups; linear or branched $C_2$-$C_6$ alkynyl, optionally substituted with one or more, the same or different, $R^a$ groups; halogen, —CN, —$NO_2$; wherein $R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl; and Nu is a nucleoside.

In yet another embodiment, the compounds of the present disclosure are represented by Formula (VId)

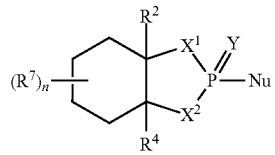

wherein $R^2$ and $R^4$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

$R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

$R^7$ is hydrogen; $CD_3$, OH, halogen, CN, $CF_3$, linear or branched $C_1$-$C_6$ alkyl; linear or branched $C_2$-$C_6$ alkenyl, or linear or branched $C_2$-$C_6$ alkynyl;

$X^1$ and $X^2$ are independently O, S or $NR^c$, wherein $R^c$ is hydrogen or $C_1$-$C_4$ alkyl;

Y is O, S or $NR^c$;

n is 0, 1, 2, 3 or 4; and

Nu is a nucleoside.

In yet another embodiment, the compounds of the present disclosure are represented by any one of Formula (VIe):

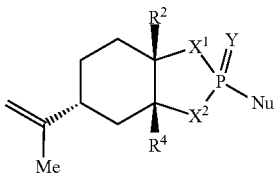

(VIe)

wherein $R^2$ and $R^4$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

$R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

provided that either the carbon bearing the $R^1$ or $R^2$ groups, the carbon bearing the $R^3$ or $R^4$ groups, or both, is chiral;

$X^1$ and $X^2$ are independently O, S or $NR^c$, wherein $R^c$ is hydrogen or $C_1$-$C_4$ alkyl;

Y is O, S or $NR^c$; and

Nu is a nucleoside.

In one embodiment, the nucleoside is a ribonucleoside. In another embodiment, the nucleoside is deoxyribonucleoside.

Nucleosides can be naturally occurring nucleosides, or non-naturally occurring nucleoside analogs. "Nucleoside analogs" as used herein are variants of natural nucleosides, such as DNA or RNA nucleosides, by virtue of modifications in the sugar and/or base moieties. Analogs could in principle be merely "silent" or "equivalent" to the natural nucleosides in the context of an oligonucleotide, i.e. have no functional effect on the way the oligonucleotide works. Such "equivalent" analogs can nevertheless be useful if, for example, they are easier or cheaper to manufacture, or are more stable to storage or manufacturing conditions, or represent a tag or label. In some embodiments, however, the analogs will have a functional effect on the way in which the oligonucleotide functions; for example by producing increased binding affinity to the target and/or increased resistance to intracellular nucleases and/or increased ease of transport into the cell.

Useful nucleosides employed herein can also include modified sugars. 2'-sugar modifications include fluoro, O-alkyl, O-alkylamino, O-alkylalkoxy, protected O-alkylamino, O-alkylaminoalkyl, O-alkyl imidazole, and polyethers of the formula (O-alkyl)$_m$, where m is 1 to about 10. Preferred among these polyethers are linear and cyclic polyethylene glycols (PEGs), and PEG-containing groups, such as crown ethers and those which are disclosed by Ouchi et al., *Drug Design and Discovery* 1992, 9, 93; Ravasio et al., *J. Org. Chem.* 1991, 56, 4329; and Delgardo et. al., *Critical Reviews in Therapeutic Drug Carrier Systems* 1992, 9, 249, each of which is hereby incorporated by reference in its entirety. Further nucleosides embodying sugar modifications are disclosed in Cook, Anti-Cancer Drug Design, 1991, 6, 585-607 and US Publication No. 2016/237427, hereby incorporated by reference in their entirety. Fluoro, O-alkyl, O-alkylamino, O-alkyl imidazole, O-alkylaminoalkyl, and alkyl amino substitutions are described in U.S. Pat. No. 6,166,197, entitled "Oligomeric Compounds having Pyrimidine Nucleotide(s) with 2' and 5' Substitutions," hereby incorporated by reference in its entirety.

Additional useful nucleosides having 2'-sugar modifications include 2'-SR and 2'-$NR_2$ groups, where each R is, independently, hydrogen, a protecting group or substituted or unsubstituted alkyl, alkenyl, or alkynyl. 2'-SR nucleosides are disclosed in U.S. Pat. No. 5,670,633, issued Sep. 23, 1997, hereby incorporated by reference in its entirety.

Useful nucleosides also include nucleosides derivatized with selenium (Se). Examples of Se-derivatized nucleosides include nucleosides where O-atom at the positions 2', and/or 5' of the sugar have been replaced with Se. Other examples include oxygen replacement with Se in the furanose ring, nucleobases and non-bridging phosphates. Such nucleic acids are described in, for example, Pallan et al., *Nat. Protoc.,* 2(3):647-51 (2007), and *Nat. Protoc.,* 2(3); 640-646 (2007), hereby incorporated by reference in their entirety.

Other examples of suitable nucleosides include boron containing nucleosides, such as those described in Schinazi et al., *Nucleosides and Nucleotides,* 17(635-647 (1998); *Biochem.,* 35(18):5741-5746 (1996); *J. Org. Chem.,* 79(8): 3465-3472 (2014), hereby incorporated by reference in their entirety.

Additional useful nucleoside analogs include, but are not limited to, Locked Nucleic Acid (LNA); 2'-O-alkyl-RNA; 2'-amino-DNA; 2'-fluoro-DNA; arabino nucleic acid (ANA); 2'-fluoro-ANA, hexitol nucleic acid (HNA), intercalating nucleic acid (INA), constrained ethyl nucleoside (cEt), 2'-O-methyl nucleic acid (2'-OMe), 2'-O-methoxyethyl nucleic acid (2'-MOE), or any combination thereof.

"Hexitol nucleic acids" or "HNA" are composed of phosphorylated 2,3-dideoxy-D-arabino-hexitol units with a nucleobase situated in the 2-[S]-position.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)-0-2'.

"2'-O-methoxyethyl" (also 2'-MOE and 2'-O(CH$_2$)$_2$—OCH$_3$ and MOE) refers to an O-methoxy-ethyl modification at the 2' position of a furanosyl ring. A 2'-O-methoxyethyl modified sugar is a modified sugar.

"2'-F" refers to modification of the 2' position of the furanosyl sugar ring to comprise a fluoro group.

As used herein, "2'-OMe" or "2'-OCH$_3$" or "2'-O-methyl" each refers to modification at the 2' position of the furanosyl sugar ring to comprise a —OCH$_3$ group.

Examples of suitable nucleotide analogs are provided by WO2007/031091, which is incorporated by reference in its entirety, or are referenced therein.

Incorporation of affinity-enhancing nucleotide analogs in an oligomer, such as LNA or 2'-substituted sugars, can allow the size of the specifically binding oligomer to be reduced, and can also reduce the upper limit to the size of the oligomer before non-specific or aberrant binding takes place.

In some embodiments, the nucleoside is a nucleoside analog that includes a bicyclic sugar. Non-limiting examples of the bicyclic sugar includes cEt, 2',4'-constrained 2'-O-methoxyethyl (cMOE), LNA, α-LNA, β-LNA, 2'-O,4'-C-ethylene-bridged nucleic acids (ENA), amino-LNA, oxy-LNA, or thio-LNA.

The term "LNA" refers to a bicyclic nucleoside analog, known as "Locked Nucleic Acid". It can refer to an LNA monomer, or, when used in the context of an "LNA oligonucleotide," LNA refers to an oligonucleotide containing one or more such bicyclic nucleotide analogs. LNA nucleosides are characterized by the presence of a linker group (such as a bridge) between C2' and C4' of the ribose sugar ring. This bridge includes, but is not limited to, a biradical (bivalent group) selected from —CH$_2$—O—, —CH$_2$—S—, —CH$_2$—NH—, —CH$_2$—N(CH$_3$)—, —CH$_2$—CH$_2$—O—, —CH$_2$—CH(CH$_3$)—, —CH$_2$—CH$_2$—S—, —CH$_2$—CH$_2$—NH—, —CH$_2$—CH$_2$—CH$_2$—, —CH$_2$—CH$_2$—CH$_2$—O—, —CH$_2$—CH$_2$—CH(CH$_3$)—, —CH═CH—CH$_2$—, —CH$_2$—O—CH$_2$—O—, —CH$_2$—NH—O—, —CH$_2$—N(CH$_3$)—O—, —CH$_2$—O—CH$_2$—, —CH(CH$_3$)—O—, and —CH(CH$_2$—O—CH$_3$)—O—, and/or, —CH$_2$—CH$_2$—, and —CH═CH— For all chiral centers, asymmetric groups can be found in either R or S orientation.

In some embodiments, the biradical can be —C(R$^a$R$^b$)—O—C(R$^c$R$^d$)—O—, wherein R$^a$, R$^b$, R$^c$, and R$^d$ are independently selected from the group consisting of hydrogen, halogen, C$_{1-6}$ alkyl, substituted C$_{1-6}$ alkyl, C$_{2-6}$ alkenyl, substituted C$_{2-6}$ alkenyl, C$_{2-6}$ alkynyl or substituted C$_{2-6}$ alkynyl, C$_{1-6}$ alkoxyl, substituted C$_{1-6}$ alkoxyl, acyl, substituted acyl, C$_{1-6}$ aminoalkyl or substituted C$_{1-6}$ aminoalkyl, such as hydrogen.

Suitable bicyclic nucleosides are disclosed in WO 2007/134181, WO2008/154401, WO2008/150729, WO2009/067647 (alpha-L-bicyclic nucleic acids analogs) and WO2009006478A, all of which are hereby incorporated by reference in its entirety.

Further bicyclic nucleoside analogs and their use in antisense oligonucleotides are disclosed in WO2011/115818, WO2011/085102, WO2011/017521, WO2009/100320, WO2010/036698, WO2009/124295 and WO2009/006478, each of which are incorporated by reference herein in their entireties.

The term "thio-LNA" comprises a locked nucleoside in which Y in general Formula III below is selected from S or —CH$_2$—S—. Thio-LNA can be in both beta-D and alpha-L-configuration.

The term "amino-LNA" comprises a locked nucleoside in which Y in general Formula III below is selected from —N(H)—, N(R)—, CH$_2$—N(H)—, and —CH$_2$—N(R)— where R is selected from hydrogen and C$_{1-4}$-alkyl. Amino-LNA can be in both beta-D and alpha-L-configuration.

The term "oxy-LNA" comprises a locked nucleoside in which Y in general Formula III below represents —O—. Oxy-LNA can be in both beta-D and alpha-L-configuration.

The term "ENA" comprises a locked nucleoside in which Y in general Formula III below is —CH$_2$—O— (where the oxygen atom of —CH$_2$—O— is attached to the 2'-position relative to the base B). Re is hydrogen or methyl.

In some exemplary embodiments LNA is selected from beta-D-oxy-LNA, alpha-L-oxy-LNA, beta-D-amino-LNA and beta-D-thio-LNA.

In some embodiments the nucleoside analogs can be, for example: 2'-O-alkyl-RNA units, 2'-amino-DNA units, 2'-fluoro-DNA units, LNA units, arabino nucleic acid (ANA) units, 2'-fluoro-ANA units, HNA units, INA (intercalating nucleic acid—Christensen, 2002. Nucl. Acids. Res. 2002 30: 4918-4925, hereby incorporated by reference) units and 2'-MOE units.

The term "nucleobase" refers to the base moiety of a nucleotide and covers both naturally occurring as well as non-naturally occurring variants. Thus, "nucleobase" covers not only the known purine and pyrimidine heterocycles but also heterocyclic analogs and tautomers thereof.

Typical nucleobases include, but are not limited to adenine, guanine, cytosine, thymidine, uracil, xanthine, hypoxanthine, 5-methylcytosine, isocytosine, pseudoisocytosine, 5-bromouracil, 5-propynyluracil, 6-aminopurine, 2-aminopurine, inosine, diaminopurine, and 2-chloro-6-aminopurine.

In some embodiments, the nucleoside comprises a naturally-occurring nucleobase, such as adenine, guanine, cytosine, uridine, thymine, 5-methyl cytosine, etc. In other embodiments, the nucleoside comprises other natural nucleobases, as well as modified nucleobases, such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally- and non-naturally-occurring nucleobases include those disclosed in U.S. Pat. No. 3,687,808 (Merigan et al.); in Sanghvi, in *Antisense Research and Application*, Chapter 15, S. T. Crooke and B. Lebleu, Eds., CRC Press, 1993; in Englisch et al., *Angewandte Chemie*, International Edition, 1991, 30, 613-722 (particularly, pages 622 and 623); in the Concise Encyclopedia of Polymer Science and Engineering, J. I. Kroschwitz, Ed., John Wiley & Sons, 1990, pages 858-859; in Zhang, et al., Nature, 2017, 551, 644-647 (hydrophobic bases); in Feldman and Romesberg, *Acc. Chem. Res.* 2018, 51, 394-403; and in Cook, Anti-Cancer Drug Design, 1991, 6, 585-607, each of which is hereby incorporated by reference in its entirety.

Other examples of modifications of nucleosides and nucleobases described herein include, but are not limited to the following: 2-methylthio-N6-(cis-hydroxyisopentenyl) adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methylthio-N6-isopentenyladenosine; 7-deaza-adenosine; N1-methyl-adenosine; N6, N6 (dimethyl)adenine; N6-cis-hydroxy-isopentenyladenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl) adenine; 2-(halo)adenine; 2-(propyl)adenine; 2'-amino-2'-deoxy-adenosine triphosphate; 2'-azido-2'-deoxy-adenosine triphosphate; 2'-deoxy-2'-a-aminoadenosine triphosphate; 2'-deoxy-2'-a-azidoadenosine triphosphate; 6-(alkyl)adenine; 6-(methyl)adenine; 7 (deaza)adenine; 8 (alkynyl) adenine; 8-(alkenyl)adenine; 8-(alkyl)adenine; 8-(alkynyl) adenine; 8-(amino)adenine; 8-(halo)adenine; 8-(hydroxyl) adenine; 8-(thioalkyl)adenine; 8-(thiol)adenine; 8-azidoadenosine; aza adenine; deaza adenine; N6 (methyl)adenine; N6-(isopentyl)adenine; 7-deaza-8-aza-adenosine; 7-methyladenine; 1-deazaadenosine triphosphate; 2'fluoro-N6-Bz-deoxyadenosine triphosphate; 2'-methoxy-2-amino-adenosine triphosphate; 2'O-methyl-N6-Bz-deoxyadenosine triphosphate; 2'-a-Ethynyladenosine triphosphate; 2-amino-adenine; 2-aminoadenosine triphosphate; 2-amino-adenosine triphosphate; 2'-a-trifluoromethyladenosine triphosphate; 2-azidoadenosine triphosphate; 2'-b-ethynyladenosine triphosphate; 2-bromoadenosine triphosphate; 2'-b-trifluoromethyladenosine triphosphate; 2-chloroadenosine triphosphate; 2'-deoxy-2',2'-difluoroadenosine triphosphate; 2'-deoxy-2'-a-mercaptoadenosine triphosphate; 2'-deoxy-2'-a-thiomethoxyadenosine triphosphate; 2'-deoxy-2'-b-aminoadenosine triphosphate; 2'-deoxy-2'-b-azidoadenosine triphosphate; 2'-deoxy-2'-b-bromoadenosine triphosphate; 2'-deoxy-2'-b-chloroadenosine triphosphate; 2'-deoxy-2'-b-fluoroadenosine triphosphate; 2'-deoxy-2'-b-iodoadenosine triphosphate; 2'-deoxy-2'-b-mercaptoadenosine triphosphate; 2'-deoxy-2'-b-thiomethoxyadenosine triphosphate; 2-fluoroadenosine triphosphate; 2-iodoadenosine triphosphate; 2-mercaptoadenosine triphosphate; 2-methoxy-adenine; 2-methylthio-adenine; 2-trifluoromethyladenosine triphosphate; 3-deaza-3-bromoadenosine triphosphate; 3-deaza-3-chloroadenosine triphosphate; 3-deaza-3-fluoroadenosine triphosphate; 3-deaza-3-iodoadenosine triphosphate; 3-deazaadenosine triphosphate; 4'-azidoadenosine triphosphate; 4'-carbocyclic adenosine triphosphate; 4'-ethynyladenosine triphosphate; 5'-homo-adenosine triphosphate; 8-aza-adenosine triphosphate; 8-bromoadenosine triphosphate; 8-Trifluoromethyladenosine triphosphate; 9-deazaadenosine triphosphate; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; pseudo-iso-cytidine; pyrrolo-cytidine; α-thiocytidine; 2-(thio)cytosine; 2'-amino-2'-deoxy-cytidine triphosphate; 2'-azido-2'-deoxycytidine triphosphate; 2'-deoxy-2'-a-aminocytidine triphosphate; 2'-deoxy-2'-a-azidocytidine triphosphate; 3 (deaza) 5 (aza)cytosine; 3 (methyl) cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl)cytosine; 5-(trifluoromethyl) cytosine; 5-bromo-cytidine; 5-iodo-cytidine; 5-propynyl cytosine; 6-(azo)cytosine; 6-aza-cytidine; aza cytosine; deaza cytosine; N4 (acetyl)cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; zebularine; (E)-5-(2-bromo-vinyl)cytidine triphosphate; 2,2'-anhydro-cytidine triphosphate hydrochloride; 2'fluor-N4-Bz-cytidine triphosphate; 2'fluoro-N4-acetyl-cytidine triphosphate; 2'-O-methyl-N4-acetyl-cytidine triphosphate; 2'O-methyl-N4-Bz-cytidine triphosphate; 2'-a-ethynylcytidine triphosphate; 2'-a-trifluoromethylcytidine triphosphate; 2'-b-ethynylcytidine triphosphate; 2'-b-trifluoromethylcytidine triphosphate; 2'-deoxy-2',2'-difluorocytidine triphosphate; 2'-deoxy-2'-a-mercaptocytidine triphosphate; 2'-deoxy-2'-a-thiomethoxycytidine triphosphate; 2'-deoxy-2'-b-aminocytidine triphosphate; 2'-deoxy-2'-b-azidocytidine triphosphate; 2'-deoxy-2'-b-bromocytidine triphosphate; 2'-deoxy-2'-b-chlorocytidine triphosphate; 2'-deoxy-2'-b-fluorocytidine triphosphate; 2'-deoxy-2'-b-iodocytidine triphosphate; 2'-deoxy-2'-b-mercaptocytidine triphosphate; 2'-deoxy-2'-b-thiomethoxycytidine triphosphate; 2'-O-methyl-5-(1-propynyl) cytidine triphosphate; 3'-ethynylcytidine triphosphate; 4'-azidocytidine triphosphate; 4'-carbocyclic cytidine triphosphate; 4'-ethynylcytidine triphosphate; 5-(1-propynyl) ara-cytidine triphosphate; 5-(2-chloro-phenyl)-2-thiocytidine triphosphate; 5-(4-amino-phenyl)-2-thiocytidine triphosphate; 5-aminoallyl-cytidine triphosphate; 5-cyano-cytidine triphosphate; 5-ethynylara-cytidine triphosphate; 5-ethynylcytidine triphosphate; 5'-homo-cytidine triphosphate; 5-methoxycytidine triphosphate; 5-trifluoromethyl-cytidine triphosphate; N4-amino-cytidine triphosphate; N4-benzoyl-cytidine triphosphate; pseudoisocytidine; 7-methylguanosine; N2,2'-O-dimethylguanosine; N2-methylguanosine; wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; archaeosine; methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxyguanosine triphosphate; 2'-Azido-2'-deoxyguanosine triphosphate; 2'-deoxy-2'-a-aminoguanosine triphosphate; 2'-deoxy-2'-a-azidoguanosine triphosphate; 6-(alkyl)guanine; 6-methyl-guanosine; 7-(alkyl)guanine; 7-(deaza)guanine; 7-(methyl)guanine; 8-(alkenyl)guanine; 8-(alkyl)guanine; 8-(alkynyl)guanine; 8-(amino)guanine; 8-(halo) guanine; 8-(hydroxyl)guanine; 8-(thioalkyl)guanine; 8-(thiol)guanine; aza guanine; deaza guanine; N-(methyl) guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-me-guanosine triphosphate; 2'fluoro-N2-isobutyl-guanosine triphosphate; 2'O- methyl-N2-isobutyl-guanosine triphosphate; 2'-a-ethynylguanosine triphosphate; 2'-a-trifluoromethylguanosine triphosphate; 2'-b-ethynylguanosine triphosphate; 2'-b-trifluoromethylguanosine triphosphate; 2'-deoxy-2',2'-difluoroguanosine triphosphate; 2'-deoxy-2'-a-mercaptoguanosine triphosphate; 2'-deoxy-2'-a-thiomethoxyguanosine triphosphate; 2'-deoxy-2'-b-aminoguanosine triphosphate; 2'-deoxy-2'-b-azidoguanosine triphosphate; 2'-deoxy-2'-b-bromoguanosine triphosphate; 2'-deoxy-2'-b-chloroguanosine triphosphate; 2'-deoxy-2'-b-fluoroguanosine triphosphate; 2'-deoxy-2'-b-iodoguanosine triphosphate; 2'-deoxy-2'-b-mercaptoguanosine triphosphate; 2'-deoxy-2'-b-thiomethoxyguanosine triphosphate; 4'-azidoguanosine triphosphate; 4'-carbocyclic guanosine triphosphate; 4'-ethynylguanosine triphosphate; 5'-homo-guanosine triphosphate; 8-bromo-guanosine triphosphate; 9-deazaguanosine triphosphate; N2-isobutyl-guanosine triphosphate; 1-methylinosine; inosine; 1,2'-O-dimethylinosine; 7-methylinosine; 2'-O-methylinosine; epoxyqueuosine; galactosyl-queuosine; mannosylqueuosine; queuosine; allyamino-thymidine; aza thymidine; deaza thymidine; deoxythymidine; 2-thiouridine; 3-methyluridine; 5-carboxymethyluridine; 5-hydroxyuridine; 5-methyluridine; 5-taurinomethyl-2-thiouridine; 5-taurinomethyluridine; dihydrouridine; pseudouridine; 1-methyl-3-(3-amino-5-carboxypropyl)pseudouridine; 1-methylpseduouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-methyl-pseudo-uridine triphosphate; 4-thiouridine; 5-(carboxyhydroxymethyl)uridine; 5-(carboxyhydroxymethyl)uridine methyl ester; 5,2'-O-dimethyluridine; 5,6-dihydro-uridine; 5-aminomethyl-2-thiouridine; 5-carbamoylmethyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyluridine; 5-carbamoylmethyluridine triphosphate; 5-methoxycarbonylmethyl-2'-O-methyluridine; 5-methoxycarbonylmethyl-2-thiouridine; 5-methoxycarbonylmethyluridine; 5-methoxyuridine; 5-methyl-2-thiouridine; 5-methylaminomethyl-2-selenouridine; 5-methylaminomethyl-2-thiouridine; 5-methylaminomethyluridine; 5-methyldihydrouridine; 5-oxyacetic acid-uridine triphosphate; 5-oxyacetic acid-methyl ester-uridine triphosphate; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-uridine triphosphate; 5-(isopentenylaminomethyl)-2-thiouridine triphosphate; 5-(isopentenylaminomethyl)-2'-O-methyluridine triphosphate; 5-(iso-pentenylaminomethyl)uridine triphosphate; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine triphosphate; 1-methyl-3-(3-amino-3-carboxypropyl) pseudo-uridine triphosphate; 1-methyl-pseudo-uridine triphosphate; 1-ethyl-pseudo-uridine triphosphate; 2 (thio) pseudouracil; 2' deoxy uridine; 2' fluorouridine; 2-(thio) uracil; 2,4-(dithio)psuedouracil; 2' methyl, 2'amino, 2'azido, 2'fluro-guanosine; 2'-amino-2'-deoxy-uridine triphosphate; 2'-azido-2'-deoxy-uridine triphosphate; 2'-azido-deoxyuridine triphosphate; 2' deoxy uridine; 2' fluorouridine; 2'-deoxy-2'-a-aminouridine triphosphate; 2'-deoxy-2'-a-azidouridine triphosphate; 2-methylpseudouridine; 3 (3 amino-3 carboxypropyl)uracil; 4-(thio)pseudouracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio)uracil; 5 (methylaminomethyl)-4 (thio) uracil; 5 (propynyl)uracil; 5 (trifluoromethyl)uracil; 5-(2-aminopropyl)uracil; 5-(alkyl)-2-(thio)pseudouracil; 5-(alkyl)-2,4 (dithio)pseudouracil; 5-(alkyl)-4 (thio) pseudouracil; 5-(alkyl)pseudouracil; 5-(alkyl)uracil; 5-(alkynyl)uracil; 5-(allylamino)uracil; 5-(cyanoalkyl)uracil; 5-(dialkylaminoalkyl)uracil; 5-(dimethylaminoalkyl) uracil; 5-(guanidiniumalkyl)uracil; 5-(halo)uracil; 5-(1,3-diazole-1-alkyl)uracil; 5-(methoxy)uracil; 5-(methoxycarbonylmethyl)-2-(thio)uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio) uracil; 5-(propynyl)uracil; 5-(trifluoromethyl)uracil; 5-aminoallyl-uridine; 5-bromo-uridine; 5-iodo-uridine; 5-uracil; 6-(azo)uracil; 6-aza-uridine; allyamino-uracil; aza uracil; deaza uracil; N3 (methyl)uracil; pseudo-uridine triphosphate-1-2-ethanoic acid; pseudouracil; 4-thio-pseudo-uridine triphosphate; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; dihydropseudouridine; (±)1-(2-hydroxypropyl)pseudouridine triphosphate; (2R)-1-(2-hydroxypropyl)pseudouridine triphosphate; (2S)-1-(2-hydroxypropyl)pseudouridine triphosphate; (E)-5-(2-bromo-vinyl)ara-uridine triphosphate; (E)-5-(2-bromo-vinyl)uridine triphosphate; (Z)-5-(2-Bromo-vinyl)ara-uridine triphosphate; (Z)-5-(2-bromo-vinyl)uridine triphosphate; 1-(2,2,2-trifluoroethyl)-pseudo-uridine triphosphate; 1-(2,2,3,3,3-pentafluoropropyl)pseudouridine triphosphate; 1-(2,2-diethoxyethyl)pseudouridine triphosphate; 1-(2,4,6-trimethylbenzyl)pseudouridine triphosphate; 1-(2,4,6-trimethyl-benzyl)pseudo-uridine triphosphate; 1-(2,4,6-trimethyl-phenyl)pseudo-uridine triphosphate; 1-(2-amino-2-carboxyethyl)pseudo-uridine triphosphate; 1-(2-amino-ethyl)pseudo-uridine triphosphate; 1-(2-hydroxyethyl)pseudouridine triphosphate; 1-(2-methoxyethyl) pseudouridine triphosphate; 1-(3,4-bis-trifluoromethoxy-benzyl)pseudouridine triphosphate; 1-(3,4-dimethoxybenzyl)pseudouridine triphosphate; 1-(3-amino-3-carboxypropyl)pseudo-uridine triphosphate; 1-(3-aminopropyl)pseudo-uridine triphosphate; 1-(3-cyclopropyl-prop-2-ynyl)pseudouridinetriphosphate; 1-(4-amino-4-carboxybutyl)pseudo-uridine triphosphate; 1-(4-amino-benzyl)pseudo-uridine triphosphate; 1-(4-amino-butyl) pseudo-uridine triphosphate; 1-(4-amino-phenyl)pseudouridine triphosphate; 1-(4-azidobenzyl)pseudouridine triphosphate; 1-(4-bromobenzyl)pseudouridine triphosphate; 1-(4-chlorobenzyl)pseudouridine triphosphate; 1-(4-fluorobenzyl)pseudouridine triphosphate; 1-(4-iodobenzyl) pseudouridine triphosphate; 1-(4-methanesulfonylbenzyl)

pseudouridine triphosphate; 1-(4-methoxybenzyl)pseudouridine triphosphate; 1-(4-methoxy-benzyl)pseudo-uridine triphosphate; 1-(4-methoxy-phenyl)pseudo-uridine triphosphate; 1-(4-methyl-benzyl)pseudo-uridine triphosphate; 1-(4-nitro-benzyl)pseudo-uridine triphosphate; 1-(4-nitro-phenyl)pseudo-uridine triphosphate; 1-(4-thiomethoxybenzyl)pseudouridine triphosphate; 1-(4-trifluoromethoxybenzyl)pseudouridine triphosphate; 1-(4-trifluoromethylbenzyl)pseudouridine triphosphate; 1-(5-amino-pentyl)pseudo-uridine triphosphate; 1-(6-aminohexyl)pseudo-uridine triphosphate; 1,6-dimethyl-pseudouridine triphosphate; 1-[3-(2-{2-[2-(2-aminoethoxy)-ethoxy]-ethoxy}-ethoxy)-propionyl]pseudouridine triphosphate; 1-{3-[2-(2-aminoethoxy)-ethoxy]-propionyl}pseudouridine triphosphate; 1-acetylpseudouridine triphosphate; 1-alkyl-6-(1-propynyl)-pseudo-uridine triphosphate; 1-alkyl-6-(2-propynyl)-pseudo-uridine triphosphate; 1-alkyl-6-allyl-pseudo-uridine triphosphate; 1-alkyl-6-ethynyl-pseudo-uridine triphosphate; 1-alkyl-6-homoallyl-pseudo-uridine triphosphate; 1-alkyl-6-vinyl-pseudo-uridine triphosphate; 1-allylpseudouridine triphosphate; 1-aminomethyl-pseudo-uridine triphosphate; 1-benzoylpseudouridine triphosphate; 1-benzyloxymethylpseudouridine triphosphate; 1-benzyl-pseudo-uridine triphosphate; 1-biotinyl-PEG2-pseudouridine triphosphate; 1-biotinylpseudouridine triphosphate; 1-butyl-pseudo-uridine triphosphate; 1-cyanomethylpseudouridine triphosphate; 1-cyclobutylmethyl-pseudo-uridine triphosphate; 1-cyclobutyl-pseudo-uridine triphosphate; 1-cycloheptylmethyl-pseudo-uridine triphosphate; 1-cycloheptyl-pseudo-uridine triphosphate; 1-cyclohexylmethyl-pseudo-uridine triphosphate; 1-cyclohexyl-pseudo-uridine triphosphate; 1-cyclooctylmethyl-pseudo-uridine triphosphate; 1-cyclooctyl-pseudo-uridine triphosphate; 1-cyclopentylmethyl-pseudo-uridine triphosphate; 1-cyclopentyl-pseudo-uridine triphosphate; 1-cyclopropylmethyl-pseudo-uridine triphosphate; 1-cyclopropyl-pseudo-uridine triphosphate; 1-hexyl-pseudo-uridine triphosphate; 1-homoallylpseudouridine triphosphate; 1-hydroxymethylpseudouridine triphosphate; 1-iso-propyl-pseudo-uridine triphosphate; 1-me-2-thio-pseudo-uridine triphosphate; 1-me-4-thio-pseudo-uridine triphosphate; 1-me-alpha-thio-pseudo-uridine triphosphate; 1-methanesulfonylmethylpseudouridine triphosphate; 1-methoxymethylpseudouridine triphosphate; 1-methyl-6-(2,2,2-trifluoroethyl)pseudo-uridine triphosphate; 1-methyl-6-(4-morpholino)-pseudo-uridine triphosphate; 1-methyl-6-(4-thiomorpholino)-pseudo-uridine triphosphate; 1-methyl-6-(substituted phenyl)pseudo-uridine triphosphate; 1-methyl-6-amino-pseudo-uridine triphosphate; 1-methyl-6-azido-pseudo-uridine triphosphate; 1-methyl-6-bromo-pseudo-uridine triphosphate; 1-methyl-6-butyl-pseudo-uridine triphosphate; 1-methyl-6-chloro-pseudo-uridine triphosphate; 1-methyl-6-cyano-pseudo-uridine triphosphate; 1-methyl-6-dimethylamino-pseudo-uridine triphosphate; 1-methyl-6-ethoxy-pseudo-uridine triphosphate; 1-methyl-6-ethylcarboxylate-pseudo-uridine triphosphate; 1-methyl-6-ethyl-pseudo-uridine triphosphate; 1-methyl-6-fluoro-pseudo-uridine triphosphate; 1-methyl-6-formyl-pseudo-uridine triphosphate; 1-methyl-6-hydroxyamino-pseudo-uridine triphosphate; 1-methyl-6-hydroxy-pseudo-uridine triphosphate; 1-methyl-6-iodo-pseudo-uridine triphosphate; 1-methyl-6-iso-propyl-pseudo-uridine triphosphate; 1-methyl-6-methoxy-pseudo-uridine triphosphate; 1-methyl-6-methylamino-pseudo-uridine triphosphate; 1-methyl-6-phenyl-pseudo-uridine triphosphate; 1-methyl-6-propyl-pseudo-uridine triphosphate; 1-methyl-6-tert-butyl-pseudo-uridine triphosphate; 1-methyl-6-trifluoromethoxy-pseudo-uridine triphosphate; 1-methyl-6-trifluoromethyl-pseudo-uridine triphosphate; 1-morpholinomethylpseudouridine triphosphate; 1-pentyl-pseudo-uridine triphosphate; 1-phenyl-pseudo-uridine triphosphate; 1-pivaloylpseudouridine triphosphate; 1-propargylpseudouridine triphosphate; 1-propyl-pseudo-uridine triphosphate; 1-propynyl-pseudouridine; 1-p-tolyl-pseudo-uridine triphosphate; 1-tert-Butyl-pseudo-uridine triphosphate; 1-thiomethoxymethylpseudouridine triphosphate; 1-thiomorpholinomethylpseudouridine triphosphate; 1-trifluoroacetylpseudouridine triphosphate; 1-trifluoromethyl-pseudo-uridine triphosphate; 1-vinylpseudouridine triphosphate; 2,2'-anhydro-uridine triphosphate; 2'-bromo-deoxyuridine triphosphate; 2'-F-5-methyl-2'-deoxy-uridine triphosphate; 2'-methoxy-5-methyl-uridine triphosphate; 2'-methoxy-pseudo-uridine triphosphate; 2'-a-ethynyluridine triphosphate; 2'-a-trifluoromethyluridine triphosphate; 2'-b-ethynyluridine triphosphate; 2'-b-trifluoromethyluridine triphosphate; 2'-deoxy-2',2'-difluorouridinetriphosphate; 2'-deoxy-2'-a-mercaptouridine triphosphate; 2'-deoxy-2'-a-thiomethoxyuridine triphosphate; 2'-deoxy-2'-b-aminouridine triphosphate; 2'-deoxy-2'-b-azidouridine triphosphate; 2'-deoxy-2'-b-bromouridine triphosphate; 2'-deoxy-2'-b-chlorouridine triphosphate; 2'-deoxy-2'-b-fluorouridine triphosphate; 2'-deoxy-2'-b-iodouridine triphosphate; 2'-deoxy-2'-b-mercaptouridine triphosphate; 2'-deoxy-2'-b-thiomethoxyuridine triphosphate; 2-methoxy-4-thio-uridine; 2-methoxyuridine; 2'-O-methyl-5-(1-propynyl)uridine triphosphate; 3-alkyl-pseudo-uridine triphosphate; 4'-azidouridine triphosphate; 4'-carbocyclic uridinetriphosphate; 4'-ethynyluridine triphosphate; 5-(1-propynyl)ara-uridine triphosphate; 5-(2-ruranyl)uridine triphosphate; 5-cyanouridine triphosphate; 5-dimethylaminouridine triphosphate; 5'-homo-uridine triphosphate; 5-iodo-2'-fluoro-deoxyuridine triphosphate; 5-phenylethynyluridine triphosphate; 5-trideuteromethyl-6-deuterouridine triphosphate; 5-trifluoromethyl-uridine triphosphate; 5-vinylarauridine triphosphate; 6-(2,2,2-trifluoroethyl)-pseudo-uridine triphosphate; 6-(4-morpholino)-pseudo-uridine triphosphate; 6-(4-thiomorpholino)-pseudouridine triphosphate; 6-(substituted-phenyl)-pseudo-uridine triphosphate; 6-amino-pseudo-uridine triphosphate; 6-azido-pseudo-uridine triphosphate; 6-bromo-pseudo-uridine triphosphate; 6-butyl-pseudo-uridine triphosphate; 6-chloro-pseudo-uridine triphosphate; 6-cyano-pseudo-uridine triphosphate; 6-dimethylamino-pseudo-uridine triphosphate; 6-ethoxy-pseudo-uridine triphosphate; 6-ethylcarboxylate-pseudo-uridine triphosphate; 6-ethyl-pseudo-uridine triphosphate; 6-fluoro-pseudo-uridine triphosphate; 6-formyl-pseudo-uridine triphosphate; 6-hydroxyamino-pseudo-uridine triphosphate; 6-hydroxy-pseudo-uridine triphosphate; 6-iodo-pseudo-uridine triphosphate; 6-iso-propyl-pseudo-uridine triphosphate; 6-methoxy-pseudo-uridine triphosphate; 6-methylamino-pseudo-uridine triphosphate; 6-methyl-pseudo-uridine triphosphate; 6-phenyl-pseudo-uridine triphosphate; 6-propyl-pseudo-uridine triphosphate; 6-tert-butyl-pseudo-uridine triphosphate; 6-trifluoromethoxy-pseudo-uridine triphosphate; 6-trifluoromethyl-pseudo-uridine triphosphate; alpha-thio-pseudo-uridine triphosphate; pseudouridine 1-(4-methylbenzenesulfonic acid) triphosphate; pseudouridine 1-(4-methylbenzoic acid) triphosphate; pseudouridine triphosphate 1-[3-(2-ethoxy)]propionic acid; pseudouridine triphosphate 1-[3-{2-(2-[2-(2-ethoxy)-ethoxy]-ethoxy)-ethoxy}]propionic acid; pseudouridine triphosphate 1-[3-{2-(2-[2-{2(2-ethoxy)-ethoxy}-ethoxy]-ethoxy)-ethoxy}]propionic acid; pseudouridine triphosphate 1-[3-{2-(2-[2-ethoxy]-ethoxy)-ethoxy}] propionic acid; pseudouridine triphosphate 1-[3-{2-(2-ethoxy)-ethoxy}]propionic acid; pseudouridine triphosphate 1-methylphosphonic acid; pseudouridine triphosphate 1-methylphosphonic acid diethyl ester; pseudo-uridine triphosphate-N1-3-propionic acid; pseudo-uridine triphosphate-N1-4-butanoic acid; pseudo-uridine triphosphate-N1-5-pentanoic acid; pseudo-uridine triphosphate-N1-6-hexanoic acid; pseudo-uridine triphosphate-N1-7-heptanoic acid; pseudo-uridine triphosphate-N1-methyl-p-benzoic acid; pseudo-uridine triphosphate-N1-p-benzoic acid;

wybutosine; hydroxywybutosine; isowyosine; peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl)isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1,3-(diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazinl-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; aminoindolyl; anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; difluorotolyl; hypoxanthine; imidizopyridinyl; inosinyl; isocarbostyrilyl; isoguanisine; N2-substituted purines; N6-methyl-2-amino-purine; N6-substituted purines; N-alkylated derivative; napthalenyl; nitrobenzimidazolyl; nitroimidazolyl; nitroindazolyl; nitropyrazolyl; nubularine; 06-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; oxoformycin triphosphate; para-(aminoalkylhydroxy)-6-phenyl-pyrrolo-pyrimidin-2-on-3-yl; para-substituted-6-phenyl-pyrrolo-pyrimidin-2-on-3-yl; pentacenyl; phenanthracenyl; phenyl; pyrenyl; pyridopyrimidin-3-yl; 2-oxo-7-amino-pyridopyrimidin-3-yl; pyrrolo-pyrimidin-2-on-3-yl; pyrrolopyrimidinyl; pyrrolopyrizinyl; stilbenzyl; substituted 1,2,4-triazoles; tetracenyl; tubercidine; xanthine; xanthosine-5)-triphosphate; 2-thio-zebularine; 5-aza-2-thio-zebularine; 7-deaza-2-amino-purine; pyridin-4-one ribonucleoside; 2-amino-riboside-triphosphate; formycin A triphosphate; formycin B triphosphate; pyrrolosine triphosphate; 2-hydroxyl-ara-adenosine triphosphate; 2-hydroxyl-ara-cytidine triphosphate; 2-hydroxyl-ara-uridine triphosphate; 2-hydroxyl-ara-guanosine triphosphate; 5-(2-carbomethoxyvinyl)uridine triphosphate; and N6-(19-amino-pentaoxanonadecyl)adenosine triphosphate.

In some embodiments, a nucleobase or a modified nucleobase of the nucleoside comprises a protecting group. Suitable protecting groups are described above. A skilled artisan will appreciate that the selection of a protecting group will be dictated by the nature of the nucleobase or the modified nucleobase. For example, an amine can be protected by Ac, iBu, Bn, or Bz.

In another embodiment, Compounds of the Disclosure are any one or more of the compounds of Table 3.

TABLE 3

| Cpd. No. | Structure | Name |
|---|---|---|
| 3-1 | 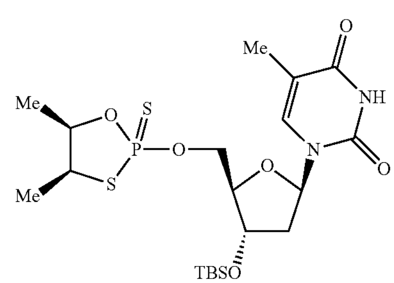 [SMILES: Cc1cn([C@H]2C[C@H](O[Si](C)(C)C(C)(C)C)[C@@H](COP3(=S)O[C@H](C)[C@H](C)S3)O2)c(=O)[nH]c1=O] | 1-((2R,4S,5R)-4-((tert-butyldimethylsilyl)oxy)-5-((((4S,5R)-4,5-dimethyl-2-sulfido-1,3,2-oxathiaphospholan-2-yl)oxy)methyl)tetrahydrofuran-2-yl)-5-methylpyrimidine-2,4(1H,3H)-dione |
| 3-2 | 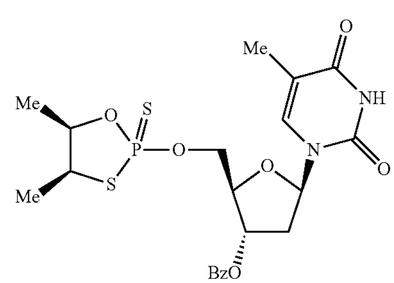 | (2R,3S,5R)-2-((((4S,5R)-4,5-dimethyl-2-sulfido-1,3,2-oxathiaphospholan-2-yl)oxy)methyl)-5-(5-methyl-2,4-dioxo-3,4-dihydropyrimidin-1(2H)-yl)tetrahydrofuran-3-yl benzoate |

TABLE 3-continued

| Cpd. No. | Structure | Name |
|---|---|---|
| 3-3 | 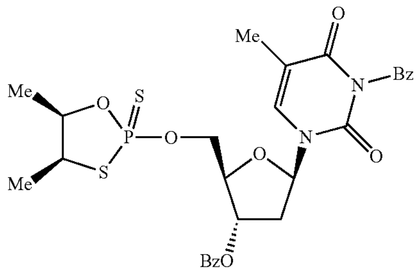 | (2R,3S,5R)-5-(3-benzoyl-5-methyl-2,4-dioxo-3,4-dihydropyrimidin-1(2H)-yl)-2-((((4S,5R)-4,5-dimethyl-2-sulfido-1,3,2-oxathiaphospholan-2-yl)oxy)methyl)tetrahydrofuran-3-yl benzoate |
| 3-4 | 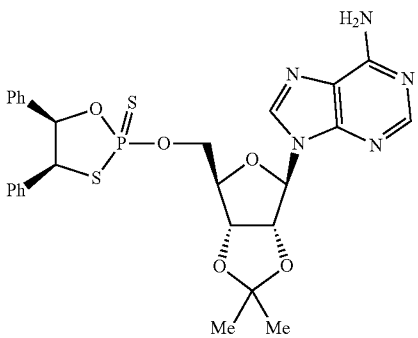 [SMILES: CC1(C)O[C@@H]2[C@H](O1)[C@@H](COP1(=S)O[C@H](c3ccccc3)[C@H](c3ccccc3)S1)O[C@H]2n1cnc2c(N)ncnc21] | (4S,5R)-2-(((3aR,4R,6R,6aR)-6-(6-amino-9H-purin-9-yl)-2,2-dimethyltetrahydrofuro[3,4-d][1,3]dioxol-4-yl)methoxy)-4,5-diphenyl-1,3,2-oxathiaphospholane 2-sulfide |
| 3-5 | 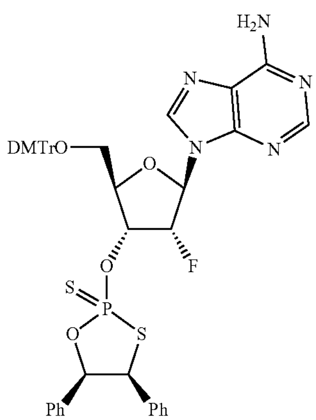 | (4S,5R)-2-(((2R,3R,4R,5R)-5-(6-amino-9H-purin-9-yl)-2-((bis(4-methoxyphenyl)(phenyl)methoxy)methyl)-4-fluorotetrahydrofuran-3-yl)oxy)-4,5-diphenyl-1,3,2-oxathiaphospholane 2-sulfide |
| 3-6 | 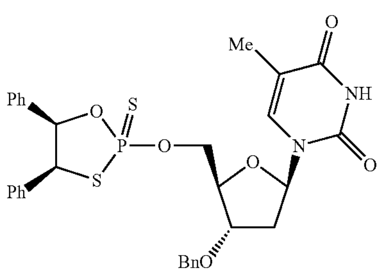 [SMILES: Cc1cn([C@H]2C[C@H](OCc3ccccc3)[C@@H](COP3(=S)O[C@H](c4ccccc4)[C@H](c4ccccc4)S3)O2)c(=O)[nH]c1=O] | 1-((2R,4S,5R)-4-(benzyloxy)-5-((((4S,5R)-4,5-diphenyl-2-sulfido-1,3,2-oxathiaphospholan-2-yl)oxy)methyl)tetrahydrofuran-2-yl)-5-methylpyrimidine-2,4(1H,3H)-dione |

TABLE 3-continued

| Cpd. No. | Structure | Name |
|---|---|---|
| 3-7 | 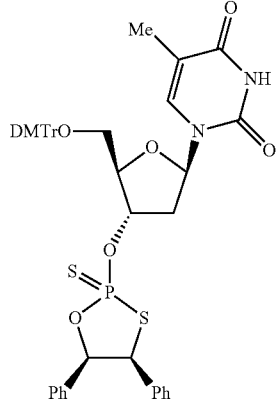 | 1-((2R,4S,5R)-5-((bis(4-methoxyphenyl)(phenyl)methoxy)methyl)-4-(((4S,5R)-4,5-diphenyl-2-sulfido-1,3,2-oxathiaphospholan-2-yl)oxy)tetrahydrofuran-2-yl)-5-methylpyrimidine-2,4(1H,3H)-dione |
| 3-8 | 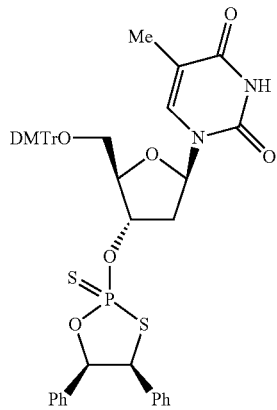 | 1-((2R,4S,5R)-5-((bis(4-methoxyphenyl)(phenyl)methoxy)methyl)-4-(((4S,5R)-4,5-diphenyl-2-sulfido-1,3,2-oxathiaphospholan-2-yl)oxy)tetrahydrofuran-2-yl)-5-methylpyrimidine-2,4(1H,3H)-dione |
| 3-9 | 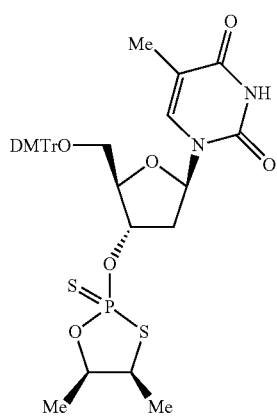 | 1-((2R,4S,5R)-5-((bis(4-methoxyphenyl)(phenyl)methoxy)methyl)-4-(((4S,5R)-4,5-dimethyl-2-sulfido-1,3,2-oxathiaphospholan-2-yl)oxy)tetrahydrofuran-2-yl)-5-methylpyrimidine-2,4(1H,3H)-dione |
| 3-10 | 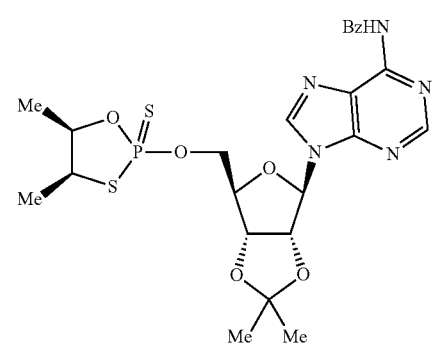 | N-(9-((3aR,4R,6R,6aR)-6-((((4S,5R)-4,5-dimethyl-2-sulfido-1,3,2-oxathiaphospholan-2-yl)oxy)methyl)-2,2-dimethyltetrahydrofuro[3,4-d][1,3]dioxol-4-yl)-9H-purin-6-yl)benzamide |

TABLE 3-continued

| Cpd. No. | Structure | Name |
|---|---|---|
| 3-11 | 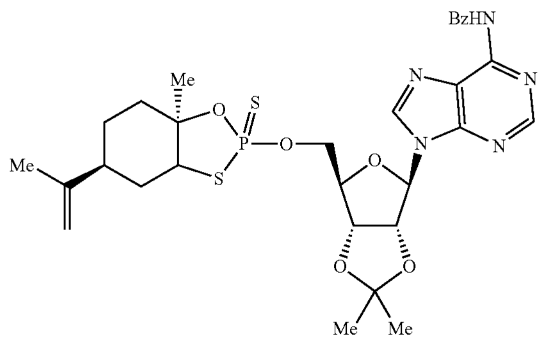 | N-(9-((3aR,4R,6R,6aR)-2,2-dimethyl-6-(((((5S,7aR)-7a-methyl-5-(prop-1-en-2-yl)-2-sulfidohexahydrobenzo[d][1,3,2]oxathiaphosphol-2-yl)oxy)methyl)tetrahydrofuro[3,4-d][1,3]dioxol-4-yl)-9H-purin-6-yl)benzamide |
| 3-12 | 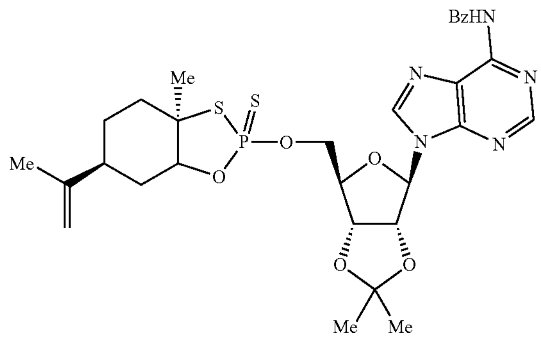 | N-(9-((3aR,4R,6R,6aR)-2,2-dimethyl-6-(((((3aR,6S)-3a-methyl-6-(prop-1-en-2-yl)-2-sulfidohexahydrobenzo[d][1,3,2]oxathiaphosphol-2-yl)oxy)methyl)tetrahydrofuro[3,4-d][1,3]dioxol-4-yl)-9H-purin-6-yl)benzamide |
| 3-13 | 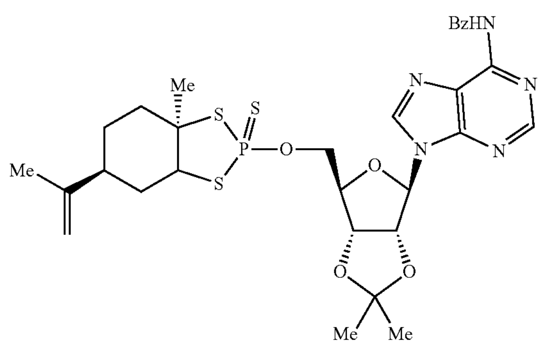 | N-(9-((3aR,4R,6R,6aR)-2,2-dimethyl-6-(((((3aR,6S)-3a-methyl-6-(prop-1-en-2-yl)-2-sulfidohexahydrobenzo[d][1,3,2]dithiaphosphol-2-yl)oxy)methyl)tetrahydrofuro[3,4-d][1,3]dioxol-4-yl)-9H-purin-6-yl)benzamide |
| 3-14 | 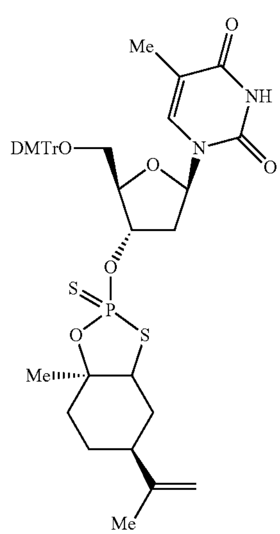 | 1-((2R,4S,5R)-5-((bis(4-methoxyphenyl)(phenyl)methoxy)methyl)-4-(((5S,7aR)-7a-methyl-5-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |

TABLE 3-continued

| Cpd. No. | Structure | Name |
|---|---|---|
| 3-15 | 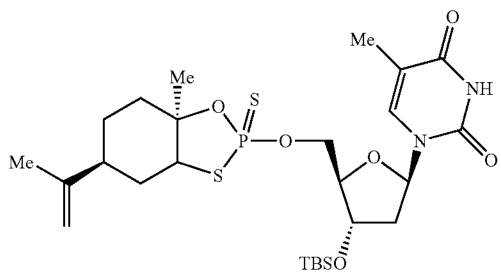 [SMILES: C=C(C)[C@H]1CC[C@@]2(C)OP(=S)(OC[C@H]3O[C@@H](n4cc(C)c(=O)[nH]c4=O)C[C@@H]3O[Si](C)(C)C(C)(C)C)SC2C1] | 1-((2R,4S,5R)-4-((tert-butyldimethylsilyl)oxy)-5-(((((5S,7aR)-7a-methyl-5-(prop-1-en-2-yl)-2-sulfidohexahydrobenzo[d][1,3,2]oxathiaphosphol-2-yl)oxy)methyl)tetrahydrofuran-2-yl)-5-methylpyrimidine-2,4(1H,3H)-dione |
| 3-16 | 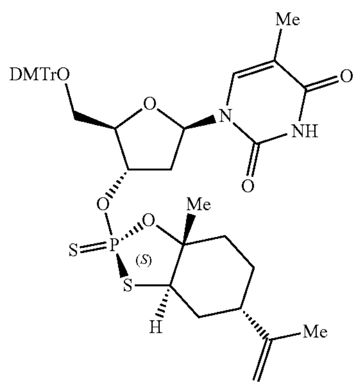 | 1-((2R,4S,5R)-5-((bis(4-methoxyphenyl)(phenyl)methoxy)methyl)-4-(((2S,3aR,5S,7aR)-7a-methyl-5-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-17 | 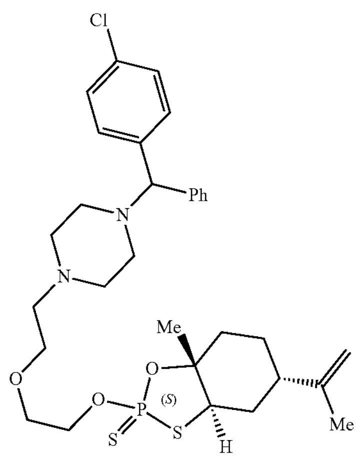 | (2S,3aR,5S,7aR)-2-(2-(2-(4-((4-chlorophenyl)(phenyl)methyl)piperazin-1-yl)ethoxy)ethoxy)-7a-methyl-5-(prop-1-en-2-yl)hexahydrobenzo[d][1,3,2]oxathiaphosphole 2-sulfide |
| 3-18 | 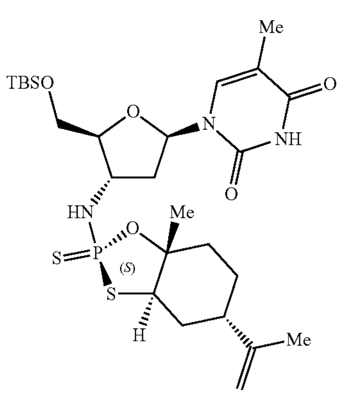 | 1-((2R,4S,5S)-5-(((tert-butyldimethylsilyl)oxy)methyl)-4-(((2S,3aR,5S,7aR)-7a-methyl-5-(prop-1-en-2-yl)-2-sulfidohexahydrobenzo[d][1,3,2]oxathiaphosphol-2-yl)amino)tetrahydrofuran-2-yl)-5-methylpyrimidine-2,4(1H,3H)-dione |

TABLE 3-continued

| Cpd. No. | Structure | Name |
|---|---|---|
| 3-19 | 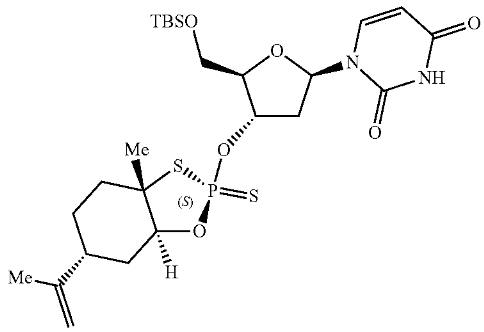 | 1-((2R,4S,5R)-5-(((tert-butyldimethylsilyl)oxy)methyl)-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)pyrimidine-2,4(1H,3H)-dione |
| 3-20 | 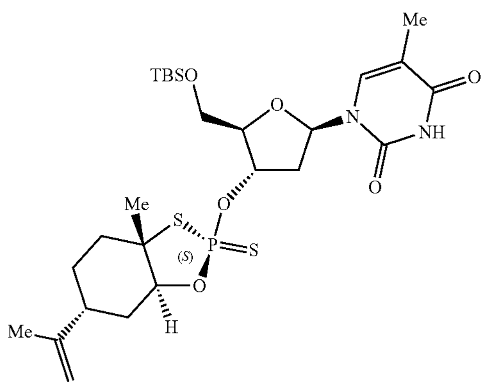 | 1-((2R,4S,5R)-5-(((tert-butyldimethylsilyl)oxy)methyl)-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-21 | 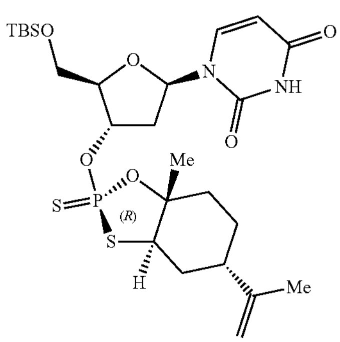 | 1-((2R,4S,5R)-5-(((tert-butyldimethylsilyl)oxy)methyl)-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)pyrimidine-2,4(1H,3H)-dione |
| 3-22 | 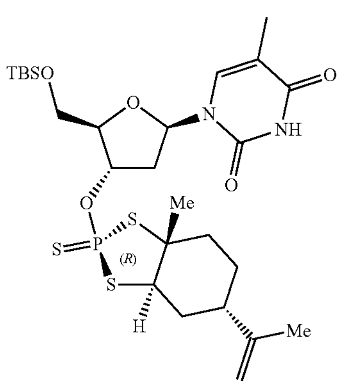 | 1-((2R,4S,5R)-5-(((tert-butyldimethylsilyl)oxy)methyl)-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |

TABLE 3-continued

| Cpd. No. | Structure | Name |
|---|---|---|
| 3-23 | 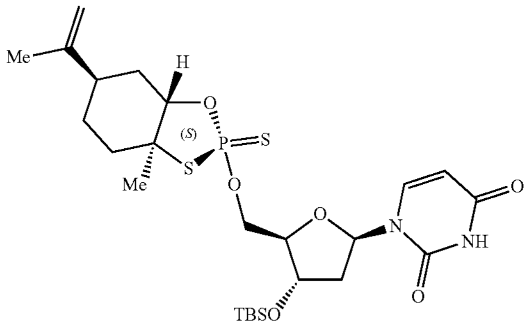 | 1-((2R,4S,5R)-4-((tert-butyldimethylsilyl)oxy)-5-((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidine-2,4(1H,3H)-dione |
| 3-24 | 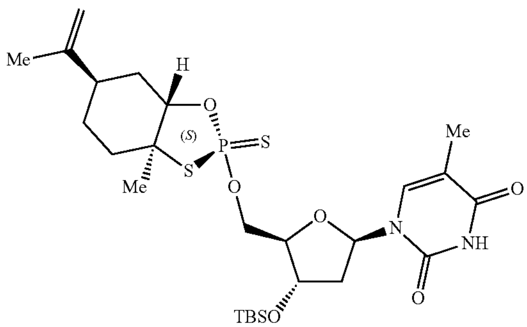 | 1-((2R,4S,5R)-4-((tert-butyldimethylsilyl)oxy)-5-((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-5-methylpyrimidine-2,4(1H,3H)-dione |
| 3-25 | 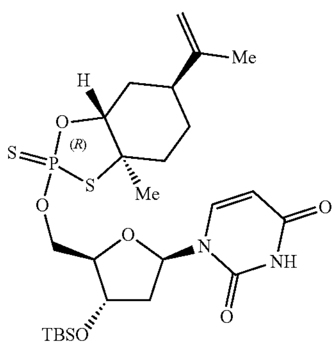 | 1-((2R,4S,5R)-4-((tert-butyldimethylsilyl)oxy)-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidine-2,4(1H,3H)-dione |
| 3-26 | 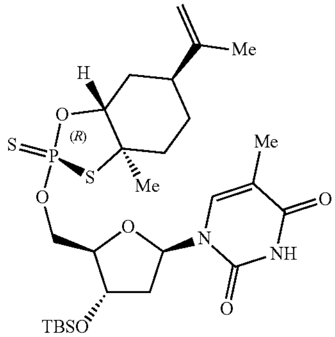 | 1-((2R,4S,5R)-4-((tert-butyldimethylsilyl)oxy)-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-5-methylpyrimidine-2,4(1H,3H)-dione |

TABLE 3-continued

| Cpd. No. | Structure | Name |
|---|---|---|
| 3-27 | 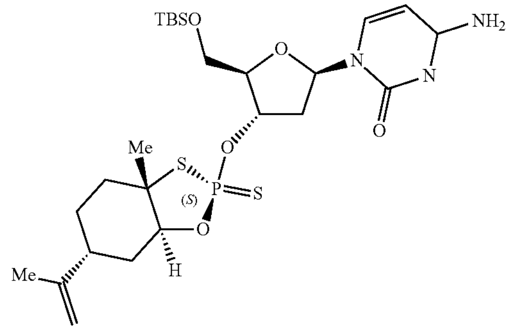 | 4-amino-1-((2R,4S,5R)-5-(((tert-butyldimethylsilyl)oxy)methyl)-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)pyrimidin-2(1H)-one |
| 3-28 | 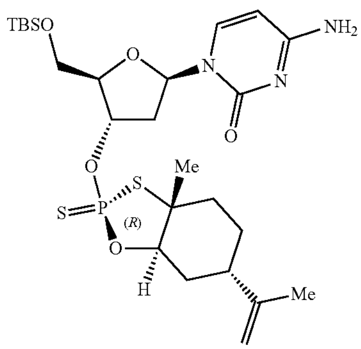 | 4-amino-1-((2R,4S,5R)-5-(((tert-butyldimethylsilyl)oxy)methyl)-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)pyrimidin-2(1H)-one |
| 3-29 | 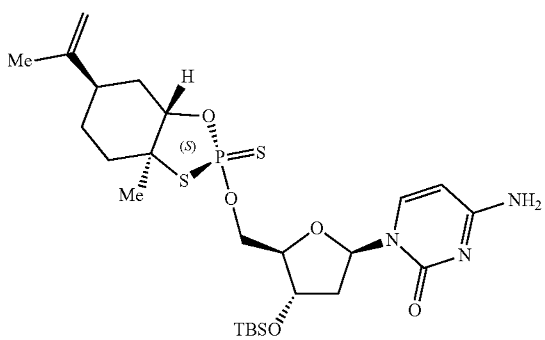 | 4-amino-1-((2R,4S,5R)-4-((tert-butyldimethylsilyl)oxy)-5-((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidin-2(1H)-one |
| 3-30 | 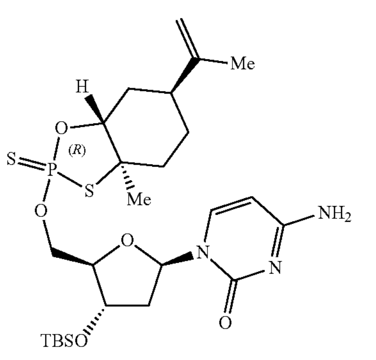 | 4-amino-1-((2R,4S,5R)-4-((tert-butyldimethylsilyl)oxy)-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidin-2(1H)-one |

TABLE 3-continued

| Cpd. No. | Structure | Name |
|---|---|---|
| 3-31 | 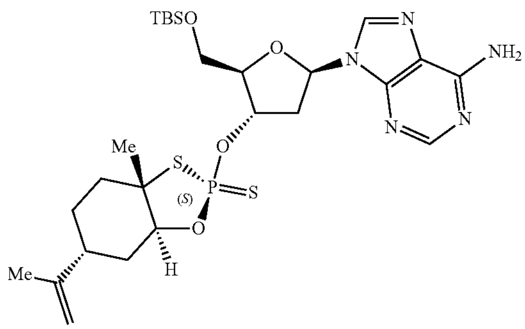 | (2S,3aS,6R,7aS)-2-(((2R,3S,5R)-5-(6-amino-9H-purin-9-yl)-2-(((tert-butyldimethylsilyl)oxy)methyl)tetrahydrofuran-3-yl)oxy)-3a-methyl-6-(prop-1-en-2-yl)hexahydrobenzo[d][1,3,2]oxathiaphosphole 2-sulfide |
| 3-32 | 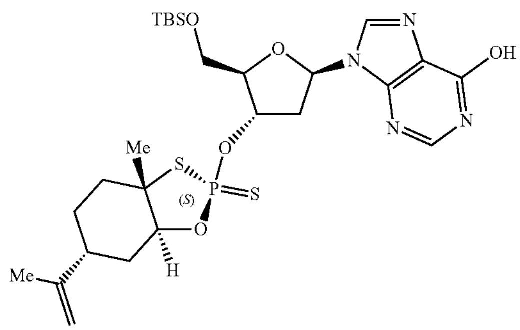 | (2S,3aS,6R,7aS)-2-(((2R,3S,5R)-2-(((tert-butyldimethylsilyl)oxy)methyl)-5-(6-hydroxy-9H-purin-9-yl)tetrahydrofuran-3-yl)oxy)-3a-methyl-6-(prop-1-en-2-yl)hexahydrobenzo[d][1,3,2]oxathiaphosphole 2-sulfide |
| 3-33 | 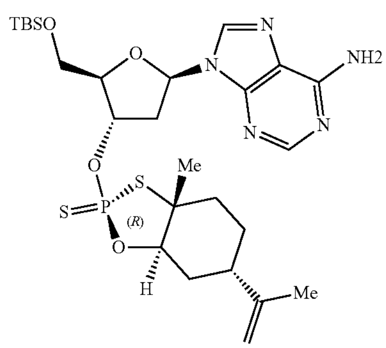 | (2R,3aR,6S,7aR)-2-(((2R,3S,5R)-5-(6-amino-9H-purin-9-yl)-2-(((tert-butyldimethylsilyl)oxy)methyl)tetrahydrofuran-3-yl)oxy)-3a-methyl-6-(prop-1-en-2-yl)hexahydrobenzo[d][1,3,2]oxathiaphosphole 2-sulfide |
| 3-34 | 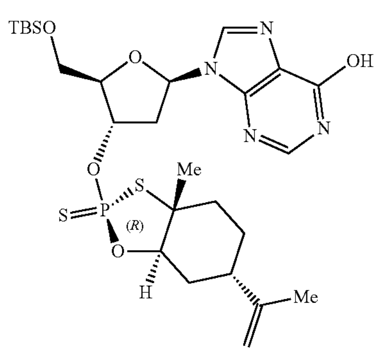 | (2R,3aR,6S,7aR)-2-(((2R,3S,5R)-2-(((tert-butyldimethylsilyl)oxy)methyl)-5-(6-hydroxy-9H-purin-9-yl)tetrahydrofuran-3-yl)oxy)-3a-methyl-6-(prop-1-en-2-yl)hexahydrobenzo[d][1,3,2]oxathiaphosphole 2-sulfide |

TABLE 3-continued

| Cpd. No. | Structure | Name |
|---|---|---|
| 3-35 | | (2S,3aS,6R,7aS)-2-(((2R,3S,5R)-5-(6-amino-9H-purin-9-yl)-3-((tert-butyldimethylsilyl)oxy)tetrahydrofuran-2-yl)methoxy)-3a-methyl-6-(prop-1-en-2-yl)hexahydrobenzo[d][1,3,2]oxathiaphosphole 2-sulfide |
| 3-35 | | (2S,3aS,6R,7aS)-2-(((2R,3S,5R)-3-((tert-butyldimethylsilyl)oxy)-5-(6-hydroxy-9H-purin-9-yl)tetrahydrofuran-2-yl)methoxy)-3a-methyl-6-(prop-1-en-2-yl)hexahydrobenzo[d][1,3,2]oxathiaphosphole 2-sulfide |
| 3-36 | 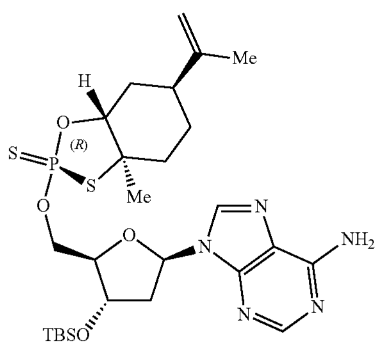 | (2R,3aR,6S,7aR)-2-(((2R,3S,5R)-5-(6-amino-9H-purin-9-yl)-3-((tert-butyldimethylsilyl)oxy)tetrahydrofuran-2-yl)methoxy)-3a-methyl-6-(prop-1-en-2-yl)hexahydrobenzo[d][1,3,2]oxathiaphosphole 2-sulfide |
| 3-37 | 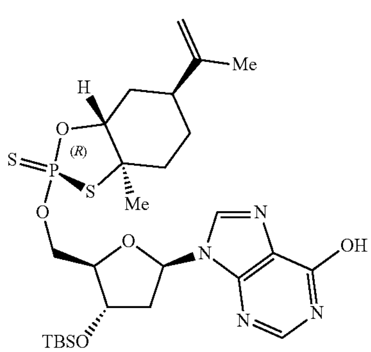 | (2R,3aR,6S,7aR)-2-(((2R,3S,5R)-3-((tert-butyldimethylsilyl)oxy)-5-(6-hydroxy-9H-purin-9-yl)tetrahydrofuran-2-yl)methoxy)-3a-methyl-6-(prop-1-en-2-yl)hexahydrobenzo[d][1,3,2]oxathiaphosphole 2-sulfide |

TABLE 3-continued

| Cpd. No. | Structure | Name |
|---|---|---|
| 3-38 | 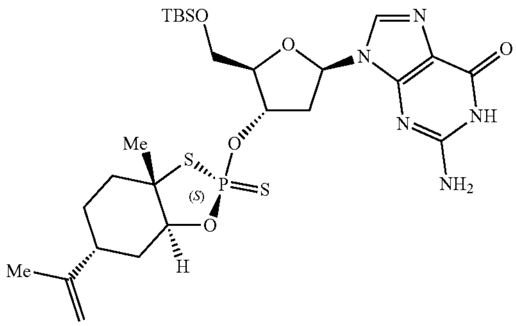 | 2-amino-9-((2R,4S,5R)-5-(((tert-butyldimethylsilyl)oxy)methyl)-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-1,9-dihydro-6H-purin-6-one |
| 3-39 | 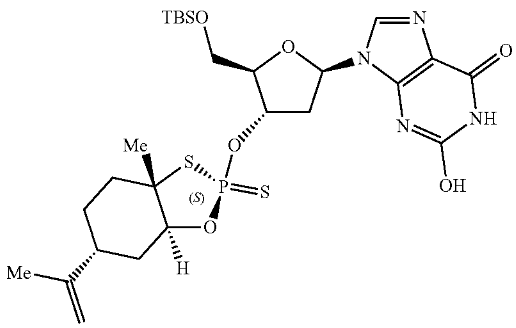 | 9-((2R,4S,5R)-5-(((tert-butyldimethylsilyl)oxy)methyl)-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-2-hydroxy-1,9-dihydro-6H-purin-6-one |
| 3-40 | 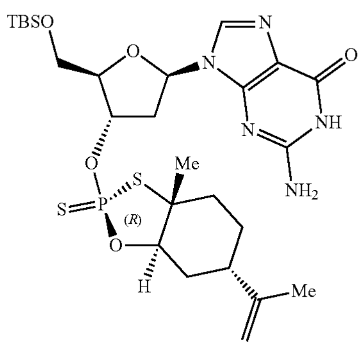 | 2-amino-9-((2R,4S,5R)-5-(((tert-butyldimethylsilyl)oxy)methyl)-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-1,9-dihydro-6H-purin-6-one |
| 3-41 | 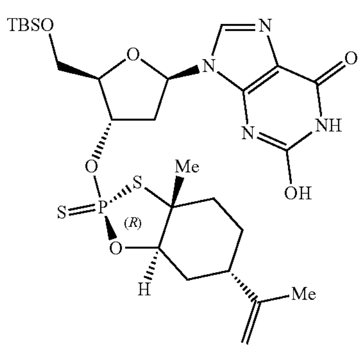 | 9-((2R,4S,5R)-5-(((tert-butyldimethylsilyl)oxy)methyl)-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-2-hydroxy-1,9-dihydro-6H-purin-6-one |

TABLE 3-continued

| Cpd. No. | Structure | Name |
|---|---|---|
| 3-42 | 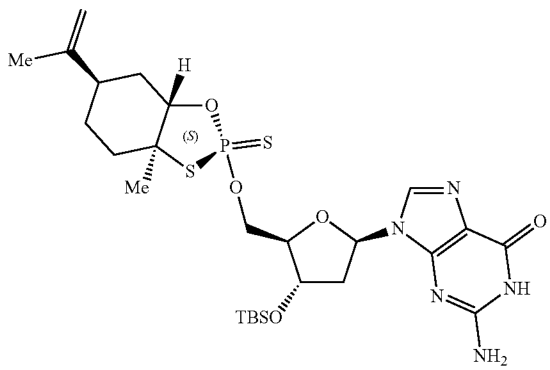 | 2-amino-9-((2R,4S,5R)-4-((tert-butyldimethylsilyl)oxy)-5-((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-1,9-dihydro-6H-purin-6-one |
| 3-43 | 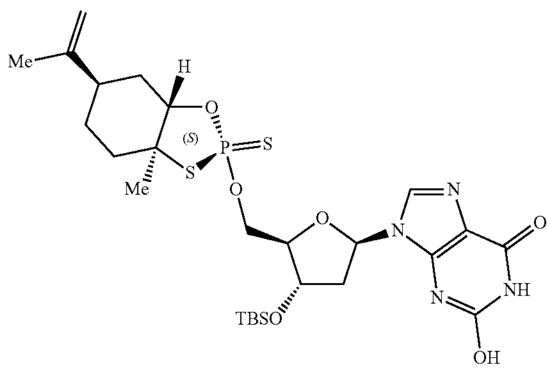 | 9-((2R,4S,5R)-4-((tert-butyldimethylsilyl)oxy)-5-((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-2-hydroxy-1,9-dihydro-6H-purin-6-one |
| 3-44 | 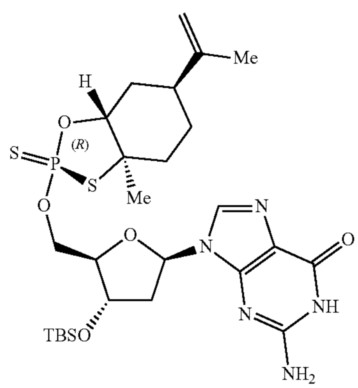 | 2-amino-9-((2R,4S,5R)-4-((tert-butyldimethylsilyl)oxy)-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-1,9-dihydro-6H-purin-6-one |
| 3-45 | 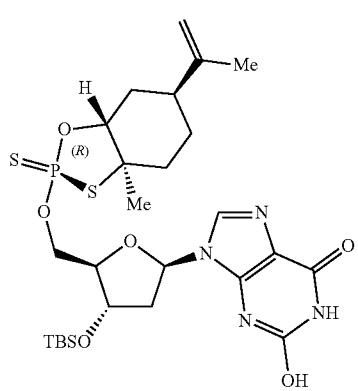 | 9-((2R,4S,5R)-4-((tert-butyldimethylsilyl)oxy)-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-2-hydroxy-1,9-dihydro-6H-purin-6-one |

TABLE 3-continued

| Cpd. No. | Structure | Name |
|---|---|---|
| 3-46 | 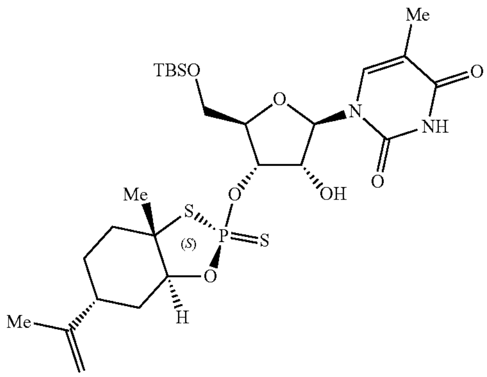 | 1-((2R,3R,4S,5R)-5-(((tert-butyldimethylsilyl)oxy)methyl)-3-hydroxy-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-47 | 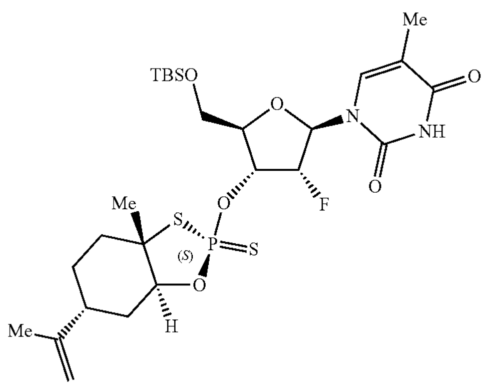 | 1-((2R,3R,4R,5R)-5-(((tert-butyldimethylsilyl)oxy)methyl)-3-fluoro-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-48 | 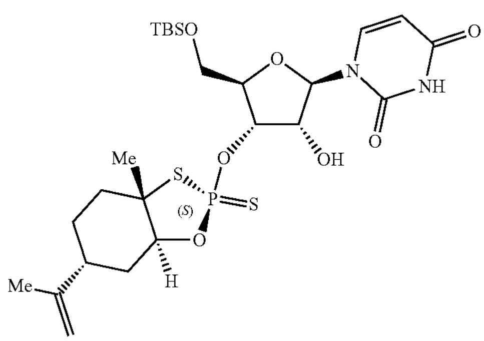 | 1-((2R,3R,4S,5R)-5-(((tert-butyldimethylsilyl)oxy)methyl)-3-hydroxy-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)pyrimidine-2,4(1H,3H)-dione |
| 3-49 | 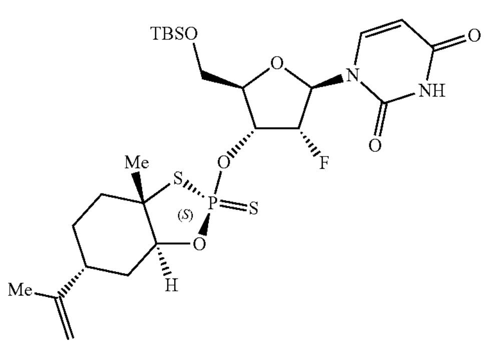 | 1-((2R,3R,4R,5R)-5-(((tert-butyldimethylsilyl)oxy)methyl)-3-fluoro-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)pyrimidine-2,4(1H,3H)-dione |

TABLE 3-continued

| Cpd. No. | Structure | Name |
|---|---|---|
| 3-50 | 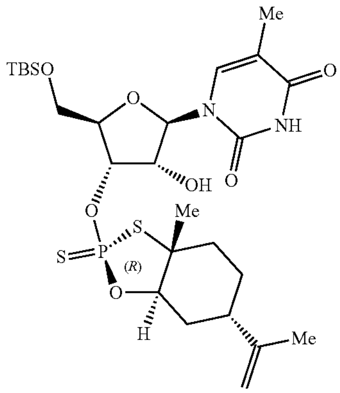 | 1-((2R,3R,4S,5R)-5-(((tert-butyldimethylsilyl)oxy)methyl)-3-hydroxy-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-51 | 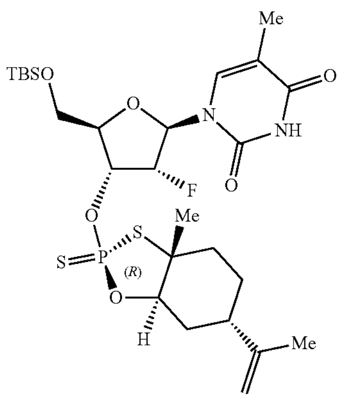 | 1-((2R,3R,4R,5R)-5-(((tert-butyldimethylsilyl)oxy)methyl)-3-fluoro-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-52 | 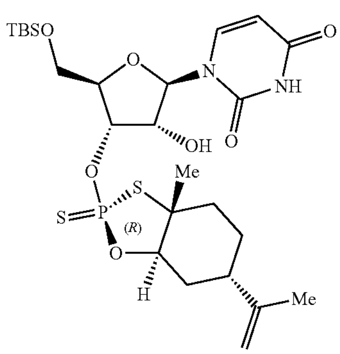 | 1-((2R,3R,4S,5R)-5-(((tert-butyldimethylsilyl)oxy)methyl)-3-hydroxy-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)pyrimidine-2,4(1H,3H)-dione |
| 3-53 | 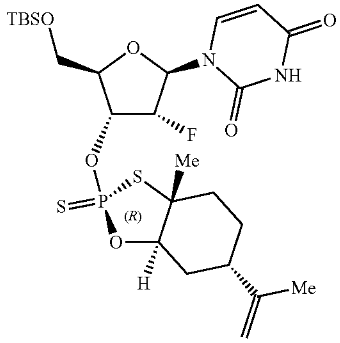 | 1-((2R,3R,4R,5R)-5-(((tert-butyldimethylsilyl)oxy)methyl)-3-fluoro-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)pyrimidine-2,4(1H,3H)-dione |

TABLE 3-continued

| Cpd. No. | Structure | Name |
|---|---|---|
| 3-54 | 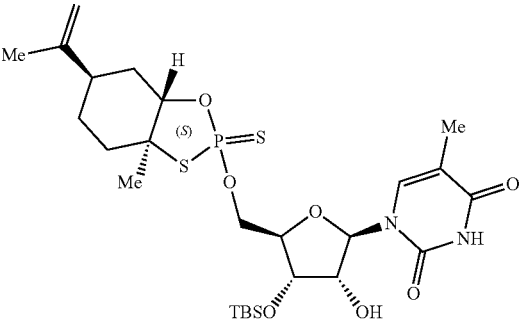 | 1-((2R,3R,4S,5R)-4-((tert-butyldimethylsilyl)oxy)-3-hydroxy-5-(((((2S,3aS,6R, 7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-5-methylpyrimidine-2,4(1H,3H)-dione |
| 3-55 | 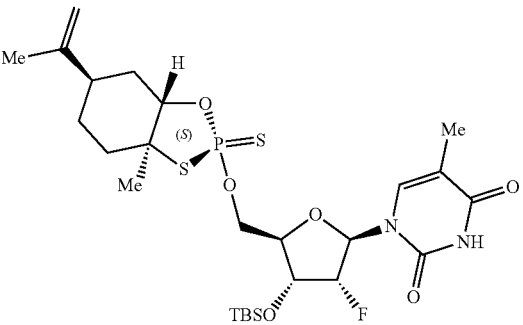 | 1-((2R,3R,4R,5R)-4-((tert-butyldimethylsilyl)oxy)-3-fluoro-5-(((((2S,3aS,6R, 7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-5-methylpyrimidine-2,4(1H,3H)-dione |
| 3-56 | 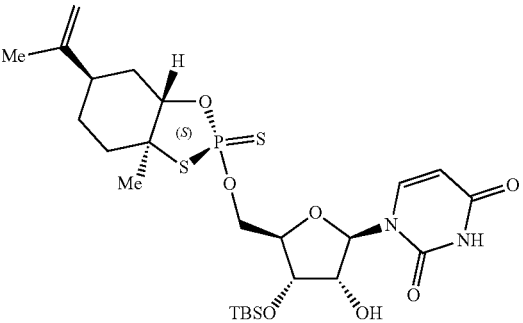 | 1-((2R,3R,4S,5R)-4-((tert-butyldimethylsilyl)oxy)-3-hydroxy-5-(((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidine-2,4(1H,3H)-dione |
| 3-57 | 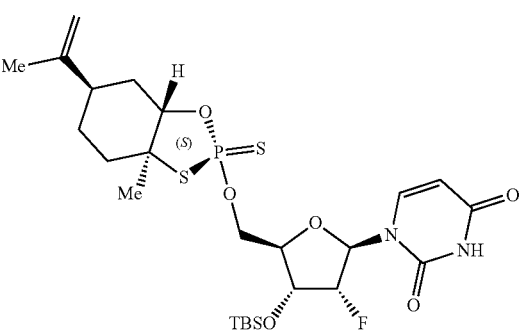 | 1-((2R,3R,4R,5R)-4-((tert-butyldimethylsilyl)oxy)-3-fluoro-5-(((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidine-2,4(1H,3H)-dione |

TABLE 3-continued

| Cpd. No. | Structure | Name |
|---|---|---|
| 3-58 | 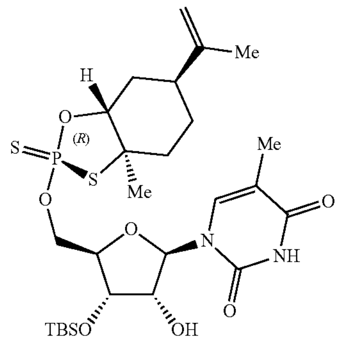 | 1-((2R,3R,4S,5R)-4-((tert-butyldimethylsilyl)oxy)-3-hydroxy-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-5-methylpyrimidine-2,4(1H,3H)-dione |
| 3-59 | 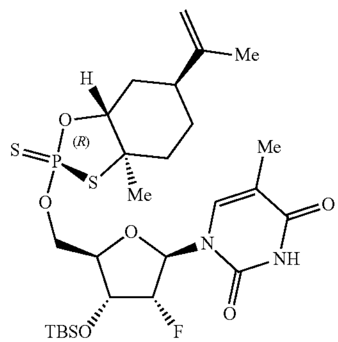 | 1-((2R,3R,4R,5R)-4-((tert-butyldimethylsilyl)oxy)-3-fluoro-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-5-methylpyrimidine-2,4(1H,3H)-dione |
| 3-60 | 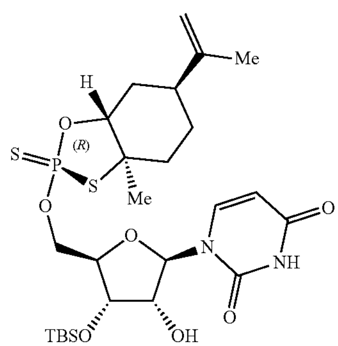 | 1-((2R,3R,4S,5R)-4-((tert-butyldimethylsilyl)oxy)-3-hydroxy-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidine-2,4(1H,3H)-dione |
| 3-61 | 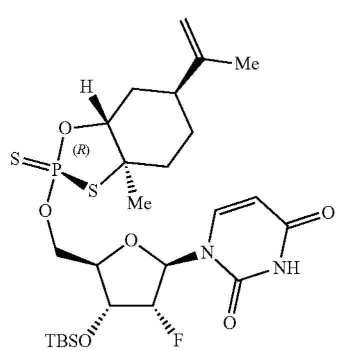 | 1-((2R,3R,4R,5R)-4-((tert-butyldimethylsilyl)oxy)-3-fluoro-5-((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidine-2,4(1H,3H)-dione |

TABLE 3-continued

| Cpd. No. | Structure | Name |
|---|---|---|
| 3-62 | 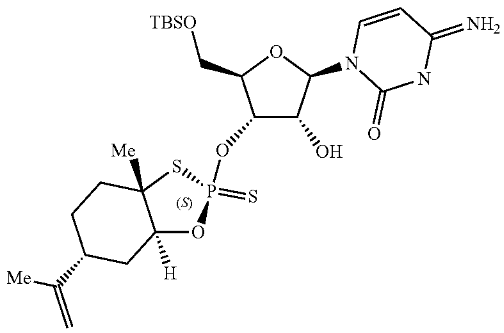 | 4-amino-1-((2R,3R,4S,5R)-5-(((tert-butyldimethylsilyl)oxy)methyl)-3-hydroxy-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)pyrimidin-2(1H)-one |
| 3-63 | 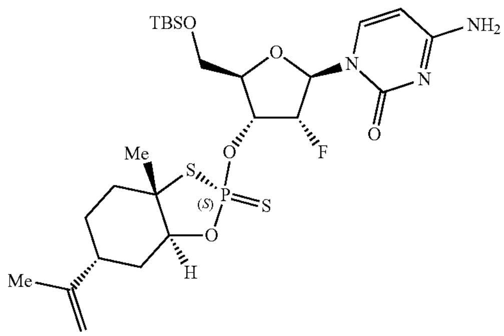 | 4-amino-1-((2R,3R,4R,5R)-5-(((tert-butyldimethylsilyl)oxy)methyl)-3-fluoro-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)pyrimidin-2(1H)-one |
| 3-64 | 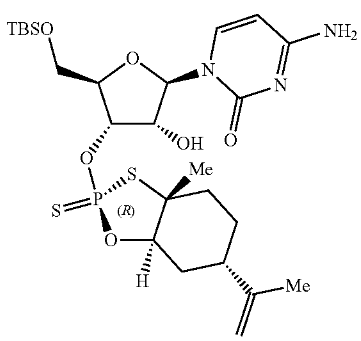 | 4-amino-1-((2R,3R,4S,5R)-5-(((tert-butyldimethylsilyl)oxy)methyl)-3-hydroxy-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)pyrimidin-2(1H)-one |
| 3-65 | 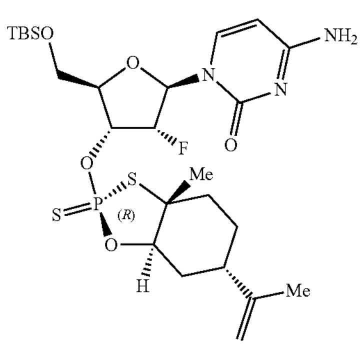 | 4-amino-1-((2R,3R,4R,5R)-5-(((tert-butyldimethylsilyl)oxy)methyl)-3-fluoro-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)pyrimidin-2(1H)-one |

TABLE 3-continued

| Cpd. No. | Structure | Name |
|---|---|---|
| 3-66 | 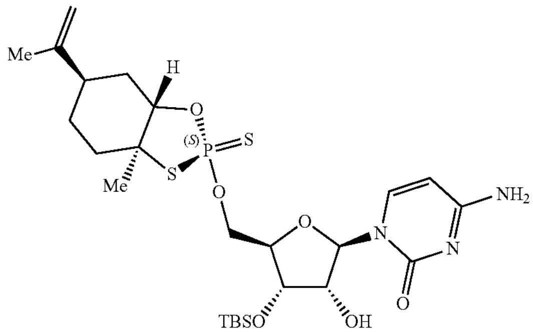 | 4-amino-1-((2R,3R,4S,5R)-4-((tert-butyldimethylsilyl)oxy)-3-hydroxy-5-(((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidin-2(1H)-one |
| 3-67 | 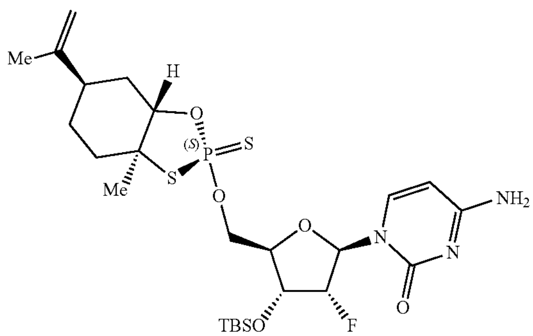 | 4-amino-1-((2R,3R,4R,5R)-4-((tert-butyldimethylsilyl)oxy)-3-fluoro-5-(((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidin-2(1H)-one |
| 3-68 | 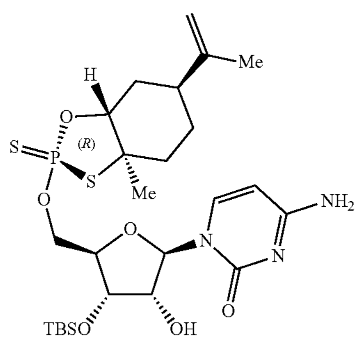 | 4-amino-1-((2R,3R,4S,5R)-4-((tert-butyldimethylsilyl)oxy)-3-hydroxy-5-(((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidin-2(1H)-one |
| 3-69 | 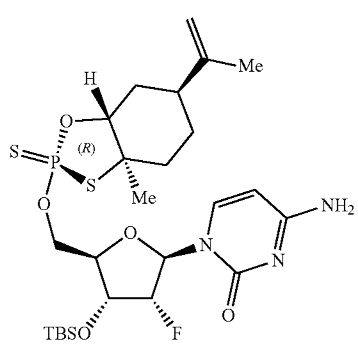 | 4-amino-1-((2R,3R,4R,5R)-4-((tert-butyldimethylsilyl)oxy)-3-fluoro-5-(((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)pyrimidin-2(1H)-one |

TABLE 3-continued

| Cpd. No. | Structure | Name |
|---|---|---|
| 3-70 | 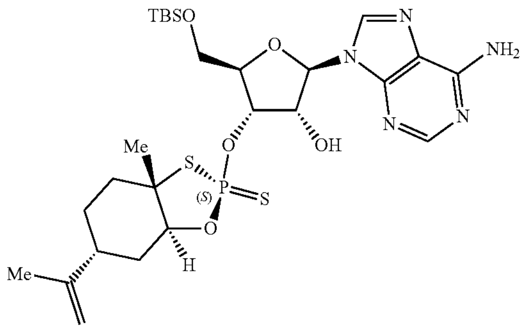 | (2S,3aS,6R,7aS)-2-(((2R,3S,4R,5R)-5-(6-amino-9H-purin-9-yl)-2-(((tert-butyldimethylsilyl)oxy)methyl)-4-hydroxytetrahydrofuran-3-yl)oxy)-3a-methyl-6-(prop-1-en-2-yl)hexahydrobenzo[d][1,3,2]oxathiaphosphole 2-sulfide |
| 3-71 | 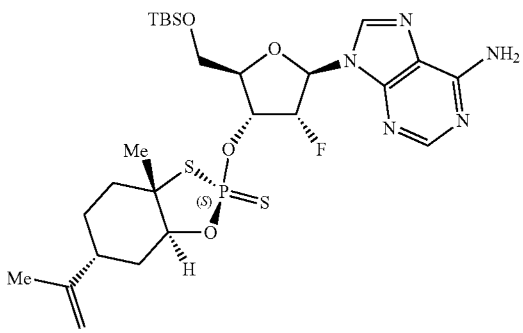 | (2S,3aS,6R,7aS)-2-(((2R,3R,4R,5R)-5-(6-amino-9H-purin-9-yl)-2-(((tert-butyldimethylsilyl)oxy)methyl)-4-fluorotetrahydrofuran-3-yl)oxy)-3a-methyl-6-(prop-1-en-2-yl)hexahydrobenzo[d][1,3,2]oxathiaphosphole 2-sulfide |
| 3-72 | 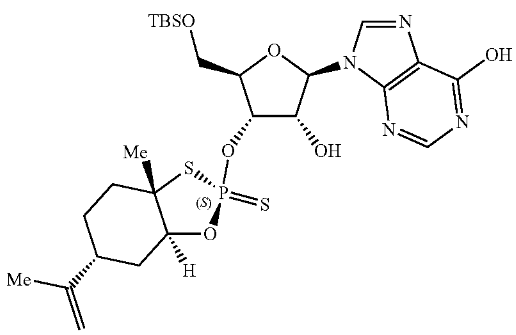 | (2S,3aS,6R,7aS)-2-(((2R,3S,4R,5R)-2-(((tert-butyldimethylsilyl)oxy)methyl)-4-hydroxy-5-(6-hydroxy-9H-purin-9-yl)tetrahydrofuran-3-yl)oxy)-3a-methyl-6-(prop-1-en-2-yl)hexahydrobenzo[d][1,3,2]oxathiaphosphole 2-sulfide |
| 3-73 | 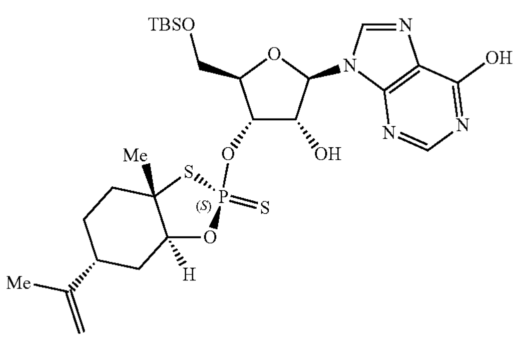 | (2S,3aS,6R,7aS)-2-(((2R,3R,4R,5R)-2-(((tert-butyldimethylsilyl)oxy)methyl)-4-fluoro-5-(6-hydroxy-9H-purin-9-yl)tetrahydrofuran-3-yl)oxy)-3a-methyl-6-(prop-1-en-2-yl)hexahydrobenzo[d][1,3,2]oxathiaphosphole 2-sulfide |

TABLE 3-continued

| Cpd. No. | Structure | Name |
|---|---|---|
| 3-74 | 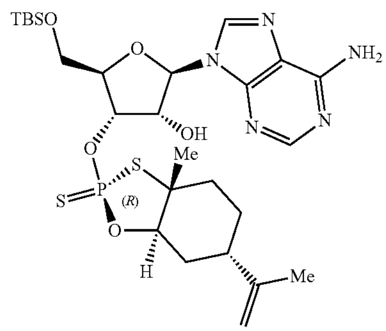 | (2R,3aR,6S,7aR)-2-(((2R,3S,4R,5R)-5-(6-amino-9H-purin-9-yl)-2-(((tert-butyldimethylsilyl)oxy)methyl)-4-hydroxytetrahydrofuran-3-yl)oxy)-3a-methyl-6-(prop-1-en-2-yl)hexahydrobenzo[d][1,3,2]oxathiaphosphole 2-sulfide |
| 3-75 | 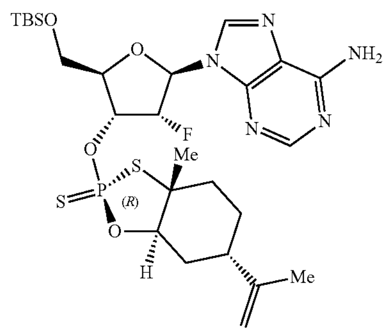 | (2R,3aR,6S,7aR)-2-(((2R,3R,4R,5R)-5-(6-amino-9H-purin-9-yl)-2-(((tert-butyldimethylsilyl)oxy)methyl)-4-fluorotetrahydrofuran-3-yl)oxy)-3a-methyl-6-(prop-1-en-2-yl)hexahydrobenzo[d][1,3,2]oxathiaphosphole 2-sulfide |
| 3-76 | 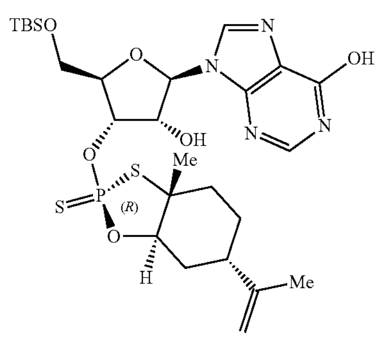 | (2R,3aR,6S,7aR)-2-(((2R,3S,4R,5R)-2-(((tert-butyldimethylsilyl)oxy)methyl)-4-hydroxy-5-(6-hydroxy-9H-purin-9-yl)tetrahydrofuran-3-yl)oxy)-3a-methyl-6-(prop-1-en-2-yl)hexahydrobenzo[d][1,3,2]oxathiaphosphole 2-sulfide |
| 3-77 | 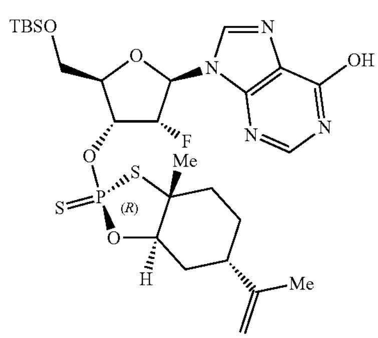 | (2R,3aR,6S,7aR)-2-(((2R,3R,4R,5R)-2-(((tert-butyldimethylsilyl)oxy)methyl)-4-fluoro-5-(6-hydroxy-9H-purin-9-yl)tetrahydrofuran-3-yl)oxy)-3a-methyl-6-(prop-1-en-2-yl)hexahydrobenzo[d][1,3,2]oxathiaphosphole 2-sulfide |

TABLE 3-continued

| Cpd. No. | Structure | Name |
|---|---|---|
| 3-78 | | (2S,3aS,6R,7aS)-2-(((2R,3S,4R,5R)-5-(6-amino-9H-purin-9-yl)-3-((tert-butyldimethylsilyl)oxy)-4-hydroxytetrahydrofuran-2-yl)methoxy)-3a-methyl-6-(prop-1-en-2-yl)hexahydrobenzo[d][1,3,2]oxathiaphosphole 2-sulfide |
| 3-79 | | (2S,3aS,6R,7aS)-2-(((2R,3R,4R,5R)-5-(6-amino-9H-purin-9-yl)-3-((tert-butyldimethylsilyl)oxy)-4-fluorotetrahydrofuran-2-yl)methoxy)-3a-methyl-6-(prop-1-en-2-yl)hexahydrobenzo[d][1,3,2]oxathiaphosphole 2-sulfide |
| 3-78 | | (2S,3aS,6R,7aS)-2-(((2R,3S,4R,5R)-3-((tert-butyldimethylsilyl)oxy)-4-hydroxy-5-(6-hydroxy-9H-purin-9-yl)tetrahydrofuran-2-yl)methoxy)-3a-methyl-6-(prop-1-en-2-yl)hexahydrobenzo[d][1,3,2]oxathiaphosphole 2-sulfide |
| 3-79 | | (2S,3aS,6R,7aS)-2-(((2R,3R,4R,5R)-3-((tert-butyldimethylsilyl)oxy)-4-fluoro-5-(6-hydroxy-9H-purin-9-yl)tetrahydrofuran-2-yl)methoxy)-3a-methyl-6-(prop-1-en-2-yl)hexahydrobenzo[d][1,3,2]oxathiaphosphole 2-sulfide |

TABLE 3-continued

| Cpd. No. | Structure | Name |
|---|---|---|
| 3-80 | 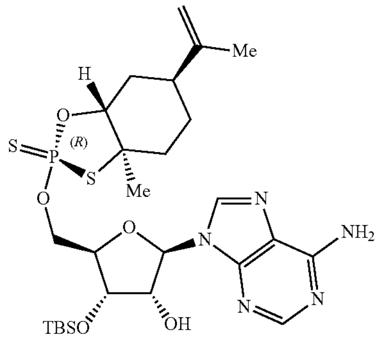 | (2R,3aR,6S,7aR)-2-(((2R,3S,4R,5R)-5-(6-amino-9H-purin-9-yl)-3-((tert-butyldimethylsilyl)oxy)-4-hydroxytetrahydrofuran-2-yl)methoxy)-3a-methyl-6-(prop-1-en-2-yl)hexahydrobenzo[d][1,3,2]oxathiaphosphole 2-sulfide |
| 3-81 | 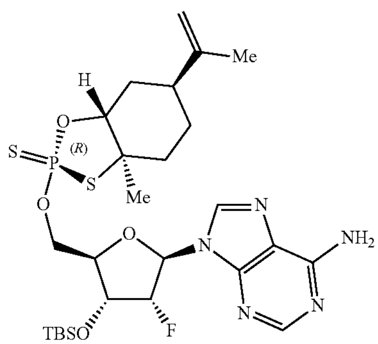 | (2R,3aR,6S,7aR)-2-(((2R,3R,4R,5R)-5-(6-amino-9H-purin-9-yl)-3-((tert-butyldimethylsilyl)oxy)-4-fluorotetrahydrofuran-2-yl)methoxy)-3a-methyl-6-(prop-1-en-2-yl)hexahydrobenzo[d][1,3,2]oxathiaphosphole 2-sulfide |
| 3-82 | 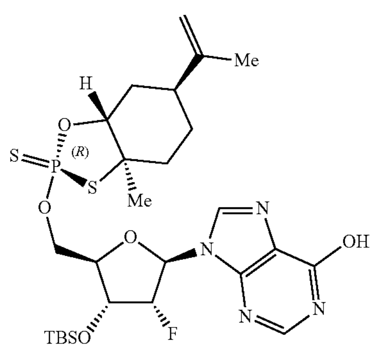 | (2R,3aR,6S,7aR)-2-(((2R,3R,4R,5R)-3-((tert-butyldimethylsilyl)oxy)-4-fluoro-5-(6-hydroxy-9H-purin-9-yl)tetrahydrofuran-2-yl)methoxy)-3a-methyl-6-(prop-1-en-2-yl)hexahydrobenzo[d][1,3,2]oxathiaphosphole 2-sulfide |
| 3-83 | 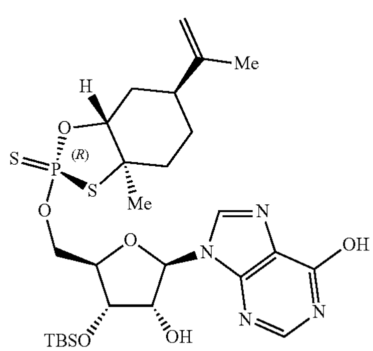 | (2R,3aR,6S,7aR)-2-(((2R,3S,4R,5R)-3-((tert-butyldimethylsilyl)oxy)-4-hydroxy-5-(6-hydroxy-9H-purin-9-yl)tetrahydrofuran-2-yl)methoxy)-3a-methyl-6-(prop-1-en-2-yl)hexahydrobenzo[d][1,3,2]oxathiaphosphole 2-sulfide |

TABLE 3-continued

| Cpd. No. | Structure | Name |
|---|---|---|
| 3-84 | 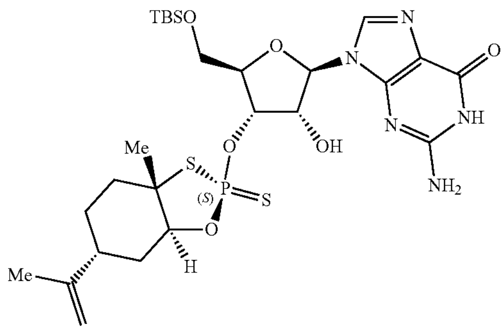 | 2-amino-9-((2R,3R,4S,5R)-5-(((tert-butyldimethylsilyl)oxy)methyl)-3-hydroxy-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-1,9-dihydro-6H-purin-6-one |
| 3-85 | 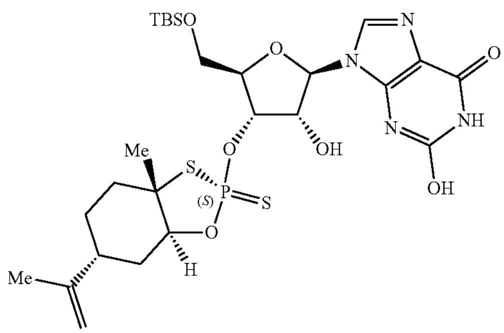 | 9-((2R,3R,4S,5R)-5-(((tert-butyldimethylsilyl)oxy)methyl)-3-hydroxy-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-2-hydroxy-1,9-dihydro-6H-purin-6-one |
| 3-86 | 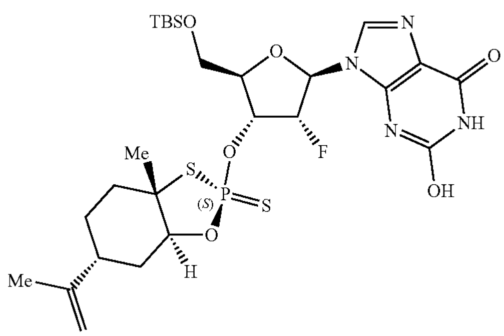 | 9-((2R,3R,4R,5R)-5-(((tert-butyldimethylsilyl)oxy)methyl)-3-fluoro-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-2-hydroxy-1,9-dihydro-6H-purin-6-one |
| 3-87 | 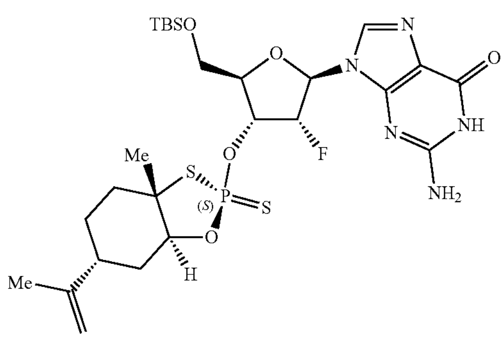 | 2-amino-9-((2R,3R,4R,5R)-5-(((tert-butyldimethylsilyl)oxy)methyl)-3-fluoro-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-1,9-dihydro-6H-purin-6-one |

TABLE 3-continued

| Cpd. No. | Structure | Name |
|---|---|---|
| 3-88 | 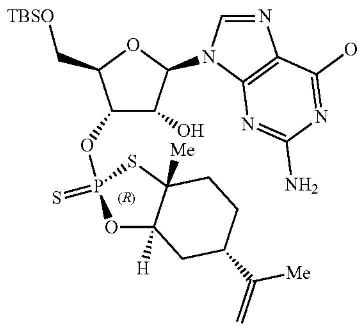 | 2-amino-9-((2R,3R,4S,5R)-5-(((tert-butyldimethylsilyl)oxy)methyl)-3-hydroxy-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-1,9-dihydro-6H-purin-6-one |
| 3-89 | 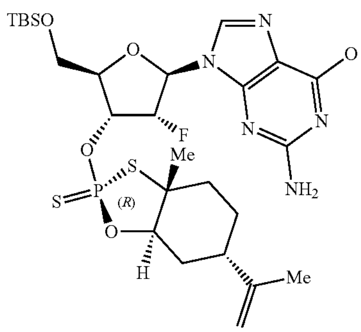 | 2-amino-9-((2R,3R,4R,5R)-5-(((tert-butyldimethylsilyl)oxy)methyl)-3-fluoro-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-1,9-dihydro-6H-purin-6-one |
| 3-90 | 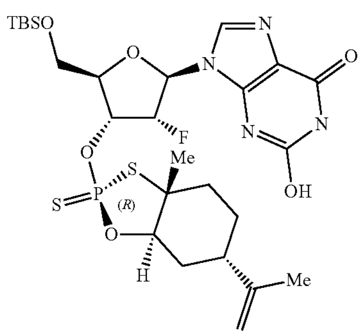 | 9-((2R,3R,4R,5R)-5-(((tert-butyldimethylsilyl)oxy)methyl)-3-fluoro-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-2-hydroxy-1,9-dihydro-6H-purin-6-one |
| 3-91 | 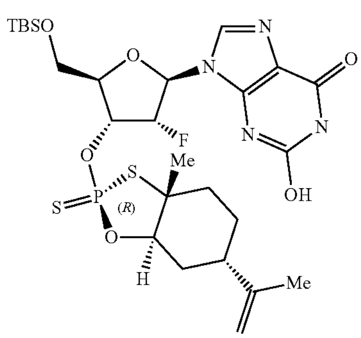 | 9-((2R,3R,4S,5R)-5-(((tert-butyldimethylsilyl)oxy)methyl)-3-hydroxy-4-(((2R,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-2-hydroxy-1,9-dihydro-6H-purin-6-one |

TABLE 3-continued

| Cpd. No. | Structure | Name |
|---|---|---|
| 3-92 | 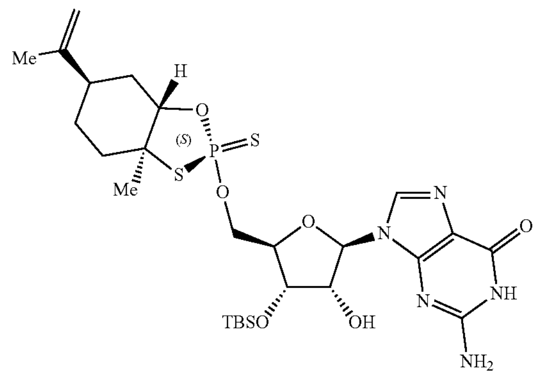 | 2-amino-9-((2R,3R,4S,5R)-4-((tert-butyldimethylsilyl)oxy)-3-hydroxy-5-(((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-1,9-dihydro-6H-purin-6-one |
| 3-93 | 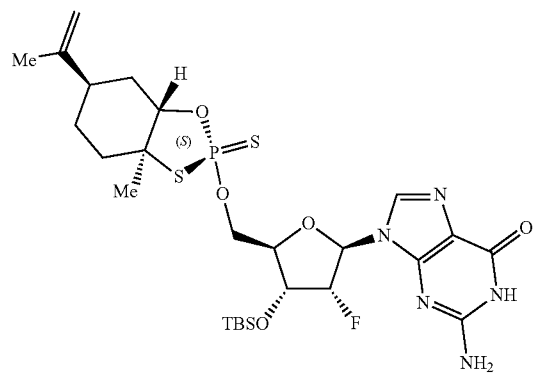 | 2-amino-9-((2R,3R,4R,5R)-4-((tert-butyldimethylsilyl)oxy)-3-fluoro-5-(((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-1,9-dihydro-6H-purin-6-one |
| 3-94 | 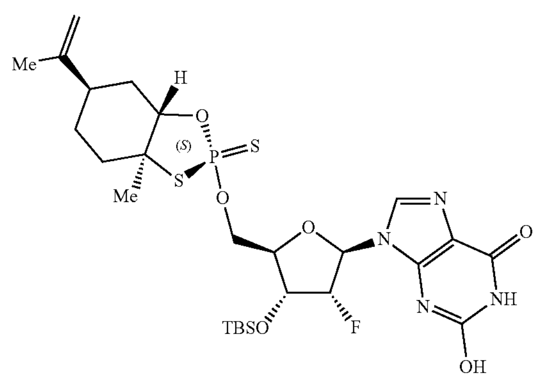 | 9-((2R,3R,4R,5R)-4-((tert-butyldimethylsilyl)oxy)-3-fluoro-5-(((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-2-hydroxy-1,9-dihydro-6H-purin-6-one |
| 3-95 | 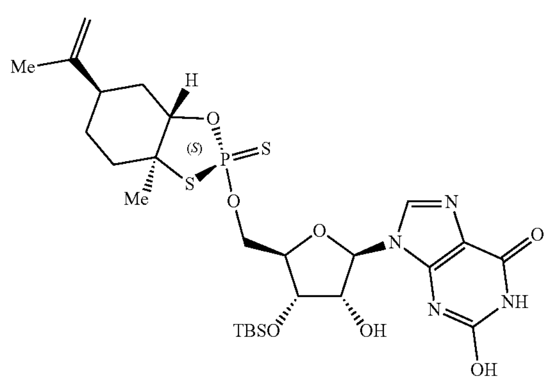 | 9-((2R,3R,4S,5R)-4-((tert-butyldimethylsilyl)oxy)-3-hydroxy-5-(((((2S,3aS,6R,7aS)-3a-methyl-6-(prop-1-en-2-yl)-2-sulfidohexahydrobenzo[d][1,3,2]oxathiaphosphol-2-yl)oxy)methyl)tetrahydrofuran-2-yl)-2-hydroxy-1,9-dihydro-6H-purin-6-one |

TABLE 3-continued

| Cpd. No. | Structure | Name |
|---|---|---|
| 3-96 | 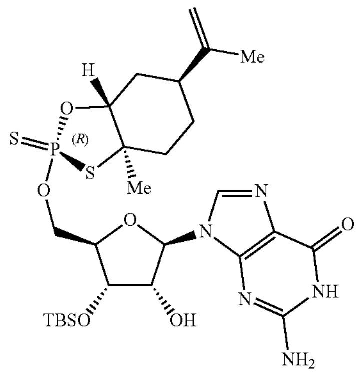 | 2-amino-9-((2R,3R,4S,5R)-4-((tert-butyldimethylsilyl)oxy)-3-hydroxy-5-(((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-1,9-dihydro-6H-purin-6-one |
| 3-97 | 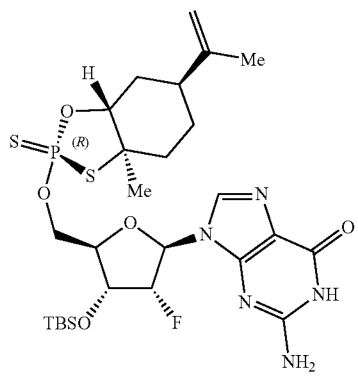 | 2-amino-9-((2R,3R,4R,5R)-4-((tert-butyldimethylsilyl)oxy)-3-fluoro-5-(((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-1,9-dihydro-6H-purin-6-one |
| 3-98 | 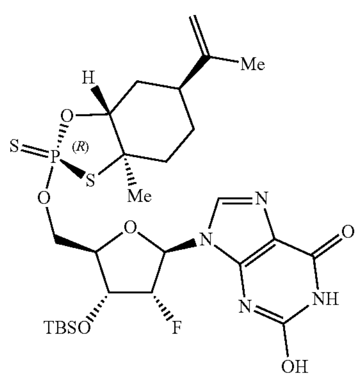 | 9-((2R,3R,4R,5R)-4-((tert-butyldimethylsilyl)oxy)-3-fluoro-5-(((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-2-hydroxy-1,9-dihydro-6H-purin-6-one |
| 3-99 | 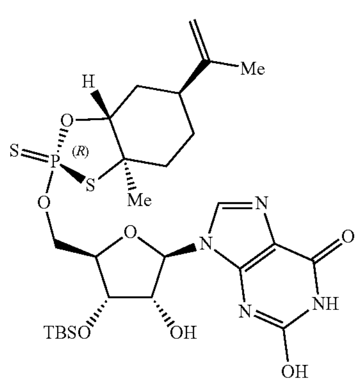 | 9-((2R,3R,4S,5R)-4-((tert-butyldimethylsilyl)oxy)-3-hydroxy-5-(((((2R,3aR,6S,7aR)-3a-methyl-6-(prop-1-en-2-yl)-2-sulfidohexahydrobenzo[d][1,3,2]oxathiaphosphol-2-yl)oxy)methyl)tetrahydrofuran-2-yl)-2-hydroxy-1,9-dihydro-6H-purin-6-one |

TABLE 3-continued

| Cpd. No. | Structure | Name |
|---|---|---|
| 3-100 | 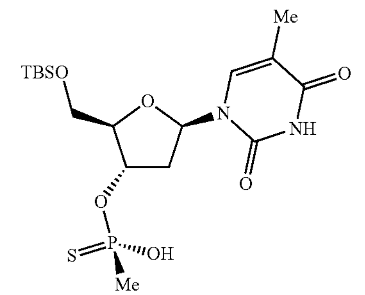 [SMILES: Cc1cn([C@H]2C[C@H](O[P@](C)(O)=S)[C@@H](CO[Si](C)(C)C(C)(C)C)O2)c(=O)[nH]c1=O] | O-((2R,3S,5R)-2-(((tert-butyldimethylsilyl)oxy)methyl)-5-(5-methyl-2,4-dioxo-3,4-dihydropyrimidin-1(2H)-yl)tetrahydrofuran-3-yl) O-hydrogen (S)-methylphosphonothioate |
| 3-101 | 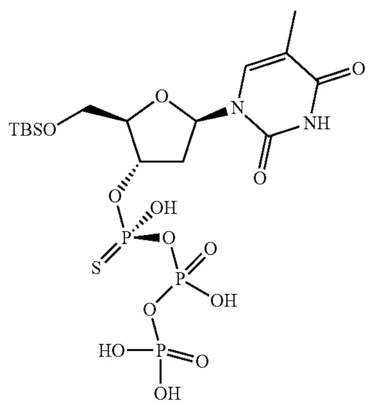 [SMILES: Cc1cn([C@H]2C[C@H](O[P@](O)(=S)OP(=O)(O)OP(=O)(O)O)[C@@H](CO[Si](C)(C)C(C)(C)C)O2)c(=O)[nH]c1=O] | Thymidine-5-(((tert-butyldimethylsilyl)oxy)-3-[(Rp)-α-thio]-triphosphate |
| 3-102 | 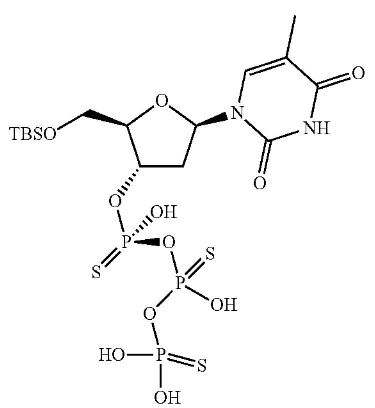 | Thymidine-5-(((tert-butyldimethylsilyl)oxy)-3-[(Rp)-α-thio]-[γ-thio]-triphosphate |
| 3-103 | 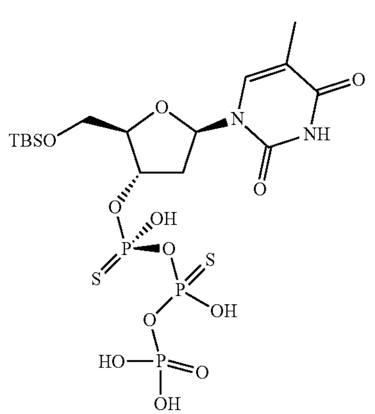 [SMILES: Cc1cn([C@H]2C[C@H](O[P@](O)(=S)OP(O)(=S)OP(O)(O)=S)[C@@H](CO[Si](C)(C)C(C)(C)C)O2)c(=O)[nH]c1=O] | Thymidine-5-(((tert-butyldimethylsilyl)oxy)-3-[(Rp)-α-thio]-[ß-thio]-triphosphate |

TABLE 3-continued

| Cpd. No. | Structure | Name |
|---|---|---|
| 3-104 | 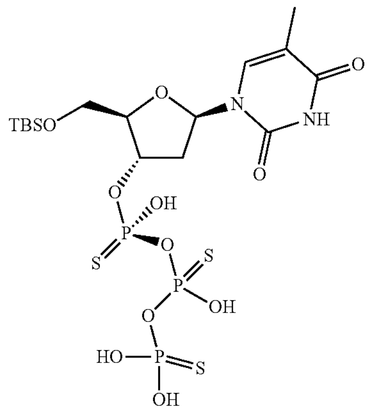 [SMILES: Cc1cn([C@H]2C[C@H](O[P@](O)(=S)OP(O)(=S)OP(O)(O)=S)[C@@H](CO[Si](C)(C)C(C)(C)C)O2)c(=O)[nH]c1=O] | Thymidine-5-(((tert-butyldimethylsilyl)oxy)-3-[(Rp)-α-thio]-[β-thio]-[γ-thio]-triphosphate |
| 3-105 | 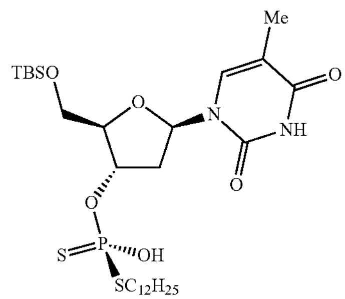 | O-((2R,3S,5R)-2-(((tert-butyldimethylsilyl)oxy)methyl)-5-(5-methyl-2,4-dioxo-3,4-dihydropyrimidin-1(2H)-yl)tetrahydrofuran-3-yl) S-dodecyl O-hydrogen (R)-phosphorodithioate |
| 3-106 | 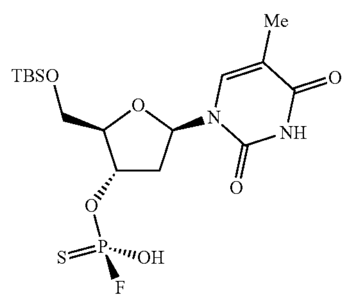 [SMILES: Cc1cn([C@H]2C[C@H](O[P@@](O)(F)=S)[C@@H](CO[Si](C)(C)C(C)(C)C)O2)c(=O)[nH]c1=O] | O-((2R,3S,5R)-2-(((tert-butyldimethylsilyl)oxy)methyl)-5-(5-methyl-2,4-dioxo-3,4-dihydropyrimidin-1(2H)-yl)tetrahydrofuran-3-yl) O-hydrogen (S)-phosphorofluoridothioate |
| 3-107 | 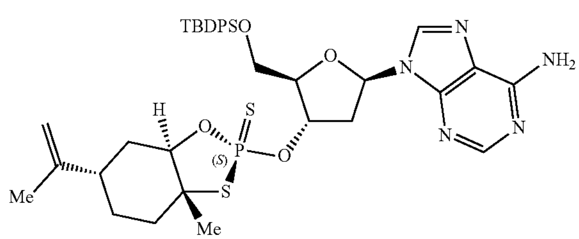 | (2S,3aR,6S,7aR)-2-(((2R,3S,5R)-5-(6-amino-9H-purin-9-yl)-2-(((tert-butyldiphenylsilyl)oxy)methyl)tetrahydrofuran-3-yl)oxy)-3a-methyl-6-(prop-1-en-2-yl)hexahydrobenzo[d][1,3,2]oxathiaphosphole 2-sulfide |
| 3-108 | 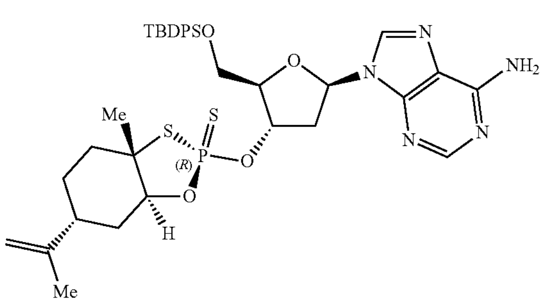 | (2R,3aS,6R,7aS)-2-(((2R,3S,5R)-5-(6-amino-9H-purin-9-yl)-2-(((tert-butyldiphenylsilyl)oxy)methyl)tetrahydrofuran-3-yl)oxy)-3a-methyl-6-(prop-1-en-2-yl)hexahydrobenzo[d][1,3,2]oxathiaphosphole 2-sulfide |

TABLE 3-continued

| Cpd. No. | Structure | Name |
|---|---|---|
| 3-109 | 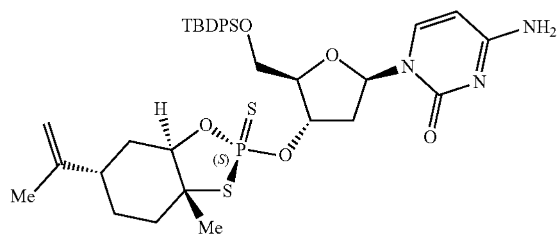 | 4-amino-1-((2R,4S,5R)-5-(((tert-butyldiphenylsilyl)oxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)pyrimidin-2(1H)-one |
| 3-110 | 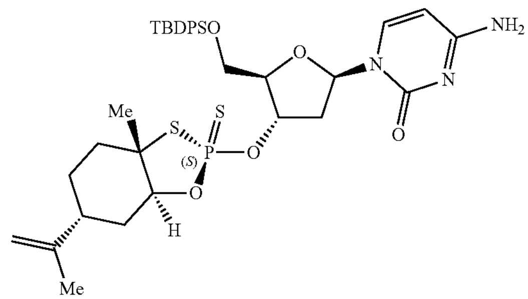 | 4-amino-1-((2R,4S,5R)-5-(((tert-butyldiphenylsilyl)oxy)methyl)-4-(((2R,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)pyrimidin-2(1H)-one |
| 3-111 | 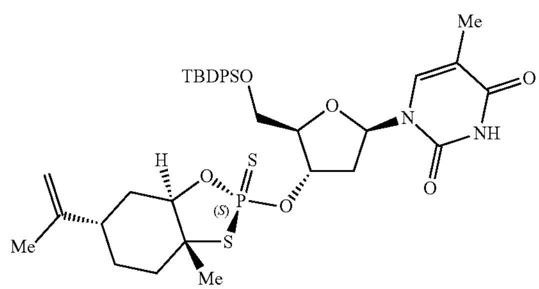 | 1-((2R,4S,5R)-5-(((tert-butyldiphenylsilyl)oxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-112 | 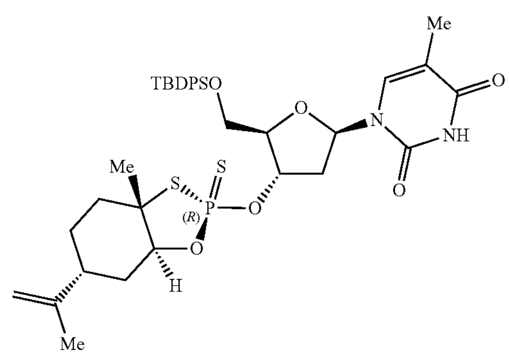 | 1-((2R,4S,5R)-5-(((tert-butyldiphenylsilyl)oxy)methyl)-4-(((2R,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-113 | 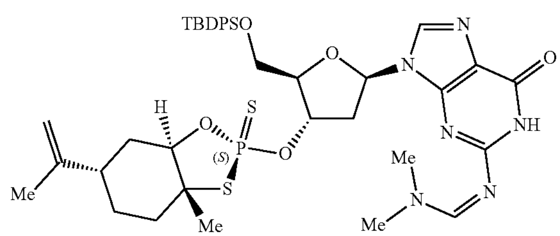 | (Z)-N'-(9-((2R,4S,5R)-5-(((tert-butyldiphenylsilyl)oxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-6-oxo-6,9-dihydro-1H-purin-2-yl)-N,N-dimethylformimidamide |

TABLE 3-continued

| Cpd. No. | Structure | Name |
|---|---|---|
| 3-114 | 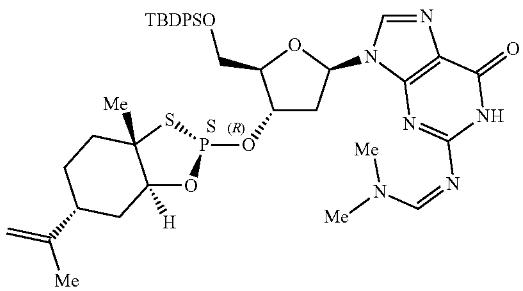 | (Z)-N'-(9-((2R,4S,5R)-5-(((tert-butyldiphenylsilyl)oxy)methyl)-4-(((2R,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-6-oxo-6,9-dihydro-1H-purin-2-yl)-N,N-dimethylformimidamide |
| 3-115 | 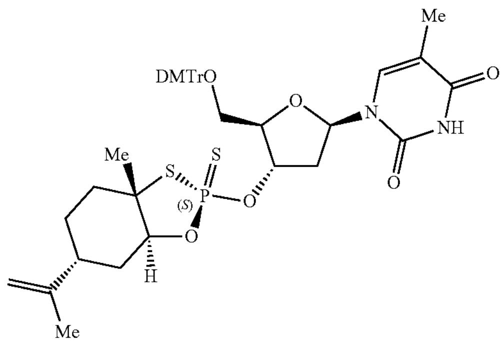 | 1-((2R,4S,5R)-5-((bis(4-methoxyphenyl)(phenyl)methoxy)methyl)-4-(((2R,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |
| 3-116 | 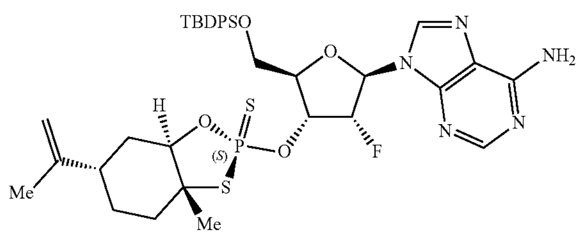 | (2S,3aR,6S,7aR)-2-(((2R,3R,4R,5R)-5-(6-amino-9H-purin-9-yl)-2-(((tert-butyldimethylsilyl)oxy)methyl)-4-fluorotetrahydrofuran-3-yl)oxy)-3a-methyl-6-(prop-1-en-2-yl)hexahydrobenzo[d][1,3,2]oxathiaphosphole 2-sulfide |
| 3-117 | 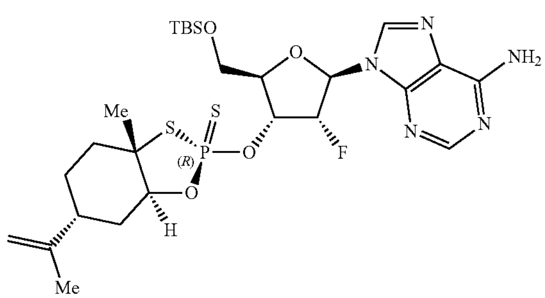 | (2R,3aS,6R,7aS)-2-(((2R,3R,4R,5R)-5-(6-amino-9H-purin-9-yl)-2-(((tert-butyldimethylsilyl)oxy)methyl)-4-fluorotetrahydrofuran-3-yl)oxy)-3a-methyl-6-(prop-1-en-2-yl)hexahydrobenzo[d][1,3,2]oxathiaphosphole 2-sulfide |
| 3-118 | 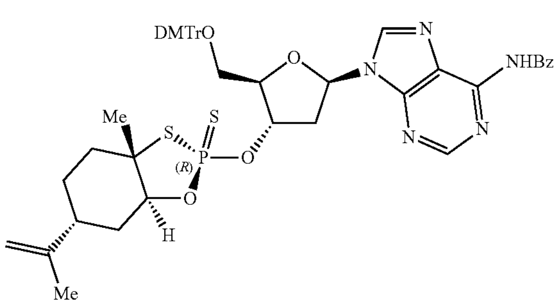 | N-(9-((2R,4S,5R)-5-((bis(4-methoxyphenyl)(phenyl)methoxy)methyl)-4-(((2R,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-9H-purin-6-yl)benzamide |

TABLE 3-continued

| Cpd. No. | Structure | Name |
|---|---|---|
| 3-119 | 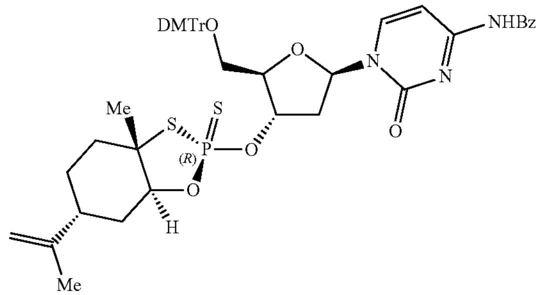 | N-(1-((2R,4S,5R)-5-((bis(4-methoxyphenyl)(phenyl)methoxy)methyl)-4-(((2R,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-2-oxo-1,2-dihydropyrimidin-4-yl)benzamide |
| 3-120 | 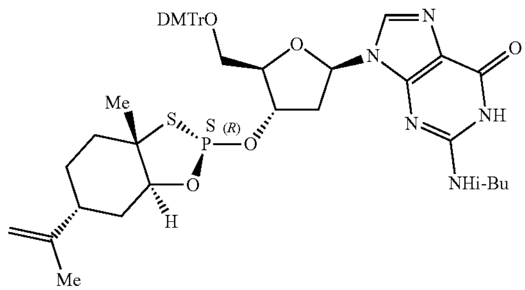 | 9-((2R,4S,5R)-5-((bis(4-methoxyphenyl)(phenyl)methoxy)methyl)-4-(((2R,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-2-(isobutylamino)-1,9-dihydro-6H-purin-6-one |
| 3-121 | 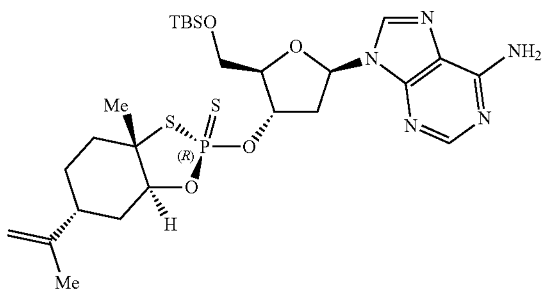 | (2R,3aS,6R,7aS)-2-(((2R,3S,5R)-5-(6-amino-9H-purin-9-yl)-2-(((tert-butyldimethylsilyl)oxy)methyl)tetrahydrofuran-3-yl)oxy)-3a-methyl-6-(prop-1-en-2-yl)hexahydrobenzo[d][1,3,2]oxathiaphosphole 2-sulfide |
| 3-122 | 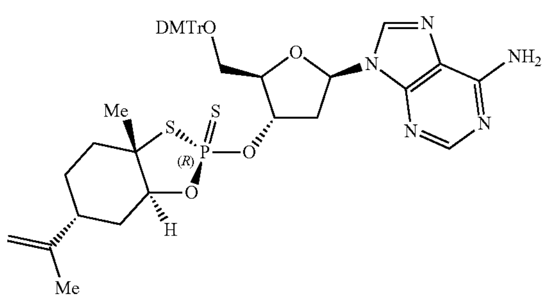 | (2R,3aS,6R,7aS)-2-(((2R,3S,5R)-5-(6-amino-9H-purin-9-yl)-2-((bis(4-methoxyphenyl)(phenyl)methoxy)methyl)tetrahydrofuran-3-yl)oxy)-3a-methyl-6-(prop-1-en-2-yl)hexahydrobenzo[d][1,3,2]oxathiaphosphole 2-sulfide |
| 3-123 | 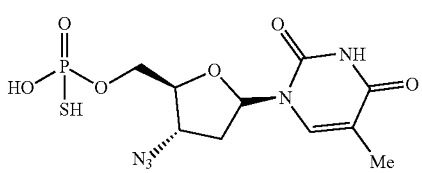 | O-(((2S,3S,5S)-3-azido-5-(5-methyl-2,4-dioxo-3,4-dihydropyrimidin-1(2H)-yl)tetrahydrofuran-2-yl)methyl) O,S-dihydrogen phosphorothioate |
| 3-124 | 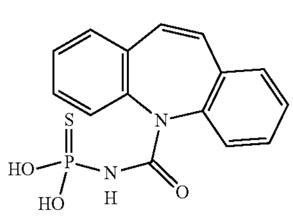 | (5H-dibenzo[b,f]azepine-5-carbonyl)phosphoramidothioic O,O-acid |

TABLE 3-continued

| Cpd. No. | Structure | Name |
|---|---|---|
| 3-125 | 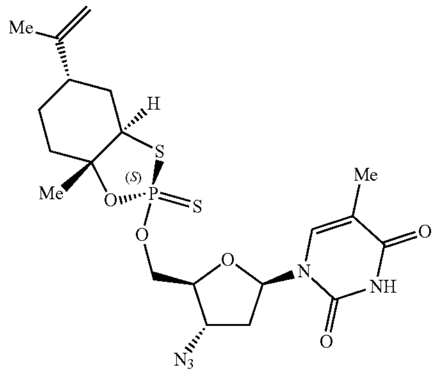 | 1-((2R,4S,5S)-4-azido-5-((((2S,3aR,5S,7aR)-7a-methyl-5-(prop-1-en-2-yl)-2-sulfidohexahydrobenzo[d][1,3,2]oxathiaphosphol-2-yl)oxy)methyl)tetrahydrofuran-2-yl)-5-methylpyrimidine-2,4(1H,3H)-dione |
| 3-126 | 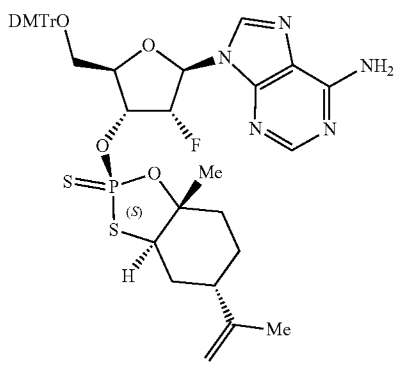 | (2S,3aR,5S,7aR)-2-(((2R,3R,4R,5R)-5-(6-amino-9H-purin-9-yl)-2-((bis(4-methoxyphenyl)(phenyl)methoxy)methyl)-4-fluorotetrahydrofuran-3-yl)oxy)-7a-methyl-5-(prop-1-en-2-yl)hexahydrobenzo[d][1,3,2]oxathiaphosphole 2-sulfide |
| 3-127 | 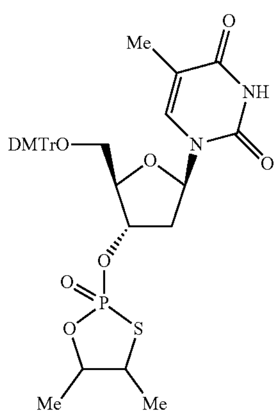 | 1-((2R,4S,5R)-5-((bis(4-methoxyphenyl)(phenyl)methoxy)methyl)-4-((4,5-dimethyl-2-oxido-1,3,2-oxathiaphospholan-2-yl)oxy)tetrahydrofuran-2-yl)-5-methylpyrimidine-2,4(1H,3H)-dione |
| 3-128 | 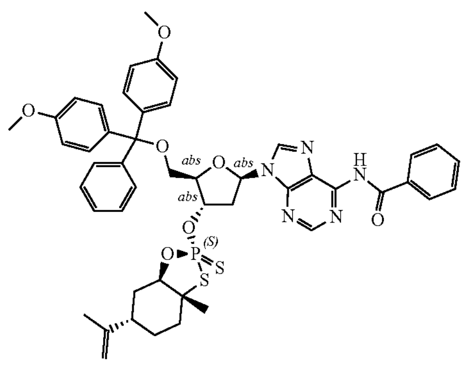 | N-(9-((2R,4S,5R)-5-((bis(4-methoxyphenyl)(phenyl)methoxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-9H-purin-6-yl)benzamide |

TABLE 3-continued

| Cpd. No. | Structure | Name |
|---|---|---|
| 3-129 | 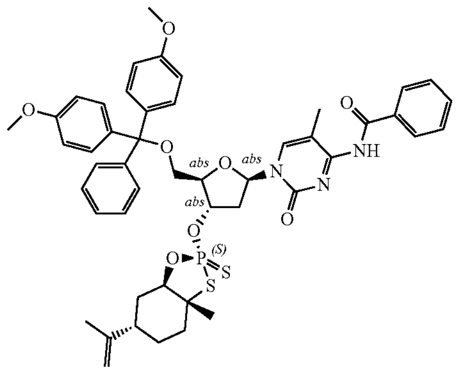 | N-(1-((2R,4S,5R)-5-((bis(4-methoxyphenyl)(phenyl)methoxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-5-methyl-2-oxo-1,2-dihydropyrimidin-4-yl)benzamide |
| 3-130 | 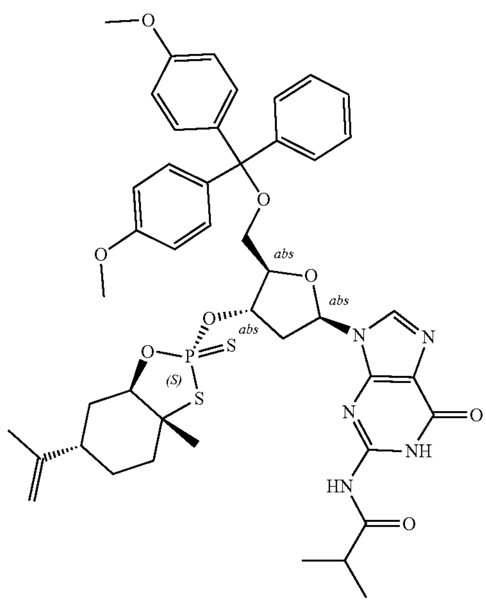 | N-(9-((2R,4S,5R)-5-((bis(4-methoxyphenyl)(phenyl)methoxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)oxy)tetrahydrofuran-2-yl)-6-oxo-6,9-dihydro-1H-purin-2-yl)isobutyramide |
| 3-131 | 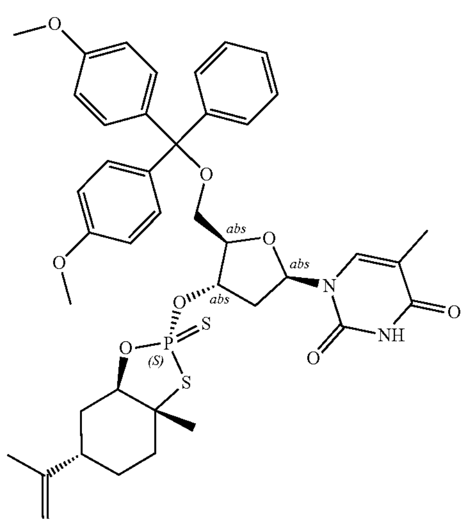 | 1-((2R,4S,5R)-5-((bis(4-methoxyphenyl)(phenyl)methoxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione |

TABLE 3-continued

| Cpd. No. | Structure | Name |
|---|---|---|
| 3-132 | 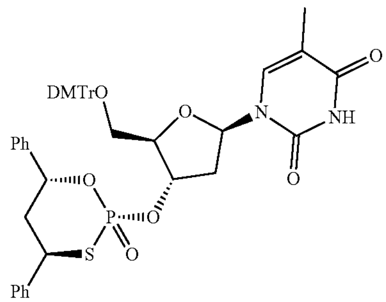 | 1-((2R,4S,5R)-5-((bis(4-methoxyphenyl)(phenyl)methoxy)methyl)-4-(((2R,4R,6R)-2-oxido-4,6-diphenyl-1,3,2-oxathiaphosphinan-2-yl)oxy)tetrahydrofuran-2-yl)-5-methylpyrimidine-2,4(1H,3H)-dione |
| 3-133 | 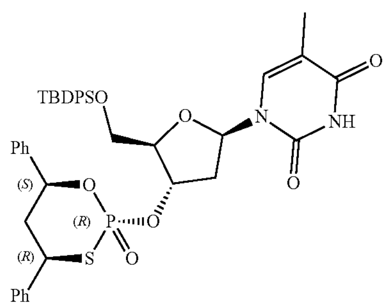 | 1-((2R,4S,5R)-5-(((tert-butyldiphenylsilyl)oxy)methyl)-4-(((2R,4R,6S)-2-oxido-4,6-diphenyl-1,3,2-oxathiaphosphinan-2-yl)oxy)tetrahydrofuran-2-yl)-5-methylpyrimidine-2,4(1H,3H)-dione |
| 3-134 | 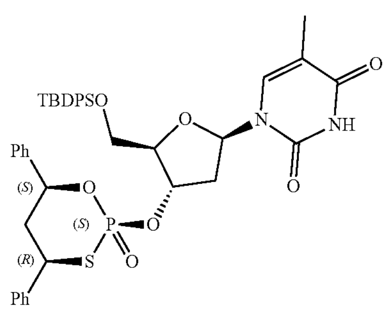 | 1-((2R,4S,5R)-5-(((tert-butyldiphenylsilyl)oxy)methyl)-4-(((2S,4R,6S)-2-oxido-4,6-diphenyl-1,3,2-oxathiaphosphinan-2-yl)oxy)tetrahydrofuran-2-yl)-5-methylpyrimidine-2,4(1H,3H)-dione |
| 3-135 | 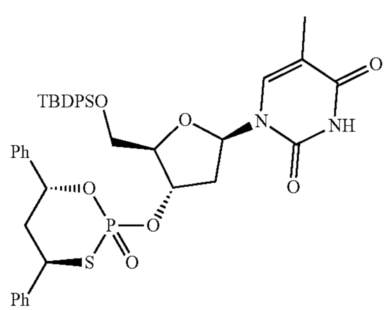 | 1-((2R,4S,5R)-5-(((tert-butyldiphenylsilyl)oxy)methyl)-4-(((4R,6R)-2-oxido-4,6-diphenyl-1,3,2-oxathiaphosphinan-2-yl)oxy)tetrahydrofuran-2-yl)-5-methylpyrimidine-2,4(1H,3H)-dione |

In one embodiment, Compounds of the Disclosure are compounds selected from the group consisting of compounds 3-1 to 3-100, 3-105, 3-106, and 3-123 to 3-127. In another embodiment, Compounds of the Disclosure are compounds selected from the group consisting of compounds 3-101 to 3-104 and 3-107 to 3-122. In another embodiment, Compounds of the Disclosure are compounds selected from the group consisting of compounds 3-128 to 3-135.

In yet another embodiment, Compounds of the Disclosure are compounds represented by Formula (IVa):

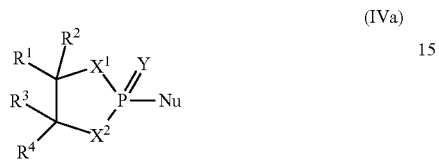

(IVa)

wherein
$R^1$, $R^2$, $R^3$, and $R^4$ are hydrogen;
$X^1$ and $X^2$ are independently O, S or NR;
Y is O, S or NR;
$R^c$ is hydrogen or $C_1$-$C_4$ alkyl; and
Nu is a nucleoside.

In another embodiment, Compounds of the Disclosure are compounds represented by Formula (IVa) above: wherein $R^1$, $R^2$, $R^3$, and $R^4$ are hydrogen; $X^1$ and $X^2$ are S; and Y is S.

In another embodiment, Compounds of the Disclosure are any one or more of the compounds of Table 4.

TABLE 4

| | | |
|---|---|---|
| 4-1 | (structure) | 1-((2R,4S,5R)-5-(((tert-butyldimethylsilyl)oxy)methyl)-4-((2-sulfido-1,3,2-dithiaphospholan-2-yl)oxy)tetrahydrofuran-2-yl)-5-methylpyrimidine-2,4(1H,3H)-dione |
| 4-2 | (structure) | 1-((2R,3R,4S,5R)-5-(((tert-butyldimethylsilyl)oxy)methyl)-3-hydroxy-4-((2-sulfido-1,3,2-dithiaphospholan-2-yl)oxy)tetrahydrofuran-2-yl)-5-methylpyrimidine-2,4(1H,3H)-dione |
| 4-3 | (structure) | 1-((2R,3R,4R,5R)-5-(((tert-butyldimethylsilyl)oxy)methyl)-3-fluoro-4-((2-sulfido-1,3,2-dithiaphospholan-2-yl)oxy)tetrahydrofuran-2-yl)-5-methylpyrimidine-2,4(1H,3H)-dione |

TABLE 4-continued

| | | |
|---|---|---|
| 4-4 | | 1-((2R,3R,4R,5R)-5-(((tert-butyldimethylsilyl)oxy)methyl)-3-fluoro-4-((2-sulfido-1,3,2-dithiaphospholan-2-yl)oxy)tetrahydrofuran-2-yl)pyrimidine-2,4(1H,3H)-dione |
| 4-5 | | 1-((2R,3R,4S,5R)-5-(((tert-butyldimethylsilyl)oxy)methyl)-3-hydroxy-4-((2-sulfido-1,3,2-dithiaphospholan-2-yl)oxy)tetrahydrofuran-2-yl)pyrimidine-2,4(1H,3H)-dione |
| 4-6 | | 1-((2R,4S,5R)-5-(((tert-butyldimethylsilyl)oxy)methyl)-4-((2-sulfido-1,3,2-dithiaphospholan-2-yl)oxy)tetrahydrofuran-2-yl)pyrimidine-2,4(1H,3H)-dione |
| 4-7 | | 1-((2R,4S,5R)-4-((tert-butyldimethylsilyl)oxy)-5-(((2-sulfido-1,3,2-dithiaphospholan-2-yl)oxy)methyl)tetrahydrofuran-2-yl)-5-methylpyrimidine-2,4(1H,3H)-dione |
| 4-8 | | 1-((2R,3R,4S,5R)-4-((tert-butyldimethylsilyl)oxy)-3-hydroxy-5-(((2-sulfido-1,3,2-dithiaphospholan-2-yl)oxy)methyl)tetrahydrofuran-2-yl)-5-methylpyrimidine-2,4(1H,3H)-dione |
| 4-9 | | 1-((2R,3R,4R,5R)-4-((tert-butyldimethylsilyl)oxy)-3-fluoro-5-(((2-sulfido-1,3,2-dithiaphospholan-2-yl)oxy)methyl)tetrahydrofuran-2-yl)-5-methylpyrimidine-2,4(1H,3H)-dione |

TABLE 4-continued

| | Structure | Name |
|---|---|---|
| 4-10 | 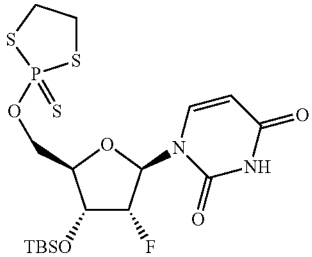 [SMILES: CC(C)(C)[Si](C)(C)O[C@H]1[C@@H](F)[C@H](n2ccc(=O)[nH]c2=O)O[C@@H]1COP1(=S)SCCS1] | 1-((2R,3R,4R,5R)-4-((tert-butyldimethylsilyl)oxy)-3-fluoro-5-(((2-sulfido-1,3,2-dithiaphospholan-2-yl)oxy)methyl)tetrahydrofuran-2-yl)pyrimidine-2,4(1H,3H)-dione |
| 4-11 | 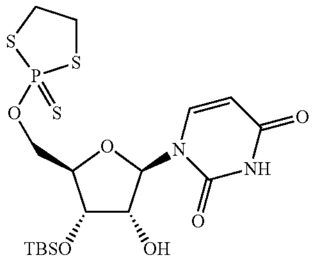 [SMILES: CC(C)(C)[Si](C)(C)O[C@H]1[C@@H](O)[C@H](n2ccc(=O)[nH]c2=O)O[C@@H]1COP1(=S)SCCS1] | 1-((2R,3R,4S,5R)-4-((tert-butyldimethylsilyl)oxy)-3-hydroxy-5-(((2-sulfido-1,3,2-dithiaphospholan-2-yl)oxy)methyl)tetrahydrofuran-2-yl)pyrimidine-2,4(1H,3H)-dione |
| 4-12 | 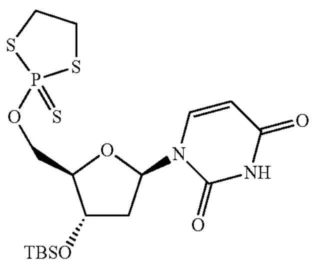 [SMILES: CC(C)(C)[Si](C)(C)O[C@H]1C[C@H](n2ccc(=O)[nH]c2=O)O[C@@H]1COP1(=S)SCCS1] | 1-((2R,4S,5R)-4-((tert-butyldimethylsilyl)oxy)-5-(((2-sulfido-1,3,2-dithiaphospholan-2-yl)oxy)methyl)tetrahydrofuran-2-yl)pyrimidine-2,4(1H,3H)-dione |
| 4-13 | 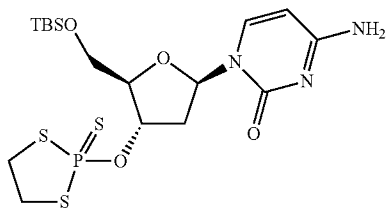 [SMILES: CC(C)(C)[Si](C)(C)OC[C@H]1O[C@@H](n2ccc(N)nc2=O)C[C@@H]1OP1(=S)SCCS1] | 4-amino-1-((2R,4S,5R)-5-(((tert-butyldimethylsilyl)oxy)methyl)-4-((2-sulfido-1,3,2-dithiaphospholan-2-yl)oxy)tetrahydrofuran-2-yl)pyrimidin-2(1H)-one |
| 4-14 | 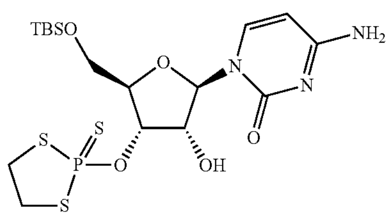 [SMILES: CC(C)(C)[Si](C)(C)OC[C@H]1O[C@@H](n2ccc(N)nc2=O)[C@H](O)[C@@H]1OP1(=S)SCCS1] | 4-amino-1-((2R,3R,4S,5R)-5-(((tert-butyldimethylsilyl)oxy)methyl)-3-hydroxy-4-((2-sulfido-1,3,2-dithiaphospholan-2-yl)oxy)tetrahydrofuran-2-yl)pyrimidin-2(1H)-one |
| 4-15 | 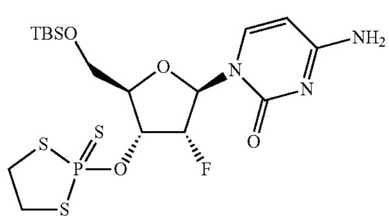 [SMILES: CC(C)(C)[Si](C)(C)OC[C@H]1O[C@@H](n2ccc(N)nc2=O)[C@H](F)[C@@H]1OP1(=S)SCCS1] | 4-amino-1-((2R,3R,4R,5R)-5-(((tert-butyldimethylsilyl)oxy)methyl)-3-fluoro-4-((2-sulfido-1,3,2-dithiaphospholan-2-yl)oxy)tetrahydrofuran-2-yl)pyrimidin-2(1H)-one |

TABLE 4-continued

| | | |
|---|---|---|
| 4-16 | | 4-amino-1-((2R,4S,5R)-4-((tert-butyldimethylsilyl)oxy)-5-(((2-sulfido-1,3,2-dithiaphospholan-2-yl)oxy)methyl)tetrahydrofuran-2-yl)pyrimidin-2(1H)-one |
| 4-17 | | 4-amino-1-((2R,3R,4S,5R)-4-((tert-butyldimethylsilyl)oxy)-3-hydroxy-5-(((2-sulfido-1,3,2-dithiaphospholan-2-yl)oxy)methyl)tetrahydrofuran-2-yl)pyrimidin-2(1H)-one |
| 4-18 | | 4-amino-1-((2R,3R,4R,5R)-4-((tert-butyldimethylsilyl)oxy)-3-fluoro-5-(((2-sulfido-1,3,2-dithiaphospholan-2-yl)oxy)methyl)tetrahydrofuran-2-yl)pyrimidin-2(1H)-one |
| 4-19 | | 2-(((2R,3S,5R)-5-(6-amino-9H-purin-9-yl)-2-(((tert-butyldimethylsilyl)oxy)methyl)tetrahydrofuran-3-yl)oxy)-1,3,2-dithiaphospholane 2-sulfide |
| 4-20 | | 2-(((2R,3S,4R,5R)-5-(6-amino-9H-purin-9-yl)-2-(((tert-butyldimethylsilyl)oxy)methyl)-4-hydroxytetrahydrofuran-3-yl)oxy)-1,3,2-dithiaphospholane 2-sulfide |
| 4-21 | | 2-(((2R,3R,4R,5R)-5-(6-amino-9H-purin-9-yl)-2-(((tert-butyldimethylsilyl)oxy)methyl)-4-fluorotetrahydrofuran-3-yl)oxy)-1,3,2-dithiaphospholane 2-sulfide |
| 4-22 | | 2-(((2R,3R,4R,5R)-2-(((tert-butyldimethylsilyl)oxy)methyl)-4-fluoro-5-(6-hydroxy-9H-purin-9-yl)tetrahydrofuran-3-yl)oxy)-1,3,2-dithiaphospholane 2-sulfide |

TABLE 4-continued

| | | |
|---|---|---|
| 4-23 | (structure) | 2-(((2R,3S,4R,5R)-2-(((tert-butyldimethylsilyl)oxy)methyl)-4-hydroxy-5-(6-hydroxy-9H-purin-9-yl)tetrahydrofuran-3-yl)oxy)-1,3,2-dithiaphospholane 2-sulfide |
| 4-24 | (structure) | 2-(((2R,3S,5R)-2-(((tert-butyldimethylsilyl)oxy)methyl)-5-(6-hydroxy-9H-purin-9-yl)tetrahydrofuran-3-yl)oxy)-1,3,2-dithiaphospholane 2-sulfide |
| 4-25 | (structure) | 2-(((2R,3S,4R,5R)-3-((tert-butyldimethylsilyl)oxy)-4-hydroxy-5-(6-hydroxy-9H-purin-9-yl)tetrahydrofuran-2-yl)methoxy)-1,3,2-dithiaphospholane 2-sulfide |
| 4-26 | (structure) | 2-(((2R,3R,4R,5R)-3-((tert-butyldimethylsilyl)oxy)-4-fluoro-5-(6-hydroxy-9H-purin-9-yl)tetrahydrofuran-2-yl)methoxy)-1,3,2-dithiaphospholane 2-sulfide |
| 4-27 | (structure) | 2-(((2R,3S,5R)-3-((tert-butyldimethylsilyl)oxy)-5-(6-hydroxy-9H-purin-9-yl)tetrahydrofuran-2-yl)methoxy)-1,3,2-dithiaphospholane 2-sulfide |
| 4-28 | (structure) | 2-(((2R,3S,5R)-5-(6-amino-9H-purin-9-yl)-3-((tert-butyldimethylsilyl)oxy)tetrahydrofuran-2-yl)methoxy)-1,3,2-dithiaphospholane 2-sulfide |

TABLE 4-continued

| | | |
|---|---|---|
| 4-29 | (structure) | 2-(((2R,3S,4R,5R)-5-(6-amino-9H-purin-9-yl)-3-((tert-butyldimethylsilyl)oxy)-4-hydroxytetrahydrofuran-2-yl)methoxy)-1,3,2-dithiaphospholane 2-sulfide |
| 4-30 | (structure) | 2-(((2R,3R,4R,5R)-5-(6-amino-9H-purin-9-yl)-3-((tert-butyldimethylsilyl)oxy)-4-fluorotetrahydrofuran-2-yl)methoxy)-1,3,2-dithiaphospholane 2-sulfide |
| 4-31 | (structure) | 2-amino-9-((2R,3R,4R,5R)-5-(((tert-butyldimethylsilyl)oxy)methyl)-3-fluoro-4-((2-sulfido-1,3,2-dithiaphospholan-2-yl)oxy)tetrahydrofuran-2-yl)-1,9-dihydro-6H-purin-6-one |
| 4-32 | (structure) | 2-amino-9-((2R,3R,4S,5R)-5-(((tert-butyldimethylsilyl)oxy)methyl)-3-hydroxy-4-((2-sulfido-1,3,2-dithiaphospholan-2-yl)oxy)tetrahydrofuran-2-yl)-1,9-dihydro-6H-purin-6-one |
| 4-33 | (structure) | 2-amino-9-((2R,4S,5R)-5-(((tert-butyldimethylsilyl)oxy)methyl)-4-((2-sulfido-1,3,2-dithiaphospholan-2-yl)oxy)tetrahydrofuran-2-yl)-1,9-dihydro-6H-purin-6-one |
| 4-34 | (structure) | 9-((2R,4S,5R)-5-(((tert-butyldimethylsilyl)oxy)methyl)-4-((2-sulfido-1,3,2-dithiaphospholan-2-yl)oxy)tetrahydrofuran-2-yl)-2-hydroxy-1,9-dihydro-6H-purin-6-one |
| 4-35 | (structure) | 9-((2R,3R,4S,5R)-5-(((tert-butyldimethylsilyl)oxy)methyl)-3-hydroxy-4-((2-sulfido-1,3,2-dithiaphospholan-2-yl)oxy)tetrahydrofuran-2-yl)-2-hydroxy-1,9-dihydro-6H-purin-6-one |

TABLE 4-continued

| | | |
|---|---|---|
| 4-36 | 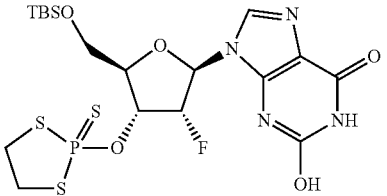 [SMILES: CC(C)(C)[Si](C)(C)OC[C@H]1O[C@@H](n2cnc3c(=O)[nH]c(O)nc32)[C@H](F)[C@@H]1OP1(=S)SCCS1] | 9-((2R,3R,4R,5R)-5-(((tert-butyldimethylsilyl)oxy)methyl)-3-fluoro-4-((2-sulfido-1,3,2-dithiaphospholan-2-yl)oxy)tetrahydrofuran-2-yl)-2-hydroxy-1,9-dihydro-6H-purin-6-one |
| 4-37 | 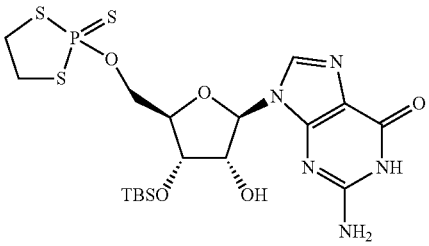 | 2-amino-9-((2R,3R,4S,5R)-4-((tert-butyldimethylsilyl)oxy)-3-hydroxy-5-(((2-sulfido-1,3,2-dithiaphospholan-2-yl)oxy)methyl)tetrahydrofuran-2-yl)-1,9-dihydro-6H-purin-6-one |
| 4-38 | 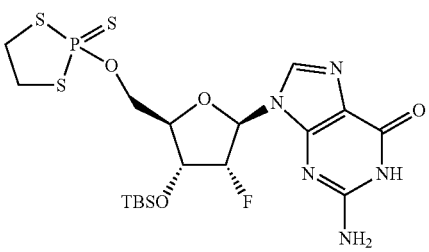 [SMILES: CC(C)(C)[Si](C)(C)O[C@H]1[C@@H](O)[C@H](n2cnc3c(=O)[nH]c(N)nc32)O[C@@H]1COP1(=S)SCCS1] | 2-amino-9-((2R,3R,4R,5R)-4-((tert-butyldimethylsilyl)oxy)-3-fluoro-5-(((2-sulfido-1,3,2-dithiaphospholan-2-yl)oxy)methyl)tetrahydrofuran-2-yl)-1,9-dihydro-6H-purin-6-one |
| 4-39 | 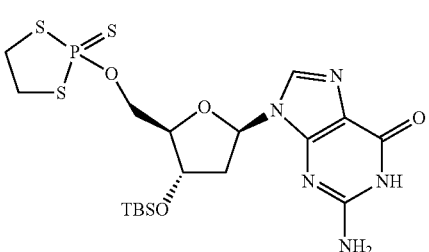 [SMILES: CC(C)(C)[Si](C)(C)O[C@H]1C[C@H](n2cnc3c(=O)[nH]c(O)nc32)O[C@@H]1COP1(=S)SCCS1] | 2-amino-9-((2R,4S,5R)-4-((tert-butyldimethylsilyl)oxy)-5-(((2-sulfido-1,3,2-dithiaphospholan-2-yl)oxy)methyl)tetrahydrofuran-2-yl)-1,9-dihydro-6H-purin-6-one |
| 4-40 | 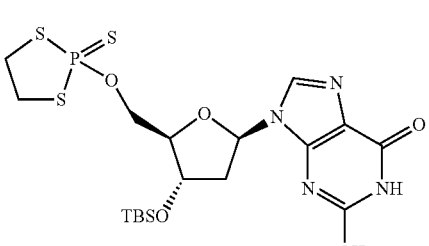 | 9-((2R,4S,5R)-4-((tert-butyldimethylsilyl)oxy)-5-(((2-sulfido-1,3,2-dithiaphospholan-2-yl)oxy)methyl)tetrahydrofuran-2-yl)-2-hydroxy-1,9-dihydro-6H-purin-6-one |
| 4-41 | 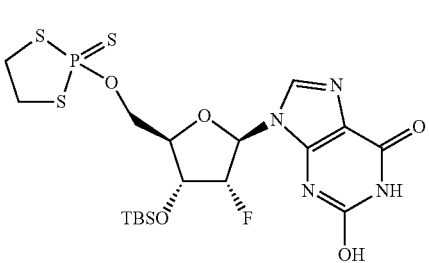 [SMILES: CC(C)(C)[Si](C)(C)O[C@H]1[C@@H](F)[C@H](n2cnc3c(=O)[nH]c(O)nc32)O[C@@H]1COP1(=S)SCCS1] | 9-((2R,3R,4R,5R)-4-((tert-butyldimethylsilyl)oxy)-3-fluoro-5-(((2-sulfido-1,3,2-dithiaphospholan-2-yl)oxy)methyl)tetrahydrofuran-2-yl)-2-hydroxy-1,9-dihydro-6H-purin-6-one |

TABLE 4-continued

| | | |
|---|---|---|
| 4-42 | [structure] | 9-((2R,3R,4S,5R)-4-((tert-butyldimethylsilyl)oxy)-3-hydroxy-5-(((2-sulfido-1,3,2-dithiaphospholan-2-yl)oxy)methyl)tetrahydrofuran-2-yl)-2-hydroxy-1,9-dihydro-6H-purin-6-one |
| 4-43 | [structure] | 1-((2R,4S,5R)-5-(((tert-butyldiphenylsilyl)oxy)methyl)-4-((2-sulfido-1,3,2-dithiaphospholan-2-yl)oxy)tetrahydrofuran-2-yl)-5-methylpyrimidine-2,4(1H,3H)-dione |
| 4-44 | [structure] | N-(1-((2R,4S,5R)-5-(((tert-butyldimethylsilyl)oxy)methyl)-4-((2-sulfido-1,3,2-dithiaphospholan-2-yl)oxy)tetrahydrofuran-2-yl)-2-oxo-1,2-dihydropyrimidin-4-yl)benzamide |
| 4-45 | [structure] | N-(9-((2R,4S,5R)-5-(((tert-butyldimethylsilyl)oxy)methyl)-4-((2-sulfido-1,3,2-dithiaphospholan-2-yl)oxy)tetrahydrofuran-2-yl)-6-oxo-6,9-dihydro-1H-purin-2-yl)isobutyramide |
| 4-46 | [structure] | N-(9-((3aR,4R,6R,6aR)-2,2-dimethyl-6-(((2-sulfido-1,3,2-dithiaphospholan-2-yl)oxy)methyl)tetrahydrofuro[3,4-d][1,3]dioxol-4-yl)-9H-purin-6-yl)benzamide |

In one embodiment, Compounds of the Disclosure are compounds selected from the group consisting of compounds 4-1 to 4-42 and compound 4-46. In another embodiment, Compounds of the Disclosure are compounds selected from the group consisting of compounds 4-43 to 4-45.

Definitions

Unless otherwise stated, the following terms used in this application, including the specification and claims, have the definitions given below. It must be noted that, as used in the specification and the appended claims, the singular forms "a" "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise. Furthermore, use of the term "including" as well as other forms, such as "include", "includes" and "included" is not limiting.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

The present disclosure is intended to include all isotopes of atoms occurring in the present compounds. Isotopes include those atoms having the same atomic number but different mass numbers. By way of general example and without limitation, isotopes of hydrogen include deuterium and tritium. The isotopes of hydrogen can be denoted as $^1H$ (hydrogen), $^2H$ (deuterium) and $^3H$ (tritium). They are also commonly denoted as D for deuterium and T for tritium. In the application, $CD_3$ denotes a methyl group wherein all of the hydrogen atoms are deuterium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

In the present disclosure, the term "compound" is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

In the present disclosure, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

In the present disclosure, the term "stereoisomer" refers to all possible different isomeric as well as conformational forms that a compound may possess (e.g., a compound of any formula described herein), in particular all possible stereochemically and conformationally isomeric forms, all diastereomers, enantiomers and/or conformers of the basic molecular structure. Some compounds of the present disclosure may exist in different tautomeric forms, all of the latter being included within the scope of the present disclosure.

In the present disclosure, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

In the present disclosure, the term "diastereomer," means stereoisomers that are not mirror images of one another and are non-superimposable on one another.

In the present disclosure, the term "nucleic acid" encompasses poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified phosphorous-atom bridges. The term encompasses nucleic acids containing any combinations of nucleobases, modified nucleobases, sugars, modified sugars, phosphate bridges or modified phosphorous atom bridges. Examples include, and are not limited to, nucleic acids containing ribose moieties, nucleic acids containing deoxyribose moieties, nucleic acids containing both ribose and deoxyribose moieties, nucleic acids containing ribose and modified ribose moieties. The prefix "poly-" refers to a nucleic acid containing about 1 to about 10,000 nucleotide monomer units, and the prefix "oligo-" refers to a nucleic acid containing about 1 to about 200 nucleotide monomer units. The term "nucleic acid" can also encompass CDNs.

In the present disclosure, the terms "nucleobase" and "nucleosidic base moiety," used interchangeably, refer to the parts of nucleic acids that are involved in the hydrogen-bonding that binds one nucleic acid strand to the complementary strand in a sequence-specific manner. The most common naturally-occurring nucleobases are adenine (A), guanine (G), uracil (U), cytosine (C), and thymine (T).

In the present disclosure, nucleobases can be represented by abbreviation A, G, U, C, T, Hyp. Abbreviation A refers to adenine; G refers to guanine; U refers to uracil; C refers to cytosine; T refers to thymine; Hyp refers to hypoxanthine.

In the present disclosure, the terms "modified nucleobase" and "modified nucleosidic base moiety," used interchangeably, refer to a moiety that can replace a nucleobase. The modified nucleobase mimics the spatial arrangement, electronic properties, or some other physicochemical property of the nucleobase and retains the property of hydrogen-bonding that binds one nucleic acid strand to another in a sequence-specific manner. A modified nucleobase generally can pair with naturally occurring bases (e.g., uracil, thymine, adenine, cytosine, guanine) without substantially affecting the melting behavior, recognition by intracellular enzymes or activity of the oligonucleotide duplex. The terms "modified nucleobase" and "modified nucleosidic base moiety," used interchangeably, is further intended to include heterocyclic compounds that can serve as nucleosidic bases, including certain 'universal bases' that are not nucleosidic bases in the most classical sense but serve as nucleosidic bases. Especially mentioned as a universal base is 3-nitropyrrole.

In the present disclosure, the term "nucleoside" refers to a compound, glycosylamine, wherein a nucleobase (a nitrogenous base, such as adenine, guanine, thymine, uracil, 5-methyluracil, etc.) or a modified nucleobase is covalently bound to a five-carbon sugar (ribose or deoxyribose) or a modified sugar.

In the present disclosure, the term "sugar" refers to a monosaccharide in closed and/or open form. Sugars include, but are not limited to, ribose, deoxyribose, pentofuranose, pentopyranose, morpholinos, carbocyclic analogs, hexopyranose moieties and bicyclic sugars such as those found in locked nucleic acids. Examples of locked nucleic acids include, without limitation, those disclosed in WO2016/079181. Examples of Compounds of the Disclosure (IV) having modified sugars include, without limitation, the following:

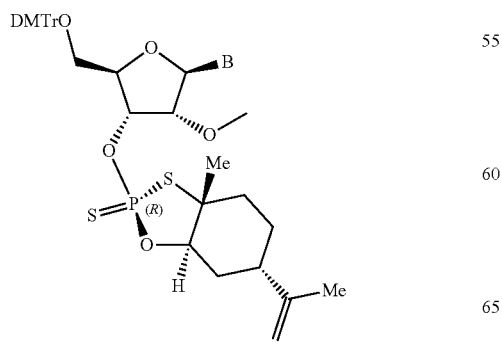

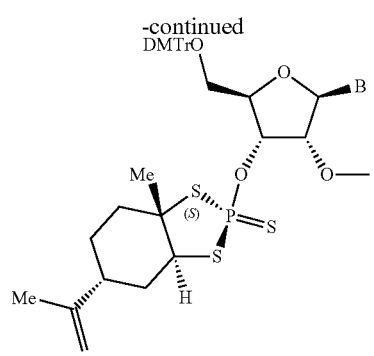

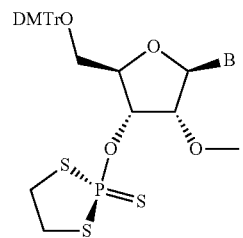

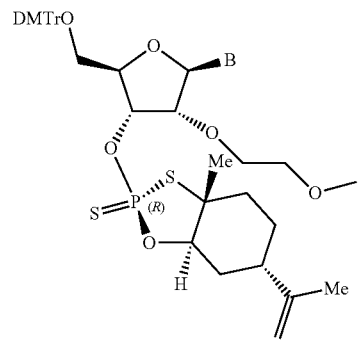

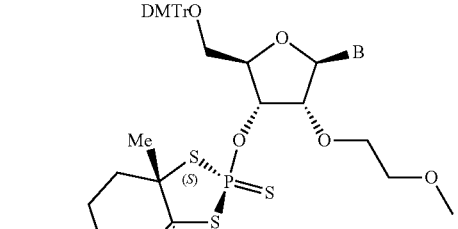

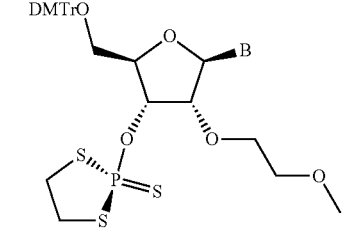

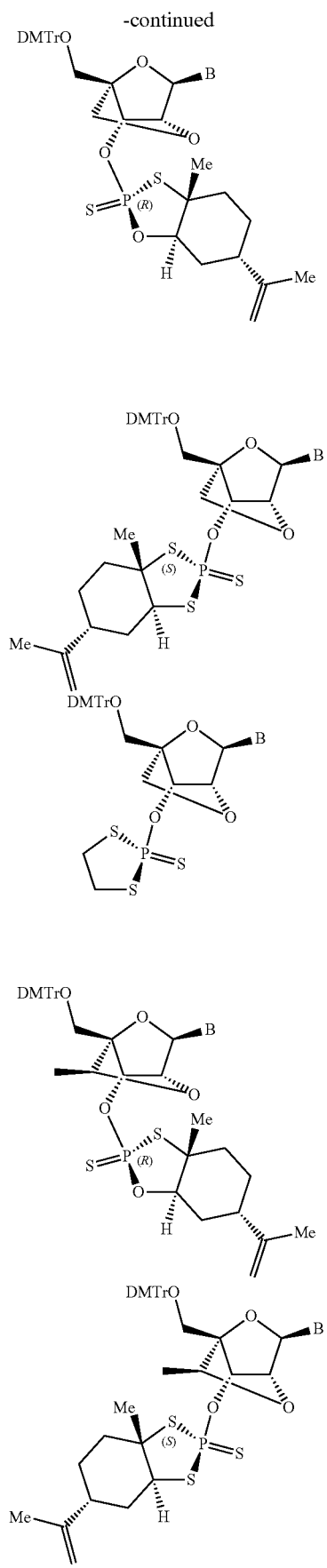

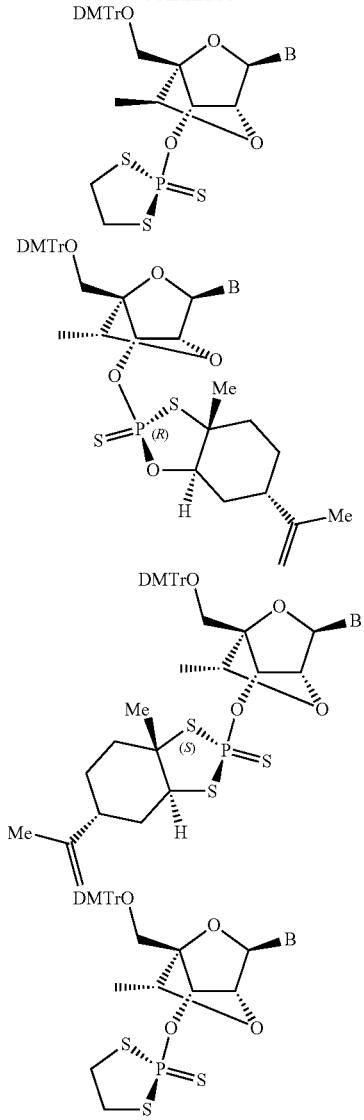

wherein B is the Base.

In the present disclosure, the term "modified sugar" refers to a moiety that can replace a sugar. The modified sugar mimics the spatial arrangement, electronic properties, or some other physicochemical property of a sugar.

In the present disclosure, the term "nucleotide" refers to a moiety wherein a nucleobase or a modified nucleobase is covalently linked to a sugar or modified sugar, and the sugar or modified sugar is covalently linked to a phosphate group or a modified phosphorous-atom moiety, such a thiophosphate group.

In the present disclosure, the term "peptide" refers to a chain of amino acid monomers linked by a peptide bond. Generally, a peptide will have no more than about 50 amino acids. The term "peptide" encompasses both naturally and non-naturally occurring amino acids. A peptide can be linear or cyclic.

In the present disclosure, the term "protein" comprises one or more polypeptides arranged in a biologically-functional way. Examples of biologically-functional proteins include, but are not limited to, enzymes, antibodies, cytokines, hormones, trans-membrane proteins, etc.

In the present disclosure, the term "moiety" refers to a specific segment or functional group of a molecule. Chemical moieties are often recognized chemical entities embedded in or appended to a molecule.

In the present disclosure, the terms "solid-support" or "resin," used herein interchangeably, refer to any support which enables synthetic mass production of nucleic acids and/or peptides and can be reutilized at need. As used herein, the terms refer to a polymer that is insoluble in the media employed in the reaction steps performed to synthesize nucleic acids and/or peptides, and is derivatized to comprise reactive groups.

In the present disclosure, the term "linking moiety" refers to any moiety optionally positioned between the terminal nucleoside and the solid support or between the terminal nucleoside and another nucleoside, nucleotide, or nucleic acid.

In the present disclosure, the term "purified," when used in relation to nucleic acids, refers to one that is separated from at least one contaminant. As used herein, a "contaminant" is any substance that makes another unfit, impure or inferior. Thus, a purified oligonucleotide is present in a form or setting different from that which existed prior to subjecting it to a purification method.

In the present disclosure, the term "alkyl" as used by itself or as part of another group refers to unsubstituted straight- or branched-chain aliphatic hydrocarbons containing one to twelve carbon atoms, i.e., $C_{1-12}$ alkyl, or the number of carbon atoms designated, e.g., a $C_1$ alkyl such as methyl, a $C_2$ alkyl such as ethyl, a $C_3$ alkyl such as propyl or isopropyl, and so on. In one embodiment, the alkyl group is a $C_{1-10}$ alkyl. In another embodiment, the alkyl group is a $C_{1-6}$ alkyl. In another embodiment, the alkyl group is a $C_{1-4}$ alkyl. Non-limiting exemplary $C_{1-10}$ alkyl groups include methyl, ethyl, propyl, isopropyl, butyl, sec-butyl, tert-butyl, isobutyl, 3-pentyl, hexyl, heptyl, octyl, nonyl, and decyl. Non-limiting exemplary $C_{1-6}$ alkyl groups include methyl, ethyl, propyl, isopropyl, butyl, sec-butyl, tert-butyl, iso-butyl, and hexyl. Non-limiting exemplary $C_{1-4}$ alkyl groups include methyl, ethyl, propyl, isopropyl, butyl, sec-butyl, tert-butyl, and iso-butyl.

In the present disclosure, the term "optionally substituted alkyl" is an alkyl group as defined above, that has one or more of $R^a$ groups.

In the present disclosure, the term "cycloalkyl" as used by itself or as part of another group refers to unsubstituted saturated and partially unsaturated, e.g., containing one or two double bonds, cyclic aliphatic hydrocarbons containing one to three rings having from three to twelve carbon atoms, i.e., $C_{3-12}$ cycloalkyl, or the number of carbons designated. In one embodiment, the cycloalkyl group has two rings. In one embodiment, the cycloalkyl group has one ring. In another embodiment, the cycloalkyl is saturated. In another embodiment, the cycloalkyl is unsaturated. In another embodiment, the cycloalkyl group is a $C_{3-8}$ cycloalkyl group. In another embodiment, the cycloalkyl group is a $C_{3-7}$ cycloalkyl group. In another embodiment, the cycloalkyl group is a $C_{5-7}$ cycloalkyl group. In another embodiment, the cycloalkyl group is a $C_{3-6}$ cycloalkyl group. The term "cycloalkyl" includes groups wherein a ring —$CH_2$— is replaced with a —C(=O)—. Non-limiting exemplary cycloalkyl groups include cyclopropyl, cyclobutyl, cyclopentyl, cyclohexyl, cycloheptyl, cyclooctyl, norbornyl, decalin, adamantyl, cyclohexenyl, cyclopentenyl, cyclohexenyl, and cyclopentanone.

In the present disclosure, the term "optionally substituted cycloalkyl" is a cycloalkyl group as defined above, that has one or more of $R^a$ groups.

The term optionally substituted cycloalkyl includes cycloalkyl groups having a fused optionally substituted aryl, e.g., phenyl, or fused optionally substituted heteroaryl, e.g., pyridyl. An optionally substituted cycloalkyl having a fused optionally substituted aryl or fused optionally substituted heteroaryl group may be attached to the remainder of the molecule at any available carbon atom on the cycloalkyl ring. In one embodiment, the optionally substituted cycloalkyl group is a 5-, 6-, or 7-membered cycloalkyl group having a fused phenyl group, wherein the phenyl optionally substituted with one, two, or three substituents.

In the present disclosure, the term "alkenyl" as used by itself or as part of another group refers to an alkyl containing one, two or three carbon-to-carbon double bonds. In one embodiment, the alkenyl group is a $C_{2-6}$ alkenyl group. In another embodiment, the alkenyl group is a $C_{2-4}$ alkenyl group. Non-limiting exemplary alkenyl groups include ethenyl, propenyl, isopropenyl, butenyl, sec-butenyl, pentenyl, and hexenyl.

In the present disclosure, the term "optionally substituted alkenyl" as used herein by itself or as part of another group refers to an alkenyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, optionally substituted cycloalkyl, alkenyl, alkynyl, optionally substituted aryl, heteroaryl, and optionally substituted heterocyclo.

In the present disclosure, the term "alkynyl" as used by itself or as part of another group refers to an alkyl containing one to three carbon-to-carbon triple bonds. In one embodiment, the alkynyl has one carbon-to-carbon triple bond. In one embodiment, the alkynyl group is a $C_{2-6}$ alkynyl group. In another embodiment, the alkynyl group is a $C_{2-4}$ alkynyl group. Non-limiting exemplary alkynyl groups include ethynyl, propynyl, butynyl, 2-butynyl, pentynyl, and hexynyl groups.

In the present disclosure, the term "optionally substituted alkynyl" as used herein by itself or as part of another group refers to an alkynyl that is either unsubstituted or substituted with one, two or three substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, alkyl, cycloalkyl, alkenyl, alkynyl, optionally substituted aryl, optionally substituted heteroaryl, heterocyclo, and —Si(R)$_3$, wherein R is selected from the group consisting of alkyl and aryl.

In the present disclosure, the term "aryl" as used by itself or as part of another group refers to unsubstituted monocyclic or bicyclic aromatic ring systems having from six to fourteen carbon atoms, i.e., a $C_{6-14}$ aryl. Non-limiting exemplary aryl groups include phenyl (abbreviated as "Ph"), naphthyl, phenanthryl, anthracyl, indenyl, azulenyl, biphenyl, biphenylenyl, and fluorenyl groups. In one embodiment, the aryl group is a phenyl or naphthyl.

In the present disclosure, the term "optionally substituted aryl" as used herein by itself or as part of another group refers to an aryl that is either unsubstituted or substituted with one to five substituents independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, optionally substituted aryl, optionally substituted heteroaryl, optionally substituted heterocyclo, (alkoxy)alkyl, (amino)alkyl, (carboxamido)alkyl, mercaptoalkyl, and (heterocyclo)alkyl.

In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Non-limiting exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl, 3,5-dimethoxy, 4-methylphenyl, 2-fluoro-3-chlorophenyl, and 3-chloro-4-fluorophenyl. The term optionally substituted aryl includes phenyl groups having fused optionally substituted cycloalkyl and fused optionally substituted heterocyclo rings. An optionally substituted aryl having a fused optionally substituted cycloalkyl and fused optionally substituted heterocycle is attached to the remainder of the molecule at any available carbon atom on the aryl ring. Non-limiting examples include:

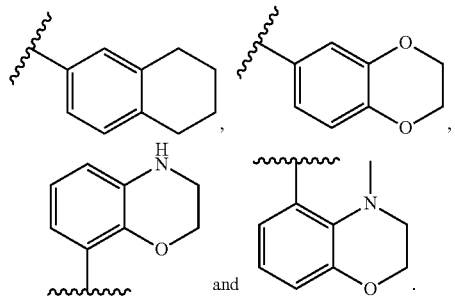

In the present disclosure, the term "aryloxy" as used by itself or as part of another group refers to an optionally substituted aryl attached to a terminal oxygen atom. A non-limiting exemplary aryloxy group is PhO⁻.

In the present disclosure, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the core of the compound.

In the present disclosure, the term "heteroaryl" or "heteroaromatic" refers to unsubstituted monocyclic and bicyclic aromatic ring systems having 5 to 14 ring atoms, i.e., a 5- to 14-membered heteroaryl, wherein at least one carbon atom of one of the rings is replaced with a heteroatom independently selected from the group consisting of oxygen, nitrogen and sulfur. In one embodiment, the heteroaryl contains 1, 2, 3, or 4 heteroatoms independently selected from the group consisting of oxygen, nitrogen and sulfur. In one embodiment, the heteroaryl has three heteroatoms. In another embodiment, the heteroaryl has two heteroatoms. In another embodiment, the heteroaryl has one heteroatom. In another embodiment, the heteroaryl is a 5- to 10-membered heteroaryl. In another embodiment, the heteroaryl is a 5- or 6-membered heteroaryl. In another embodiment, the heteroaryl has 5 ring atoms, e.g., thienyl, a 5-membered heteroaryl having four carbon atoms and one sulfur atom. In another embodiment, the heteroaryl has 6 ring atoms, e.g., pyridyl, a 6-membered heteroaryl having five carbon atoms and one nitrogen atom. Non-limiting exemplary heteroaryl groups include thienyl, benzo[b]thienyl, naphtho[2,3-b]thienyl, thianthrenyl, furyl, benzofuryl, pyranyl, isobenzofuranyl, benzooxazonyl, chromenyl, xanthenyl, 2H-pyrrolyl, pyrrolyl, imidazolyl, pyrazolyl, pyridyl, pyrazinyl, pyrimidinyl, pyridazinyl, isoindolyl, 3H-indolyl, indolyl, indazolyl, purinyl, isoquinolyl, quinolyl, phthalazinyl, naphthyridinyl, cinnolinyl, quinazolinyl, pteridinyl, 4aH-carbazolyl, carbazolyl, β-carbolinyl, phenanthridinyl, acridinyl, pyrimidinyl, phenanthrolinyl, phenazinyl, thiazolyl, isothiazolyl, phenothiazolyl, isoxazolyl, furazanyl, and phenoxazinyl. In one embodiment, the heteroaryl is thienyl (e.g., thien-2-yl and thien-3-yl), furyl (e.g., 2-furyl and 3-furyl), pyrrolyl (e.g., 1H-pyrrol-2-yl and 1H-pyrrol-3-yl), imidazolyl (e.g., 2H-imidazol-2-yl and 2H-imidazol-4-yl), pyrazolyl (e.g., 1H-pyrazol-3-yl, 1H-pyrazol-4-yl, and 1H-pyrazol-5-yl), pyridyl (e.g., pyridin-2-yl, pyridin-3-yl, and pyridin-4-yl), pyrimidinyl (e.g., pyrimidin-2-yl, pyrimidin-4-yl, and pyrimidin-5-yl), thiazolyl (e.g., thiazol-2-yl, thiazol-4-yl, and thiazol-5-yl), isothiazolyl (e.g., isothiazol-3-yl, isothiazol-4-yl, and isothiazol-5-yl), oxazolyl (e.g., oxazol-2-yl, oxazol-4-yl, and oxazol-5-yl), isoxazolyl (e.g., isoxazol-3-yl, isoxazol-4-yl, and isoxazol-5-yl), or indazolyl (e.g., 1H-indazol-3-yl). The term "heteroaryl" also includes possible N-oxides. A non-limiting exemplary N-oxide is pyridyl N-oxide.

In one embodiment, the heteroaryl is a 5- or 6-membered heteroaryl. In one embodiment, the heteroaryl is a 5-membered heteroaryl, i.e., the heteroaryl is a monocyclic aromatic ring system having 5 ring atoms wherein at least one carbon atom of the ring is replaced with a heteroatom independently selected from nitrogen, oxygen, and sulfur. Non-limiting exemplary 5-membered heteroaryl groups include thienyl, furyl, pyrrolyl, oxazolyl, pyrazolyl, imidazolyl, thiazolyl, isothiazolyl, and isoxazolyl.

In another embodiment, the heteroaryl is a 6-membered heteroaryl, e.g., the heteroaryl is a monocyclic aromatic ring system having 6 ring atoms wherein at least one carbon atom of the ring is replaced with a nitrogen atom. Non-limiting exemplary 6-membered heteroaryl groups include pyridyl, pyrazinyl, pyrimidinyl, and pyridazinyl.

In the present disclosure, the term "optionally substituted heteroaryl" as used by itself or as part of another group refers to a heteroaryl that is either unsubstituted or substituted with one to four substituents, e.g., one or two substituents, independently selected from the group consisting of halo, nitro, cyano, hydroxy, amino, alkylamino, dialkylamino, haloalkyl, hydroxyalkyl, alkoxy, haloalkoxy, aryloxy, aralkyloxy, alkylthio, carboxamido, sulfonamido, alkylcarbonyl, arylcarbonyl, alkylsulfonyl, arylsulfonyl, carboxy, carboxyalkyl, optionally substituted alkyl, optionally substituted cycloalkyl, alkenyl, alkynyl, aryl, heteroaryl, heterocyclo, (alkoxy)alkyl, (amino)alkyl, (carboxamido)alkyl, mercaptoalkyl, and (heterocyclo)alkyl. In one embodiment, the optionally substituted heteroaryl has one substituent. Any available carbon or nitrogen atom can be substituted. Non-limiting exemplary substituted heteroaryl groups include, but are not limited to:

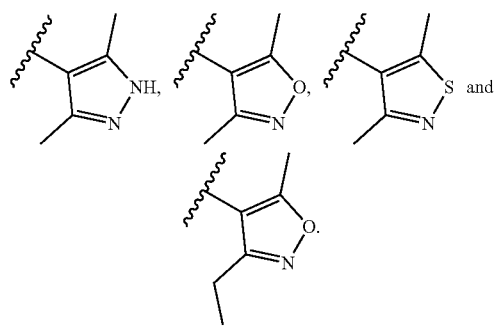

The term optionally substituted heteroaryl includes heteroaryl groups having a fused optionally substituted cycloalkyl or fused optionally substituted heterocyclo group. An optionally substituted heteroaryl having a fused optionally substituted cycloalkyl or fused optionally substituted heterocyclo group may be attached to the remainder of the molecule at any available carbon atom on the heteroaryl ring. Non-limiting examples include:

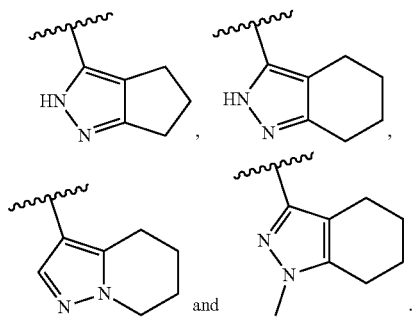

In the present disclosure, the term "halogen" is intended to include fluorine, chlorine, bromine and iodine.

In the present disclosure, the term "internucleoside linkage" refers to a naturally-occurring or modified linkage between two adjacent nucleosides in an oligonucleotide or a CDN. Naturally occurring RNA and DNA contain phosphorodiester internucleoside linkages. An example of a modified internucleoside linkage is a phosphorothioate linkage.

In the present disclosure, the term "heterochiral nucleic acids" refers to nucleic acids comprising internucleoside linkages containing phosphorous atoms in different stereochemical configurations. By analogy, the term "homochiral nucleic acids" refers to nucleic acids comprising internucleoside linkages containing phosphorous atoms in the same stereochemical configuration.

In the present disclosure, the term "leaving group" refers to a compound with a pKa of less than about 10. In some embodiments, the pKa of a leaving group is less than 7.1. Examples of a leaving group include, but are not limited to, DBU, 1,5-Diazabicyclo[4.3.0]non-5-ene (DBN), and imidazole, N-Hydroxytetrachlorophthalimide (TCNHPI), N-Hydroxyphthalimide (NHPI), N-Hydroxysuccinimide (OSu), Hydroxybenzotriazole (HOBt), 1-Hydroxy-7-azabenzotriazole (HOAt), Oxyma, and Uroninium salts. In some embodiment, the leaving group is selected from the group consisting of:

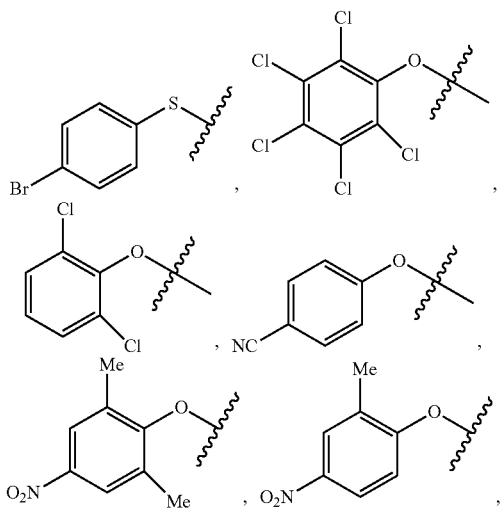

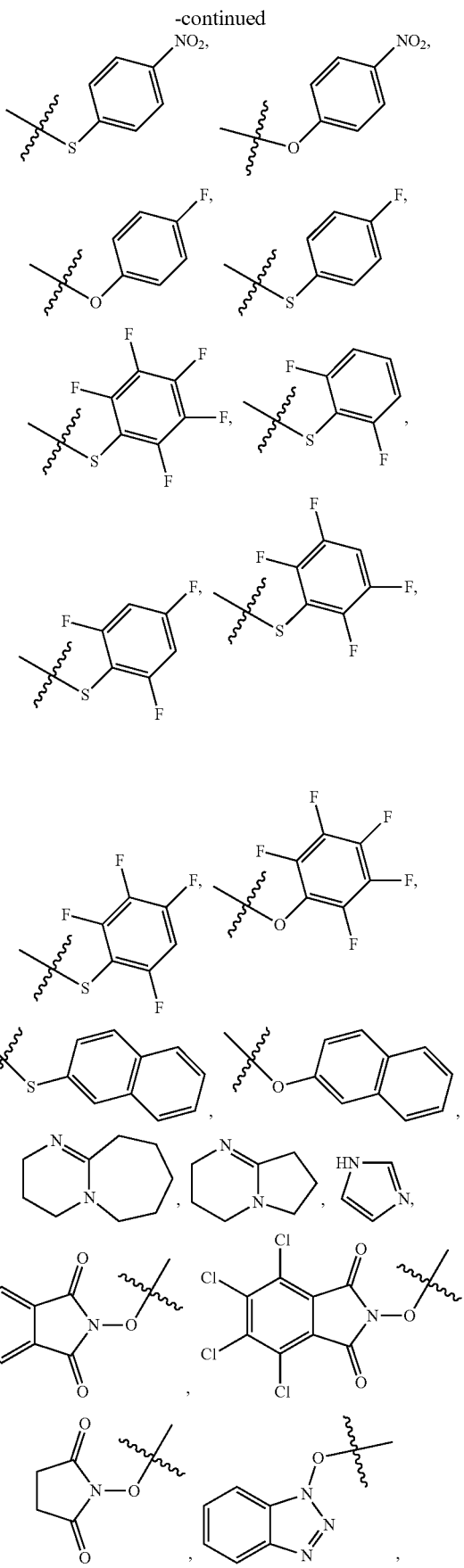

149
-continued

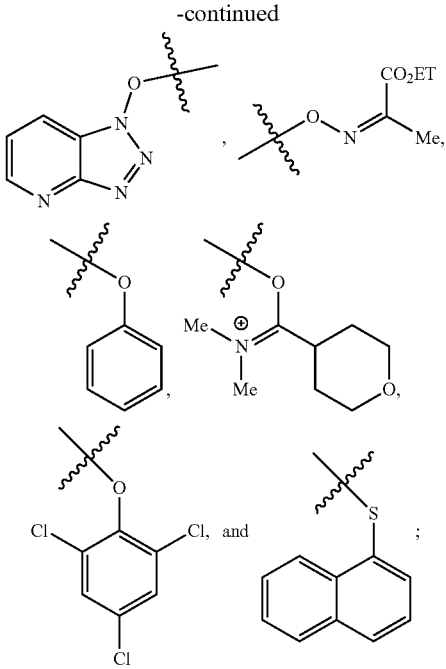

In the present disclosure, the term "protecting group" refers to a group that protects a functional group, such as alcohol, amine, carbonyl, carboxylic acid, phosphate, terminal alkyne, etc., from an unwanted chemical reaction. In some embodiments, the functional group is a nucleophile. Examples of alcohol protecting groups include, but are not limited to, acetyl (Ac), benzoyl (Bz), benzyl (Bn), β-methoxyethoxymethyl ether (MEM), dimethoxytrityl (DMT), methoxymethyl ether (MOM), methoxytrityl (MMT), p-methoxybenzyl ether (PMB), trimethylsislyl (TMS), tert-butyldimethylsilyl (TBS), tert-Butyldiphenylsilyl ether (TBDPS), tri-iso-propylsilyloxymethyl (TOM), trityl (Triphenyl methyl, Tr), pivaloyl (Piv), and the like. In one embodiment, the protecting group is the protecting group is 4,4'-dimethoxytrityl. Examples of amine protecting groups include, but are not limited to, carbobenzyloxy (Cbz), isobutyryl (iBu), p-methoxybenzyl carbonyl (MOZ), tert-butylcarbonyl (Boc), acetyl (Ac), benzoyl (Bz), benzyl (Bn), p-methoxybenzyl (PMB), p-methoxyphenyl (PMP), tosyl (Ts), and the like. Examples of carbonyl protecting groups include, but are not limited to, acetals and ketals, acylals, dithianes, and the like. Examples of carboxylic acid protecting groups include, but are not limited to, methyl esters, bezyl esters, tert-butyl esters, silyl esters, orthoesters, oxazoline, and the like. Examples of phosphate protecting groups include, but are not limited to, 2-cyanoethyl, methyl and the like. Examples of terminal alkyne protecting groups include, but are not limited to, propargyl and silyl groups. In one embodiment, a protecting group is used to protect a 5'-hydroxy group of a nucleoside used in the methods of the present disclosure. In one embodiment, the protecting group is DMT. In another embodiment, a protecting group is used to protect a nucleobase of a nucleoside used in the methods of the present disclosure. In some embodiments, the protecting group is an amine protecting group. In one embodiment, the protecting group is Ac. In another embodiment, the protecting group is Bz. In yet another embodiment, the protecting group is iBu.

150

Methods of Making Compounds of the Disclosure

In another aspect, the present disclosure provides methods of making Compounds of the Disclosure of Formulae (I)-(IIIe). In some embodiments, a method of the present disclosure comprises reacting a compound of formula (VII):

(VII)

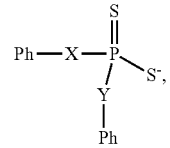

wherein X and Y are independently O or S, and
Ph is phenyl, optionally substituted with on one or more groups chosen from linear or branched $C_1$-$C_6$ alkyl, aryl, heteroaryl, halogen, —CN, or —$NO_2$,
with an epoxide or an episulfide.

In some embodiments, the methods of the present disclosure comprise reacting a compound of formula (VII) with an epoxide or an episulfide at a temperature of from about 20° C. to about 50° C. In other embodiments, the temperature is from about 30° C. to about 40° C. In one embodiment, the temperature is about 35° C. In one embodiment, the temperature is 35° C.

In some embodiments, the reaction is conducted for from about 30 min to about 4 hours. In other embodiments, the reaction is conducted for from about 1 hour to about 2 hours. In one embodiment, the reaction is conducted for about 1 hour. In one embodiment, the reaction is conducted for 1 hour.

The above reaction conditions are exemplary, and are not meant to be limiting. A skilled artisan will appreciate that the reaction conditions, such as reaction time and temperature, the identity and the amounts of the solvents and base, etc., can be varied according to the methods known in the art. In some embodiments, a reaction is conducted in an aprotic solvent at a temperature of from about 0° C. to about 100° C. for about 10 min to about 48 hours. In some embodiments, the temperature is from about 10° C. to about 80° C., from about 20° C. to about 60° C., from about 25° C. to about 40° C., from about 25° C. to about 30° C., from about 30° C. to about 40° C. In some embodiments, the time of a reaction is from about 30 min to about 40 hours, from about 30 min to about 20 hours, from about 30 min to about 10 hours, from about 30 min to about 5 hours, from about 30 min to about 3 hours, from about 1 hour to about 30 hours, from about 2 hours to about 20 hours, from about 3 hours to about 10 hours, from about 4 hours to about 8 hours, from about 5 hours to about 6 hours.

In some embodiments, an epoxide is represented by Formula (VIII):

(VIII)

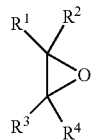

wherein
(a) $R^1$, $R^2$, $R^3$ and $R^4$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

or (b) any of $R^1$, $R^2$, $R^3$, and $R^4$ together with the carbons to which they are attached form $C_4$-$C_8$ cycloalkyl, optionally substituted with one or more, the same or different, $R^a$ groups;

wherein $R^a$ is hydrogen, deuterium, tritium; halogen; linear or branched $C_1$-$C_6$ alkyl; OH, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$ linear or branched $C_2$-$C_6$ alkenyl, optionally substituted with linear or branched $C_1$-$C_6$ alkyl; or linear or branched $C_2$-$C_6$ alkynyl, optionally substituted with a linear or branched $C_1$-$C_6$ alkyl;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

provided that either the carbon bearing the $R^1$ and $R^2$ groups, the carbon bearing the $R^3$ and $R^4$ groups, or both, is chiral.

In some embodiments, an epoxide is represented by Formula (IX).

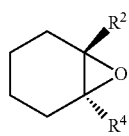

(IX)

wherein $R^2$ and $R^4$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

wherein $R^a$ is hydrogen, deuterium, tritium; halogen; linear or branched $C_1$-$C_6$ alkyl; OH, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$ linear or branched $C_2$-$C_6$ alkenyl, optionally substituted with linear or branched $C_1$-$C_6$ alkyl; or linear or branched $C_2$-$C_6$ alkynyl, optionally substituted with a linear or branched $C_1$-$C_6$ alkyl;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl.

Exemplary epoxides include, but are not limited to, the following epoxides:

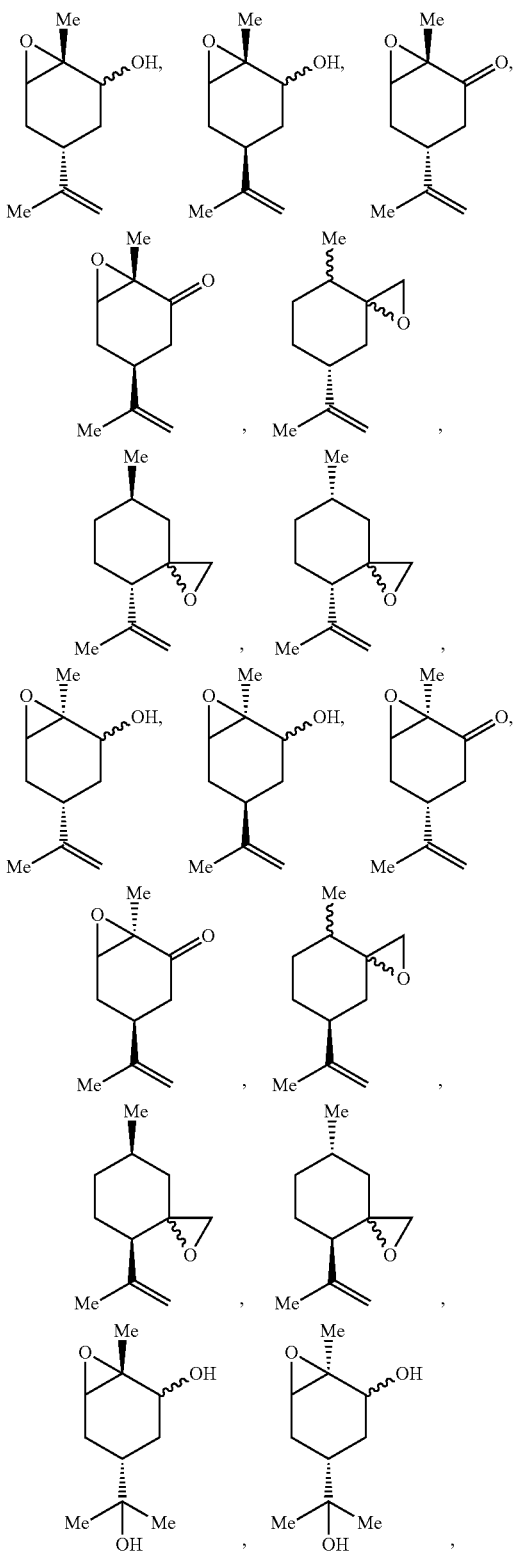

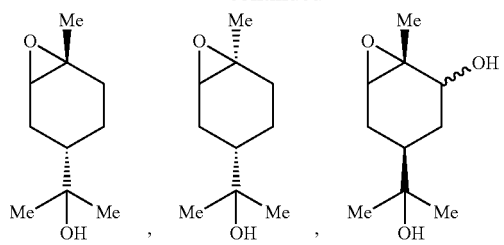
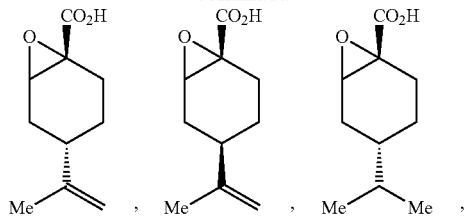
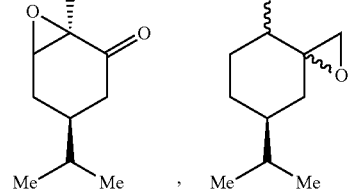
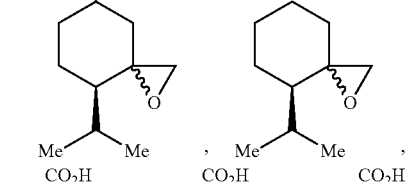
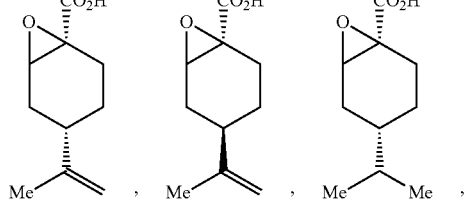
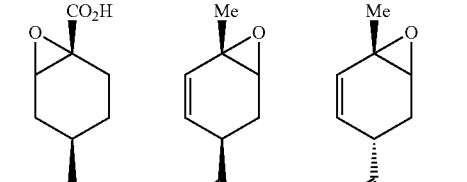
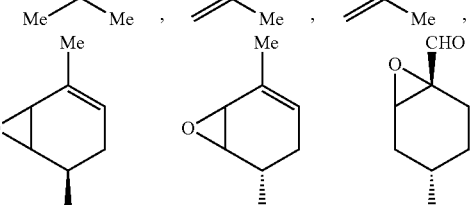
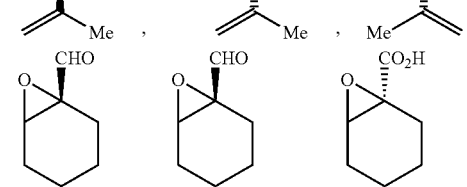
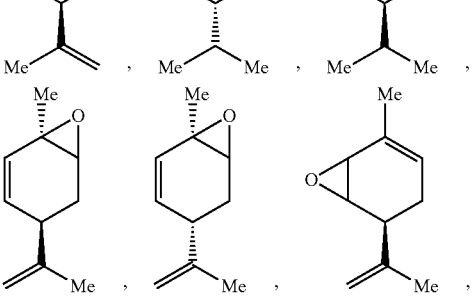

-continued
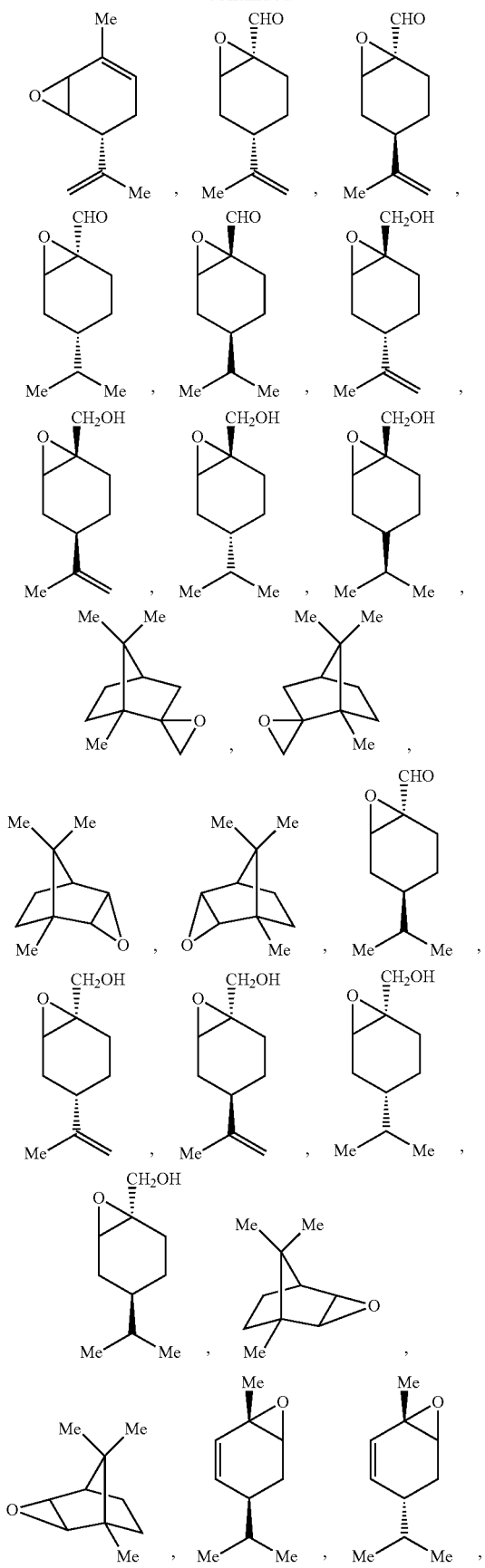
-continued
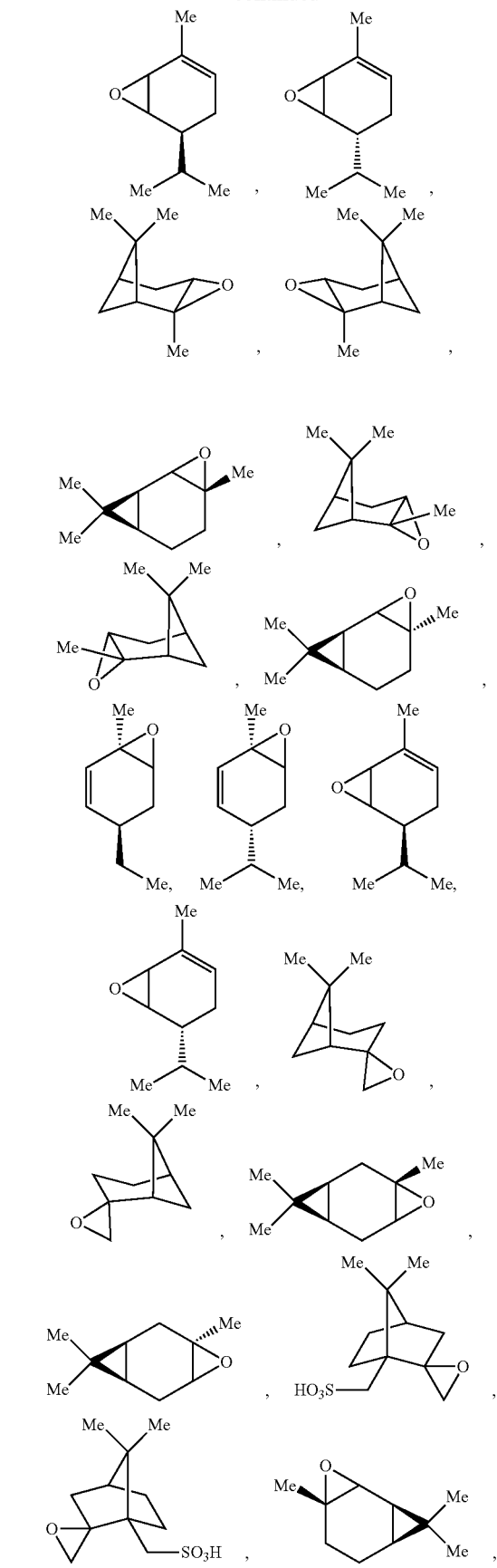

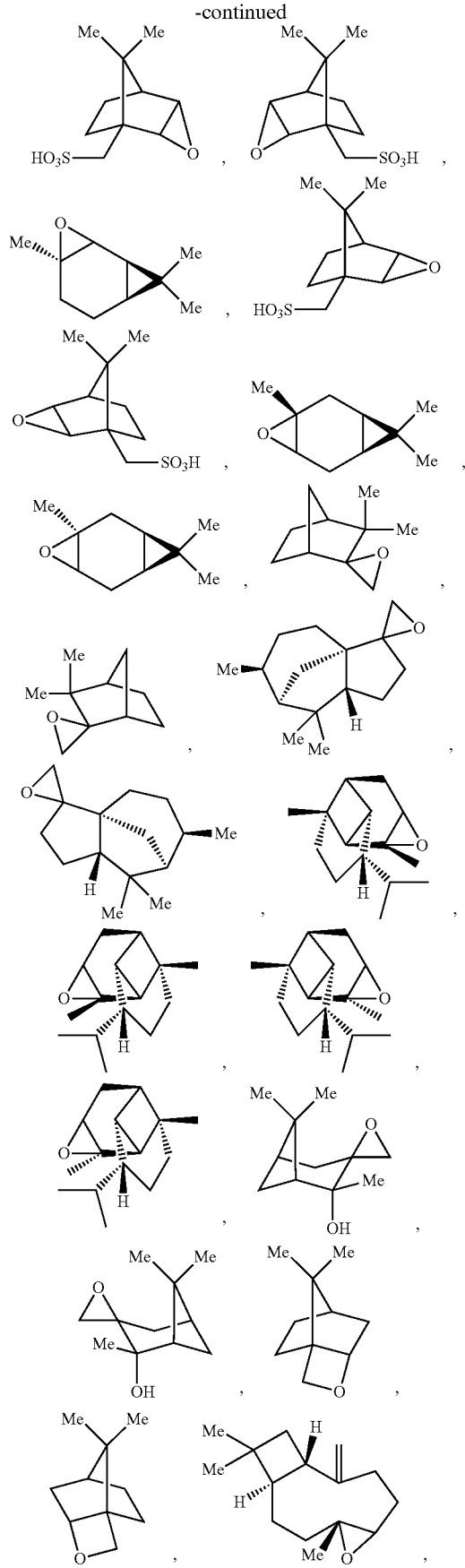
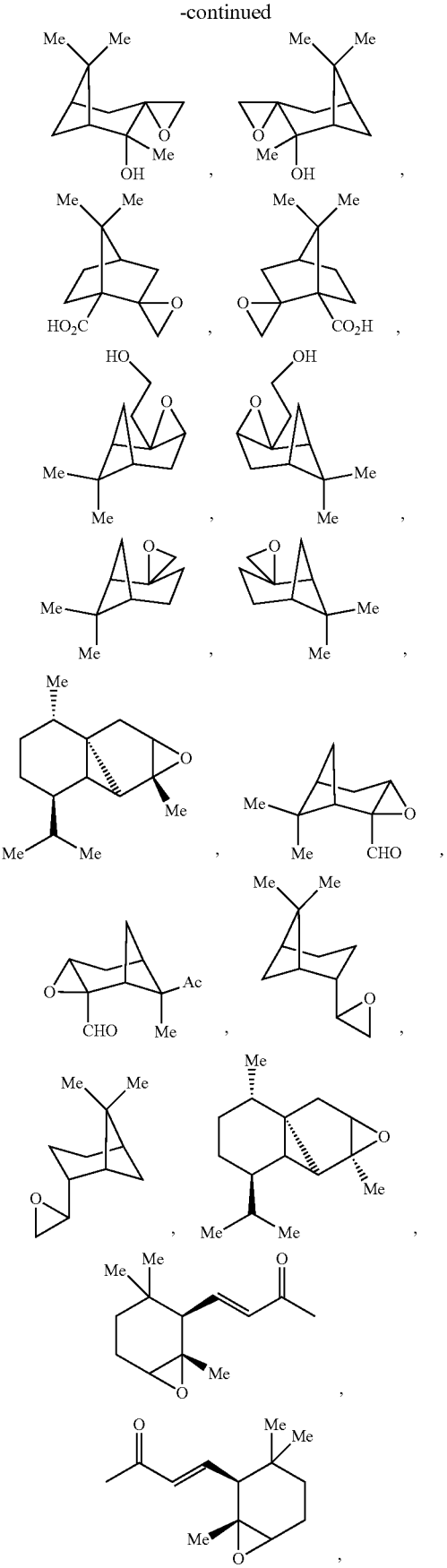

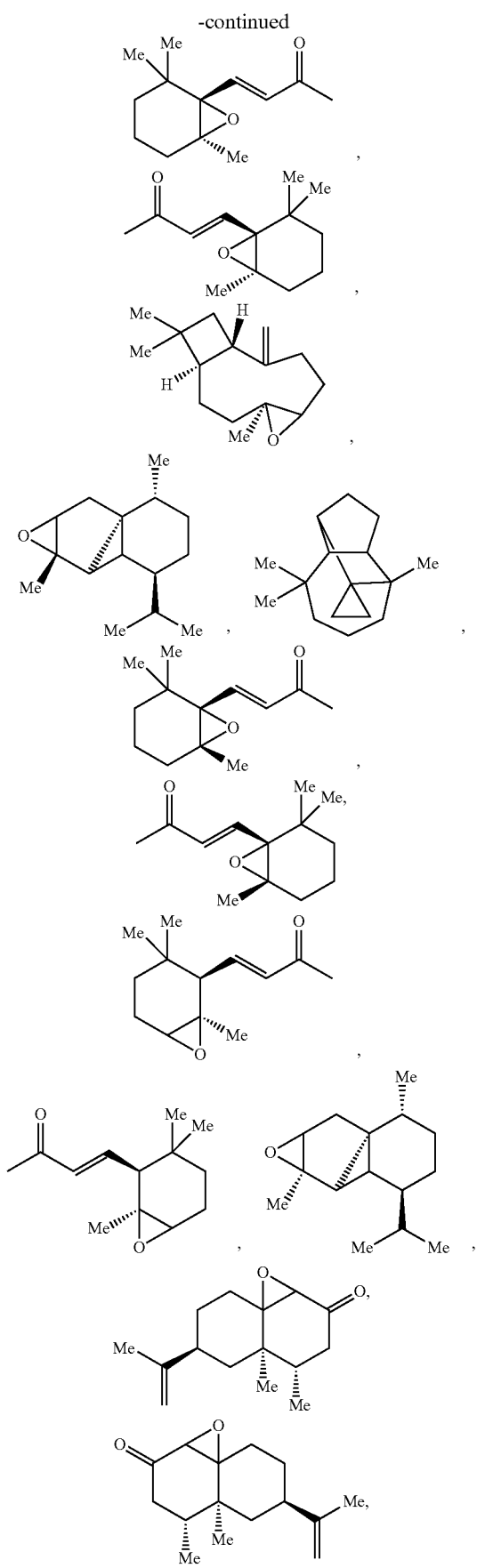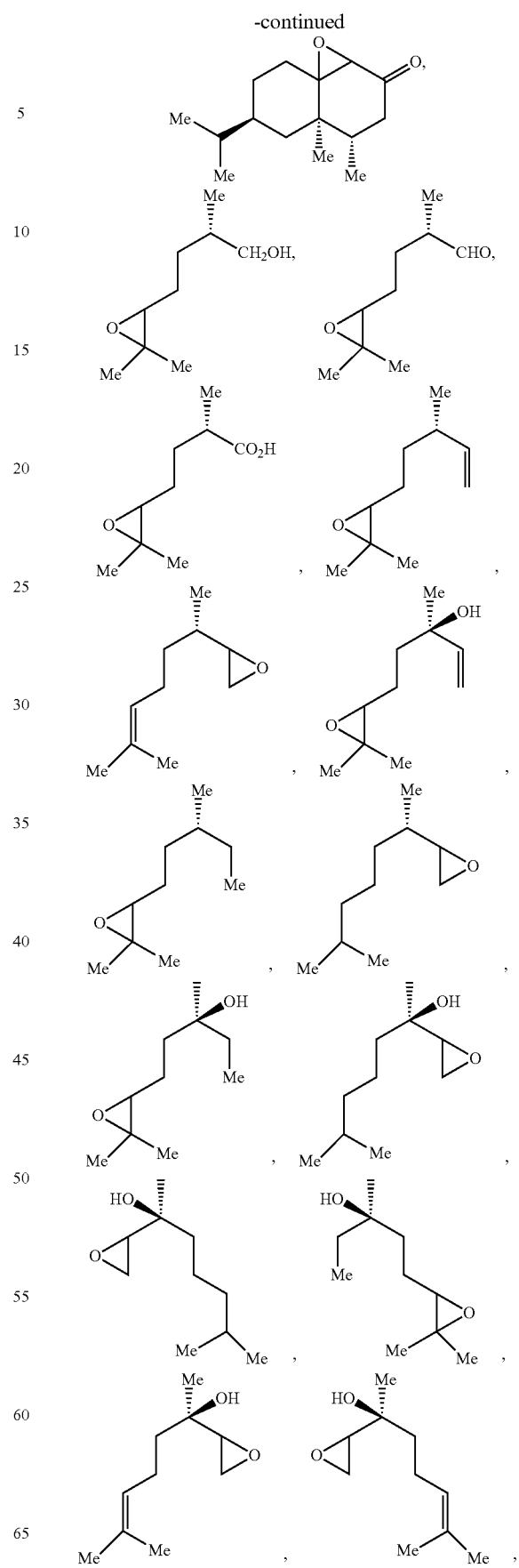

-continued
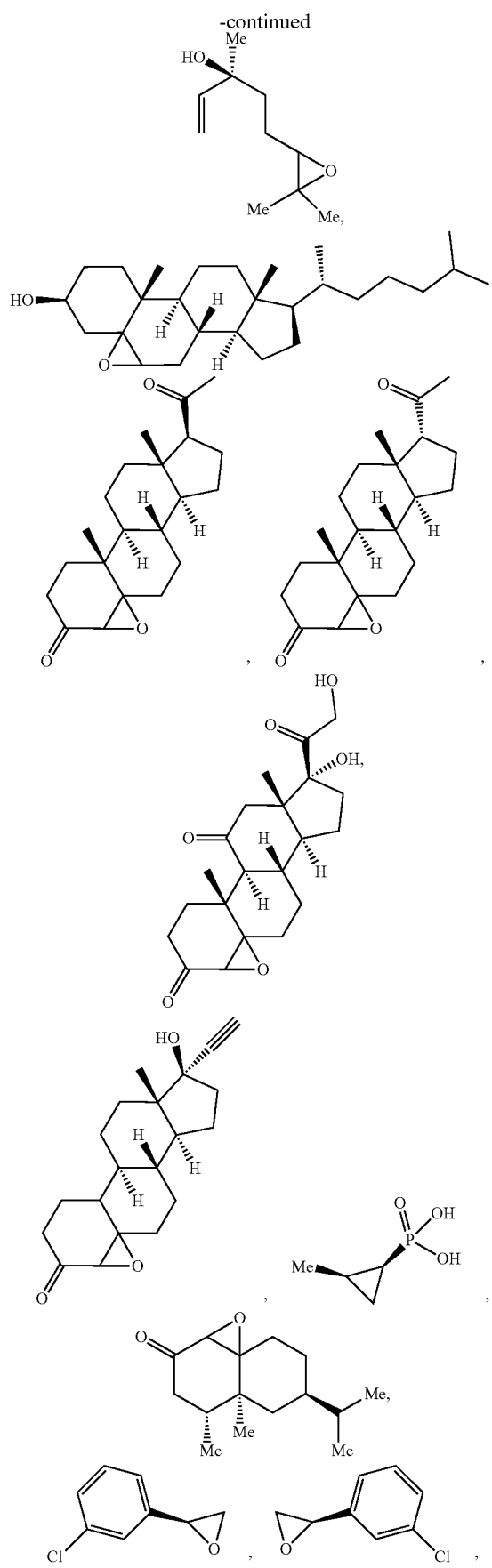
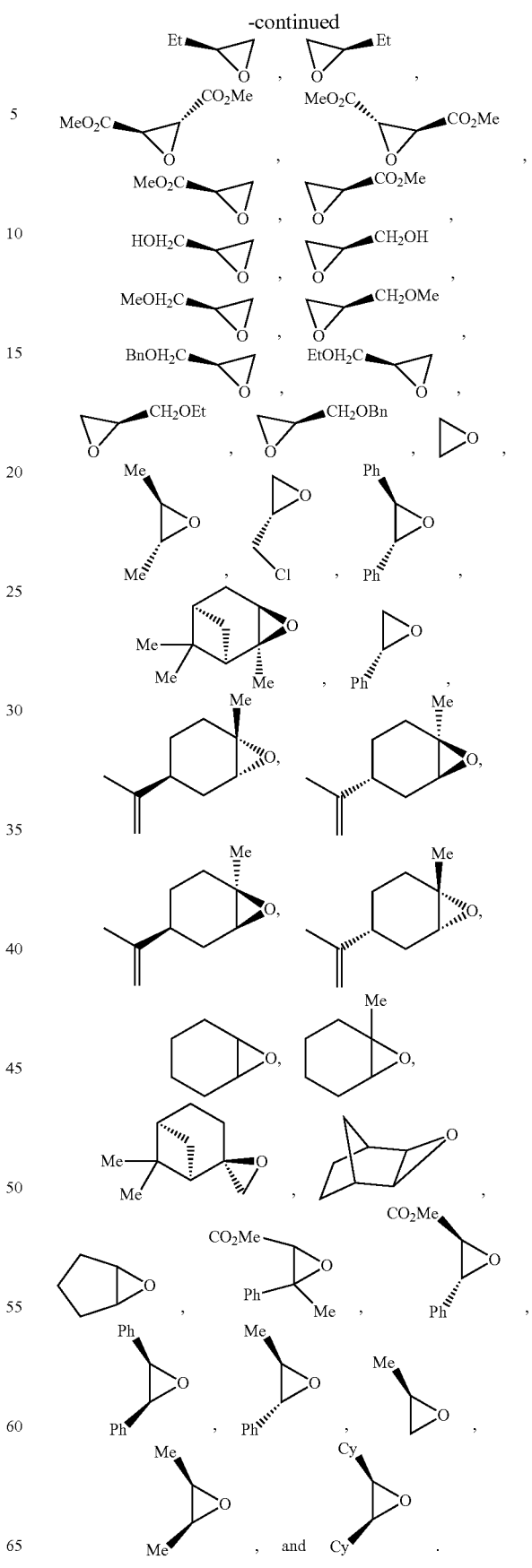

Exemplary episulfides include, but are not limited to, thiirane.
Exemplary compounds represented by Formula (VII) include, but are not limited to, the following:
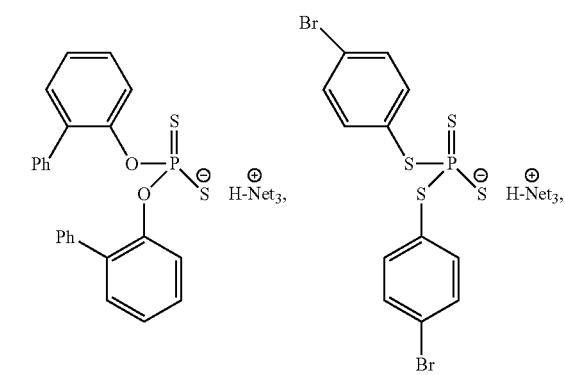
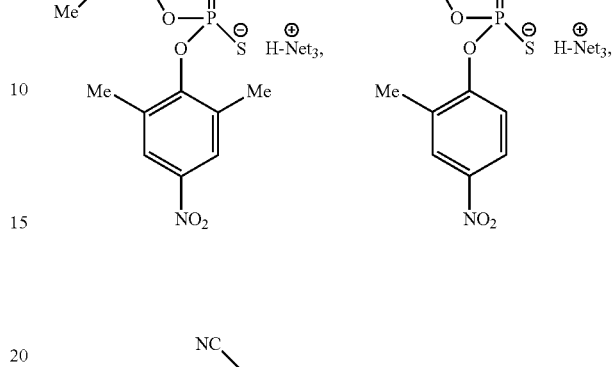
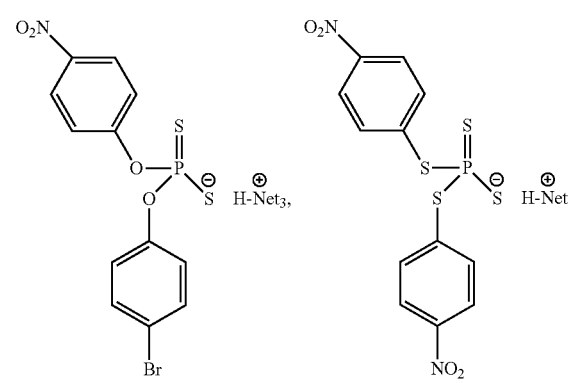
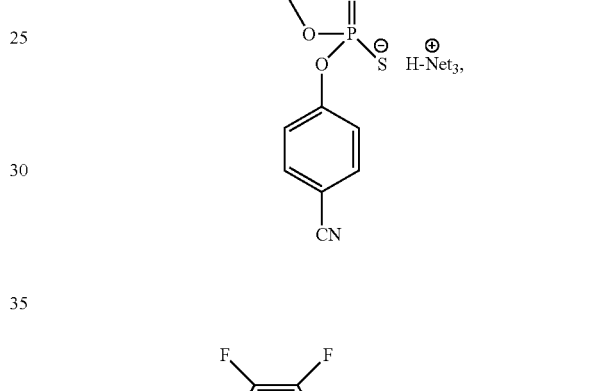
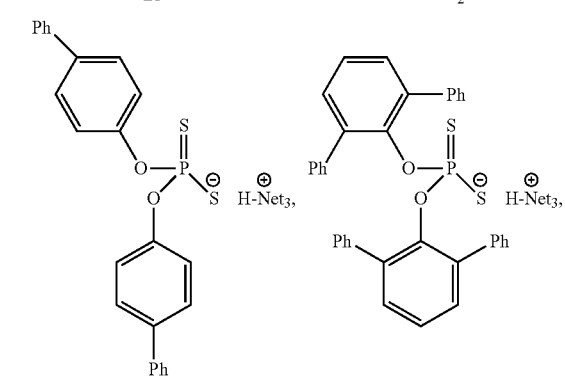
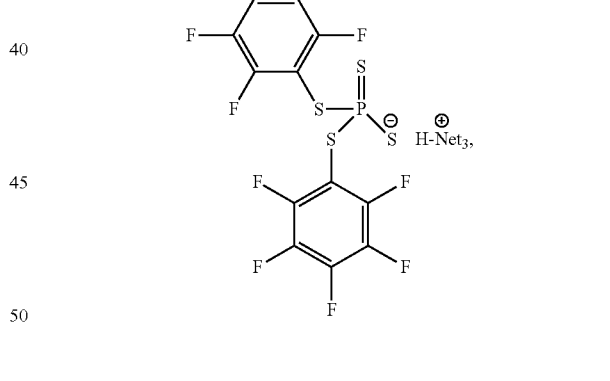
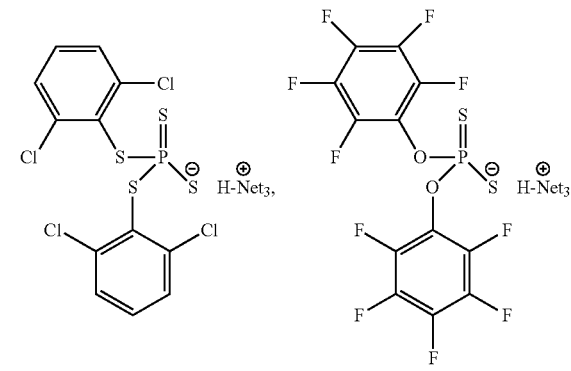
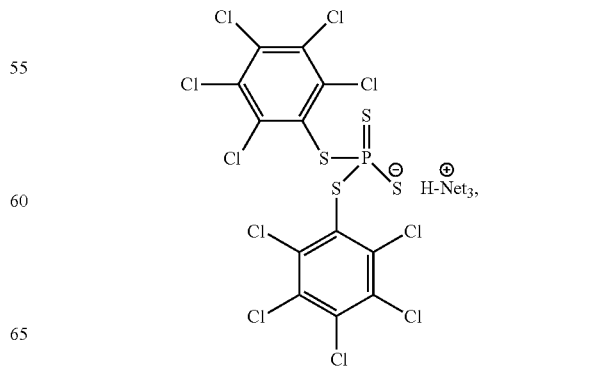

-continued

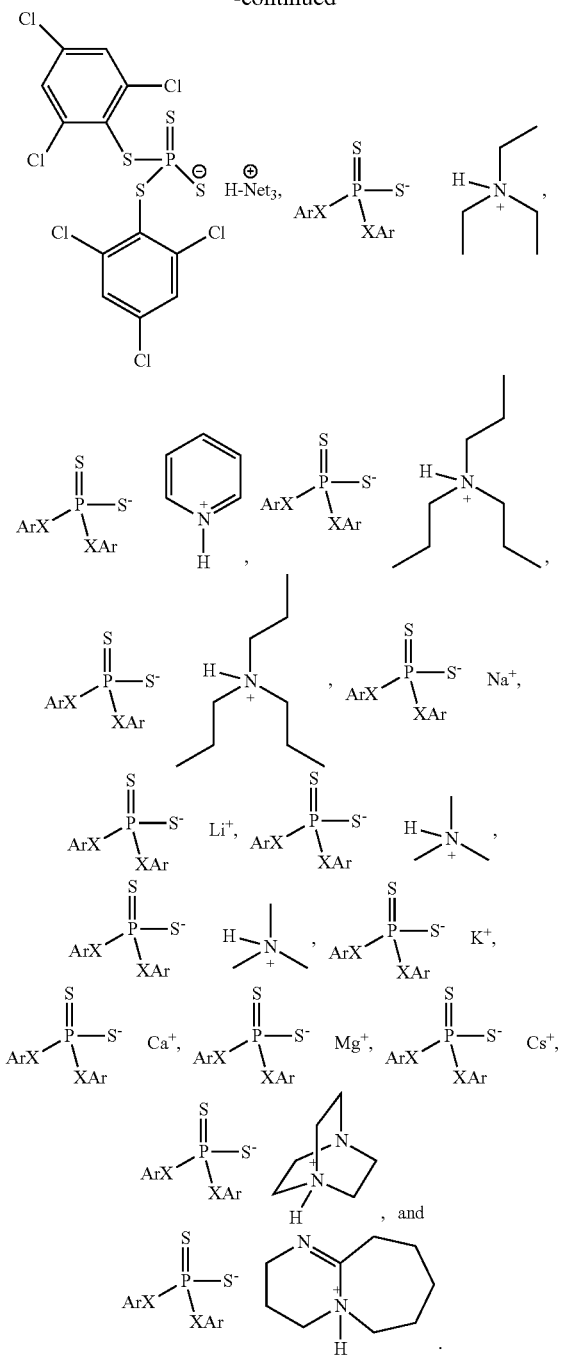

A skilled artisan would appreciate that the compounds represented by formula (VII) can be made by methods known in the art. For example, the compound can be made by the following reaction:

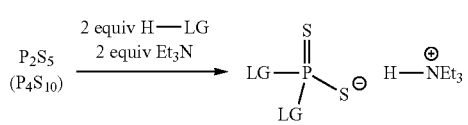

wherein LG is as defined above. In some embodiment, the reaction can be conducted at a temperature of from about 20° C. to about 50° C. A skilled artisan will appreciate that the reaction conditions, such as reaction time and temperature, the identity and the amounts of the solvents, etc., can be varied according to the methods known in the art.

In other embodiments, Compounds of the Disclosure of Formulae (I)-(IIIe) can be made by a process comprising reacting a compound of Formula (VII) with a compound of formula (IXa):

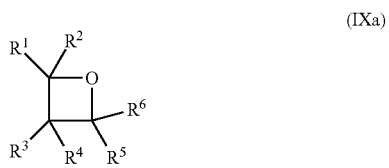

(IXa)

wherein
(a) $R^1$, $R^2$, $R^3$, $R^4$, $R^5$ and $R^6$ are independently hydrogen, deuterium, tritium; $CD_3$ or $CF_3$, linear or branched $C_1$-$C_{20}$ alkyl, optionally substituted with one or more, the same or different, $R^a$ groups; linear or branched $C_2$-$C_6$ alkenyl, optionally substituted with one or more, the same or different, $R^a$ groups; linear or branched $C_2$-$C_6$ alkynyl, optionally substituted with one or more, the same or different, $R^a$ groups; halogen, —CN, —$NO_2$; aryl, optionally substituted with one or more, the same or different, $R^a$ groups; heteroaryl, optionally substituted with one or more, the same or different, $R^a$ groups; or $C_3$-$C_8$ cycloalkyl, optionally substituted with one or more, the same or different, $R^a$ groups;
or
(b) any of $R^1$, $R^2$, $R^3$, $R^4$, $R^5$, and $R^6$ together with the carbons to which they are attached form $C_4$-$C_8$ cycloalkyl, optionally substituted with one or more, the same or different, $R^a$ groups; wherein
$R^a$ is hydrogen, deuterium, tritium; halogen; linear or branched $C_1$-$C_6$ alkyl; OH, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$ linear or branched $C_2$-$C_6$ alkenyl, optionally substituted with linear or branched $C_1$-$C_6$ alkyl; or linear or branched $C_2$-$C_6$ alkynyl, optionally substituted with a linear or branched $C_1$-$C_6$ alkyl;
$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;
provided that either the carbon bearing the $R^1$ or $R^2$ groups, the carbon bearing the $R^3$ or $R^4$ groups, or the carbon bearing the $R^4$ or $R^5$ groups or all of the above, is chiral.

In other embodiments, Compounds of the Disclosure of Formulae (I)-(IIIe) can be made by a process comprising reacting a compound of Formula (VII) with a compound of formula (IXb):

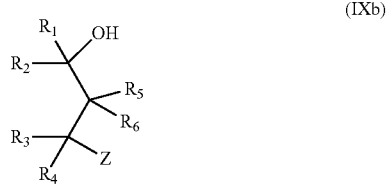

(IXb)

wherein $R^1$, $R^2$, $R^3$, $R^4$, $R^5$, and $R^6$ are as defined above; and Z is a halogen.

In another embodiment, Compounds of the Disclosure of Formulae (I)-(IIIc) can be made by reacting mercaptoethanol or mercaptopropanol and $PCl_3$. The mercaptoethanol or mercaptopropanol can be represented by the following formulae:

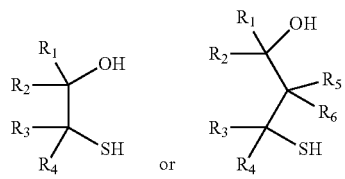

wherein $R^1$, $R^2$, $R^3$, $R^4$, $R^5$, $R^6$, LG are as defined above.

In one embodiment, Compounds of the Disclosure of Formulae (I)-(IIIe) can be made according to the following exemplary reaction scheme:

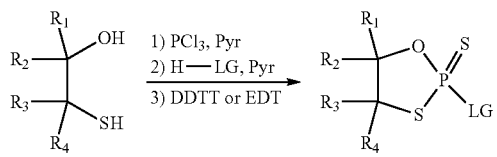

wherein $R^1$, $R^2$, $R^3$ and $R^4$ and LG are as defined above. Additional reagents that can affect the reaction between a mercaptoethanol and $PCl_3$ include, but are not limited to, potassium peroxymonosulfate (Oxone), magnesium monoperoxyphthalate (MMPP) and trichloroacetaldehyde.

In one embodiment, Compounds of the Disclosure of Formulae (I)-(IIIe) can be made according to the following exemplary reaction scheme:

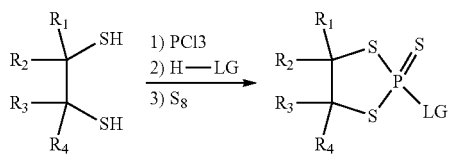

wherein $R^1$, $R^2$, $R^3$ and $R^4$ and LG are as defined above.

In some embodiments, the reactions using a mercaptoethanol are conducted in an aprotic solvent at a temperature of from about 0° C. to about 100° C. for about 10 min to about 48 hours. In some embodiments, the temperature is from about 10° C. to about 80° C., from about 20° C. to about 60° C., from about 25° C. to about 40° C., from about 25° C. to about 30° C., from about 30° C. to about 40° C. In some embodiments, the time of a reaction is from about 30 min to about 40 hours, from about 30 min to about 20 hours, from about 30 min to about 10 hours, from about 30 min to about 5 hours, from about 30 min to about 3 hours, from about 1 hour to about 30 hours, from about 2 hours to about 20 hours, from about 3 hours to about 10 hours, from about 4 hours to about 8 hours, from about 5 hours to about 6 hours.

In one embodiment, Compounds of the Disclosure of Formulae (I)-(IIIe) can be made according to the following exemplary reaction scheme:

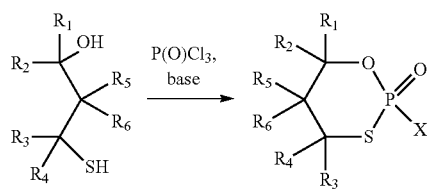

wherein $R^1$, $R^2$, $R^3$, $R^4$, $R^5$, and $R^6$ are as defined above. In one embodiment, X is a leaving group (LG) as defined above. In another embodiment, X is —OH, —Cl, or 4-nitrophenoxy. A base can be varied based on the condition. In some embodiments, the base is chosen from triethylamine, DBU, DIPEA, pyridine, 2,6-Lut., or imidazole. In another embodiment, the base is triethylamine.

The above reaction conditions are exemplary, and are not meant to be limiting. A skilled artisan will appreciate that the reaction conditions, such as reaction time and temperature, the identity and the amounts of the solvents, etc., can be varied according to the methods known in the art. A skilled artisan will also be familiar with other solvents (e.g., toluene, p-xylene, n-hexane, etc.) and sulfurization agents (e.g., the Beaucage Reagent, $K_2S_5O_6$, etc.) can be used in the above reaction.

Examples of suitable mercaptoethanols include, but are not limited to, the following:

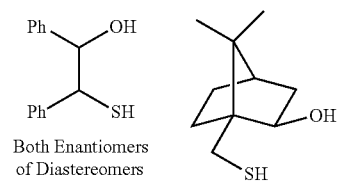

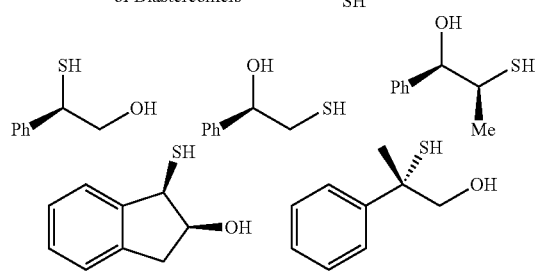

In yet another embodiment, Compounds of the Disclosure can be made according to the following reaction scheme:

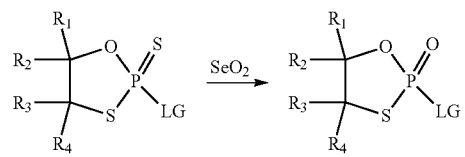

wherein $R^1$, $R^2$, $R^3$, $R^4$, and LG are as defined above.

In some embodiments, a reaction is conducted in an aprotic solvent at a temperature of from about 0° C. to about 100° C. for about 10 min to about 48 hours. In some embodiments, the temperature is from about 10° C. to about 80° C., from about 20° C. to about 60° C., from about 25° C. to about 40° C., from about 25° C. to about 30° C., from about 30° C. to about 40° C. In some embodiments, the time of a reaction is from about 30 min to about 40 hours, from about 30 min to about 20 hours, from about 30 min to about 10 hours, from about 30 min to about 5 hours, from about 30 min to about 3 hours, from about 1 hour to about 30 hours, from about 2 hours to about 20 hours, from about 3 hours to about 10 hours, from about 4 hours to about 8 hours, from about 5 hours to about 6 hours.

The above reaction conditions are exemplary, and are not meant to be limiting. A skilled artisan will appreciate that the reaction conditions, such as reaction time and temperature, the identity and the amounts of the solvents, etc., can be varied according to the methods known in the art.

In another aspect, the present disclosure provides methods for making stereo-defined organosphosphorous (V) compounds. The stereo-defined organosphosphorous (V) compounds can be made by coupling an oxathiaphospholane sulfide compound that is designed to undergo cleavage to a nucleophile, followed by a reaction with another nucleophile, thereby making a stereo-defined organophoshorous (V) compound. Examples of suitable nucleophiles include, but are not limited to, water, hydroxide anions, alcohols, alkoxide anions, carboxylate anions, thiols, thiolate anions, anions of a thiocarboxylic acid, amines, amides, etc. The methods of the present disclosure are not limited to a particular stereo-defined organophoshorous (V) compound, but can be used to prepare oligonucleotides; CDNs; conjugates comprising peptides/proteins and nucleic acids; peptide/protein-drug conjugates, etc. The nature and the origin of nucleophiles are also not limited to a particular molecule, but nucleophiles can be supplied by, for example, nucleic acids (e.g., 3'-hydroxy and 5'-hydroxy), peptides and proteins (e.g., —NH$_2$, —OH, —SH, —C(O)NH$_2$, —C(O)OH, etc.), or small molecules (—NH$_2$, —OH, —SH, —C(O)NH$_2$, —C(O)OH, etc.).

In some embodiments, Compounds of the Present Disclosure represented by any one of Formulae (I)-(IIIe) are used to prepare compounds represented by any one of Formulae (IV)-(VIe), above. In these embodiments, a method comprises reacting a compound represented by any one of Formulae (I)-(IIIe), above, with a nucleoside. In some embodiments, the reaction is conducted in the presence of a base. In some embodiments, the base is selected from the group consisting of DBU, BTMG, TMG, LiHMDS, LiOtBu, KHMDS, KOtBu, NaHMDS, NaOtBu, DABCO, NMI, DIPEA, Pyr, 2,6-Lut, and imidazole.

In some embodiments, the reaction is conducted at a temperature of from about −78° C. to about 30° C. In other embodiments, the temperature is from about −50° C. to about 30° C. In other embodiments, the temperature is from about −30° C. to about 30° C. In other embodiments, the temperature is from about −10° C. to about 30° C. In other embodiments, the temperature is from about 0° C. to about 30° C. In other embodiments, the temperature is from about 10° C. to about 30° C. In other embodiments, the temperature is from about 15° C. to about 30° C. In other embodiments, the temperature is from about 20° C. to about 30° C. In other embodiments, the temperature is from about 25° C. to about 30° C. In one embodiment, the temperature is from about 20° C. In one embodiment, the temperature is from about 25° C.

In some embodiments, the reaction is conducted for from about 10 min to about 12 hours. In other embodiments, the reaction is conducted for from about 1 hour to about 8 hours. In other embodiments, the reaction is conducted for from about 1 hour to about 6 hours. In other embodiments, the reaction is conducted for from about 1 hour to about 4 hours. In other embodiments, the reaction is conducted for from about 1 hour to about 2 hours. In one embodiment, the reaction is conducted for about 1 hour. In one embodiment, the reaction is conducted for 1 hour.

As described above the nucleoside may comprise a naturally occurring or a modified base. It may also comprise a naturally occurring or a modified sugar, as described above. In some embodiments, both the sugar and the base are naturally occurring. In other embodiments, both the sugar and the base are modified. In yet other embodiments only one (a sugar or a base) are modified. In one embodiment, the nucleoside is a ribonucleoside. In another embodiment, the nucleoside is deoxyribonucleoside.

In one embodiment, the nucleoside comprises a protecting group at the 5'-end. Suitable protecting groups are described above. In one embodiment, the protecting group is DMTr. In one embodiment, the nucleoside comprises a protecting group at the 3-end. Suitable protecting groups are described above. In one embodiment, the protecting group is TBS. In another embodiment, when the nucleoside is a deoxyribonucleoside, it can comprise a protecting group at the 2'-end. Suitable protecting groups are described above. In one embodiment, the protecting group is TOM. In another embodiment, the protecting group is TBDPS.

In another embodiment, a nucleobase or a modified nucleobase of the nucleoside comprises a protecting group. Suitable protecting groups are described above. A skilled artisan will appreciate that the selection of a protecting group will be dictated by the nature of the nucleobase or the modified nucleobase. For example, an amine can be protected by Ac, iBu, or Bz.

In some embodiments, the protecting group(s) are removed from the final product. A skilled artisan will be familiar with methods for removing protecting groups. For example, the DMTr protecting group can be removed by a weak acid, such as trichloroacetic acid (TCA, pKa 0.8) or dichloroacetic acid (DCA, pKa 1.5), in dichloromethane. The TBS, TOM, and TBDPS protecting groups can be removed by an acid or fluoride ion, such as NaF, TBAF (tetra-n-butylammonium fluoride, HF·Py, or HF·NEt$_3$. The Ac, iBu, and Bz protecting groups can be removed by a base, such as aqueous or gaseous ammonia or methylamine.

The above reaction conditions and reagents are exemplary, and are not meant to be limiting. A skilled artisan will appreciate that the reaction conditions, such as reaction time and temperature, the identity and the amounts of the solvents and base, etc., can be varied according to the methods known in the art.

Methods of Making Oligonucleotides and CDNs Comprising Stereo-Defined Thio-Phosphate Based Internucleoside Linkages In another aspect, the present disclosure provides a method for making oligonucleotides and CDNs comprising stereo-defined, enantioenriched thiophosphate-based internucleoside linkages. In some embodiments, the method comprises (a) reacting a compound of any of the Formulae (I)-(IIIe) with a nucleoside, to make a compound of any of the Formulae (IV)-(VIe), as described above, and (b) reacting the compound formed in step (a) with another nucleoside, thereby forming an internucleoside linkage.

In some embodiments, the internucleoside linkage formed by the method above is stereo-defined. In some embodiment, the internucleoside linkage formed by the method above is achiral.

In some embodiments, both reactions are conducted in the presence of a base. Suitable bases are described above. Reaction conditions for such reaction are also described above. A skilled artisan will easily be able to vary the reaction conditions, such as time, temperature, amounts of the reagents, etc., to achieve desirable yields.

In some embodiments, nucleosides can comprise naturally-occurring or modified nucleobases and sugars. Suitable naturally-occurring and modified nucleobases and sugars are described above. In some embodiments, the nucleosides can bear protecting groups. Suitable sugar and nucleobase protecting groups are described above. In one embodiment, the nucleosides in the two reactions are the same. In another embodiment, the nucleosides are different. In some embodiments, protecting groups can be removed by the methods described above.

In some embodiments, the linkage is a phosphorothioate linkage.

The method of making stereo-defined thio-phosphate internucleoside linkages is uniquely applicable for making stereo-defined CDNs. In this application, the method further comprises (c) adding a compound of any of the Formulae (I)-(IIIe), thereby forming a CDN. Exemplary, but not limiting, embodiments of the method are illustrated below:

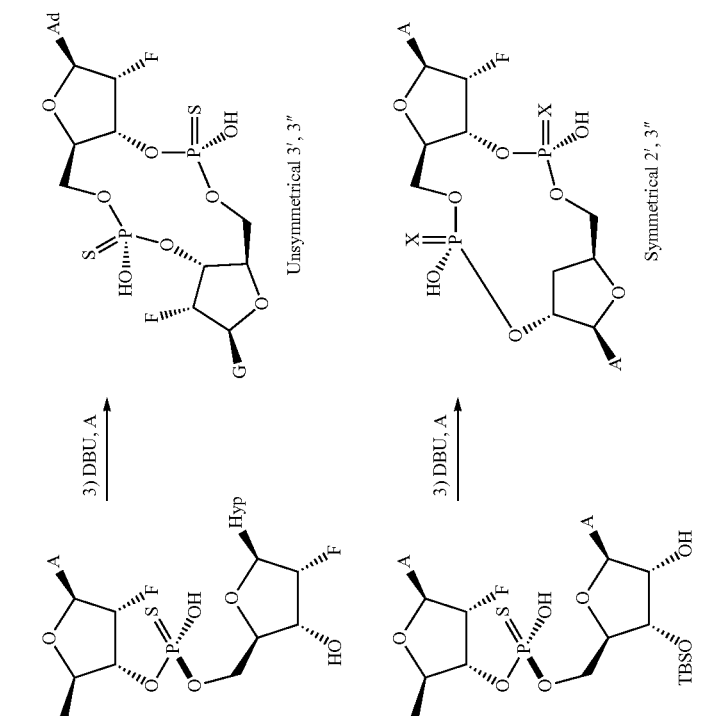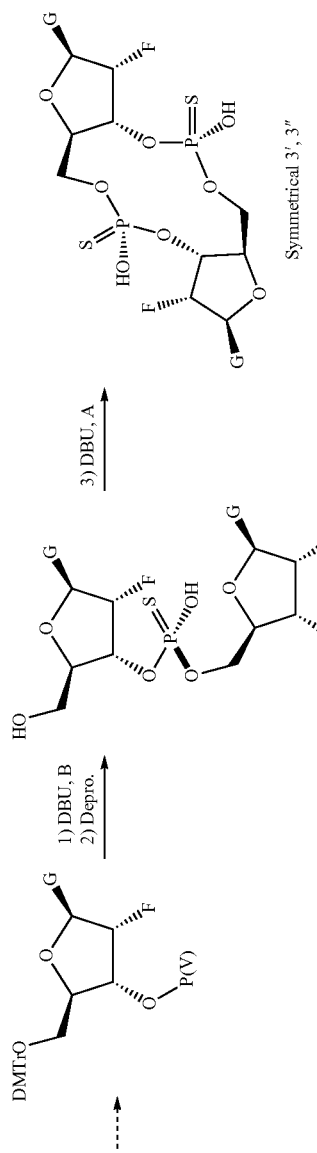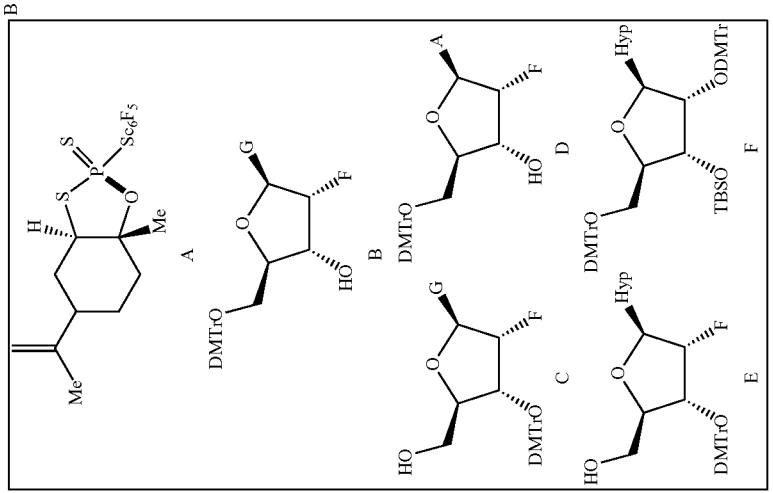
Base A: Adenine
Base G: Guanosine
Base Hyp: Hypoxanthine In some embodiments, the methods of making a CDN comprise a purification step. Purification of the CDN can be performed by methods known in the arts such as, but not limited to, HPLC based purification methods such as, but not limited to, strong anion exchange HPLC, weak anion exchange HPLC, reverse phase HPLC (RP-HPLC), and hydrophobic interaction HPLC (HIC-HPLC).

The present disclosure also provides a method for preparing a homochiral thio-phosphate-based oligonucleotide and salts thereof. In some embodiments, the method comprises.

a) reacting a compound of any of the Formulae (I)-(IIIe) with a nucleoside;
b) reacting the compound formed in step (a) with another nucleoside, thereby forming an internucleoside linkage (e.g., coupling);
c) adding a compound of any of the Formulae (I)-(IIIe);
d) adding another nucleoside, thereby coupling said nucleoside to the growing oligonucleotide; and
e) repeating steps (c) and (d) until the oligonucleotide comprises a desired number of nucleotides.

In some embodiments, both reactions are conducted in the presence of a base. Suitable bases are described above. Reaction conditions for such reaction are also described above. A skilled artisan will easily be able to vary the reaction conditions, such as time, temperature, amounts of the reagents, etc., to achieve desirable yields.

In some embodiments, nucleosides can comprise naturally-occurring or modified nucleobases and sugars. Suitable naturally-occurring and modified nucleobases and sugars are described above. Suitable sugar and nucleobase protecting groups are described above. It will be within a purview of a skilled artisan to select appropriate nucleosides, based on the eventual application of the oligonucleotides.

In some embodiments, the nucleosides can bear a protecting group. In some embodiments, the protecting group can be removed by the methods described above. In one embodiment, the 5'-hydroxy protecting group is removed after each coupling step. In one embodiment, the 2'-hydroxy protecting group is not removed until the oligonucleotide synthesis is complete. In one embodiment, the nucleobase protecting groups are not removed until the oligonucleotide synthesis is completed.

In one embodiment, the oligonucleotide is a homochiral phosphorothioate-based oligonucleotide.

Examples of the salts of the oligonucleotide include, but are not limited to, ammonium salts, such as salts of a tertiary alkylamine compound (e.g., triethylamine salts), metal salts, such as sodium salts, potassium salts, and magnesium salts, etc. The oligonucleotide or a salt thereof may be in the form of a hydrate or a solvate.

In certain embodiments, the oligonucleotide can be synthesized using iterative oligonucleotide synthesis in a solution.

In certain embodiments, the oligonucleotide can be synthesized using iterative solid-phase nucleic acid synthetic regimes. Typically, the first step in such a process is attachment of the first nucleoside containing a protected 5'-hydroxyl to a solid support (also referred to herein as "resin"), usually through a linker, using standard methods and procedures known in the art. See, e.g., Oligonucleotides and Analogues: A Practical Approach, Ekstein, F. Ed., IRL Press, N.Y., 1991, hereby incorporated by reference in its entirety. The support-bound nucleoside is then treated to remove the 5'-protecting group, using the methods described above. The solid support bound nucleoside is then reacted with a second nucleoside in the presence of a compound according to any of the Formulae (I)-(IIIe) thereby forming an internucleoside linkage.

In some embodiments, the oligonucleotide synthesis is performed on an automated synthesizer utilizing a solid support. Solid supports are substrates which are capable of serving as the solid phase in solid phase synthetic methodologies, such as those described in U.S. Pat. Nos. 4,415,732; 4,458,066; 4,500,707; 4,668,777; 4,973,679; 5,132,418; 4,725,677 and Re. 34,069. Linkers are known in the art as short molecules which serve to connect a solid support to functional groups, e.g., hydroxyl groups, of initial synthon molecules in solid phase synthetic techniques. Suitable linkers are disclosed in, for example, Oligonucleotides and Analogues: A Practical Approach, Ecstein, F., Ed., IRL Press, N.Y., 1991, Chapter 1, pages 1-23.

Suitable solid support also includes those generally known in the art to be suitable for use in solid-phase methodologies including, for example, controlled pore glass (CPG), oxalyl-controlled pore glass (see, e.g., Alul et al., Nucleic Acids Research 1991, 19, 1527, hereby incorporated by reference in its entirety), TentaGel Support; an aminopolyethyleneglycol derivatized support (see, e.g., Wright et al., Tetrahedron Letters 1993, 34, 3373, hereby incorporated by reference in its entirety) and Poros; a copolymer of polystyrene/divinylbenzene.

In some embodiments, the oligonucleotide can be made manually. In other embodiments, the oligonucleotides can be made on an automated synthesizer. In one embodiment, the synthesizer is an automated solid-phase peptide synthesizer. In one embodiment, the synthesizer is an automated solid-phase oligonucleotide synthesizer.

The extension of the oligonucleotide can be performed in the 3' to 5' direction. In one embodiment, the oligonucleotide is synthesized from the free hydroxyl at the 5'-end in repetitive cycles of chemical reactions. Alternatively, the extension of the oligonucleotide can be performed in the 5' to 3' direction. In an embodiment, the oligonucleotide is synthesized from the free hydroxyl at the 3'-end in repetitive cycles of chemical reactions.

In some embodiments, the method of making an oligonucleotide comprises a purification step. Purification can be performed by methods known in the arts such as, but not limited to, AGENCOURT® beads (Beckman Coulter Genomics, Danvers, MA), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

Figure 2:
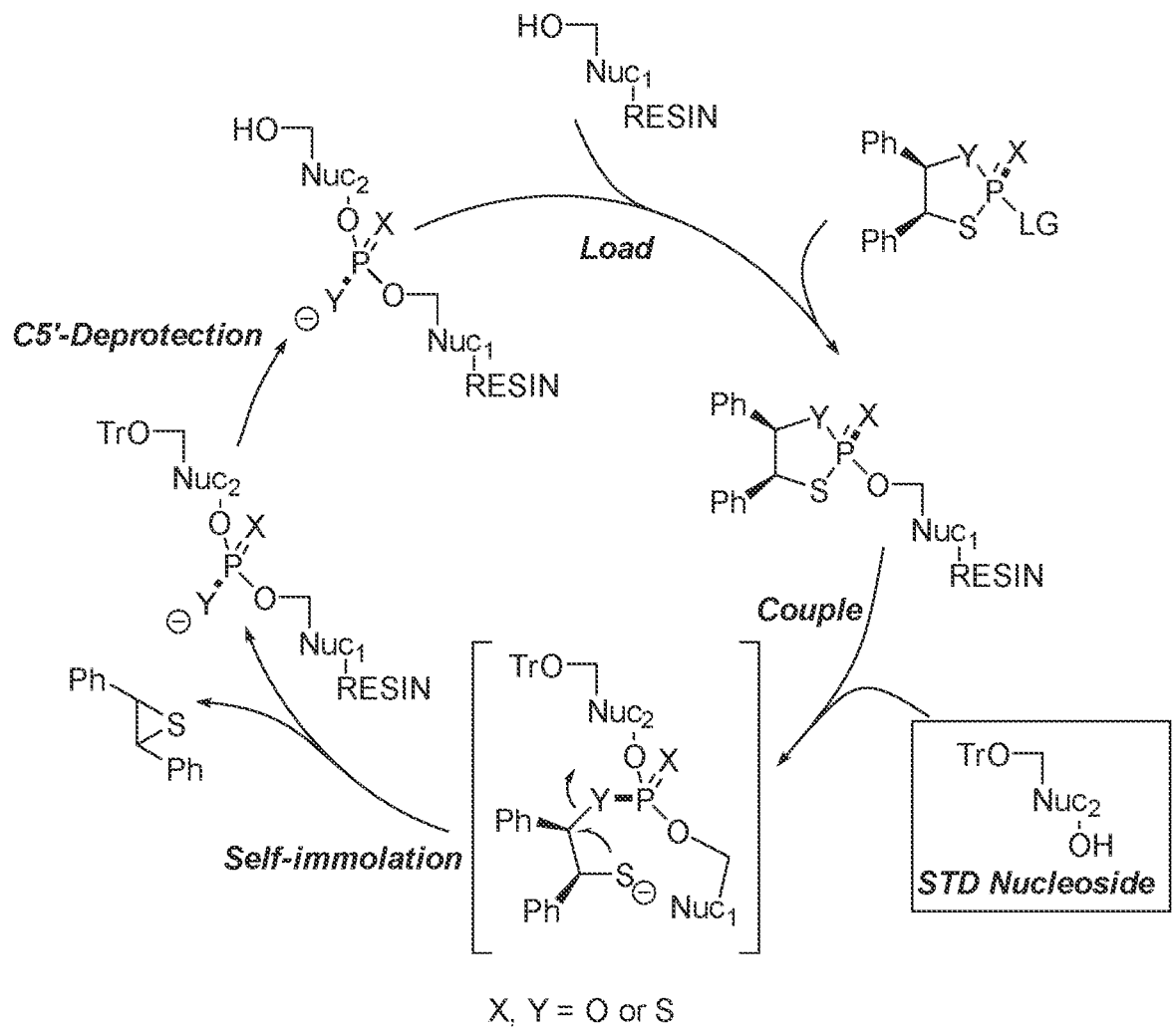
FIG. 2 is an example of a solid-phase synthesis of an oligonucleotide in accordance with a method of the present disclosure.

In some embodiments, a method of synthesizing nucleic acids is carried out according to the scheme in FIG. 2.

In some embodiments, the completed oligonucleotide is cleaved from the solid support. The cleavage step can precede or follow deprotection of protected functional groups. In certain embodiments, the oligonucleotide is left attached on the solid support for purification purposes and then cleaved from the solid support following purification.

In some embodiments, a non-hydrolyzable cap structure can be added to an oligonucleotide. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and selenophosphate nucleotides.

In other embodiments, a long chain of adenine nucleotides (poly-A tail) can be added to an oligonucleotide in order to increase stability. The poly-A polymerase can add a chain of adenine nucleotides to the 3'-end of the oligonucleotide. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

Non-limiting examples of dinucleotides and oligonucleotides that can be prepared by the methods of the present disclosure are presented in Table 5.

TABLE 5

| | | |
|---|---|---|
| 5-1 | 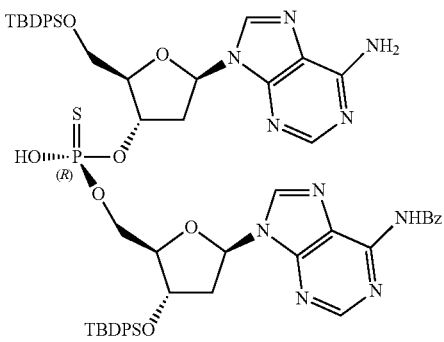 | O-((2R,3S,5R)-5-(6-amino-9H-purin-9-yl)-2-(((tert-butyldiphenylsilyl)oxy)methyl)tetrahydrofuran-3-yl) O-(((2R,3S,5R)-5-(6-benzamido-9H-purin-9-yl)-3-((tert-butyldiphenyl-silyl)oxy)tetrahydrofuran-2-yl)methyl) O-hydrogen (R)-phosphorothioate |
| 5-2 | 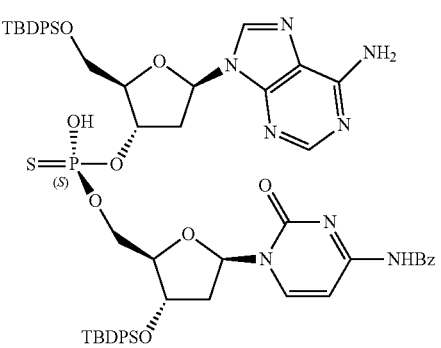 | O-((2R,3S,5R)-5-(6-amino-9H-purin-9-yl)-2-(((tert-butyldiphenyl-silyl)oxy)methyl)tetrahydrofuran-3-yl) O-(((2R,3S,5R)-5-(4-benzamido-2-oxopyrimidin-1(2H)-yl)-3-((tert-butyldiphenyl-silyl)oxy)tetrahydrofuran-2-yl)methyl) O-hydrogen (S)-phosphorothioate |
| 5-3 | 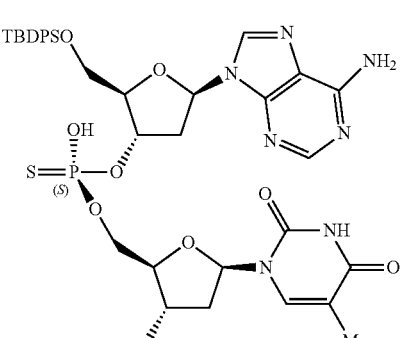 | O-((2R,3S,5R)-5-(6-amino-9H-purin-9-yl)-2-(((tert-butyldiphenyl-silyl)oxy)methyl)tetrahydrofuran-3-yl) O-(((2R,3S,5R)-3-((tert-butyldiphenyl-silyl)oxy)-5-(5-methyl-2,4-dioxo-3,4-dihydropyrimidin-1(2H)-yl)tetrahydrofuran-2-yl)methyl) O-hydrogen (S)-phosphorothioate |

TABLE 5-continued

| | Structure | Name |
|---|---|---|
| 5-4 | 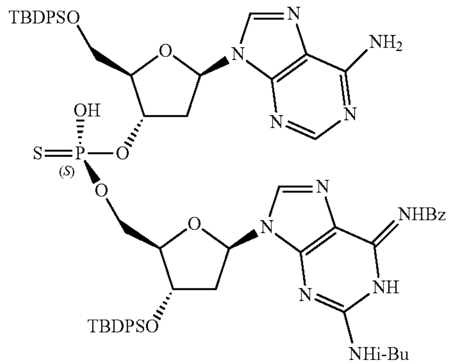 | O-((2R,3S,5R)-5-(6-amino-9H-purin-9-yl)-2-(((tert-butyldiphenyl-silyl)oxy)methyl)tetrahydrofuran-3-yl) O-(((2R,3S,5R)-3-((tert-butyldiphenyl-silyl)oxy)-5-(2-(isobutylamino)-6-oxo-1,6-dihydro-9H-purin-9-yl)tetrahydrofuran-2-yl)methyl) O-hydrogen (S)-phosphorothioate |
| 5-5 | 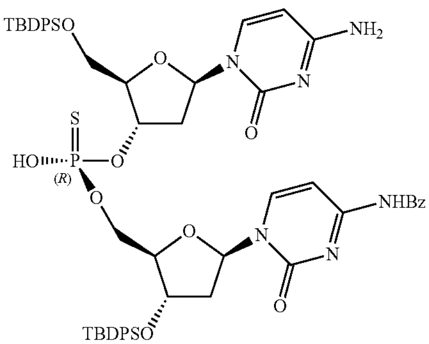 | O-((2R,3S,5R)-5-(4-amino-2-oxopyrimidin-1(2H)-yl)-2-(((tert-butyldiphenylsilyl)oxy)methyl)tetrahydrofuran-3-yl) O-(((2R,3S,5R)-5-(4-benzamido-2-oxopyrimidin-1(2H)-yl)-3-((tert-butyldiphenyl-silyl)oxy)tetrahydrofuran-2-yl)methyl) O-hydrogen (R)-phosphorothioate |
| 5-6 | 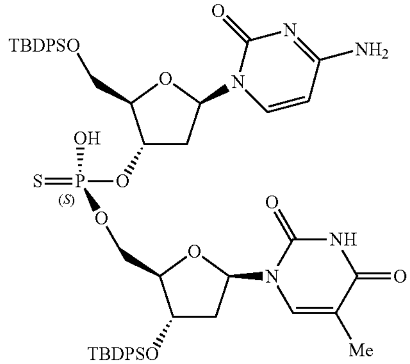 | O-((2R,3S,5R)-5-(4-amino-2-oxopyrimidin-1(2H)-yl)-2-(((tert-butyldiphenylsilyl)oxy)methyl)tetrahydrofuran-3-yl) O-(((2R,3S,5R)-3-((tert-butyldiphenyl-silyl)oxy)-5-(5-methyl-2,4-dioxo-3,4-dihydropyrimidin-1(2H)-yl)tetrahydrofuran-2-yl)methyl) O-hydrogen (S)-phosphorothioate |
| 5-7 | 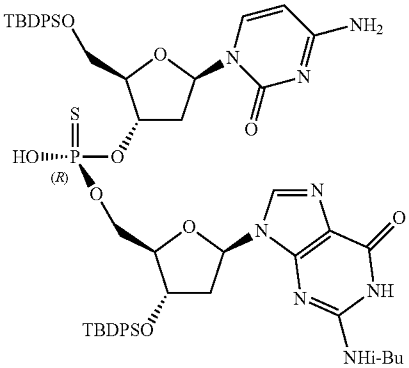 | O-((2R,3S,5R)-5-(4-amino-2-oxopyrimidin-1(2H)-yl)-2-(((tert-butyldiphenyl-silyl)oxy)methyl)tetrahydrofuran-3-yl) O-(((2R,3S,5R)-3-((tert-butyldiphenyl-silyl)oxy)-5-(2-(isobutylamino)-6-oxo-1,6-dihydro-9H-purin-9-yl)tetrahydrofuran-2-yl)methyl) O-hydrogen (R)-phosphorothioate |

TABLE 5-continued

| | | |
|---|---|---|
| 5-8 | [structure: dinucleotide with TBDPSO groups, (S)-phosphorothioate linkage, two thymine bases] | O-(((2R,3S,5R)-3-((tert-butyldiphenyl-silyl)oxy)-5-(5-methyl-2,4-dioxo-3,4-dihydropyrimidin-1(2H)-yl)tetrahydrofuran-2-yl)methyl) O-((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl) O-hydrogen (S)-phosphorothioate |
| 5-9 | [structure: dinucleotide with TBDPSO groups, (S)-phosphorothioate linkage, thymine and N-isobutyl guanine bases] | O-(((2R,3S,5R)-3-((tert-butyldiphenyl-silyl)oxy)-5-(2-(isobutylamino)-6-oxo-1,6-dihydro-9H-purin-9-yl)tetrahydrofuran-2-yl)methyl) O-((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl) O-hydrogen (S)-phosphorothioate |
| 5-10 | [structure: dinucleotide with TBDPSO groups, (R)-phosphorothioate linkage, N-formamido guanine and N-isobutyl guanine bases] | O-(((2R,3S,5R)-3-((tert-butyldiphenyl-silyl)oxy)-5-(2-(isobutylamino)-6-oxo-1,6-dihydro-9H-purin-9-yl)tetrahydro-furan-2-yl)methyl) O-((2R,3S,5R)-2-(((tert-butyldiphenylsilyl)oxy)methyl)-5-(2-formamido-6-oxo-1,6-dihydro-9H-purin-9-yl)tetrahydrofuran-3-yl) O-hydrogen (R)-phosphorothioate |
| 5-11 | [structure: dinucleotide with TBDPSO group, phosphate linkage, thymine and 3'-azido thymine] | ((2S,3S,5R)-3-azido-5-(5-methyl-2,4-dioxo-3,4-dihydropyrimidin-1(2H)-yl)tetrahydrofuran-2-yl)methyl ((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl) hydrogen phosphate |

TABLE 5-continued

| | | |
|---|---|---|
| 5-12 | 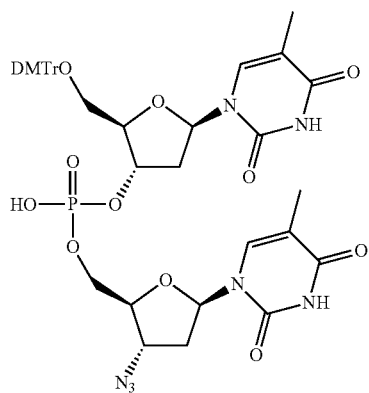 | ((2S,3S,5R)-3-azido-5-(5-methyl-2,4-dioxo-3,4-dihydropyrimidin-1(2H)-yl)tetrahydrofuran-2-yl)methyl ((2R,3S,5R)-2-((bis(4-methoxyphenyl)(phenyl)methoxy)methyl)-5-(5-methyl-2,4-dioxo-3,4-dihydropyrimidin-1(2H)-yl)tetrahydrofuran-3-yl) hydrogen phosphate |
| 5-13 | 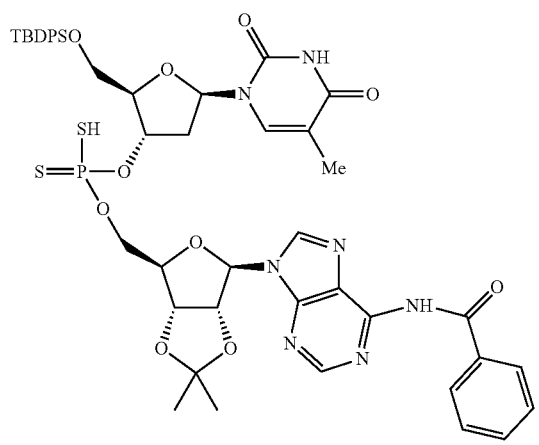 | O-(((3aR,4R,6R,6aR)-6-(6-benzamido-9H-purin-9-yl)-2,2-dimethyltetrahydrofuro[3,4-d][1,3]dioxol-4-yl)methyl) O-((2R,3S,5R)-2-(((tert-butyldimethylsilyl)oxy)methyl)-5-(5-methyl-2,4-dioxo-3,4-dihydropyrimidin-1(2H)-yl)tetrahydrofuran-3-yl) S-hydrogen phosphorodithioate |
| 5-14 | 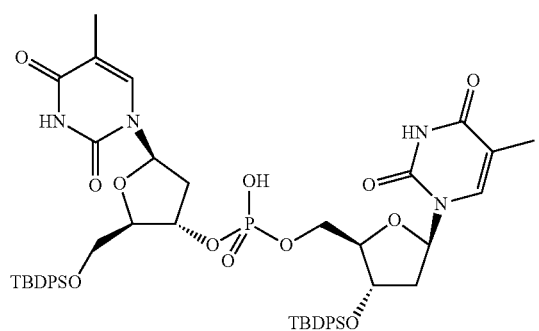 | ((2R,3S,5R)-3-((tert-butyldiphenylsilyl)oxy)-5-(5-methyl-2,4-dioxo-3,4-dihydropyrimidin-1(2H)-yl)tetrahydrofuran-2-yl)methyl ((2R,3S,5R)-2-(((tert-butyldiphenylsilyl)oxy)methyl)-5-(5-methyl-2,4-dioxo-3,4-dihydropyrimidin-1(2H)-yl)tetrahydrofuran-3-yl) hydrogen phosphate |

TABLE 5-continued

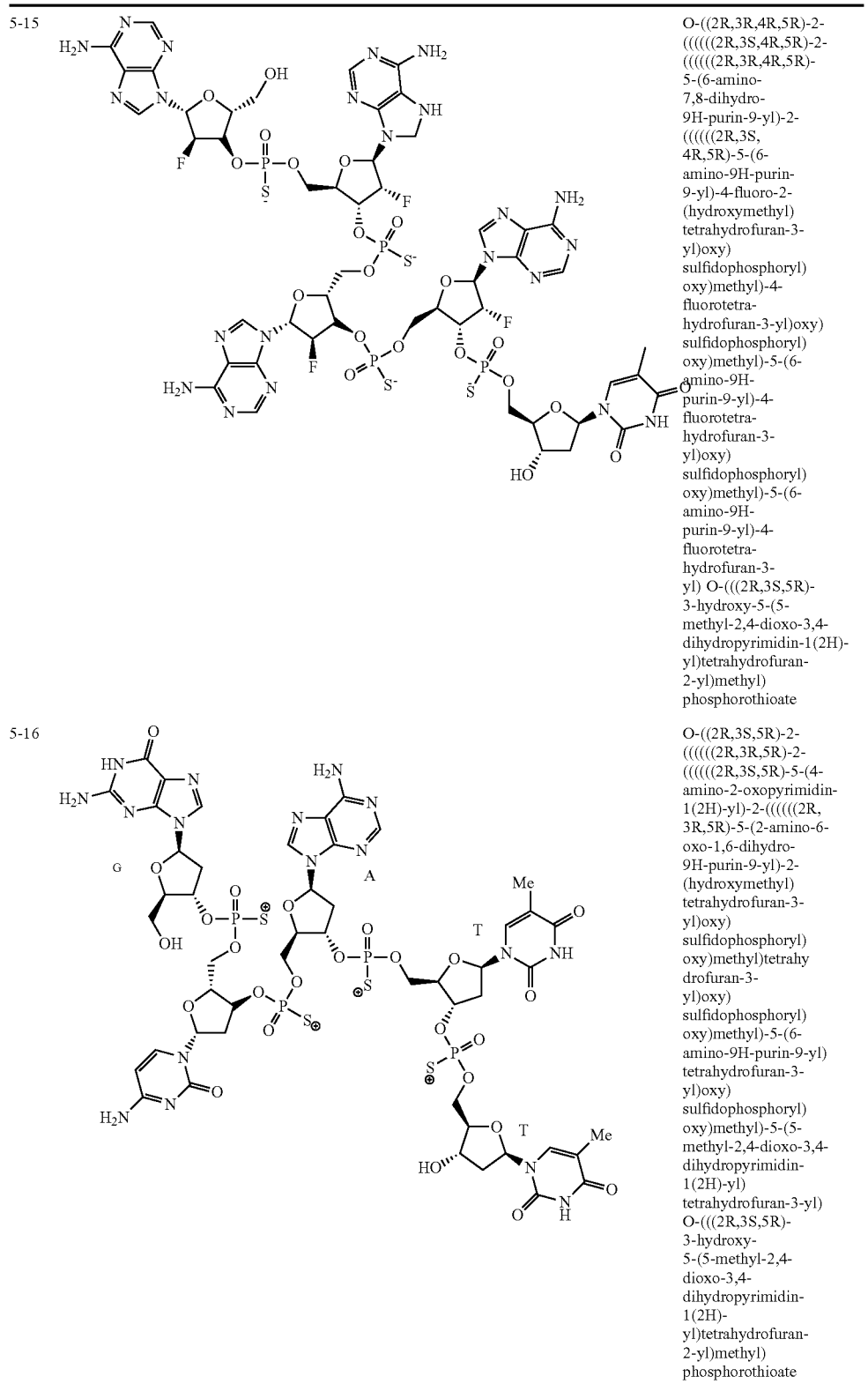

| | | |
|---|---|---|
| 5-15 | | O-((2R,3R,4R,5R)-2-(((((2R,3S,4R,5R)-2-(((((2R,3R,4R,5R)-5-(6-amino-7,8-dihydro-9H-purin-9-yl)-2-(((((2R,3S,4R,5R)-5-(6-amino-9H-purin-9-yl)-4-fluoro-2-(hydroxymethyl)tetrahydrofuran-3-yl)oxy)sulfidophosphoryl)oxy)methyl)-4-fluorotetrahydrofuran-3-yl)oxy)sulfidophosphoryl)oxy)methyl)-5-(6-amino-9H-purin-9-yl)-4-fluorotetrahydrofuran-3-yl)oxy)sulfidophosphoryl)oxy)methyl)-5-(6-amino-9H-purin-9-yl)-4-fluorotetrahydrofuran-3-yl) O-(((2R,3S,5R)-3-hydroxy-5-(5-methyl-2,4-dioxo-3,4-dihydropyrimidin-1(2H)-yl)tetrahydrofuran-2-yl)methyl) phosphorothioate |
| 5-16 | | O-((2R,3S,5R)-2-(((((2R,3R,5R)-2-(((((2R,3S,5R)-5-(4-amino-2-oxopyrimidin-1(2H)-yl)-2-(((((2R,3R,5R)-5-(2-amino-6-oxo-1,6-dihydro-9H-purin-9-yl)-2-(hydroxymethyl)tetrahydrofuran-3-yl)oxy)sulfidophosphoryl)oxy)methyl)tetrahydrofuran-3-yl)oxy)sulfidophosphoryl)oxy)methyl)-5-(6-amino-9H-purin-9-yl)tetrahydrofuran-3-yl)oxy)sulfidophosphoryl)oxy)methyl)-5-(5-methyl-2,4-dioxo-3,4-dihydropyrimidin-1(2H)-yl)tetrahydrofuran-3-yl) O-(((2R,3S,5R)-3-hydroxy-5-(5-methyl-2,4-dioxo-3,4-dihydropyrimidin-1(2H)-yl)tetrahydrofuran-2-yl)methyl) phosphorothioate |
| 5-17 | Structure see Example 13(a) | P(V)-DMT-T16 (all R) |
| 5-18 | Structure see Example 13(b) | P(V)-T16 (all R) |
| 5-19 | Structure see Example 13(c) | 17-mer<br>TAGTCGACT<br>TGGCCAAT |

In one embodiment, dinucleotides are the compound selected from group consisting of compounds 5-13, 5-15, and 5-16. In another embodiment, oligonucleotides are the compound selected from group consisting of compounds 5-17 and 5-18. In another embodiment, dinucleotides are the compound selected from group consisting of compounds 5-1 to 5-10 and compound 5-14. In another embodiment, dinucleotides and oligonucleotides are the compound selected from group consisting of compounds 5-11, 5-12, and 5-19.

Non-limiting examples of CDNs that can be prepared by the methods of the present disclosure are presented in Table 6.

TABLE 6

| Cpd. No. | Structure |
|---|---|
| 6-1 | 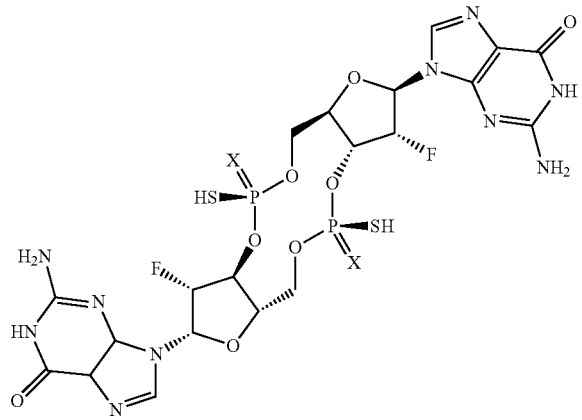 |
| 6-2 | 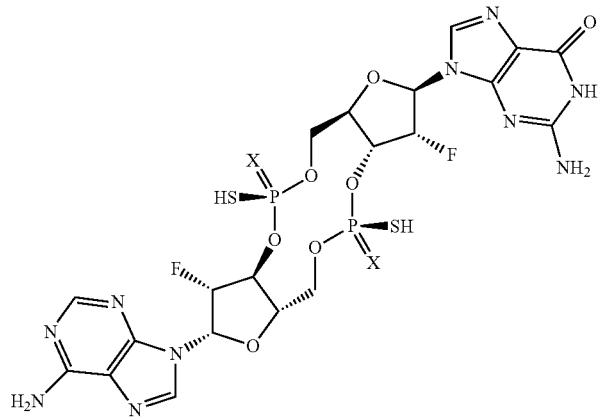 |
| 6-3 | 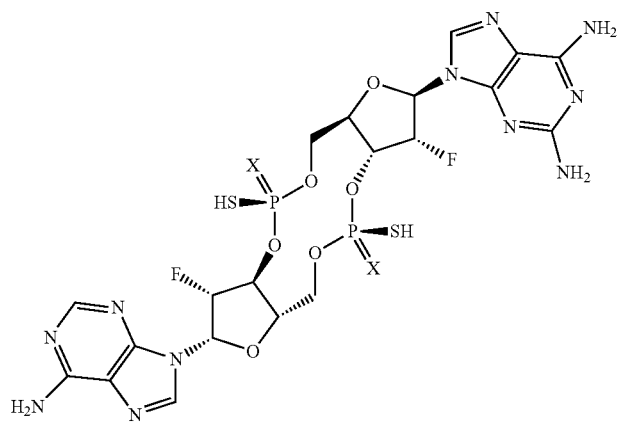 |

TABLE 6-continued
| Cpd. No. | Structure |
|---|---|
| 6-4 | 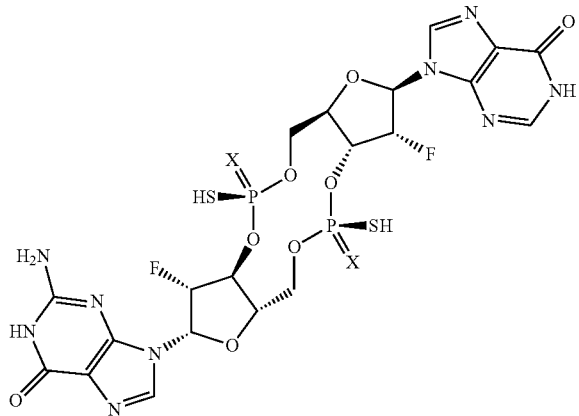 |
| 6-5 | 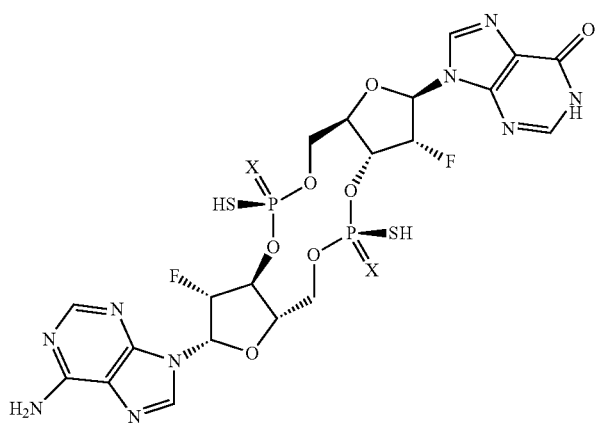 |
| 6-6 | 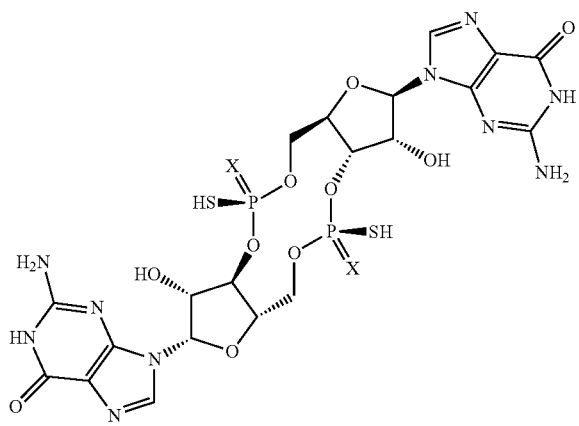 |

TABLE 6-continued
| Cpd. No. | Structure |
|---|---|
| 6-7 | 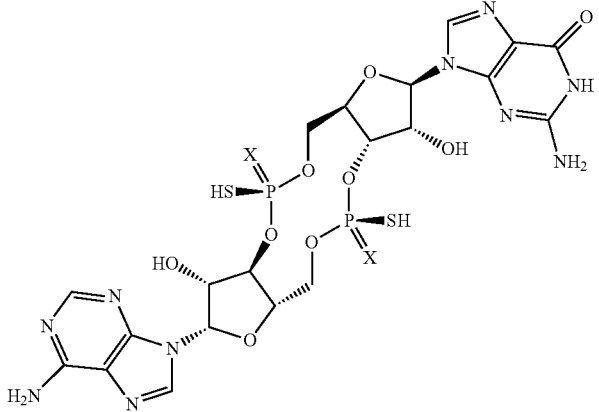 |
| 6-8 | 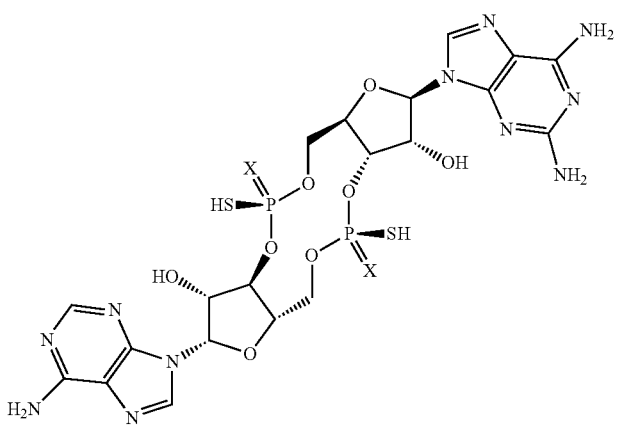 |
| 6-9 | 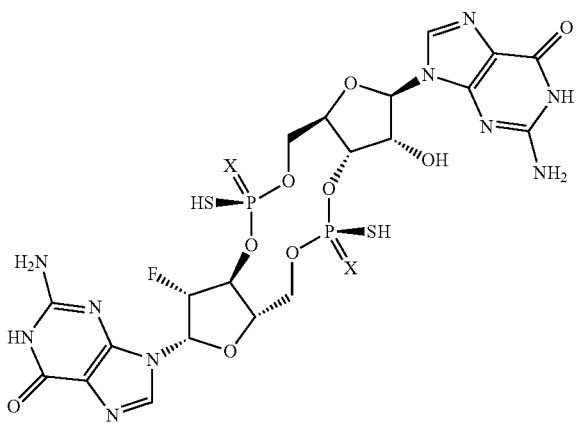 |

TABLE 6-continued
| Cpd. No. | Structure |
|---|---|
| 6-10 | 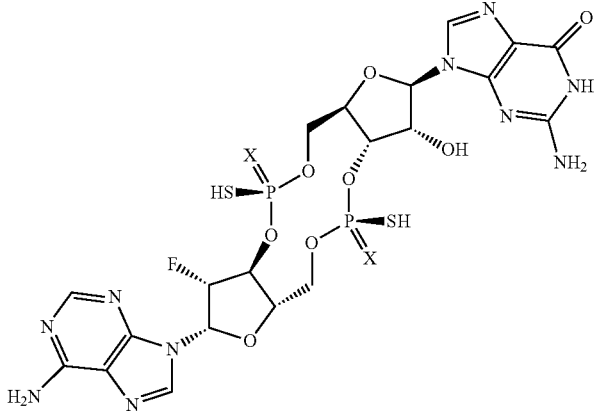 |
| 6-11 | 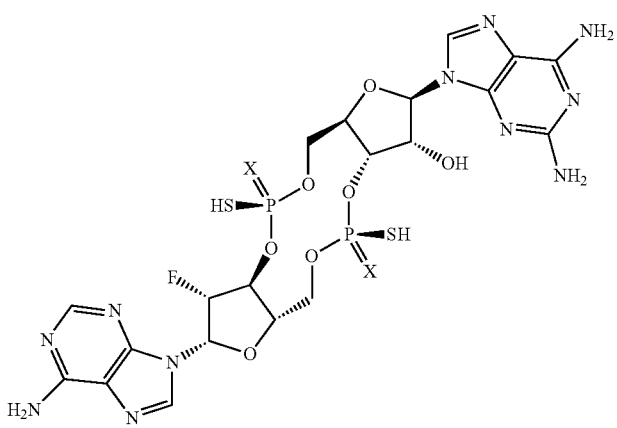 |
| 6-12 | 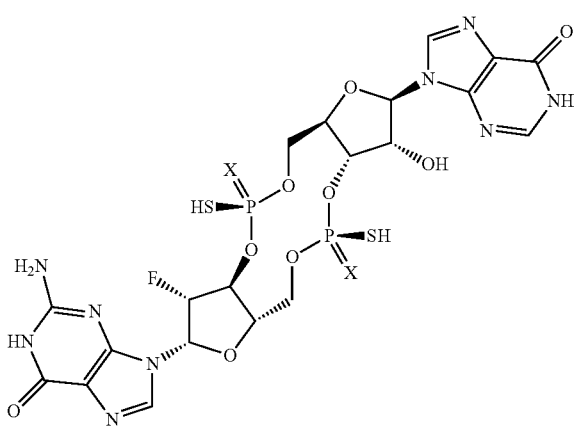 |

TABLE 6-continued
| Cpd. No. | Structure |
|---|---|
| 6-13 | 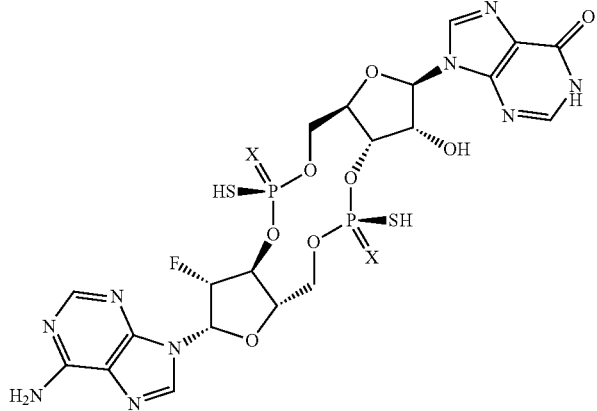 |
| 6-14 | 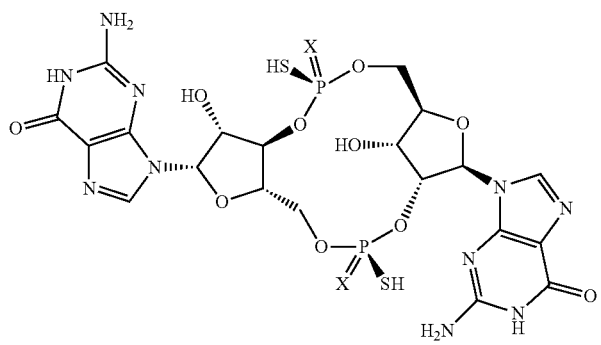 |
| 6-15 | 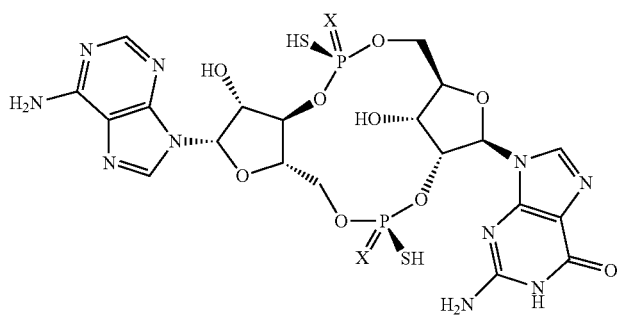 |
| 6-16 | 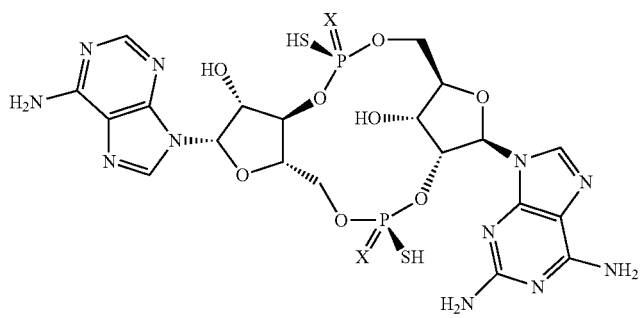 |

TABLE 6-continued
| Cpd. No. | Structure |
|---|---|
| 6-17 | 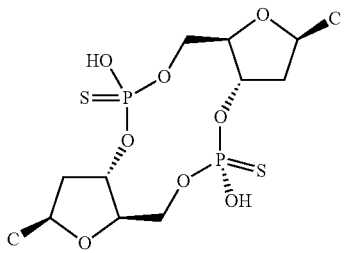 |
| 6-18 | 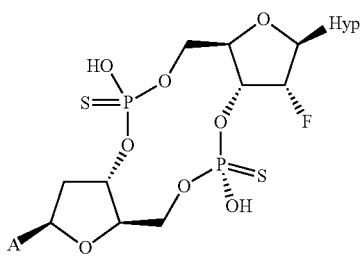 |
| 6-19 | 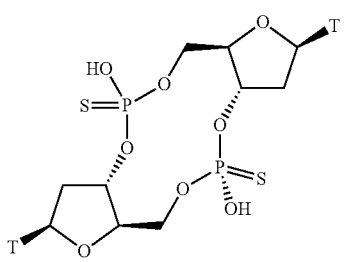 |
| 6-20 | 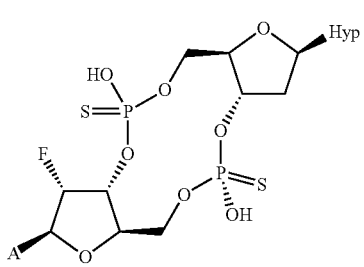 |

TABLE 6-continued

| Cpd. No. | Structure |
|---|---|
| 6-21 | 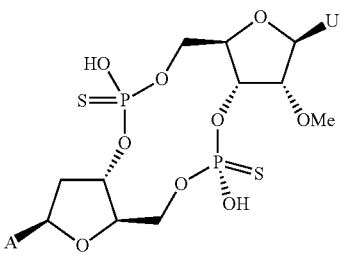 |
| 6-22 | 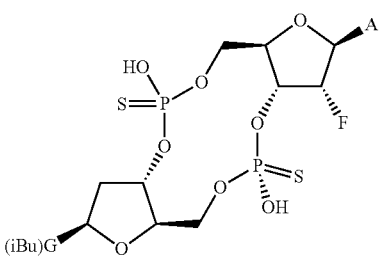 |
| 6-23 | 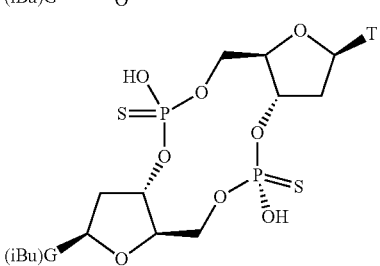 |

For compounds of Table 6, when X is O, all structures are (R/S—P) combinations; and when X is S, all (R/S—P) combinations.

Methods of Making Peptide/Protein-Nucleic Acid Conjugates

In another aspect, the present disclosure provides a method for making peptide/protein-nucleic acid (e.g., nucleosides, nucleotides, oligonucleotides, polynucleotides) conjugates comprising P(V)-based linkages. In some embodiments, the linkages are achiral. In some embodiments, the linkages are stereo-defined thiophosphate linkages. In some embodiments, the method comprises (a) reacting a compound of any of the Formulae (I)-(IIIe) with a nucleophile and (b) reacting the compound formed in step (a) with another nucleophile, thereby forming a stereo-defined linkage. In one embodiment, one of the nucleophiles is supplied by nucleic acids (e.g., 3'-hydroxy and 5'-hydroxy), and another nucleophile is supplies by a peptide or a protein (e.g., —NH$_2$, —OH, —SH, —C(O)NH$_2$, —C(O)OH, etc.).

In some embodiments, both reactions are conducted in the presence of a base. Suitable bases are described above for preparing oligonucleotides comprising stereo-defined thiophosphate linkages. Reaction conditions for such reactions are also described above. A skilled artisan will easily be able to vary the reaction conditions, such as time, temperature, amounts of the reagents, etc., to achieve desirable yields.

In one embodiment, the peptide is about 50 amino acids long, about 40 amino acids long, about 30 amino acids long, about 20 amino acids long, about 10 amino acids long, about 5 amino acids long, about 2 amino acids long, or about 1 amino acid long. In some embodiments, the peptide comprises only naturally-occurring amino acids. In other embodiments, the peptide comprises naturally- and non-naturally-occurring amino acids.

In one embodiment, the nucleic acid is a nucleoside (naturally-occurring or modified). In another embodiment, the nucleic acid is a nucleotide (naturally-occurring or modified). In one embodiment, the nucleic acid is an oligonucleotide comprising only naturally-occurring nucleosides. In one embodiment, the nucleic acid is an oligonucleotide comprising naturally-occurring and modified nucleosides. In another embodiment, the nucleic acid is an oligonucleotide comprising only modified nucleosides. Suitable naturally-occurring and modified nucleobases and sugars are described above. It will be within a purview of a skilled artisan to select appropriate nucleosides, based on the eventual application of the conjugates.

Examples of suitable proteins include, but are not limited to, enzymes, antibodies, cytokines, hormones, trans-membrane proteins, etc. More specific examples of proteins that can be used include, but are not limited to, polyclonal and monoclonal antibodies, including but are not limited to fully human antibodies; single chain antibodies; fragments of antibodies; chimeric antibodies and antigen-binding fragments thereof; domain antibodies and antigen-binding fragments thereof; interferons (e.g., alpha, beta, gamma); lymphokines (IL-2, IL-3, IL-4, IL-6); protein hormones, such as insulin; and enzymes.

In some embodiments, the methods of making peptide/protein-nucleic acid comprise a purification step. Purification can be performed by methods known in the arts such as, but not limited to, HPLC based purification methods such as, but not limited to, strong anion exchange HPLC, weak anion exchange HPLC, reverse phase HPLC (RP-HPLC), and hydrophobic interaction HPLC (HIC-HPLC).

In some embodiments, the nucleosides and/or amino acids can bear a protecting group. Suitable protecting groups are described above. In some embodiments, the protecting group can be removed by the methods described above.

Non-limiting examples of conjugates that can be prepared by the methods of the present disclosure are presented in Table 7.

TABLE 7

| Cpd. No. | Structure |
|---|---|
| 7-1 | 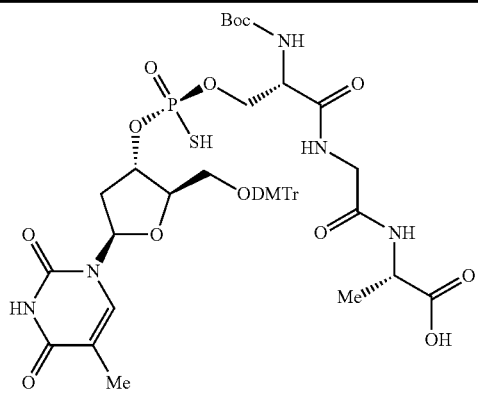 |
| 7-2 | 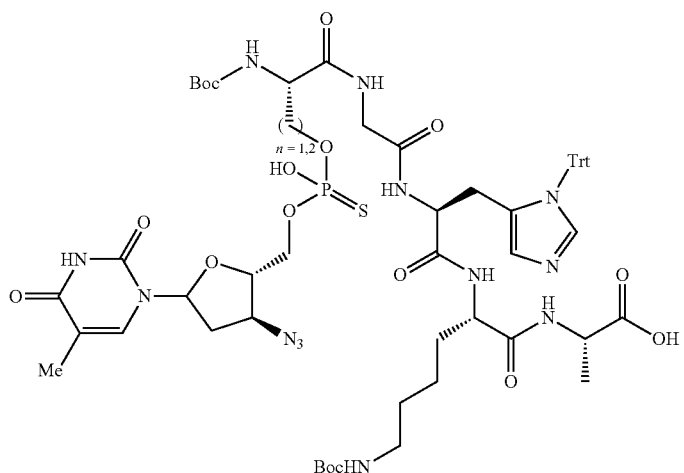 |
| 7-3 | 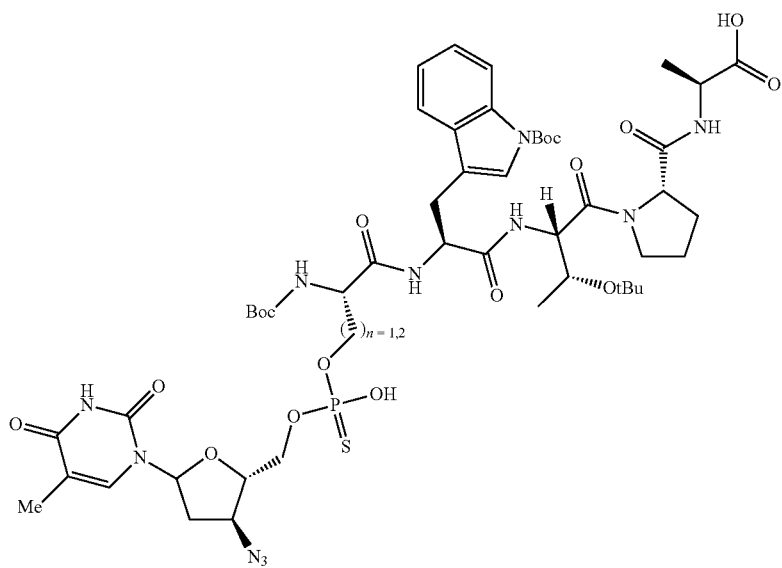 |

TABLE 7-continued
| Cpd. No. | Structure |
|---|---|
| 7-4 | 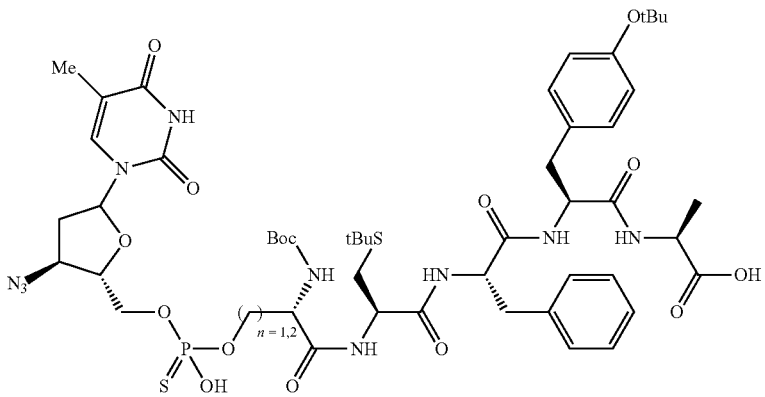 |
| 7-5 | 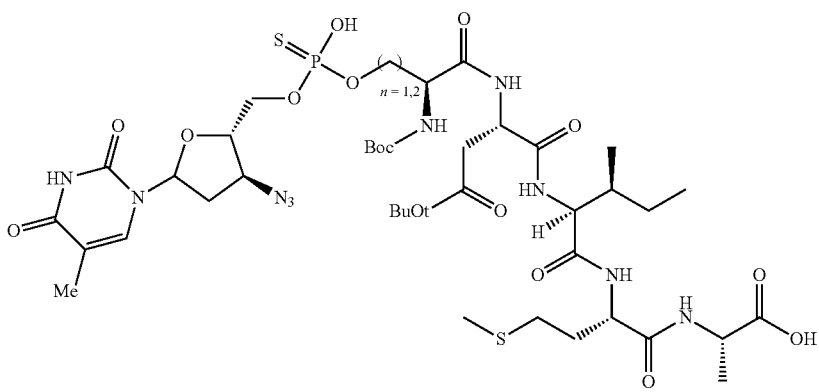 |
| 7-6 | 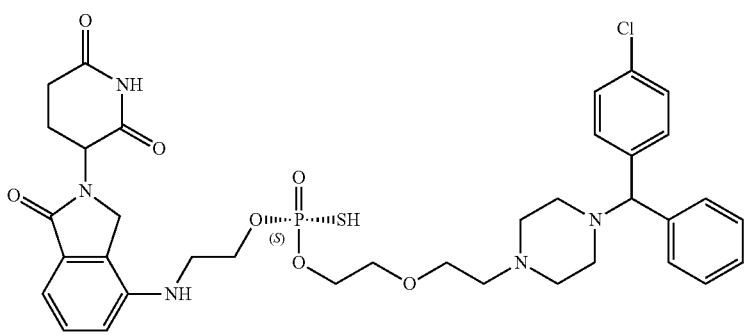 |
| 7-7 | 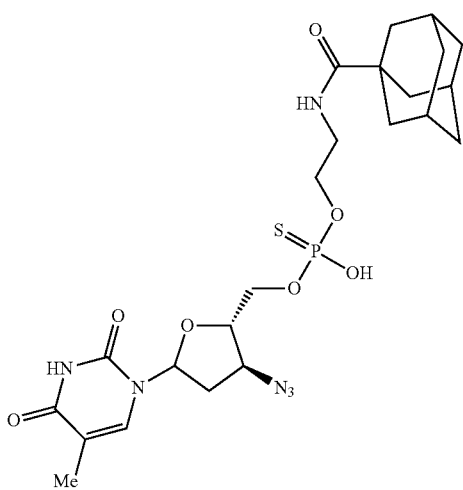 [SMILES: Cc1cn(C2C[C@H](N=[N+]=[N-])[C@@H](COP(O)(=S)OCCNC(=O)C34CC5CC(CC(C5)C3)C4)O2)c(=O)[nH]c1=O] |

TABLE 7-continued
| Cpd. No. | Structure |
|---|---|
| 7-8 | 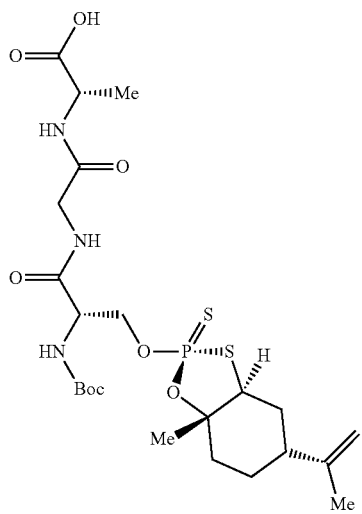 |
| 7-9 | 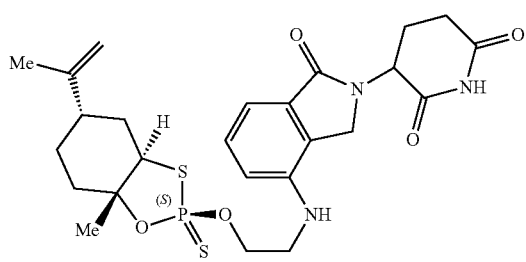 |
| 7-10 | 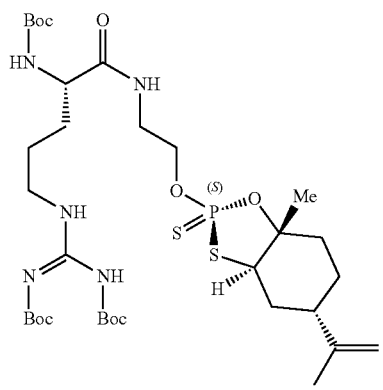 |
| 7-11 | 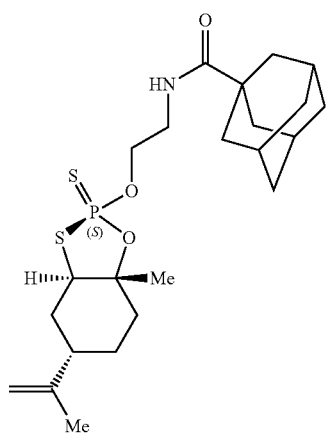 |

TABLE 7-continued

| Cpd. No. | Structure |
|---|---|
| 7-12 | 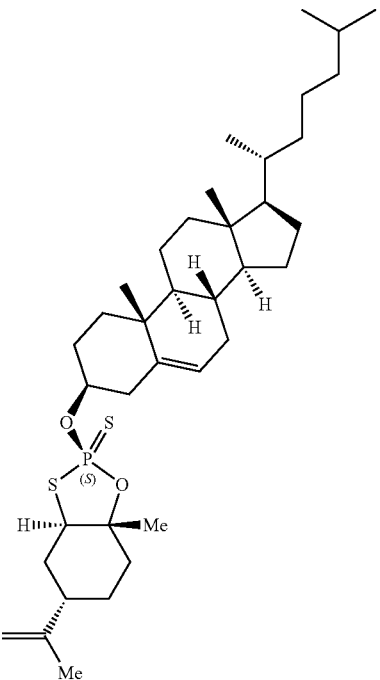 |
| 7-13 | 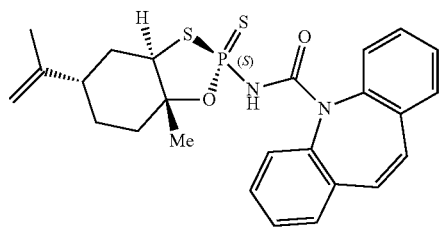 |
| 7-14 | 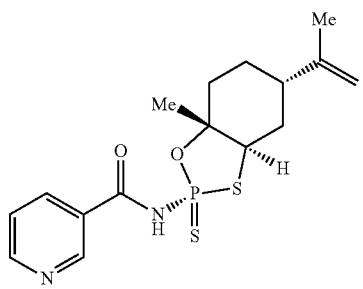 [SMILES: C=C(C)[C@H]1CC[C@@]2(C)O[P@@](=S)(NC(=O)c3cccnc3)S[C@@H]2C1] |

Control of Chirality at the Phosphorous Atom

The methods described herein are useful for controlling the configuration of each phosphorus atom in an organosphosphorous (V) compound (for example, an internucleoside linkage). The novel reagents described herein permit the specific control of the chirality at the phosphorus atom. For example, in embodiments pertaining to oligonucleotides containing thiophosphate internucleoside linkages, either a $R_P$ or $S_P$ configuration can be selected in each synthesis cycle, permitting control of the overall three dimensional structure of the nucleic acid product. In some embodiments, the selection of $R_P$ or $S_P$ configurations is made to confer a specific three dimensional superstructure to the nucleic acid chain.

In some embodiments, each phosphorous atom can have a $R_P$ configuration. In other embodiments, each phosphorous atom can have a $S_P$ configuration. In another embodiment, each phosphorous atom independently can have a $R_P$ configuration or a $S_P$ configuration. In another embodiment, the phosphorous atoms alternate between $R_P$ and $S_P$ such as $R_P$, $S_P$, $R_P$ or $S_P$, $R_P$, $S_P$ throughout the nucleic acid. In other specific embodiments, the phosphorous atoms contain repeated configurations of $R_P$, $R_P$, $S_P$, $S_P$ throughout the nucleic acid. In yet other embodiments, the nucleic acid comprises all $R_P$ configurations. In further embodiments, the nucleic acid comprises all $S_P$ moieties. In some embodiments, the 5' and 3' terminal internucleoside linkages are of the $S_P$ configuration and the internal internucleoside linkages are all of the $R_P$ configuration. The embodiments described herein serve as examples of how the configuration can be controlled using these methods. The nucleic acids (oligonucleotides and CDNs) described herein are not limited to these configuration patterns. It will be evident to one skilled in the art that other variations and alternations in the $R_P$ and $S_P$ configurations are possible and depend on the use and applications of the nucleic acid.

Purity Determination of Phosphorous Configurations

The purity of the configuration at each phosphorous atom in a organosphosphorous (V) compound (e.g., an oligonucleotide, a CDN, a peptide-oligonucleotide conjugate, etc.) is determined using conventional analytical methods such as, but not limited to, $^{31}P$ NMR spectroscopy or reverse-phase HPLC. Using methods described herein, in an embodiment, each phosphorous atom of a organosphosphorous (V) compound can be more than 80% diastereomerically pure. In an embodiment, each phosphorous atom of a organosphosphorous (V) compound can be more than 60% diastereomerically pure. In an embodiment, each phosphorous atom of a organosphosphorous (V) compound can be more than 70% diastereomerically pure. In an embodiment, each phosphorous atom of a organosphosphorous (V) compound can be more than 85% diastereomerically pure. In an embodiment, each phosphorous atom of a organosphosphorous (V) compound can be more than 90% diastereomerically pure. In an embodiment, each phosphorous atom of a organosphosphorous (V) compound can be more than 95% diastereomerically pure. In another embodiment, each phosphorous atom of a organosphosphorous (V) compound can be more than 98% diastereomerically pure. In another embodiment, each phosphorous atom of a organosphosphorous (V) compound can be more than 99% diastereomerically pure. In an embodiment, each phosphorous atom of a organosphosphorous (V) compound can be more than about 60%, more than about 70%, more than about 80%, more than about 83%, more than about 84%, more than about 85%, more than about 86%, more than about 87%, more than about 88%, more than about 89%, more than about 90%, more than about 91%, more than about 92%, more than about 93%, more than about 94%, more than about 95%, more than about 96%, more than about 97%, more than about 98%, or more than about 99% diastereomerically pure. In one embodiment, each phosphorous atom of a organosphosphorous (V) compound can be from about 60% to about 99.9% diastereomerically pure. In one embodiment, each phosphorous atom of a organosphosphorous (V) compound can be from about 60% to about 99% diastereomerically pure. In one embodiment, each phosphorous atom of a organosphosphorous (V) compound can be from about 60% to about 70% diastereomerically pure. In one embodiment, each phosphorous atom of a organosphosphorous (V) compound can be from about 70% to about 80% diastereomerically pure. In one embodiment, each phosphorous atom of a organosphosphorous (V) compound can be from about 80% to about 90% diastereomerically pure. In one embodiment, each phosphorous atom of a organosphosphorous (V) compound can be from about 80% to about 99% diastereomerically pure. In one embodiment, each phosphorous atom of a organosphosphorous (V) compound can be from about 85% to about 95% diastereomerically pure. In one embodiment, each phosphorous atom of a organosphosphorous (V) compound can be from about 90% to about 95% diastereomerically pure. In one embodiment, each phosphorous atom of a nucleic acid can be from about 95% to about 99% diastereomerically pure. In one embodiment, each phosphorous atom of a organosphosphorous (V) compound can be from about 90% to about 99.9% diastereomerically pure.

The amount of a particular configuration over another configuration affects the three-dimensional structure of a organosphosphorous (V) compound, such as nucleic acids, as well as their stability. Accordingly, different configurations affect the biological, chemical, and physical properties of the nucleic acids. In one embodiment, the nucleic acid comprises a greater percentage of $S_P$ configuration than $R_P$ configuration. In another embodiment, the nucleic acid comprises a greater percentage of $R_P$ configuration than $S_P$ configuration. In another embodiment, the nucleic acid comprises the same percentage of $R_P$ configuration as $S_P$ configuration. In one embodiment, the nucleic acid can comprise 0-20% $R_P$ configuration. In one embodiment, the nucleic acid can comprise 20-40% R configuration. In one embodiment, the nucleic acid can comprise 40-60% R configuration. In one embodiment, the nucleic acid can comprise 60-80% R configuration. In one embodiment, the nucleic acid can comprise 80-100% R configuration. In one embodiment, the nucleic acid can comprise 0-20% $R_P$ configuration. In one embodiment, the nucleic acid can comprise 20-40% $S_P$ configuration. In one embodiment, the nucleic acid can comprise 40-60% $S_P$ configuration. In one embodiment, the nucleic acid can comprise 60-80% $S_P$ configuration. In one embodiment, the nucleic acid can comprise 80-100% $S_P$ configuration.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather is defined by the claims appended hereto.

Example 1(a)

Preparation of the Limonene-P(V) Reagents

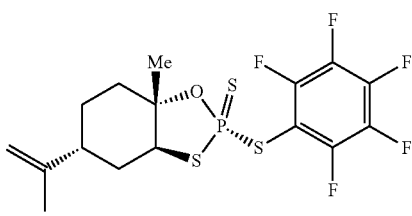

Compound 1-31

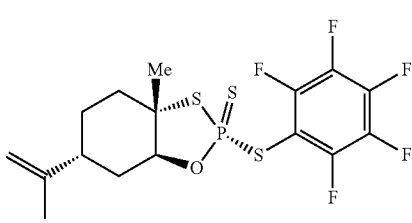

Compound 1-33

Preparation of Thio-Phosphoric Acid Triethylamine.

Step (1): To a mixture of phosphorus pentasulfide (30.0 g, 132 mmol, 98 mass %) in toluene (240 mL, 8 mL/g) was charged pentafluorothiophenol (PFTP) (55 g, 266.58 mmol, 97 mass %) at 21° C. The batch was inert by flushing with $N_2$ for 2 min. Triethylamine (TEA) (39 mL, 277 mmol, 99 mass %) was added over a period of 0.5 hours. The batch temperature went to 45° C. at the end of the addition. At the end of TEA addition, the batch became a nearly clear yellow solution and then gradually turned cloudy in 0.5 hours. The batch temperature slowly dropped to ambient temperature over 0.5 hours (by air cooling). HPLC analysis of a sample at 3 hours indicated that relative area percent ("RAP") of PFTP vs. product was less than 5%.

Step (2): The mixture was stirred at ambient temperature overnight. The slurry was then filtered, and the reactor was rinsed with toluene (30 mL×2) and the rinses were applied to the cake washes. The filtration was rapid, and HPLC analysis of the cake indicated very little loss of product.

Steps (3) and (4): The combined filtrates were concentrated under vacuum to 105 g (~3.5 v). Methanol (180 mL, 6 v) was added, followed by heptane (180 mL, 6 v). The biphasic mixture was stirred for 15 min. Water (150 mL, 5 v) was added over 30 min. After 35 mL of water was added, seed (0.3 g, 1%) was added. After the seed was added, a slurry was formed within a minute.

Step (5): After the addition of water was complete, the batch was mixed for 1 h. The batch was filtered. The reactor was rinsed with a mixture of 3:2 water/methanol (75 mL), and the rinse was applied for the cake wash. The filter cake was washed with water (90 mL×2), then heptane (45 mL×2). The cake was dried in vacuo for 15 h at 50° C. 73 g of thio-phosphoric acid TEA salt was collected as a white solid (93% as-is yield). The product was characterized by $^1H$ NMR (500 MHz, chloroform-d) δ 8.99-8.60 (m, 1H), 3.40-3.20 (m, 6H), 1.51-1.36 (m, 9H); and P NMR δ 99.35. Process flow diagram for preparing thio-phosphoric acid TEA salt is shown below:

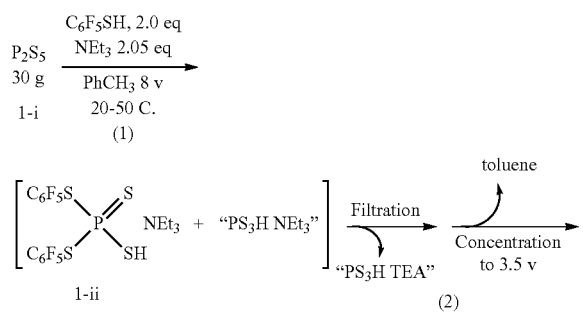

Preparation of the Limonene P(V) Reagent A (Compound 1-31) from Trans-Limonene.

Step (1): A solution of bis[(2,3,4,5,6-pentafluorophenyl) sulfanyl]-sulfido-thioxophosphane triethylammonium (1.00 g, 1.68 mmol, 100 mass %) and (1R,3R,6S)-3-isopropenyl-6-methyl-7-oxabicyclo[4.1.0]heptane (0.383 g, 2.52 mmol, 100 mass %) in dichloromethane (DCM) (5.0 mL, 5 v) was made inert by flushing with nitrogen. Trifluoroacetic acid (0.19 mL, 2.52 mmol, 100 mass %) was added at 21° C. The mixture was then heated at 35° C. for one hour. HPLC analysis of a sample indicated that RAP of P—SH SM vs. product was less than 3%.

Steps (2) and (3): The reaction mixture was cooled to ambient temperature, and hexanes (10 mL, 10 v) was added into the batch (a biphasic mixture). The resulting stream was washed with water (5 mL), saturated $NaHCO_3$ (10 mL), and 10% $KH_2PO_4$ (3 mL). The organic phase was filtered through a $MgSO_4$ pad, and concentrated to ~3 mL. Methanol (5 mL) was added, the batch was concentrated to ~3 mL. Addition of methanol (5 mL) was repeated and the reaction mixture was concentrated to ~3 mL. The mixture was cooled to 5-10° C. and stirred for 5 min. The resulting slurry was filtered, and the reactor and cake were washed with cold methanol (1 mL). The cake was dried, and weighed 0.56 g in 75% as-is yield. The product was characterized by $^1H$ NMR (500 MHz, chloroform-d) δ 5.09-4.95 (m, 1H), 4.81-4.66 (m, 1H), 3.07-2.89 (m, 1H), 2.44 (br s, 1H), 2.18-2.09 (m, 2H), 2.09-2.03 (m, 1H), 1.80-1.70 (m, 2H), 1.69-1.67 (m, 6H), 1.61-1.53 (m, 3H); and P NMR δ 101.61. Process flow diagram for preparing limonene P(V) reagent A is shown below:

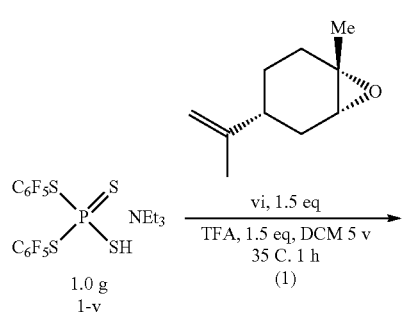

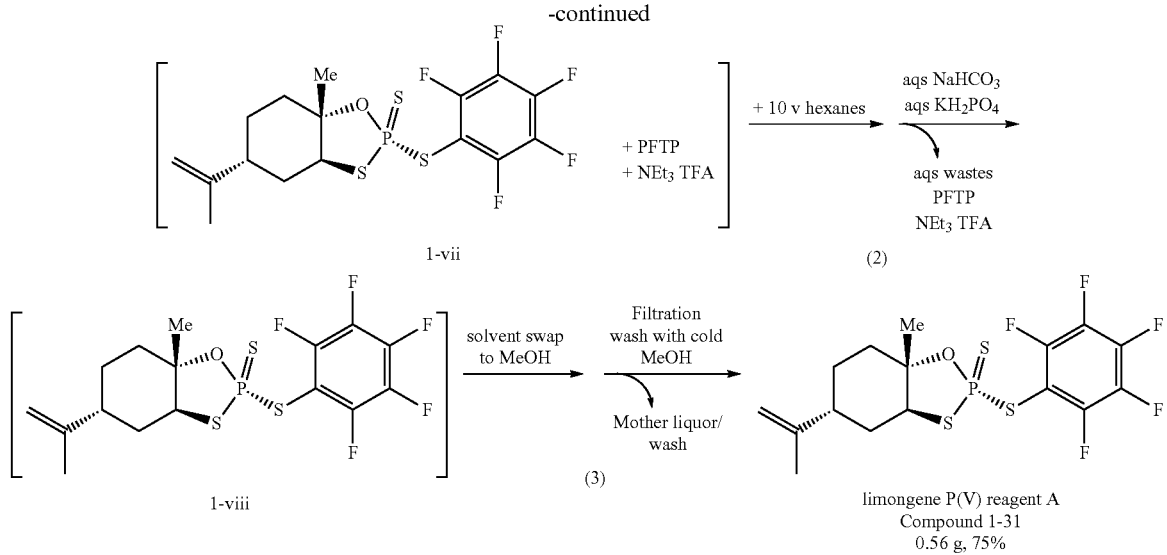
Preparation of the Limonene P(V) Reagent B (Compound 1-33) from Cis-Limonene.
The preparation of limonene P(V) B used the same procedure of making limonene P(V) A except that tran-limonene was replaced by cis-limonene. Process flow diagram for preparing limonene P(V) reagent B is shown below:
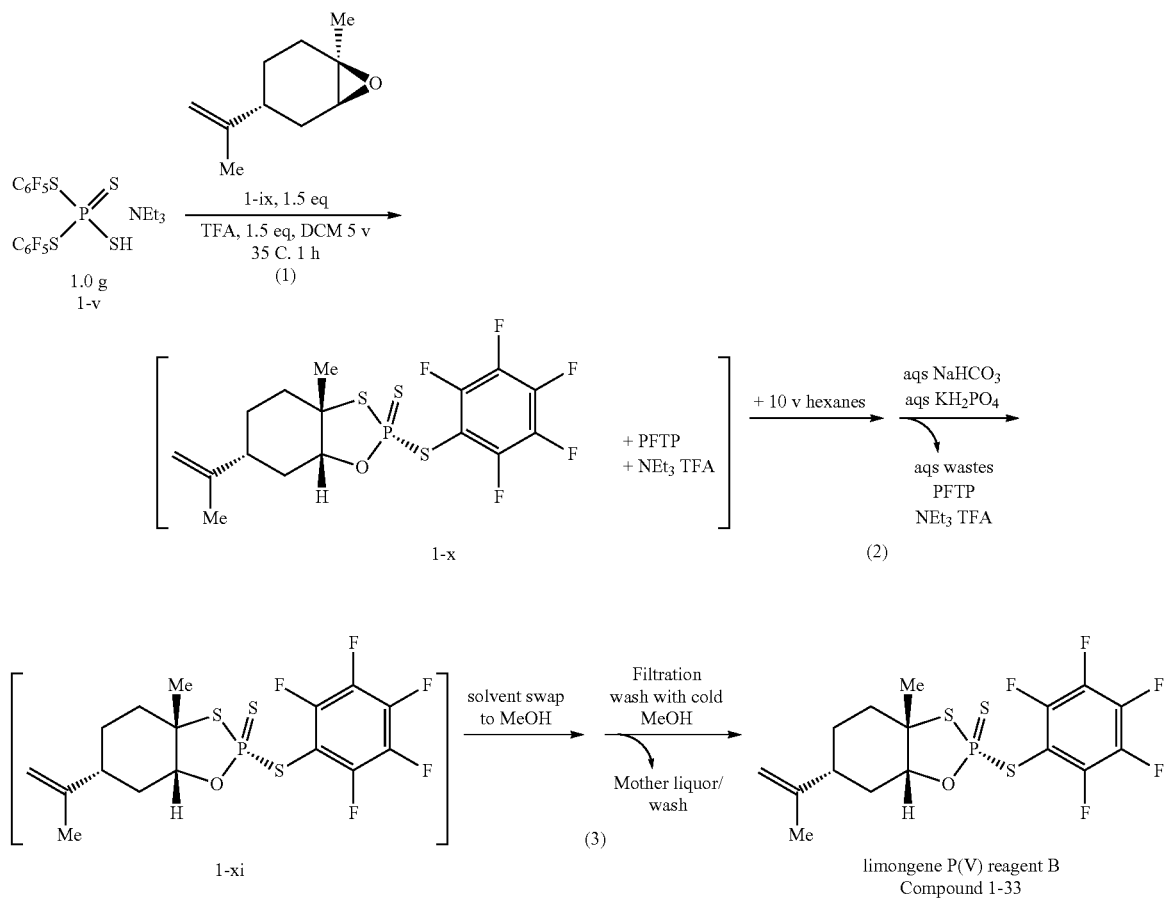

Example 1(b)

Alternative Preparation of Limonene P(V) Reagent B (Compound 1-33) from Cis-Limonene

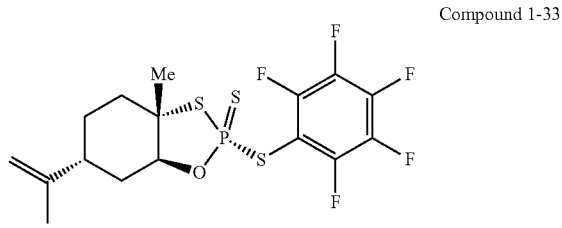 [SMILES: C=C(C)[C@@H]1CC[C@]2(C)S[P@](=S)(Sc3c(F)c(F)c(F)c(F)c3F)O[C@H]2C1]

Compound 1-33

Step (1): The thio-phosphoric TEA salt was prepared according to the procedure described below.

To a solution of thio-phosphoric acid TEA salt (232 g, 389.6 mmol, 100 mass %) and cis-(+)-limonene oxide (90 g, 591.21 mmol, 100 mass %) in chloroform (2.5 L, contains 0.5-1% EtOH as a stabilizer) was added dibutyl phosphate (DBP) (83 mL, 439.1 mmol, 100 mass %) at room temperature under nitrogen. Then, dichloroacetic acid (72 mL, 872.2 mmol, 100 mass %) was added immediately, with rinse of chloroform (50 mL). After the addition of the acids, the batch temp increased to 26° C. The resulting mixture was warmed to 55-60° C. over about 40 min. After 2.5 hours, the reaction gave two diastereomers with a ratio of about 8:1. The HPLC retention time for these two diastereomers is 1.932 min and 1.993 min respectively.

Step (2): The batch from step (1) was concentrated to about 1.3 L at 35-60° C. under vacuum (200 torr) over ~2 hours. To this mixture, hexane was added (2 L). The resulting batch was quickly washed with 10% aqueous $K_2HPO_4$ (1.5 L). The batch was agitated for less than 5 min and allowed for phase separation. After separation, the organic layer was washed with 10% aqueous $KH_2PO_4$ (0.5 L), then water (0.5 L) to remove PFTP, DCA, DBP, and $NEt_3$. Then the organic layer was concentrated to 0.6 L at 30-60° C. under vacuum (200 torr) over 2 hours.

Step (3): To the batch from step (2) MeOH (0.75 L) was added and the batch was concentrated to about 0.5 L at 30-60° C. under vacuum. Then MeOH (1.0 L) was added and the batch was concentrated to about 1.5 L at 30-60° C. under vacuum. The resulting slurry was heated to about 60° C. and stirred until all solids were dissolved. The batch was then cooled to 20° C. over a period of 1 hour. Water (100 mL) was added at 30-40° C. during the cooling period. The batch was stirred at 20° C. for 15-24 h. The resulting slurry was filtered. The filtrate was recycled and the new slurry was transferred into the filter. The filter cake was washed with 10% water in MeOH (100 mL) to afford two diastereomers with a ratio of greater than 20:1 (in this experiment, the diastereomer ratio (d.r.) is 98:2). If the ratio is less than 20:1, then the cake is re-dissolved in MeOH (10 L/kg of cake) at 60° C., followed by cooling to 20° C., and water (0.7 L/kg of cake) is added and mixed with the batch for 15-24 h. Then, the filtration gives a cake with the desired purity.

The cake (125 g) was then dissolved in DCM (0.3 L). The batch was solvent-swapped to heptane, and distilled to 0.5 L. After stirring for 1 h at 20° C., the slurry was filtered. The filtrate was recycled and the new slurry was transferred into the filter. The filter cake was washed with heptane (50 mL×2) and dried under vacuum at 50° C. to afford the desired product (105 g, yield 59%, d.r.>99:1; ee>99:1.) The chiral HPLC retention time of two enantiomers is 7.743 min and 8.199 min respectively. $^1$H NMR (500 MHz, chloroform-d) δ 5.09-4.95 (m, 1H), 4.81-4.66 (m, 1H), 3.07-2.89 (m, 1H), 2.44 (br s, 1H), 2.18-2.09 (m, 2H), 2.09-2.03 (m, 1H), 1.80-1.70 (m, 2H), 1.69-1.67 (m, 6H), 1.61-1.53 (m, 3H); and P NMR δ 101.61.

The process flow diagram for preparing limonene P(V) reagent B according to Example 1(b) is shown below:

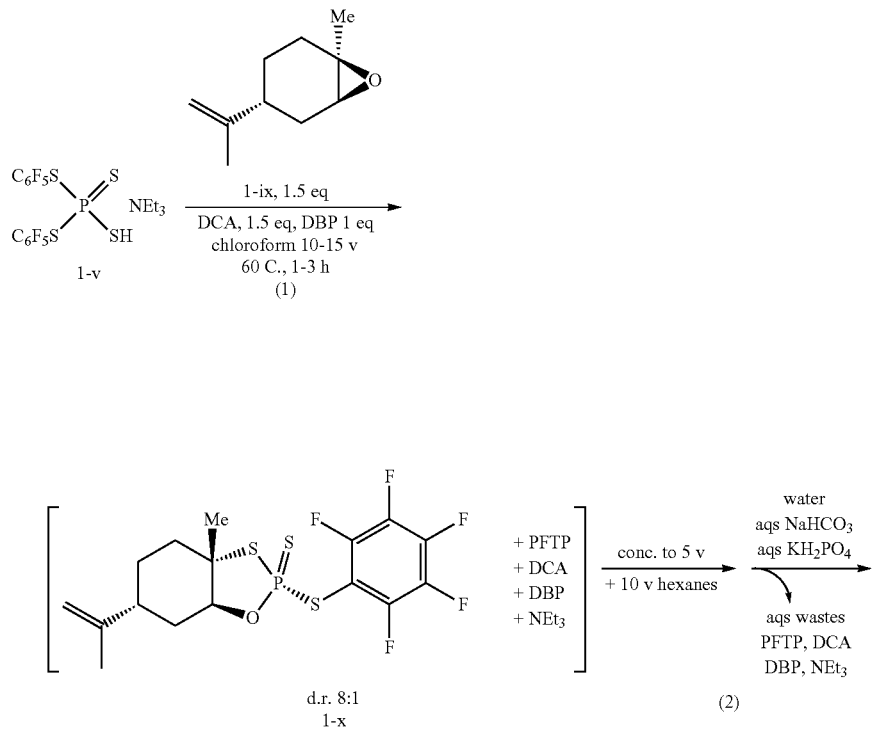

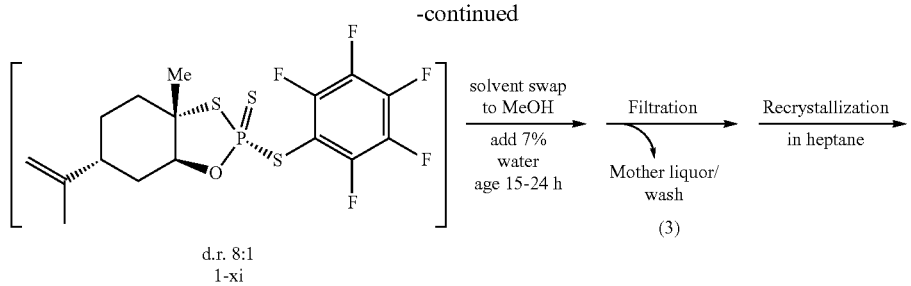

d.r. >99:1
55-62%
limongene P(V) reagent B
Compound 1-33

Example 2

Formation of a Stereo-Defined Phosphorothioate Internucleoside Linkage Using the Limonene P(V) Reagent The limonene P(V) reagent from Example 1 was used to stereoselectively form a phosphorothioate internucleoside linkage.

(a) A deoxythymidine nucleoside bearing a 5'-di-(p-methoxyphenyl)phenylmethyl ether 4',4'-dimethoxytrityl (DMTr) protecting group was reacted with either the (+) $S_P$ or the (−) $R_P$ stereoisomer of the limonene P(V) reagent (see Examples 1(a) and 1(b) in the presence of 1,8-diazabicyclo[5.4.0]undec-7-ene (DBU) at 25° C. for 10 min.

(b) To the reaction mixture, a 3'-tert-butyldimethylsilyl ether (TBS) of deoxythymidine nucleoside was added in the presence of acetonitrile (MeCN), tetrahydrofuran (THF) and tetra-n-butylammonium fluoride (TBAF). The reaction was allowed to proceed at 25° C. for several hours, yielding a dinucleotide containing a phosphorothioate internucleoside linkage. HPLC analysis showed that (S)-limonene P(V) gives (S)-nucleoside dimer, and (R)-limonene P(V) gives (R)-nucleoside dimer, with the overall retention of stereochemistry in both cases.

Example 3

Preparation of P(S)$_2$ P(V) Reagents

Method A

To a solution of O,O-bis(4-nitrophenyl) S-hydrogen phosphorodithioate triethylammonium salt (4.20 mmol) in acetonitrile (0.10 M) was added dibutylphosphate (16.8 mmol) and ethylene sulfide (16.8 mmol). The resulting solution was heated at 80° C. for 18 hours. Upon cooling to ambient temperature, the solvent was removed in vacuo and the resulting residue applied to silica gel. The product was eluted with dichloromethane/hexane (3:1). The solid obtained was dissolved in dichloromethane and precipitated from hexane affording the title compound (3.19 mmol, 76% yield) as a white solid. The reaction can be represented by the following scheme:

ii. Method B (General Scheme)

Dithiol (1.00 eq) was added to $PCl_3$ (3.00 eq) at room temperature. The mixture was stirred for 3 hours (HCl bubbles were observed during this reaction). The excess $PCl_3$ was distilled out by a simple distillation and the compound was stored under vacuum giving Intermediate 1.

Intermediate 1 (1.0 eq) in deoxygenated MeCN (0.1 M) was added dropwise to a stirred solution of Leaving Group-H (LG-H, 1.0 eq.) and DIEA (1.10 eq) in dry, degassed MeCN (73 mL) at 0° C. After stirring for 1 h at the same temperature, the reaction mixture was warmed to room temperature and stirred for an additional 2 h. The P(III) intermediate was then sulfurized with either $S_8$ (3 eq.) in $CS_2$ (20 eq.) or EDITH (1 eq.). The P(V) Reagents were obtained by crystallization from alcoholic solvents (IPA, MeOH, nBuOH, EtOH, etc.)

2-(4-nitrophenoxy)-1,3,2-dithiaphospholane 2-sulfide (Compound 2-1)

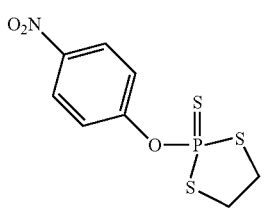 [SMILES: O=[N+]([O-])c1ccc(OP2(=S)SCCS2)cc1]

Illustration 1

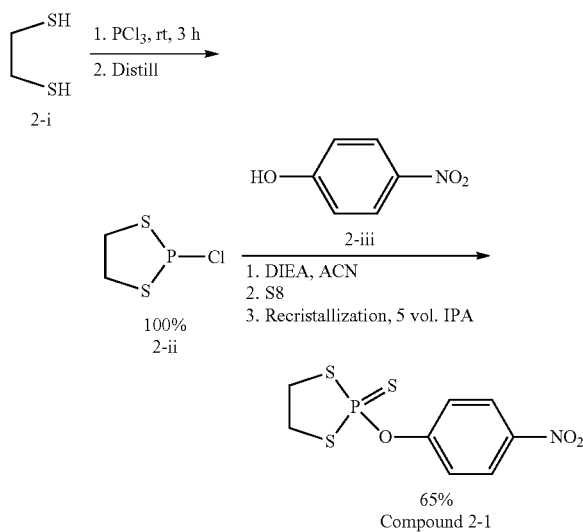

Step 1. Synthesis of 2-chloro-1,3,2-dithiaphospholane (2-ii)

32.0 mmol of phosphorus (III) chloride and 1 equiv. of ethane-1,2-dithiol were mixed at room temperature and stirred for 3 hours. Following completion of the reaction, the mixture was distilled to afford 2-chloro-1,3,2-dithiaphospholane (5.08 g, 32.0 mmol, quantitative yield).

Step 2. Synthesis of 2-(4-nitrophenoxy)-1,3,2-dithiaphospholane 2-sulfide (Compound 2-1)

To a solution of 32.0 mmol of 2-chloro-1,3,2-dithiaphospholane and 1 equiv. of 4-nitrophenol in MeCN [0.1 M] was added 1.0 equiv. of DIPEA at room temperature. The mixture was stirred for 3 h, followed by a solution of $S_8$ in $CS_2$ (8.0 equiv., 24 wt %). The resulting mixture was stirred for 3 h. The crude product was recrystallized from 2-propanol (ca. 5 mL/g of expected product) to afford 2-(4-nitrophenoxy)-1,3,2-dithiaphospholane 2-sulfide (6.0 g, 20.4 mmol, 65%).

Illustration 2

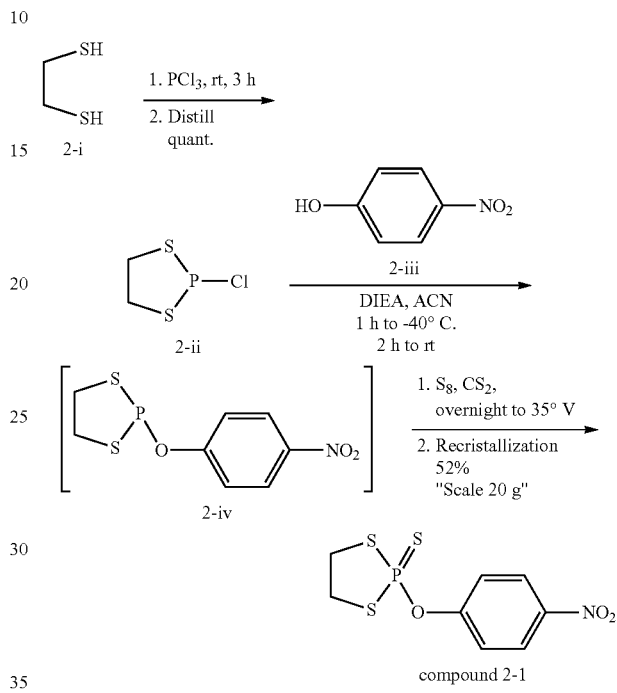

Synthesis of 2-chloro-1,3,2-dithiaphospholane (2-ii)

1,2-Ethanedithiol (1.00 eq., 27.34 g, 24.35 mL, 290.2 mmol) was added (5 min) to $PCl_3$ (3.00 eq., 119.57 g, 75.97 mL, 870.70 mmol) at room temperature. The mixture was stirred for 3 h (HCl bubbles were observed during this reaction). The $PCl_3$ excess was distilled out by a simple distillation and the compound was stored under vacuum. The compound was obtained as transparent liquid in quantitative yield (45.8 g). $^1$H NMR (400 MHz, $CDCl_3$) δ 3.82-3.65 (m, 2H), 3.65-3.48 (m, 2H). $^{13}$C NMR (150 MHz, $CDCl_3$) δ 42.82, 42.80. $^{31}$P NMR (244 MHz, $CDCl_3$) δ 167.92.

Synthesis of 2-(4-Nitrophenylthiol)-1,3,2-dithiaphospholane-2-sulfide (Compound 2-1)

2-Chloro-1,3,2-dithiophospholane (1.0 eq., 22.9 g, 145.01 mmol) in deoxygenated MeCN (229.5 mL) was added dropwise to a stirred solution of 4-Nitrophenol (1.0 eq., 20.17 g, 145.01 mmol) and DIEA (1.10 eq., 20.6 g, 27.8 mL, 159.5 mmol) in dry, degassed MeCN (73 mL) at −40° C. After stirring for 1 h at the same temperature, the reaction mixture was warmed to room temperature and stirred for an additional 2 h 30 min. The mixture was analyzed by NMR ($^{31}$P and $^1$H). The intermediate 2-(4-nitrophenoxy)-1,3,2-dithiaphospholane (3a2) was stable during this process. $^1$H NMR (400 MHz, $CDCl_3$) δ 8.03 (d, J=9.2 Hz, 2H), 7.03 (d, J=9.2 Hz, 2H), 3.17 (m, 4H). $^{31}$P NMR (244 MHz, $CDCl_3$) δ 160.56.

A solution of S₈ (3.0 eq., 13.95 g, 435.03 mmol) dissolved in $CS_2$ (20 eq., 175 mL) and was slowly added to the mixture above for 20 min., at room temperature and the resultant light yellow heterogeneous mixture was vigorously stirred overnight at 35° C.

Purification and Recrystallization: IPA (250 mL) was added at room temperature and then was warmed until complete solution. Then it was cooled to room temperature and was stirred 3 hours. The precipitated solid was filtered and washed with additional IPA (50 mL). The compound was obtained as white solid (30.0 g, 70.6%, this compound has an impurity in 7% but It can be used in the next step). The solid was solved in DCM (50 mL) and was added silica gel (10 g) and it was dried under reduced pressure. After, this solid was loaded onto a silica gel column and the mixture was washed with Hexane:DCM 1:1 (600 mL). The filtrate was concentrated under reduced pressure to dry to afford the desired compound 2-1 as white solid (22.0 g, 51.8%, Rf: 0.25 in DCM/Hexane 1:1). ¹H NMR (400 MHz, CDCl3) δ 8.26 (d, J=9.0 Hz, 2H), 7.41 (dd, J=9.1, 2.0 Hz, 2H), 3.88-3.66 (m, 4H). ¹³C NMR (150 MHz, CDCl3) δ 155.67 and 155.58, 145.33 and 145.32, 125.51 and 125.49, 122.78 and 122.75, 42.09. ³¹P NMR (244 MHz, CDCl₃) δ 120.04.

The following compounds 3b-3t were prepared by utilizing method B.

b. 2-phenoxy-1,3,2-dithiaphospholane 2-sulfide (Compound 2-2)

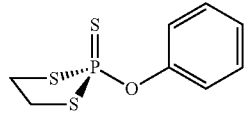

compound 2-2

The title compound was prepared using method B and LG-H is phenol. ¹H NMR (600 MHz, Chloroform-d) δ 7.40-7.33 (m, 2H), 7.29-7.21 (m, 3H), 3.76-3.66 (m, 2H), 3.64-3.56 (m, 2H). ¹³C NMR (151 MHz, Chloroform-d) δ 151.13 (d, J=13.2 Hz), 129.65 (d, J=2.4 Hz), 125.93 (d, J=2.6 Hz), 122.16 (d, J=5.0 Hz), 41.95. ³¹P NMR (202 MHz, Chloroform-d) δ 119.02 (p, J=16.3 Hz). HRMS (ESI-TOF) m/z Calcd for $C_8H_{10}OPS_3^+$ [M+H]⁺ 248.9626, found 248.9641.

c. 2-(phenylthio)-1,3,2-dithiaphospholane 2-sulfide (Compound 2-3)

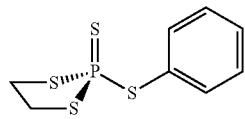

compound 2-3

The title compound was prepared using method B and LG-H is benzenethiol. ¹H NMR (600 MHz, Chloroform-d) δ 7.70-7.64 (m, 2H), 7.50-7.45 (m, 1H), 7.44-7.38 (m, 2H), 3.62-3.50 (m, 2H), 3.23-3.12 (m, 2H). ¹³C NMR (151 MHz, Chloroform-d) δ 136.64 (d, J=4.7 Hz), 130.59 (d, J=4.4 Hz), 130.51 (d, J=8.3 Hz), 129.36 (d, J=3.7 Hz), 42.92. ³¹P NMR (202 MHz, Chloroform-d) δ 108.61. HRMS (ESI-TOF) m/z Calcd for $C_8H_{10}PS_4^+$ [M+H]⁺ 264.9397, found 264.9423.

d. 2-((4-nitrophenyl)thio)-1,3,2-dithiaphospholane 2-sulfide (Compound 2-4)

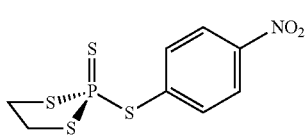

compound 2-4

The title compound was prepared using method B and LG-H is 4-nitrobenzenethiol. ¹H NMR (600 MHz, Chloroform-d) δ 8.26 (d, J=8.0 Hz, 2H), 7.83 (dd, J=8.9, 2.4 Hz, 2H), 3.77-3.66 (m, 2H), 3.54-3.44 (m, 2H). ¹³C NMR (151 MHz, Chloroform-d) δ 149.00 (d, J=4.4 Hz), 138.30 (d, J=7.8 Hz), 136.81 (d, J=4.6 Hz), 124.19 (d, J=3.0 Hz), 42.85. ³¹P NMR (202 MHz, Chloroform-d) δ 105.41 (tt, J=19.2, 16.0 Hz). HRMS (ESI-TOF) m/z Calcd for $C_8H_9NO_2PS_4^+$ [M+H]⁺ 309.9248, found 309.9240.

e. 2-(4-bromophenoxy)-1,3,2-dithiaphospholane 2-sulfide (Compound 2-5)

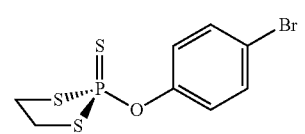

compound 2-5

The title compound was prepared using method B and LG-H is 4-bromophenol. ¹H NMR (600 MHz, Chloroform-d) δ 7.51-7.45 (m, 2H), 7.15 (d, J=12.0 Hz, 2H), 3.77-3.68 (m, 2H), 3.67-3.59 (m, 2H). 13C NMR (151 MHz, Chloroform-d) δ 150.04 (d, J=13.2 Hz), 132.69 (d, J=2.3 Hz), 123.94 (d, J=5.2 Hz), 119.17 (d, J=3.4 Hz), 42.00. 31P NMR (202 MHz, Chloroform-d) δ 119.85 (ddd, J=32.4, 18.5, 14.3 Hz). HRMS (ESI-TOF) m/z Calcd for $C_8H_9BrOPS_3^+$ [M+H]⁺ 326.8731, found 326.8758.

f. 2-(4-chlorophenoxy)-1,3,2-dithiaphospholane 2-sulfide (Compound 2-6)

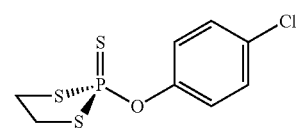

compound 2-6

The title compound was prepared using method B and LG-H is 4-chlorophenol. ¹H NMR (500 MHz, Chloroform-d) δ 7.32 (t, J=1.6 Hz, 2H), 7.21 (d, J=2.2 Hz, 2H), 3.79-3.68 (m, 2H), 3.68-3.59 (m, 2H). 13C NMR (151 MHz, Chloroform-d) δ 149.51 (d, J=13.2 Hz), 131.48 (d, J=3.3 Hz), 129.73 (d, J=2.2 Hz), 123.53 (d, J=5.2 Hz), 41.99. 31P NMR (202 MHz, Chloroform-d) δ 119.94 (ddd, J=32.5, 18.6, 14.4 Hz). HRMS (ESI-TOF) m/z Calcd for $C_8H_9ClOPS_3^+$ [M+H]⁺ 282.9236, found 282.9285.

g. 2-((4-chlorophenyl)thio)-1,3,2-dithiaphospholane 2-sulfide (Compound 2-7)

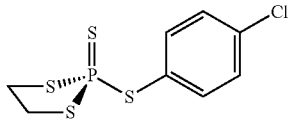

compound 2-7

The title compound was prepared using method B and LG-H is 4-chlorobenzenethiol. $^1$H NMR (600 MHz, Chloroform-d) δ 7.58 (d, J=8.5 Hz, 2H), 7.39 (dd, J=8.6, 0.9 Hz, 2H), 3.68-3.54 (m, 2H), 3.36-3.18 (m, 2H). 13C NMR (151 MHz, Chloroform-d) δ 137.69 (d, J=4.8 Hz), 137.31 (d, J=5.2 Hz), 129.65 (d, J=3.8 Hz), 128.94 (d, J=8.2 Hz), 42.92. 31P NMR (202 MHz, Chloroform-d) δ 107.82. HRMS (ESI-TOF) m/z Calcd for $C_8H_9ClPS_4^+$ [M+H]$^+$ 298.9008, found 298.9022.

h. 2-(perfluorophenoxy)-1,3,2-dithiaphospholane 2-sulfide (Compound 2-8)

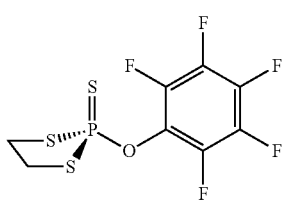

compound 2-8

The title compound was prepared using method B and LG-H is pentafluorophenol. $^1$H NMR (500 MHz, Chloroform-d) δ 3.89-3.76 (m, 4H). $^{13}$C NMR (151 MHz, Chloroform-d) δ 142.05 (m), 139.26 (m), 138.04 (m), 125.94 (d, J=14.8 Hz), 42.41. $^{31}$P NMR (202 MHz, Chloroform-d) δ 127.31 (p, J=17.8 Hz). HRMS (ESI-TOF) m/z Calcd for $C_8H_9ClPS_4^+$ [M+H]$^+$ 298.9008, found 298.9022.

i. 2-((perfluorophenyl)thio)-1,3,2-dithiaphospholane 2-sulfide (Compound 2-9)

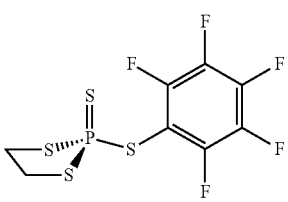

compound 2-9

The title compound was prepared using method B and LG-H is 2,3,4,5,6-pentafluorobenzenethiol. $^1$H NMR (600 MHz, Chloroform-d) δ 3.81-3.63 (m, 4H). $^{13}$C NMR (151 MHz, Chloroform-d) δ 148.30 (ddt, J=250.7, 11.1, 4.1 Hz), 143.27 (dddt, J=259.3, 13.6, 9.0, 4.7 Hz), 138.16 (m), 105.78 (m), 43.00. 31P NMR (202 MHz, Chloroform-d) δ 103.71. HRMS (ESI-TOF) m/z Calcd for $C_8H_5F_5PS_4^+$ [M+H]$^+$ 354.8926, found 354.8935.

j. 2-(4-methoxyphenoxy)-1,3,2-dithiaphospholane 2-sulfide (Compound 2-10)

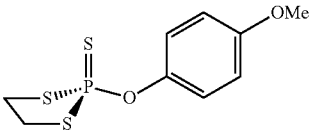

compound 2-10

The title compound was prepared using method B and LG-H is 4-methoxyphenol. $^1$H NMR (600 MHz, Chloroform-d) δ 7.21-7.15 (m, 2H), 6.89-6.83 (m, 2H), 3.80 (s, 3H), 3.73-3.64 (m, 2H), 3.61-3.53 (m, 2H). 13C NMR (126 MHz, Chloroform-d) δ 157.43 (d, J=2.9 Hz), 144.64 (d, J=13.4 Hz), 123.09 (d, J=4.8 Hz), 114.56 (d, J=2.8 Hz), 55.71, 41.95. 31P NMR (202 MHz, Chloroform-d) δ 120.24 (ddd, J=32.0, 18.0, 13.7 Hz). HRMS (ESI-TOF) m/z Calcd for $C_9H_{12}O_2PS_3^+$ [M+H]$^+$ 278.9732, found 278.9755.

k. 2-((4-methoxyphenyl)thio)-1,3,2-dithiaphospholane 2-sulfide (Compound 2-11)

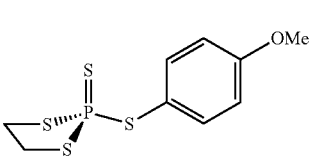

compound 2-11

The title compound was prepared using method B and LG-H is 4-methoxybenzenethiol. $^1$H NMR (500 MHz, Chloroform-d) δ 7.61-7.54 (m, 2H), 6.95-6.89 (m, 2H), 3.84 (s, 3H), 3.61-3.49 (m, 2H), 3.22-3.11 (m, 2H). 13C NMR (151 MHz, Chloroform-d) δ 161.67 (d, J=4.1 Hz), 138.22 (d, J=4.4 Hz), 121.36 (d, J=7.9 Hz), 114.89 (d, J=3.5 Hz), 55.58, 42.94. 31P NMR (202 MHz, Chloroform-d) δ 110.45-109.95 (m). HRMS (ESI-TOF) m/z Calcd for $C_9H_{12}OPS_4^+$ [M+H]$^+$ 294.9503, found 294.9527.

l. 2-(4-(trifluoromethyl)phenoxy)-1,3,2-dithiaphospholane 2-sulfide (Compound 2-12)

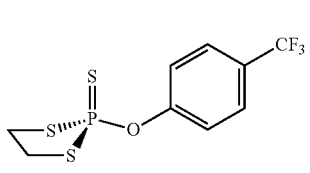

compound 2-12

The title compound was prepared using method B and LG-H is 4-(trifluoromethyl)phenol. $^1$H NMR (400 MHz, Chloroform-d) δ 7.64 (d, J=8.4 Hz, 2H), 7.42-7.33 (m, 2H), 3.83-3.61 (m, 4H). 13C NMR (151 MHz, Chloroform-d) δ 152.85 (d, J=13.0 Hz), 127.51 (qd, J=33.0, 2.7 Hz), 126.45 (p, J=3.6 Hz), 123.36 (d, J=272.2 Hz), 121.90 (d, J=5.1 Hz), 41.42. 31P NMR (202 MHz, Chloroform-d) δ 119.58 (p, J=16.3 Hz). HRMS (ESI-TOF) m/z Calcd for $C_9H_9F_3OPS_3^+$ [M+H]$^+$ 316.9500, found 316.9515.

m. 4-((2-sulfido-1,3,2-dithiaphospholan-2-yl)oxy)benzonitrile (Compound 2-13)

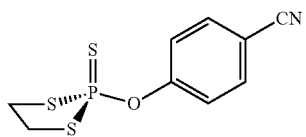
compound 2-13

The title compound was prepared using method B and LG-H is 4-hydroxybenzonitrile. $^1$H NMR (600 MHz, Chloroform-d) δ 7.75-7.63 (m, 2H), 7.37 (dd, J=8.9, 2.0 Hz, 2H), 3.84-3.63 (m, 4H). $^{13}$C NMR (151 MHz, Chloroform-d) δ 154.19 (d, J=12.6 Hz), 133.95 (d, J=2.6 Hz), 123.12 (d, J=5.3 Hz), 118.29 (d, J=1.3 Hz), 109.81 (d, J=2.7 Hz), 42.05. 31P NMR (202 MHz, Chloroform-d) δ 119.80 (p, J=17.3, 16.7 Hz). HRMS (ESI-TOF) m/z Calcd for $C_9H_9NOPS_3^+$ [M+H]$^+$ 273.9578, found 273.9587.

n. 2-(4-fluorophenoxy)-1,3,2-dithiaphospholane 2-sulfide (Compound 2-14)

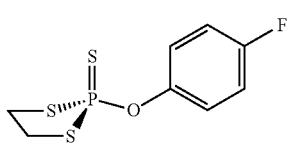
compound 2-14

The title compound was prepared using method B and LG-H is 4-fluorophenol. $^1$H NMR (500 MHz, Chloroform-d) δ 7.25-7.19 (m, 2H), 7.08-7.01 (m, 2H), 3.78-3.67 (m, 2H), 3.67-3.58 (m, 2H). 13C NMR (151 MHz, Chloroform-d) δ 160.38 (dd, J=244.9, 3.2 Hz), 146.85 (dd, J=13.3, 2.6 Hz), 123.61 (dd, J=8.5, 4.9 Hz), 116.30 (dd, J=23.6, 2.4 Hz), 41.98. 31P NMR (202 MHz, Chloroform-d) δ 120.62-120.08 (m). HRMS (ESI-TOF) m/z Calcd for $C_8H_9FOPS_3^+$ [M+H]$^+$ 266.9532, found 266.9544.

o. 2-(3,5-difluorophenoxy)-1,3,2-dithiaphospholane 2-sulfide (Compound 2-15)

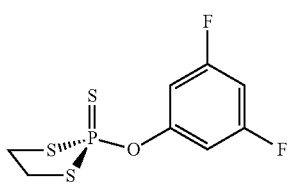
compound 2-15

The title compound was prepared using method B and LG-H is 3,5-difluorophenol. $^1$H NMR (400 MHz, Chloroform-d) δ 6.84 (dt, J=7.6, 2.3 Hz, 2H), 6.76-6.66 (m, 1H), 3.84-3.61 (m, 4H). 13C NMR (151 MHz, Chloroform-d) δ 163.04 (ddd, J=249.4, 14.9, 2.4 Hz), 152.08 (q, J=13.7 Hz), 106.35 (dd, J=28.6, 5.8 Hz), 101.84 (td, J=25.3, 2.4 Hz), 42.01. 31P NMR (202 MHz, Chloroform-d) δ 119.91 (p, J=16.7, 16.3 Hz). HRMS (ESI-TOF) m/z Calcd for $C_8H_8F_2OPS_3^+$ [M+H]$^+$ 284.9437, found 284.9449.

p. 2-(3,5-bis(trifluoromethyl)phenoxy)-1,3,2-dithiaphospholane 2-sulfide (Compound 2-16)

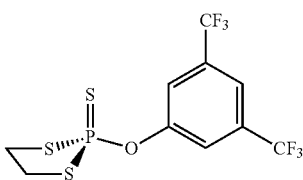
compound 2-16

The title compound was prepared using method B and LG-H is 3,5-bis(trifluoromethyl)phenol. $^1$H NMR (500 MHz, Chloroform-d) δ 7.78-7.73 (m, 1H), 7.71 (d, J=1.8 Hz, 2H), 3.88-3.67 (m, 4H). 13C NMR (151 MHz, Chloroform-d) δ 151.33 (d, J=12.4 Hz), 133.02 (m), 122.91 (m), 122.83 (d, J=1.8 Hz), 119.64 (q, J=3.7 Hz), 42.12. $^{31}$P NMR (202 MHz, Chloroform-d) δ 121.42 (t, J=16.6 Hz). HRMS (ESI-TOF) m/z Calcd for $C_8H_8F_2OPS_3^+$ [M+H]$^+$ 284.9437, found 284.9449.

q. 2-(3,4,5-trifluorophenoxy)-1,3,2-dithiaphospholane 2-sulfide (Compound 2-17)

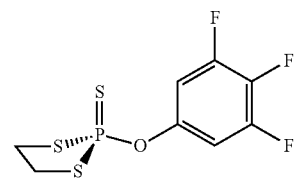
compound 2-17

The title compound was prepared using method B and LG-H is 3,4,5-trifluorophenol. $^1$H NMR (400 MHz, Chloroform-d) δ 6.95 (ddd, J=8.0, 5.8, 2.2 Hz, 2H), 3.84-3.64 (m, 4H). $^{13}$C NMR (151 MHz, Chloroform-d) δ 151.13 (dddd, J=251.3, 11.4, 5.4, 2.6 Hz), 145.45 (m), 138.49 (m), 107.59 (dt, J=19.2, 5.2 Hz), 42.03. 31P NMR (202 MHz, Chloroform-d) δ 121.62-120.89 (m). HRMS (ESI-TOF) m/z Calcd for $C_8H_7F_3OPS_3^+$ [M+H]$^+$ 302.9343, found 302.9361.

r. 2-(2,4,6-tribromophenoxy)-1,3,2-dithiaphospholane 2-sulfide (Compound 2-18)

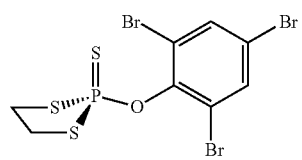
compound 2-18

The title compound was prepared using method B and LG-H is 2,4,6-tribromophenol. $^1$H NMR (600 MHz, Chloroform-d) δ 7.70 (d, J=0.9 Hz, 2H), 3.84-3.70 (m, 4H). $^{13}$C NMR (151 MHz, Chloroform-d) δ 147.43 (d, J=14.6 Hz), 134.93 (d, J=2.7 Hz), 119.84 (d, J=5.5 Hz), 119.16 (d, J=3.9

Hz), 42.16. $^{31}$P NMR (202 MHz, Chloroform-d) δ 124.00 (p, J=18.7 Hz). HRMS (ESI-TOF) m/z Calcd for $C_8H_7Br_3OPS_3^+$ [M+H]$^+$ 482.6941, found 482.6960.

s. 2-(perchlorophenoxy)-1,3,2-dithiaphospholane 2-sulfide (Compound 2-19)

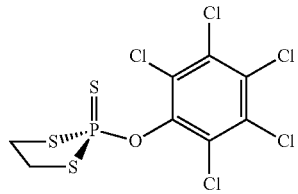

compound 2-19

The title compound was prepared using method B and LG-H is 2,3,4,5,6-pentachlorophenol. $^1$H NMR (600 MHz, Chloroform-d) δ 3.87-3.75 (m, 4H). $^{13}$C NMR (151 MHz, Chloroform-d) δ 145.56 (d, J=14.4 Hz), 131.95 (d, J=3.6 Hz), 130.92 (d, J=3.8 Hz), 128.88 (d, J=5.4 Hz), 42.29. $^{31}$P NMR (202 MHz, Chloroform-d) δ 125.13 (m). HRMS (ESI-TOF) m/z Calcd for $C_8H_7Br_3OPS_3^+$ [M+H]$^+$ 482.6941, found 482.6960.

t. 2-phenoxy-1,3,2-dithiaphosphinane 2-sulfide (Compound 2-20)

compound 2-20

The title compound was prepared using method B and LG-H is phenol and dithiol is propane-1, 3-dithiol. $^1$H NMR (500 MHz, Chloroform-d) δ 7.41-7.31 (m, 4H), 7.25-7.20 (m, 1H), 3.53-3.41 (m, 2H), 3.17-3.01 (m, 2H), 2.40-2.30 (m, 1H), 2.21-2.09 (m, 1H). $^{13}$C NMR (151 MHz, Chloroform-d) δ 150.76 (d, J=12.2 Hz), 129.76 (d, J=2.2 Hz), 125.74 (d, J=2.8 Hz), 121.46 (d, J=5.8 Hz), 32.63 (d, J=4.5 Hz), 24.43 (d, J=5.0 Hz). $^{31}$P NMR (202 MHz, Chloroform-d) δ 82.11 (tt, J=26.5, 8.1 Hz). HRMS (ESI-TOF) m/z Calcd for $C_9H_{12}OPS_3^+$ [M+H]$^+$ 262.9782, found 262.9800.

u. 2-(4-bromophenoxy)-1,3,2-dithiaphosphinane 2-sulfide (Compound 2-21)

compound 2-21

The title compound was prepared using method B and LG-H is 4-bromophenol and dithiol is propane-1, 3-dithiol. $^1$H NMR (600 MHz, Chloroform-d) δ 7.51-7.46 (m, 2H), 7.24-7.20 (m, 2H), 3.48-3.39 (m, 2H), 3.16-3.05 (m, 2H), 2.39-2.31 (m, 1H), 2.20-2.09 (m, 1H). $^{13}$C NMR (151 MHz, Chloroform-d) δ 149.71 (d, J=12.2 Hz), 132.78 (d, J=2.1 Hz), 123.28 (d, J=5.8 Hz), 118.89 (d, J=2.8 Hz), 32.63 (d, J=4.6 Hz), 24.30 (d, J=5.1 Hz). $^{31}$P NMR (202 MHz, Chloroform-d) δ 82.85 (ddt, J=26.5, 15.3, 8.0 Hz). HRMS (ESI-TOF) m/z Calcd for $C_9H_{11}BrOPS_3^+$ [M+H]$^+$ 340.8888, found 340.8897.

iii. Method C

Compound 2-9 was also prepared by Method C. The procedure below is for the purpose of illustration.

Compound 2-9

Intermediate 2-vii: To a slurry of phosphorus pentasulfide (20 g, 90 mmol, 1.0 equiv) in dichloromethane (100 mL) was charged pentafluorophenol (33 g, 180 mmol, 2.0 equiv.) under nitrogen atmosphere. Triethylamine (27 mL, 189 mmol, 2.1 equiv.) was then added over a period of 20 min. The mixture was heated at 40° C., and held at the temperature for 5 h, then cooled to ambient temperature. A mixture of MTBE and hexanes (1:1, 200 mL) was added. The resulting mixture was washed with water (200 mL×2), and concentrated to about 60 mL under vacuum. MeOH (100 mL) was added, and the resulting mixture was concentrated to about 60 mL. MeOH (50 mL) and hexanes (45 mL) were added. Water (30 mL) was then slowly added over a period of 25 min. The resulting mixture was agitated at ambient temperature for 1.5 h prior to filtration. The resulting filter cake was washed with a mixture of MeOH/water (7:3; 30 mL×2), then hexanes (25 mL×2), providing intermediate 2-vii as white solids (38 g, 76%). M.p.: 103° C. $^1$H NMR (400 MHz, CHLOROFORM-d) δ 8.79 (s, br, 1H), 3.29 (qd, J=7.3, 5.3 Hz, 6H), 1.42 (t, J=7.3 Hz, 9H). $^{13}$C NMR (101 MHz, CHLOROFORM-d) δ 143.3, 140.9, 139.3, 136.8, 46.6, 8.5. $^{31}$P NMR (162 MHz, CHLOROFORM-d) δ 114.9 (s, 1P). $^{19}$F NMR (376 MHz, CHLOROFORM-d) 6-150.94 (m, 4F), −161.53 (m, 2F), −164.08 (m, 4F). HRMS (M−H)−: calc. for $C_{12}F_{10}O_2PS_2$ 460.8918, found 460.8919.

Compound 2-9: To a mixture of 2-vii (10.0 g, 17.8 mmol, 1.0 equiv.) and ethylene sulfide (2.32 mL, 39.1 mmol, 2.2 equiv.) in dichloromethane (60 mL) was added trifluoroacetic acid (4.08 mL, 53.3 mmol, 3.0 equiv.) at ambient temperature. The reaction mixture was stirred at the temperature for 16 h, followed by addition of heptane (120 mL) and water (100 mL). After 20 min agitation, the mixture was filtered to remove the resulting white solids of thiirane polymers. The separated organic phase from the filtrate was treated with 10% aqs. $K_2HPO_4$ solution (100 mL) and triethylamine (0.013 mL, 0.5 M %) for 10 min, aqueous phase was then removed. The organic layer was mixed again with aqs. 10% $K_2HPO_4$ solution (150 mL) until completion of the conversion to the product by HPLC or $^{31}$P NMR analysis. The isolated organic layer was washed with 0.5 M aqs. $H_3PO_4$ solution (50 mL) and aqs. 10% $KH_2PO_4$ solution (50 mL), respectively. The organic stream was then filtered through an anhydrous $MgSO_4$ pad, and the resulting filtrate was concentrated under vacuum to ~35 mL. Solids were formed during the concentration. The resulting slurry was cooled to 0° C., agitated for 0.5 h, and filtered. The filter cake was washed with cold heptane (10 mL×2), providing 4.35 g of Compound 2-9 as white solids in 71% yield.

Example 4

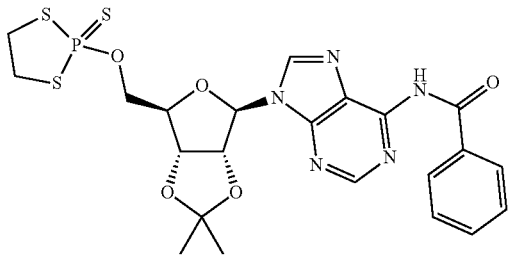 [SMILES: CC1(C)O[C@@H]2[C@H](O1)[C@@H](COP1(=S)SCCS1)O[C@H]2n1cnc2c(NC(=O)c3ccccc3)ncnc21]

N-(9-((3aR,4R,6R,6aR)-2,2-dimethyl-6-(((2-sulfido-1,3,2-dithiaphospholan-2-yl)oxy)methyl)tetrahydrofuro[3,4-d][1,3]dioxol-4-yl)-9H-purin-6-yl)benzamide (Compound 4-46)

N-(9-((3aR,4R,6R,6aR)-6-(hydroxymethyl)-2,2-dimethyltetrahydrofuro[3,4-d][1,3]dioxol-4-yl)-9H-purin-6-yl)benzamide (0.50 mmol) and 2-(4-nitrophenoxy)-1,3,2-dithiaphospholane 2-sulfide (1.00 mmol) were dissolved in acetonitrile (0.10 M) and cooled to 0° C. To this was added 4-dimethylaminopyridine (DMAP) (1.00 mmol) and the reaction was allowed to stir for 1 hour at this temperature. The acetonitrile was removed in vacuo and the resulting residue was applied to silica gel. The product was eluted with dichloromethane/acetone (10:1) affording the title compound (0.29 mmol, 58% yield) as a white solid. The reaction can be represented by the following scheme:

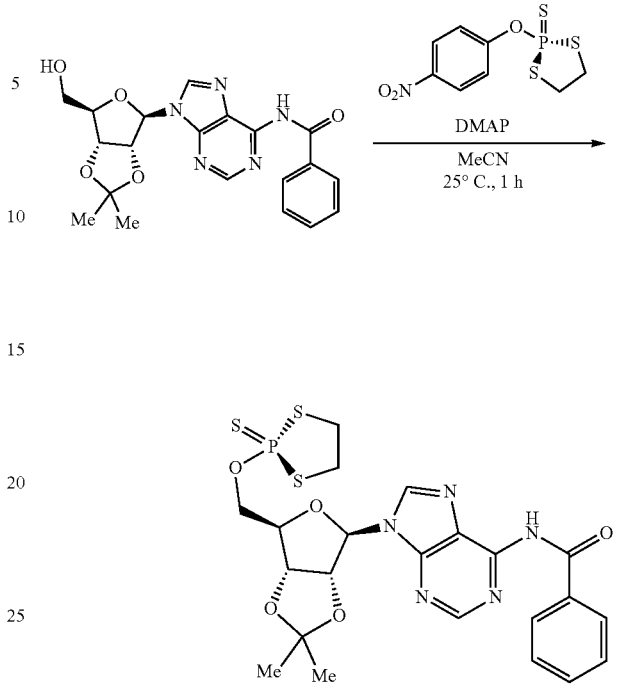

Example 5

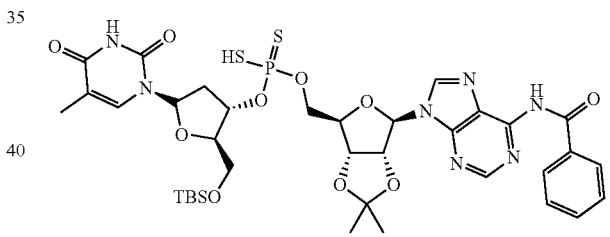

O-(((3aR,4R,6R,6aR)-6-(6-benzamido-9H-purin-9-yl)-2,2-dimethyltetrahydrofuro[3,4-d][1,3]dioxol-4-yl)methyl)O-((2R,3S,5S)-2-(((tert-butyldimethylsilyl)oxy)methyl)-5-(5-methyl-2,4-dioxo-3,4-dihydropyrimidin-1(2H)-yl)tetrahydrofuran-3-yl) S-hydrogen phosphorodithioate (Compound 5-13)

1-((2S,4S,5R)-5-(((tert-butyldimethylsilyl)oxy)methyl)-4-hydroxytetrahydrofuran-2-yl)-5-methylpyrimidine-2,4 (1H,3H)-dione (1.00 mmol) and N-(9-((3aR,4R,6R,6aR)-2,2-dimethyl-6-(((2-sulfido-1,3,2-dithiaphospholan-2-yl)oxy)methyl)tetrahydrofuro[3,4-d][1,3]dioxol-4-yl)-9H-purin-6-yl)benzamide (0.50 mmol) were dissolved in acetonitrile (0.10 M). To this was added DBU (1.50 mmol) and the reaction was allowed to stir for 1 hour. The acetonitrile was removed in vacuo and the resulting residue was applied to silica gel. The product was eluted with dichloromethane/methanol (10:1) affording the title compound (0.34 mmol, 68% yield) as a white solid. The reaction can be represented by the following scheme:

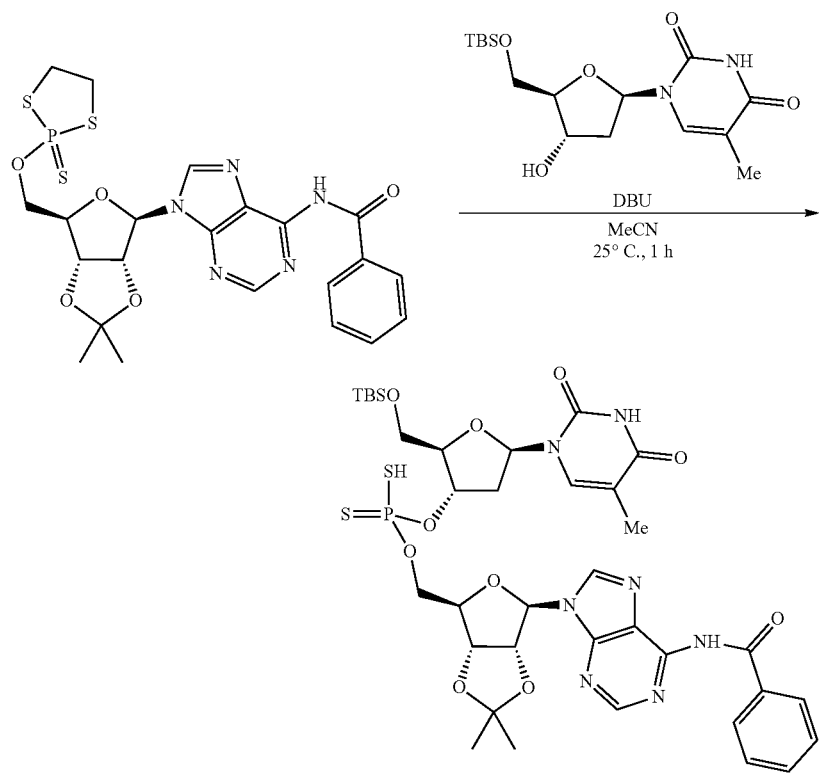

Example 6

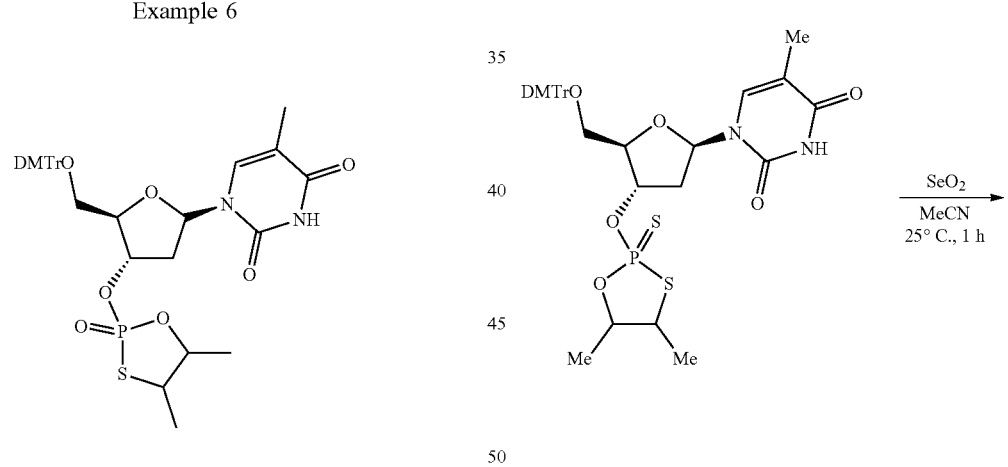

1-((2S,4S,5R)-5-((bis(4-methoxyphenyl)(phenyl)methoxy)methyl)-4-((4,5-dimethyl-2-oxido-1,3,2-oxathiaphospholan-2-yl)oxy)tetrahydrofuran-2-yl)-5-methylpyrimidine-2,4(1H,3H)-dione (Compound 3-127)

To a solution of 1-((2S,4S,5R)-5-((bis(4-methoxyphenyl)(phenyl)methoxy) methyl)-4-((4,5-dimethyl-2-sulfido-1,3,2-oxathiaphospholan-2-yl)oxy)tetrahydrofuran-2-yl)-5-methylpyrimidine-2,4(1H,3H)-dione (0.26 mmol) in acetonitrile (0.10 M) was added selenium dioxide (0.52 mmol). The reaction was allowed to stir for one hour. The reaction was filtered through celite and the solvent removed in vacuo affording the title compound (0.25 mmol, 96% yield) as a white solid. The reaction can be represented by the following scheme:

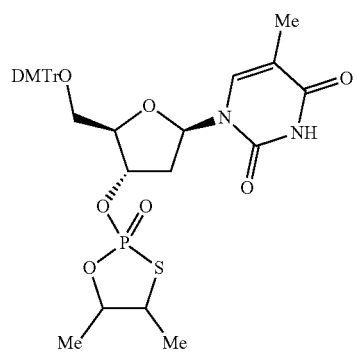

Example 7

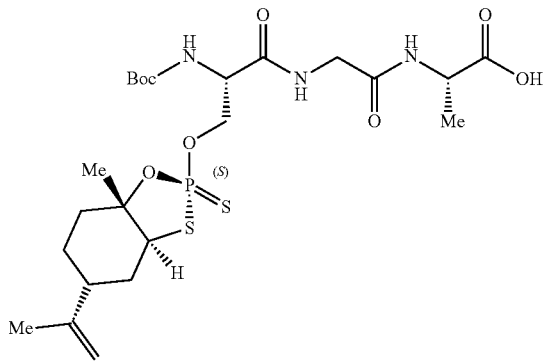

N-(tert-butoxycarbonyl)-O-((2S,3aS,5R,7aS)-7a-methyl-5-(prop-1-en-2-yl)-2-sulfidohexahydrobenzo[d][1,3,2]oxathiaphosphol-2-yl)-L-serylglycyl-L-alanine (Compound 7-8)

Resin bound peptide was prepared under standard Fmoc-SPPS conditions. To the resin bound peptide (0.010 mmol) was added (2S,3aS,5R,7aS)-7a-methyl-2-((perfluorophenyl)thio)-5-(prop-1-en-2-yl)hexahydrobenzo[d][1,3,2]oxathiaphosphole 2-sulfide (0.10 mmol) followed by triethylamine (0.10 mmol), DMAP (0.00010 mmol) and acetonitrile (0.10 M). This was agitated for 2 hours. Following standard washings and cleavage from resin, the phosphorylated peptide was isolated upon concentration.

Example 8

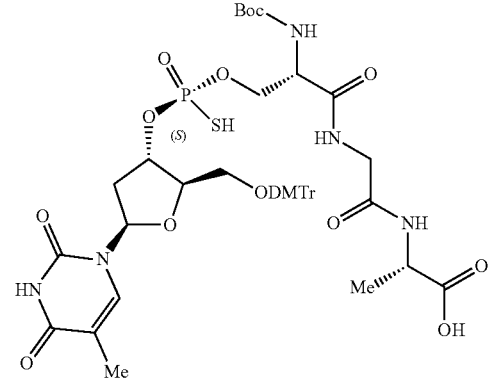

O—((S)-(((2R,3S,5R)-2-((bis(4-methoxyphenyl)(phenyl)methoxy)methyl)-5-(5-methyl-2,4-dioxo-3,4-dihydropyrimidin-1(2H)-yl)tetrahydrofuran-3-yl)oxy)(mercapto)phosphoryl)-N-(tert-butoxycarbonyl)-L-serylglycyl-L-alanine (Compound 7-1)

Resin bound peptide was prepared under standard Fmoc-SPPS conditions. To the resin bound peptide (0.010 mmol) was added 1-((2R,4S,5R)-5-((bis(4-methoxyphenyl)(phenyl)methoxy) methyl)-4-(((2S,3aR,5S,7aR)-7a-methyl-5-(prop-1-en-2-yl)-2-sulfidohexahydrobenzo[d] [1,3,2]oxathiaphosphol-2-yl)oxy)tetrahydrofuran-2-yl)-5-methylpyrimidine-2,4(1H,3H)-dione (0.030 mmol) followed by DBU (0.03 mmol) and acetonitrile (0.10 M). This was agitated for 3 hours. Following standard washings and cleavage from resin, the phosphorylated peptide was isolated upon concentration.

Example 9

Synthesis of Pentamer (Compound 5-15)

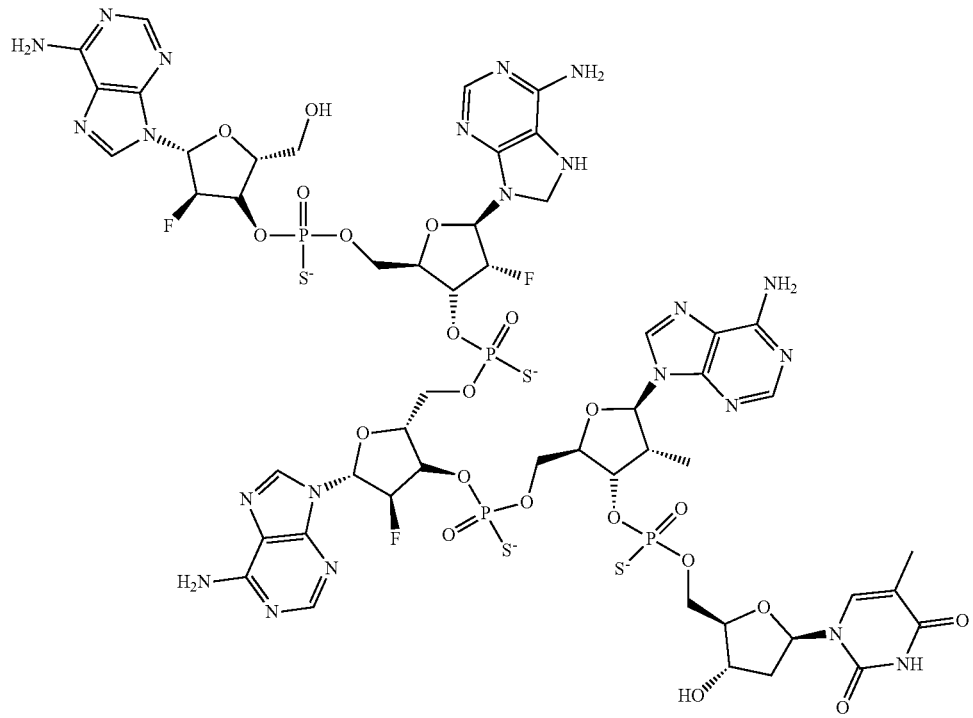

O-((2R,3R,4R,5R)-2-((((((2R,3S,4R,5R)-2-((((((2R,3R,4R,5R)-5-(6-amino-7,8-dihydro-9H-purin-9-yl)-2-((((((2R,3S,4R,5R)-5-(6-amino-9H-purin-9-yl)-4-fluoro-2-(hydroxymethyl)tetrahydrofuran-3-yl)oxy)sulfidophosphoryl)oxy)methyl)-4-fluorotetrahydrofuran-3-yl)oxy)sulfidophosphoryl)oxy)methyl)-5-(6-amino-9H-purin-9-yl)-4-fluorotetrahydrofuran-3-yl)oxy)sulfidophosphoryl)oxy)methyl)-5-(6-amino-9H-purin-9-yl)-4-fluorotetrahydrofuran-3-yl)O-(((2R,3S,5R)-3-hydroxy-5-(5-methyl-2,4-dioxo-3,4-dihydropyrimidin-1(2H)-yl)tetrahydrofuran-2-yl)methyl) phosphorothioate Step 1: Synthesis of Dimer 9-iii

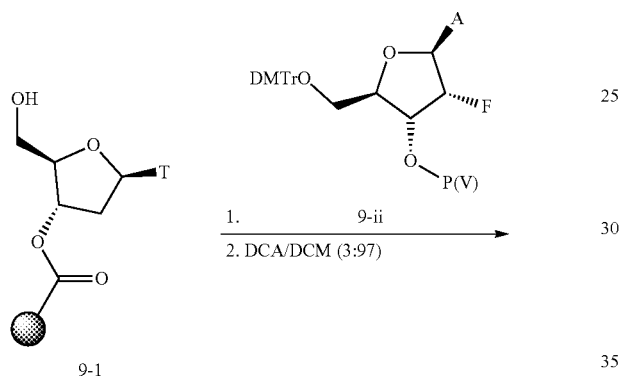

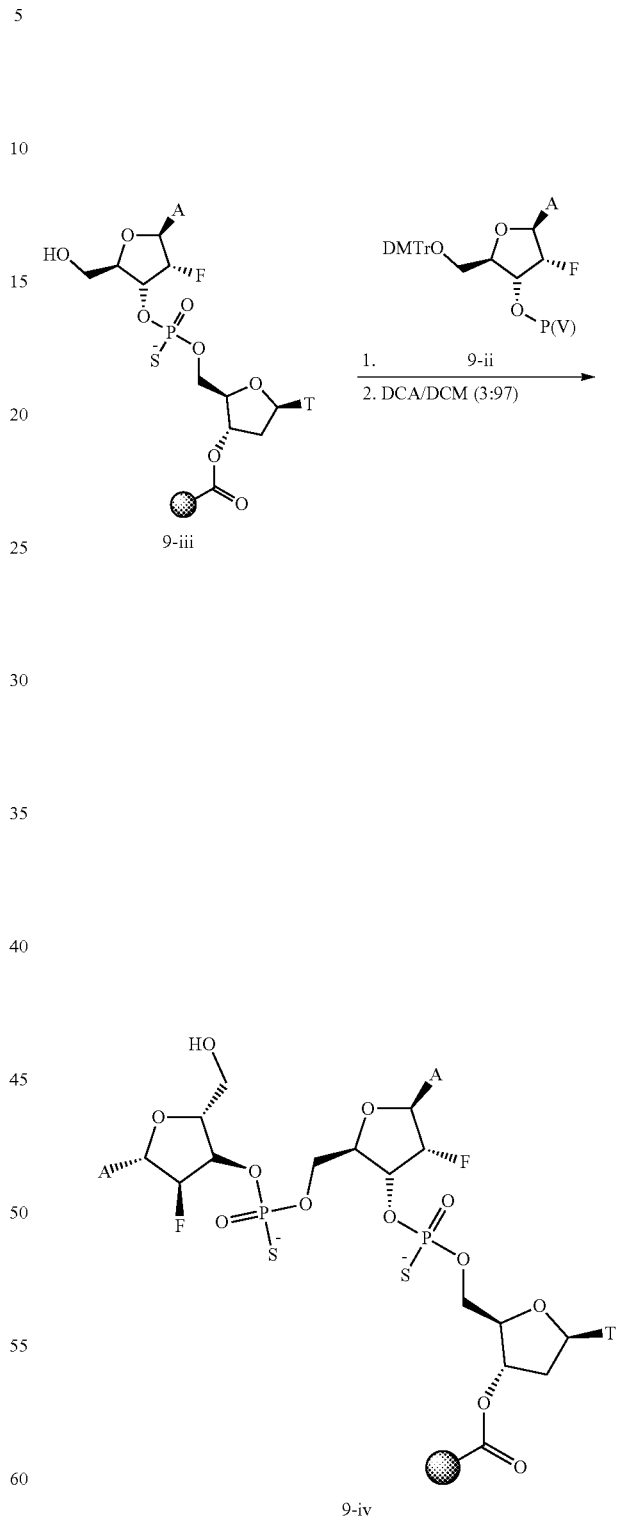

To a deprotected resin bound dT-Q-CPG (9-i, 5 umol, 98 mg) in a solid-phase peptide synthesizer (SPPS) vessel was added 20 equiv. of dry reagent P(V) reagent (9-ii). Reagent (9-ii) is made in a manner similar to the intermediate made in Example 2(a), substituting a protected deoxyadenine nucleoside for the protected deoxythymidine. Then 40 equiv. of DBU and MeCN [0.1 M relative to resin-bound substrate] were drawn into vessel. The vessel was agitated on a shaker for 6 hours. The resulted resin was deprotected with DCA/DCM (3:97, vol:vol) to afford a resin bound dimer 9-iii.

Step 2: Synthesis of Trimer 9-iv

The procedure to make a resin bound trimer 9-iv is same as step 1 above except that the starting material is resin bound dimer 9-iii in this step and the reaction was agitated on a shaker for 12 h.

Step 3: Synthesis of Tetramer 9-v
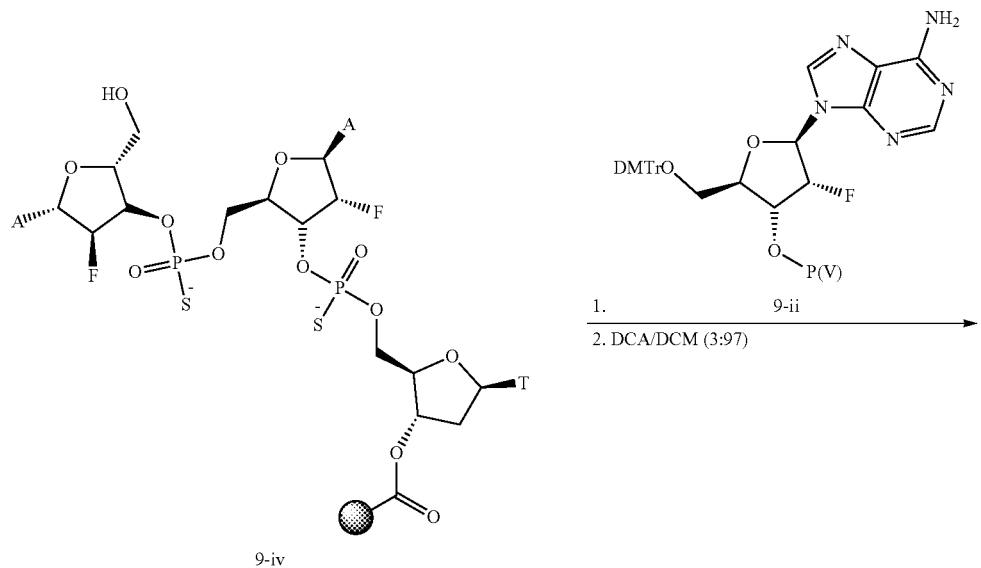
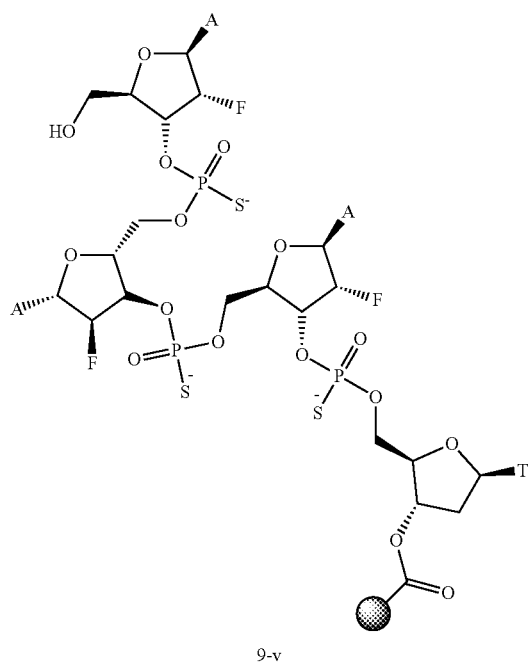

The procedure to make a resin bound tetramer 9-v is same as step 1 above except that the starting material is resin bound trimer 9-iv in this step and the reaction was agitated on a shaker for 5 h.
Step 4: Synthesis of Pentamer (Compound 5-15)
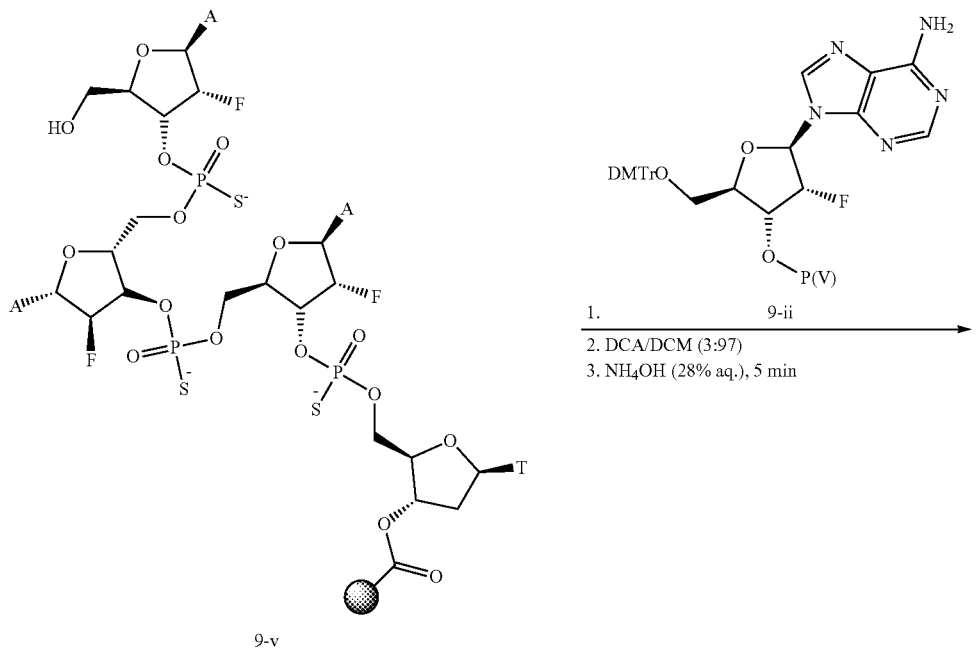
9-v
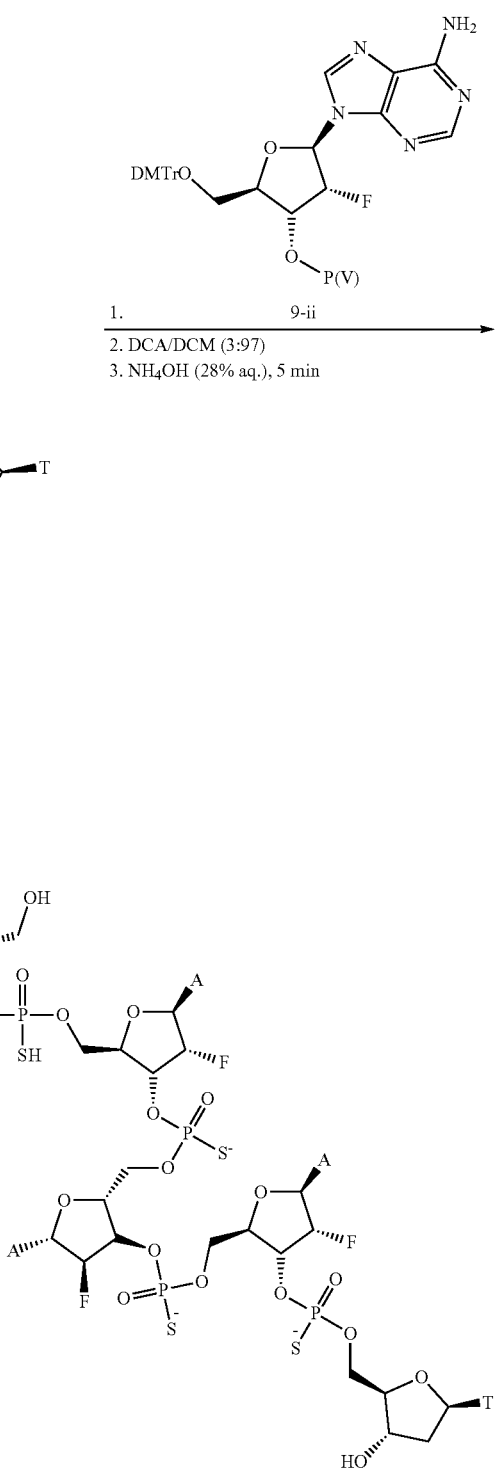
compound 5-15

The procedure to make resin-bound pentamer (compound 5-15) is same as step 1 above except that the starting material is resin bound tetramer 9-v and the reaction was agitated on a shaker for 4.5 h. After resin bound pentamer (compound 5-15) was obtained, it was cleaved from the resin with NH₄OH (28% aq.) for 5 min. The crude material was purified on a Waters Autopurification LC with a Waters BEH C18 column (19×150 mm, 5 m) using a 0.1 M aqueous ammonium formate:acetonitrile gradient (30 mL/min) at ambient temperature. HPLC analysis showed an expected mix of dimer, trimer, tetramer, and pentamer. The HPLC retention time of dimer, trimer, tetramer, and pentamer is 3.86 min, 4.52 min, 5.54 min, 6.71 min, respectively.

Example 10

Synthesis of Pentamer (Compound 5-16)

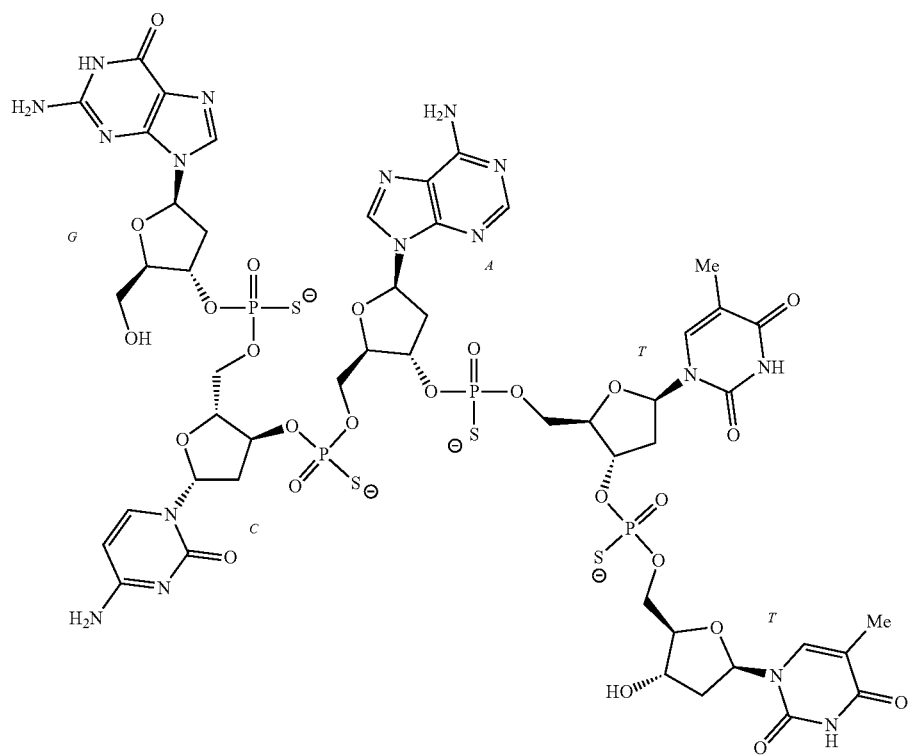

O-((2R,3S,5R)-2-(((((2R,3R,5R)-2-(((((2R,3S,5R)-5-(4-amino-2-oxopyrimidin-1(2H)-yl)-2-(((((2R,3R,5R)-5-(2-amino-6-oxo-1,6-dihydro-9H-purin-9-yl)-2-(hydroxymethyl)tetrahydrofuran-3-yl)oxy)sulfidophosphoryl)oxy)methyl)tetrahydrofuran-3-yl)oxy)sulfidophosphoryl)oxy)methyl)-5-(6-amino-9H-purin-9-yl)tetrahydrofuran-3-yl)oxy)sulfidophosphoryl)oxy)methyl)-5-(5-methyl-2,4-dioxo-3,4-dihydropyrimidin-1(2H)-yl)tetrahydrofuran-3-yl)O-(((2R,3S,5R)-3-hydroxy-5-(5-methyl-2,4-dioxo-3,4-dihydropyrimidin-1(2H)-yl)tetrahydrofuran-2-yl)methyl) phosphorothioate (Compound 5-16)

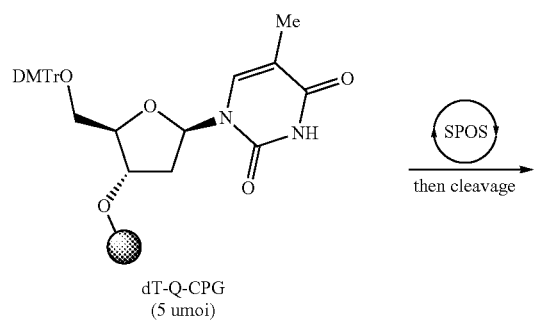

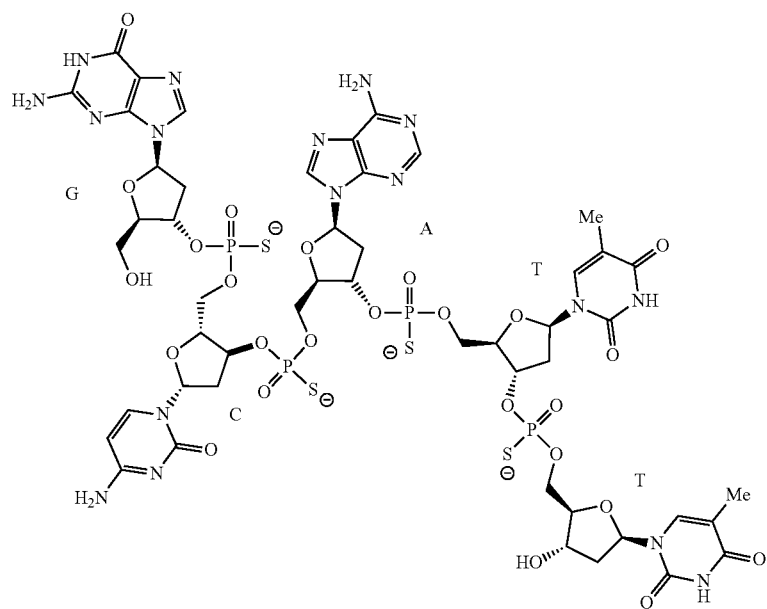

The procedure to make compound 5-16 is same as the procedure to make compound 5-15 except that the nucleotide reagents were changed correspondingly in each step and the reaction to make the resin bound tetramer was agitated on a shaker for 3 h.

Example 11

Stereoselective Synthesis of a CDN (Ammonium Salt of Compound 6-22)

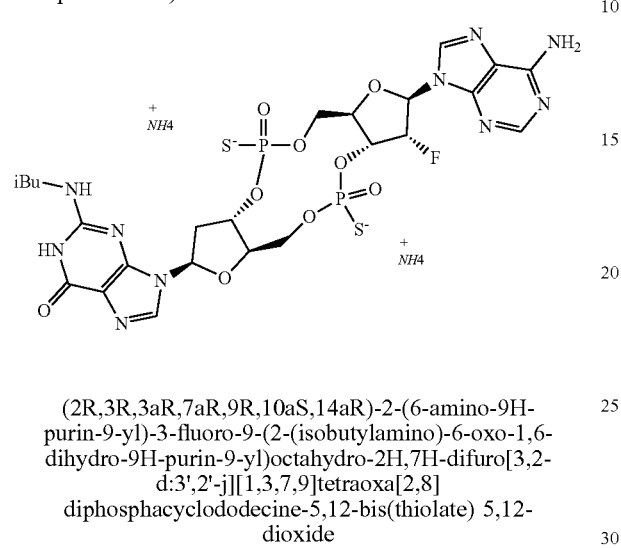

(2R,3R,3aR,7aR,9R,10aS,14aR)-2-(6-amino-9H-purin-9-yl)-3-fluoro-9-(2-(isobutylamino)-6-oxo-1,6-dihydro-9H-purin-9-yl)octahydro-2H,7H-difuro[3,2-d:3',2'-j][1,3,7,9]tetraoxa[2,8]diphosphacyclododecine-5,12-bis(thiolate) 5,12-dioxide Step 1: Synthesis of CDN Precursor 11-iii

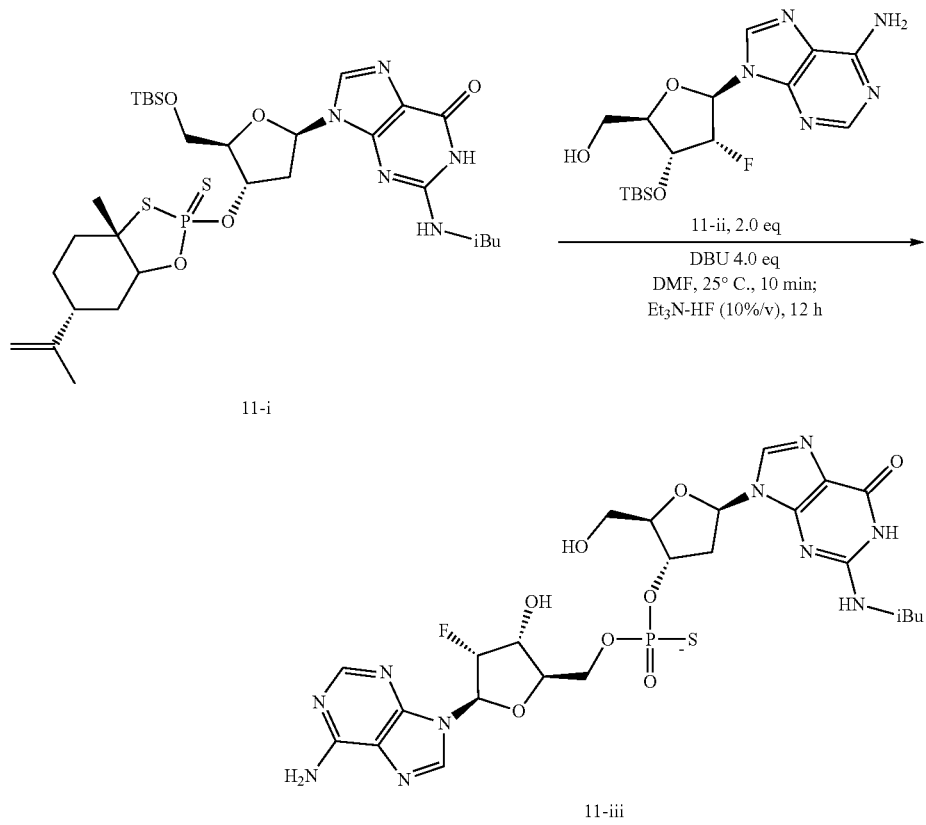

1 eq of 11-i in DMF was mixed with 2 eq. of 11-ii and 4.0 eq. DBU. The mixture was stirred at 25° C. for 10 min. After the reaction was done, triethylammonium fluoride (10%/v) was added and the resulted solution was stirred for 12 hours to afford crude 11-iii, which was purified by HPLC. Retention time in HPLC: 3.56 min. MS spectrum confirmed formation of a single isomer (11-iii) that was also stable to purification.

Step 2: Stereoselective Synthesis of CDN (Ammonium Salt of Compound 6-22)

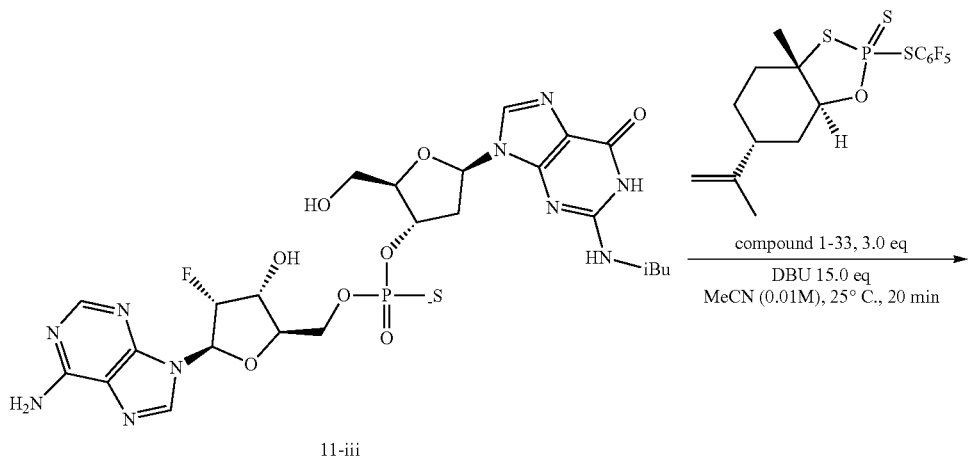

11-iii

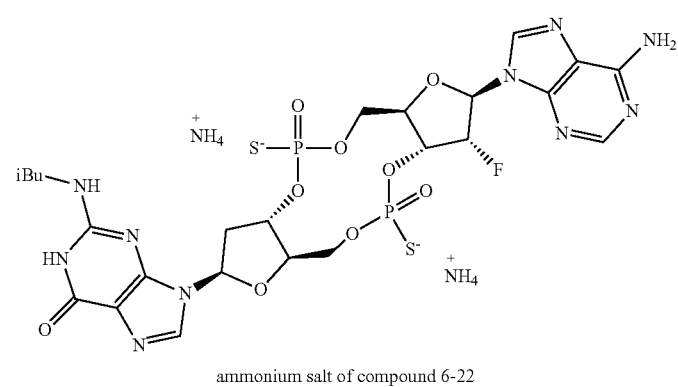

ammonium salt of compound 6-22

To an MeCN solution [0.1 M] of 11-iii, 3 eq. of 10-3 and 15.0 eq of DBU were added. The resulted solution was stirred at 25° C. for 20 min. After the reaction was done, the mixture was subject to HPLC purification affording two diastereomers of CDNs with a ratio of 7:1. The formation of two diastereomers was confirmed by mass spectrometry.

In addition to the above reactions, a base and solvent screen was conducted. It was found that NMI, imidazole, DBU, DMAP (6.0 eq.) DMAP (1.5 eq.) are all suitable bases for the reactions and THF, DMF, and MeCN are suitable solvents for the reactions.

Example 12

Synthesis of Organothiophosphates Using P(S)$_2$ Reagent a. 1-((2R,4S,5R)-5-(((tert-butyldiphenylsilyl)oxy)methyl)-4-((2-sulfido-1,3,2-dithiaphospholan-2-yl)oxy)tetrahydrofuran-2-yl)-5-methylpyrimidine-2,4(1H,3H)-dione (Compound 4-43)

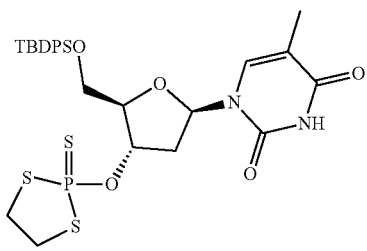

compound 4-43

The scheme to prepare compound 4-43:

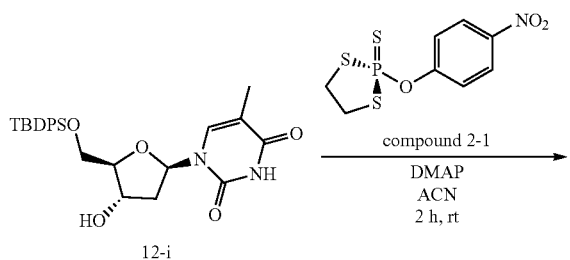

compound 4-43

To a solution of 12-i (0.5 mmol) and compound 2-1 (1.0 equiv.) in MeCN [0.1 M], was added 1.5 equiv. of DMAP. The reaction was stirred at room temperature for 16 h. Isolation by flash column chromatography (1:5 acetone: DCM) afforded compound 4-43 (0.16 g, 54%). $^1$H NMR (600 MHz, CDCl$_3$) δ 8.57 (s, 1H), 7.74-7.60 (m, 4H), 7.54-7.34 (m, 7H), 6.46 (s, 1H), 5.55 (s, 1H), 5.30 (s, 1H), 4.31 (s, 1H), 3.97 (s, 2H), 3.66 (s, 4H), 2.61 (s, 1H), 2.29 (s, 1H), 1.61 (d, J=1.2 Hz, 4H), 1.10 (s, 10H). $^{13}$C NMR (151 MHz, CDCl$_3$) δ 163.56, 150.44, 135.76, 135.39, 135.02, 132.85, 131.95, 130.42, 130.27, 128.30, 128.19, 111.80, 85.66, 85.63, 84.55, 79.20, 79.14, 63.90, 41.98, 41.73, 39.44, 39.41, 27.16, 19.54, 12.18. $^{31}$P NMR (162 MHz, CDCl$_3$) δ 122.41 (h, J=15.9 Hz). M+635.189; Rt.: 8.173 min.

b. 1-((2R,4S,5R)-5-(((tert-butyldimethylsilyl)oxy)methyl)-4-((2-sulfido-1,3,2-dithiaphospholan-2-yl)oxy)tetrahydrofuran-2-yl)-5-methylpyrimidine-2,4(1H,3H)-dione (Compound 4-1)

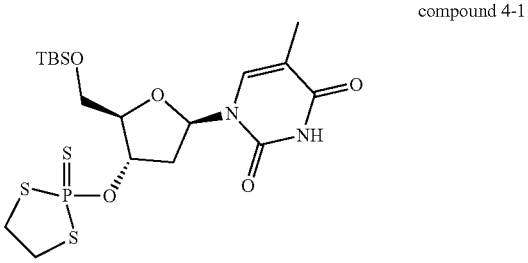 [SMILES: Cc1cn([C@H]2C[C@H](OP3(=S)SCCS3)[C@@H](CO[Si](C)(C)C(C)(C)C)O2)c(=O)[nH]c1=O]

compound 4-1

A vial was flame-dried and allowed to cool under vacuum. The vial was then placed under inert Ar atmosphere via balloon. NO$_2$-dithiaphospholane (compound 2-1, 2.0 equiv, 16.5 mg, 0.056 mmol) and 1-((2R,4S,5R)-5-(((tert-butyldimethylsilyl)oxy)methyl)-4-hydroxytetrahydrofuran-2-yl)-5-methylpyrimidine-2,4(1H,3H)-dione (1.0 equiv, 10.0 mg, 0.028 mmol) were added to the flask. Anhydrous acetonitrile (0.1M, 0.28 mL) was added, and the mixture was stirred for 5 min. DMAP (1.5 equiv, 5.15 mg, 0.042 mmol) was added, and the mixture was stirred at room temperature overnight. The crude was directly purified by TLC with elution hexanes: DCM (10% DCM in Hexane) to afford a white solid (8 mg, 56%, Rf: 0.585 (20% DCM in Hexane)). $^1$H NMR (600 MHz, CDCl$_3$) δ 8.35 (s, 1H), 7.53 (q, J=1.2 Hz, 1H), 6.42 (dd, J=9.3, 5.2 Hz, 1H), 5.35 (dd, J=13.9, 5.8 Hz, 1H), 4.41-4.29 (m, 1H), 3.92 (dd, J=7.7, 2.1 Hz, 2H), 3.79-3.62 (m, 4H), 2.53 (dd, J=13.9, 5.3 Hz, 1H), 2.18-2.09 (m, 1H), 1.92 (d, J=1.3 Hz, 3H), 0.94 (s, 9H), 0.15 (d, J=1.0 Hz, 6H). $^{13}$C NMR (151 MHz, CDCl$_3$) δ 163.49, 150.33, 135.17, 111.49, 85.91, 85.88, 84.86, 79.80, 79.74, 63.40, 42.05, 41.70, 39.52, 39.48, 26.11, 18.51, 12.65, −5.20. $^{31}$P NMR (162 MHz, Acetone) δ 122.59.

c. N-(1-((2R,4S,5R)-5-(((tert-butyldimethylsilyl)oxy)methyl)-4-((2-sulfido-1,3,2-dithiaphospholan-2-yl)oxy)tetrahydrofuran-2-yl)-2-oxo-1,2-dihydropyrimidin-4-yl)benzamide (Compound 4-44)

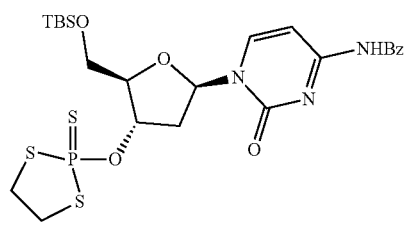

compound 4-44

A vial was flame-dried and allowed to cool under vacuum. The vial was then placed under inert Ar atmosphere via balloon. NO$_2$-dithiaphospholane (compound 2-1, 2.0 equiv, 13.2 mg, 0.0449 mmol) and N-(1-((2R,4S,5R)-5-(((tert-butyldimethylsilyl)oxy)methyl)-4-hydroxytetrahydrofuran-2-yl)-2-oxo-1,2-dihydropyrimidin-4-yl)benzamide (1.0 equiv, 10.0 mg, 0.0225 mmol) were added to the flask. Anhydrous THF (0.1M, 0.22 mL) was added, and the mixture was stirred for 5 min. DBU (1.5 equiv, 5.0 µL, 0.0337 mmol) was added, and the mixture was stirred at rt overnight. The crude was directly purified by TLC with elution hexanes: DCM (20% DCM in Hexane) to afford a white solid (6 mg, 44.6%, Rf: 0.451 (20% DCM in Hexane)). $^1$H NMR (600 MHz, CDCl$_3$) δ 8.36 (d, J=7.5 Hz, 1H), 7.91 (d, J=7.7 Hz, 2H), 7.62 (t, J=7.5 Hz, 1H), 7.55 (s broad, 1H), 7.52 (s, J=7.5 Hz, 2H), 6.44 (dd, J 7.9, 5.6 Hz, 1H), 5.34 (ddt, J=13.9, 6.2, 2.0 Hz, 1H), 4.47 (d, J=2.1 Hz, 1H), 3.95 (dd, J=4.6, 2.1 Hz, 2H), 3.78-3.62 (m, 4H), 2.91-2.79 (m, 1H), 2.25-2.14 (m, 1H), 0.92 (s, 9H), 0.14 (d, J=2.1 Hz, 6H). $^{13}$C NMR (151 MHz, CDCl$_3$) δ 162.24, 144.94, 133.45, 129.25, 127.69, 126.32, 115.92, 87.40, 86.80, 86.77, 79.46, 79.40, 63.09, 42.14, 41.59, 41.10, 41.06, 29.85, 26.07, 18.46, −5.27, −5.29. $^{31}$P NMR ($^1$H decoupled, 162 MHz, CDCl$_3$) δ 122.82-122.28 (m). $^{31}$P NMR (H decoupled, 162 MHz, CDCl$_3$) δ 122.61.

d. N-(9-((2R,4S,5R)-5-(((tert-butyldimethylsilyl)oxy)methyl)-4-((2-sulfido-1,3,2-dithiaphospholan-2-yl)oxy)tetrahydrofuran-2-yl)-6-oxo-6,9-dihydro-1H-purin-2-yl)isobutyramide (Compound 4-45)

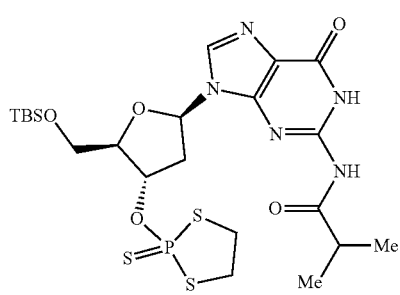

compound 4-45

A vial was flame-dried and allowed to cool under vacuum. The vial was then placed under inert Ar atmosphere via balloon. NO$_2$-dithiaphospholane (compound 2-1, 4.0 equiv, 26 mg, 0.0886 mmol) and Guanine-C(O)$^i$Pr (1.0 equiv, 10.0 mg, 0.0222 mmol) were added to the flask. Anhydrous Acetonitrile (0.1M, 0.22 mL) was added, and the mixture was stirred for 5 min. DBU (1.5 equiv, 7.0 µL, 0.0332 mmol) was added, and the mixture was stirred at rt overnight. The crude was directly purified by TLC with elution hexanes: DCM (20% DCM in Hexane) to afford a transparent oil (5.8 mg, 43%, Rf: 0.35 (20% DCM in Hexane)). $^1$H NMR (600 MHz, CDCl$_3$) δ 11.97 (s, 1H), 8.41 (s, 1H), 7.98 (s, 1H), 6.25 (s, 1H), 5.69-5.58 (m, 1H), 4.32 (d, J=3.1 Hz, 1H), 3.85 (d, J=3.0 Hz, 2H), 3.80-3.63 (m, 4H), 2.84 (d, J=6.8 Hz, 1H), 2.74 (d, J=3.8 Hz, 1H), 2.63 (s, 1H), 1.29 (dd, J=6.9, 2.1 Hz, 6H), 0.86 (s, 9H), 0.05 (d, J=21.2 Hz, 6H). $^{13}$C NMR (151 MHz, CDCl$_3$) δ 178.18, 155.45, 147.62, 147.45, 137.41, 121.73, 85.84, 85.80, 84.05, 78.76, 78.71, 62.87, 42.02, 41.92, 39.32, 39.29, 36.86, 31.09, 26.05, 19.15, 19.12, 18.52, −5.26, −5.33. $^{31}$P NMR ($^1$H coupled, 162 MHz, CDCl$_3$) δ 123.16 (dq, J=31.9, 16.0 Hz). $^{31}$P NMR ($^1$H decoupled, 162 MHz, CDCl$_3$) δ 123.21.

e. 2-(((2R,3S,5R)-5-(6-amino-9H-purin-9-yl)-2-(((tert-butyldimethylsilyl)oxy)methyl) tetrahydrofuran-3-yl)oxy)-1,3,2-dithiaphospholane 2-sulfide (Compound 4-19)

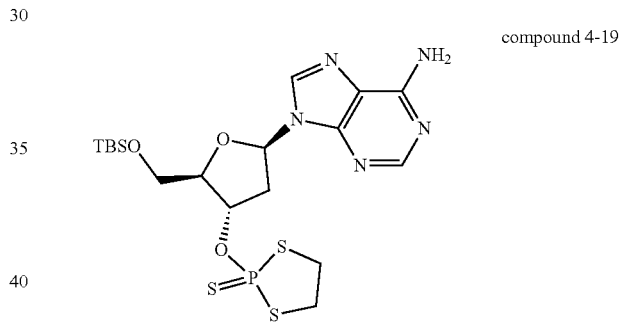

compound 4-19

A vial was flame-dried and allowed to cool under vacuum. The vial was then placed under inert Ar atmosphere via balloon. NO$_2$-dithiaphospholane (compound 2-1, 2.0 equiv, 16 mg, 0.0548 mmol) and Adenine (1.0 equiv, 10.0 mg, 0.0274 mmol) were added to the flask. Anhydrous dichloromethane (0.1M, 0.27 mL) was added, and the mixture was stirred for 5 min. DMAP (1.5 equiv, 5.0 mg, 0.0411 mmol) was added, and the mixture was stirred at rt overnight. The crude was directly purified by TLC with elution hexanes: DCM (40% DCM in Hexane) to afford a transparent oil (compound 4-19, 7.0 mg, 49%, Rf: 0.207 (40% DCM in Hexane)). $^1$H NMR (600 MHz, CDCl$_3$) δ 8.35 (s, 1H), 8.18 (s, 1H), 6.56 (d, J=1.5 Hz, 1H), 5.71 (s, 2H), 5.49 (d, J=14.0 Hz, 1H), 4.43 (d, J=2.1 Hz, 1H), 3.92 (d, J=2.9 Hz, 2H), 3.71 (dd, J=16.0, 1.7 Hz, 4H), 2.85-2.67 (m, 2H), 0.93 (s, 9H), 0.12 (s, 7H). $^{13}$C NMR (151 MHz, CDCl$_3$) δ 155.41, 153.05, 149.86, 138.84, 119.94, 86.26, 86.23, 84.31, 79.87, 79.81, 63.37, 41.92, 41.85, 40.34, 40.31, 26.14, 18.55, −5.20, −5.29. $^{31}$P NMR ($^1$H coupled, 162 MHz, CDCl$_3$) δ 122.45 (h, J=15.4 Hz). $^{31}$P NMR ($^1$H decoupled, 162 MHz, CDCl$_3$) δ 122.50.

Example 13(a)

Synthesis of P(V)-DMT-T16 (all R) (Compound 5-17)

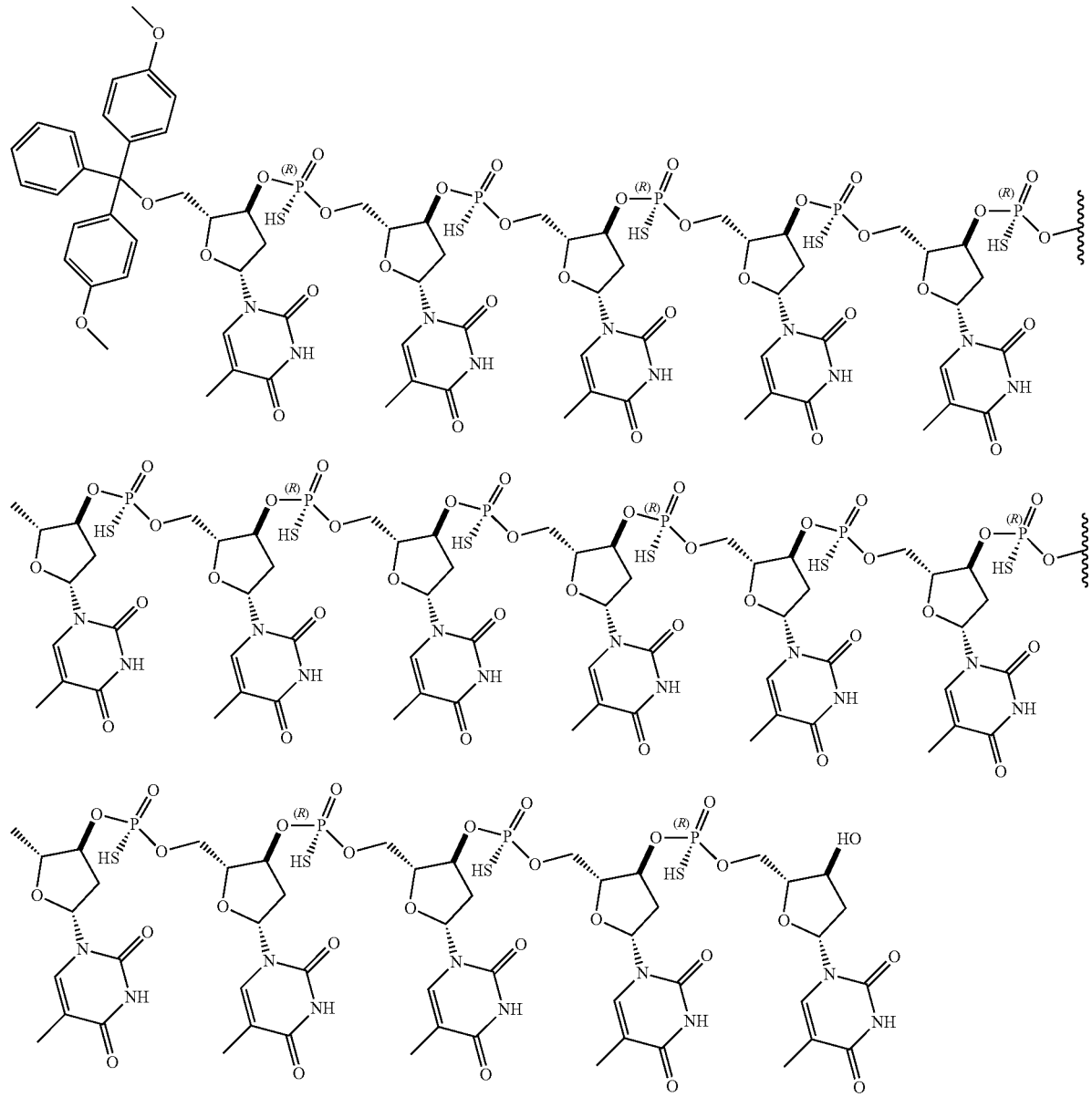

Synthesis was carried out on a BioAutomation MerMade MM12 oligonucleotide synthesizer on a 2.5 μmole scale using dT-Q-CPG 500 oligonucleotide synthesis resin (Glen Research, 20-2030-XX). Each synthesis cycle used the following parameters:

| Step | Operation | Reagents and Solvents | Wait time |
|---|---|---|---|
| 1 | Detritylation | 3% Dichloroacetic acid in dichloromethane (1 mL) | 90 sec. |
| 2 | Detritylation | 3% Dichloroacetic acid in dichloromethane (1 mL) | 90 sec. |
| 3 | ACN Wash | Acetonitrile (1.5 mL) | 20 sec. |
| 4 | ACN Wash | Acetonitrile (1.5 mL) | 20 sec. |

-continued

| Step | Operation | Reagents and Solvents | Wait time |
|---|---|---|---|
| 5 | Coupling | 0.1M (S)-ΨdT in acetonitrile (0.2 mL, 8 eq) 1.5M 1,8-diazabicyclo[5.4.0]undec-7-ene in acetonitrile (0.1 mL, 60 eq) | 300 sec. |
| 6 | Coupling | 0.1M (S)- ΨdT in acetonitrile (0.2 mL, 8 eq) 1.5M 1,8-diazabicyclo[5.4.0]undec-7-ene in acetonitrile (0.1 mL, 60 eq) | 300 sec. |
| 7 | Coupling | 0.1M (S)- ΨdT in acetonitrile (0.2 mL, 8 eq) 1.5M 1,8-diazabicyclo[5.4.0]undec-7-ene in acetonitrile (0.1 mL, 60 eq) | 300 sec. |
| 8 | ACN Wash | Acetonitrile (1.5 mL) | 20 sec. |
| 9 | ACN Wash | Acetonitrile (1.5 mL) | 20 sec. |
| 10 | Capping | 20% acetic anhydride, 30% 2,6-lutidine, 50% acetonitrile (0.4 mL) 20% N-methylimidazole in acetonitrile (0.4 mL) | 60 sec. |
| 11 | ACN Wash | Acetonitrile (1.5 mL) | 20 sec. |
| 12 | ACN Wash | Acetonitrile (1.5 mL) | 20 sec. |

(S)-ΨdT refers to the reagent 1-((2R,4S,5R)-5-((bis(4-methoxyphenyl)(phenyl)methoxy)methyl)-4-(((2S,3aS,6R,7aS)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione having the structure:

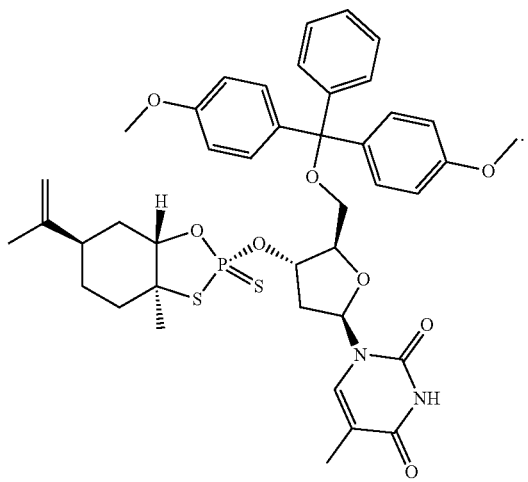 [SMILES: C=C(C)[C@@H]1CC[C@]2(C)S[P@@](=S)(O[C@H]3C[C@H](n4cc(C)c(=O)[nH]c4=O)O[C@@H]3COC(c3ccccc3)(c3ccc(OC)cc3)c3ccc(OC)cc3)O[C@H]2C1]

At the completion of the synthesis the column was subjected to two more acetonitrile washes. The column was removed from the synthesizer. Air was pulled through the column for 20 minutes. The resin in the column was treated with saturated aqueous ammonium hydroxide (3×1 mL), eluting into a 20 mL scintillation vial. The eluent was concentrated in vacuo. The residue was analyzed by LCMS (Aquity UPLC Oligo BEH, C18, 1.7μ, 2.1×50 mm; Solvent A: 97.5% water, 2.5% methanol, 0.2M 1,1,1,3,3,3-hexafluoro-2-propanol, 16 mmol triethylamine; Solvent B: 40% water, 60% methanol, 0.2M 1,1,1,3,3,3-hexafluoro-2-propanol, 16 mmol triethylamine; 10% B isocratic over 1 min, then 10% B to 60% B over 6 min then 60% B to 100% B over 0.5 min and holding at 100% B for 1.5 min, all at 1 mL/min, 65° C.) m/3−=1782 (rf 6.5 min, 34% purity at 262 nm).

Example 13(b)

Synthesis of P(V)-T16 (all R) (Compound 5-18)

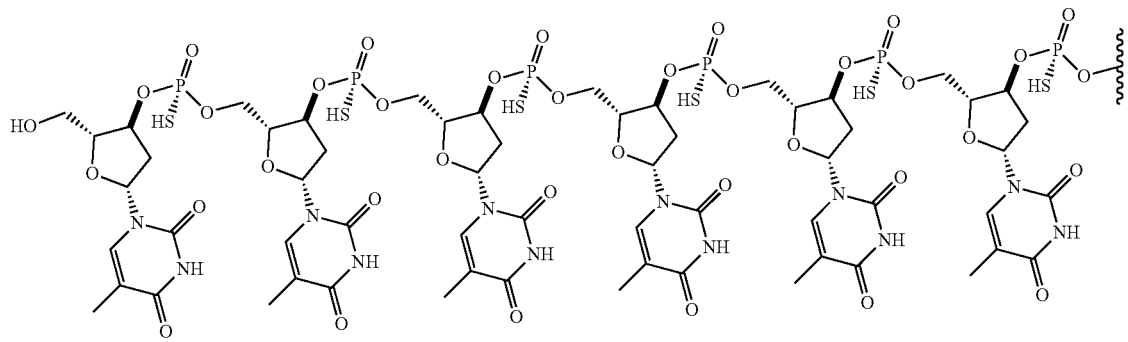

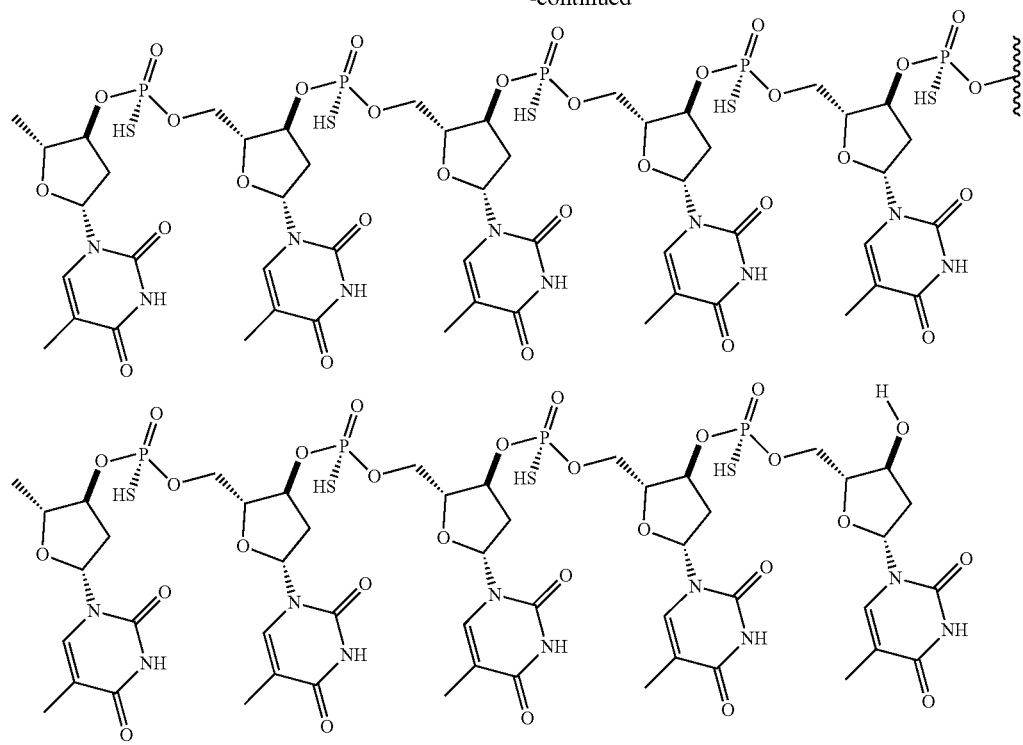

Synthesis was carried out on a BioAutomation MerMade MM12 oligonucleotide synthesizer on a 2.5 μmole scale using dT-Q-CPG 500 oligonucleotide synthesis resin (Glen Research, 20-2030-XX). Each synthesis cycle used the following parameters:

| Step | Operation | Reagents and Solvents | Wait time |
|---|---|---|---|
| 1 | Detritylation | 3% Dichloroacetic acid in dichloromethane (1 mL) | 90 sec. |
| 2 | Detritylation | 3% Dichloroacetic acid in dichloromethane (1 mL) | 90 sec. |
| 3 | ACN Wash | Acetonitrile (1.5 mL) | 20 sec. |
| 4 | ACN Wash | Acetonitrile (1.5 mL) | 20 sec. |
| 5 | Coupling | 0.1M (S)- ΨdT in acetonitrile (0.05 mL, 2 eq) 1M 1,8-diazabicyclo[5.4.0]undec-7-ene in acetonitrile (0.025 mL, 10 eq) | 120 sec. |
| 6 | Coupling | 0.1M (S)- ΨdT in acetonitrile (0.05 mL, 2 eq) 1M 1,8-diazabicyclo[5.4.0]undec-7-ene in acetonitrile (0.025 mL, 10 eq) | 120 sec. |
| 7 | Coupling | 0.1M (S)- ΨdT in acetonitrile (0.05 mL, 2 eq) 1M 1,8-diazabicyclo[5.4.0]undec-7-ene in acetonitrile (0.025 mL, 10 eq) | 120 sec. |
| 8 | Coupling | 0.1M (S)- ΨdT in acetonitrile (0.05 mL, 2 eq) 1M 1,8-diazabicyclo[5.4.0]undec-7-ene in acetonitrile (0.025 mL, 10 eq) | 120 sec. |
| 9 | Coupling | 0.1M (S)- ΨdT in acetonitrile (0.05 mL, 2 eq) 1M 1,8-diazabicyclo[5.4.0]undec-7-ene in acetonitrile (0.025 mL, 10 eq) | 120 sec. |
| 10 | Coupling | 0.1M (S)- ΨdT in acetonitrile (0.05 mL, 2 eq) 1M 1,8-diazabicyclo[5.4.0]undec-7-ene in acetonitrile (0.025 mL, 10 eq) | 120 sec. |
| 11 | ACN Wash | Acetonitrile (1.5 mL) | 20 sec. |
| 12 | ACN Wash | Acetonitrile (1.5 mL) | 20 sec. |
| 13 | Capping | 20% acetic anhydride, 30% 2,6-lutidine, 50% acetonitrile (0.4 mL) 20% N-methylimidazole in acetonitrile (0.4 mL) | 60 sec. |
| 14 | ACN Wash | Acetonitrile (1.5 mL) | 20 sec. |
| 15 | ACN Wash | Acetonitrile (1.5 mL) | 20 sec. |

At the completion of the synthesis the column was subjected to two more detritylation steps followed by two more acetonitrile washes. The column was removed from the synthesizer. Air was pulled through the column for 15 minutes. The resin was collected in a 2 dram scintillation vial. Saturated aqueous ammonium hydroxide (2 mL) was added to the vial which was then tightly sealed. The mixture was held at room temperature for 1 hour, then filtered. The filter cake was washed twice with 50% ethanol water and the filtrate was concentrated in vacuo. The resulting residue was dissolved in water (1 mL), then purified by preparatory HPLC (Waters XBridge, C18, 5μ, 19×100 mm; Solvent A: 98% water, 2% methanol, 0.4M 1,1,1,3,3,3-hexafluoro-2-propanol, 16 mmol triethylamine; Solvent B: 40% water, 60% methanol, 0.4M 1,1,1,3,3,3-hexafluoro-2-propanol, 16 mmol triethylamine; run gradient 10% B-A to 80% B-A over 25 minutes at 20 mL/min). The major UV (220 nm) peak fractions were combined. The combined fractions were concentrated to ~10 mL by centrifugal evaporation and split into two equal portions. To each portion was added 0.1M sodium hydroxide (1 mL) and 10 mM sodium hydroxide, 2M sodium chloride (3 mL), and each was partially concentrated by centrifugal evaporation for 1 hour and then desalted by gel filtration (HiPrep 26/10 Desalting, CV 53 mL×2 columns (106 mL); 100% water isocratic over 1.5 CV). The product containing fractions were combined, isolated, frozen and lyophilized. The desired product was isolated as fluffy white solid in 1.3% yield. LCMS (Aquity UPLC Oligo BEH, C18, 1.7μ, 2.1×50 mm; Solvent A: 97.5% water, 2.5% methanol, 0.2M 1,1,1,3,3,3-hexafluoro-2-propanol, 16 mmol triethylamine; Solvent B: 40% water, 60% methanol, 0.2M 1,1,1,3,3,3-hexafluoro-2-propanol, 16 mmol triethylamine; 10% B-A isocratic over 0.5 min then 10% B-A to 35% B-A over 2.25 min then 35% B-A to 100% B over 0.5 min at 1 mL/min, 65° C.) m/3-=1680.8 (rf 2.74 min, >95% purity).

Example 13(c)

Synthesis of 17-mer TAGTCGACTTGGCCAAT (Compound 5-18)

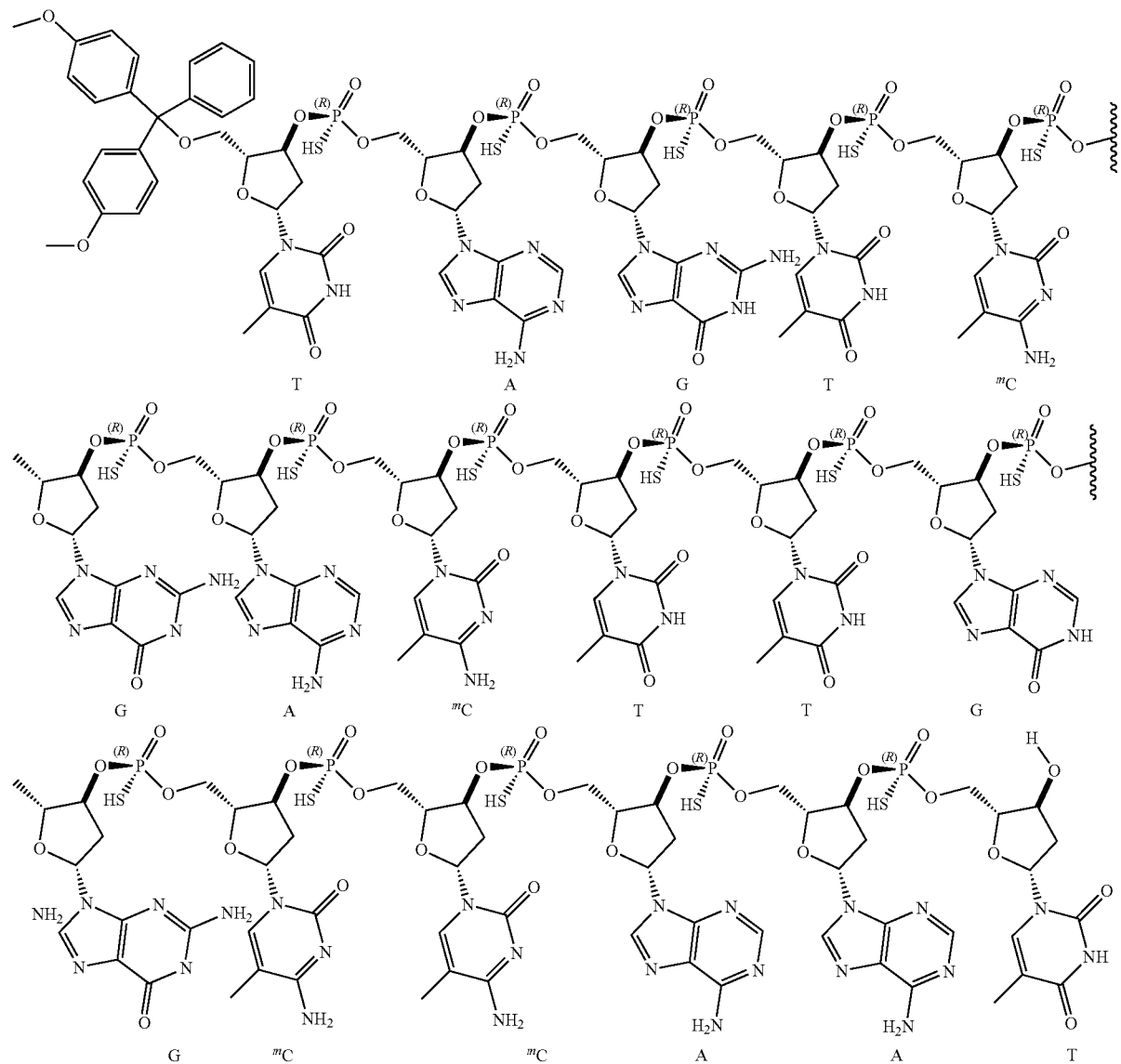

Synthesis was carried out on a BioAutomation MerMade MM12 oligonucleotide synthesizer on a 2.5 μmole scale using dT-Q-CPG 500 oligonucleotide synthesis resin (Glen Research, 20-2030-XX). The 17-mer TAGTCGACTTGGC-CAAT was designed to contain all possible dinucleotide linkages (i.e. A-C, C-A, A-G, etc.). Each synthesis cycle used the following parameters:

| Step | Operation | Reagents and Solvents | Wait time |
|---|---|---|---|
| 1 | Detritylation | 3% Dichloroacetic acid in dichloromethane (1 mL) | 90 sec. |
| 2 | Detritylation | 3% Dichloroacetic acid in dichloromethane (1 mL) | 90 sec. |
| 3 | ACN Wash | Acetonitrile (1.5 mL) | 20 sec. |
| 4 | ACN Wash | Acetonitrile (1.5 mL) | 20 sec. |
| 5 | Coupling | 0.1M (S)- Ψ-nucleoside in solvent (0.05 mL, 2 eq) 1M 1,8-diazabicyclo[5.4.0]undec-7-ene in acetonitrile (0.025 mL, 10 eq) | 120 sec. |
| 6 | Coupling | 0.1M (S)- Ψ-nucleoside in solvent (0.05 mL, 2 eq) 1M 1,8-diazabicyclo[5.4.0]undec-7-ene in acetonitrile (0.025 mL, 10 eq) | 120 sec. |
| 7 | Coupling | 0.1M (S)- Ψ-nucleoside in solvent (0.05 mL, 2 eq) 1M 1,8-diazabicyclo[5.4.0]undec-7-ene in acetonitrile (0.025 mL, 10 eq) | 120 sec. |
| 8 | Coupling | 0.1M (S)- Ψ-nucleoside in solvent (0.05 mL, 2 eq) 1M 1,8-diazabicyclo[5.4.0]undec-7-ene in acetonitrile (0.025 mL, 10 eq) | 120 sec. |
| 9 | Coupling | 0.1M (S)- Ψ-nucleoside in solvent (0.05 mL, 2 eq) 1M 1,8-diazabicyclo[5.4.0]undec-7-ene in acetonitrile (0.025 mL, 10 eq) | 120 sec. |
| 10 | Coupling | 0.1M (S)- Ψ-nucleoside in solvent (0.05 mL, 2 eq) 1M 1,8-diazabicyclo[5.4.0]undec-7-ene in acetonitrile (0.025 mL, 10 eq) | 120 sec. |
| 11 | ACN Wash | Acetonitrile (1.5 mL) | 20 sec. |
| 12 | ACN Wash | Acetonitrile (1.5 mL) | 20 sec. |
| 13 | Capping | 20% acetic anhydride, 30% 2,6-lutidine, 50% acetonitrile (0.4 mL) 20% N-methylimidazole in acetonitrile (0.4 mL) | 60 sec. |
| 14 | ACN Wash | Acetonitrile (1.5 mL) | 20 sec. |
| 15 | ACN Wash | Acetonitrile (1.5 mL) | 20 sec. |

Wherein "(S)- Ψ-nucleoside in solvent" refers to:
for deoxyadenosine: compound 3-128 (listed in Example 16) in acetonitrile;
for deoxy(5-methyl)cytosine: compound 3-129 (listed in Example 16) in acetonitrile;
for deoxyguanosine: compound 3-130 (listed in Example 16) in isobutyronitrile;
for deoxythymidine: compound 3-131 (listed in Example 16) in acetonitrile.

Following completion of the synthesis, the column containing the support was removed from the synthesizer, and dried by pulling a vacuum through it for a few minutes. The column was treated with concentrated ammonium hydroxide (3×1 mL) to cleave the linker and the eluent was collected in a red-capped pressure-rated vial. The vial was heated to 55 C overnight to cleave the base protecting groups. The mixture was filtered and the filtrate evaporated on a Biotage V10 evaporator. The sample was analyzed by LC/MS (A solvent=97.5% Water/2.5% MeOH w/0.2M HFIP/0.016M TEA, B Solvent=40% Water/60% MeOH w/0.2M HFIP/0.016M TEA) on an Acquity UPLC Oligo BEH C18 2.1×50 MM 1.7 um column, eluting with a gradient 10-100% over 3.25 min. Ions for M-3/3 (1932.45), M-4/4 (1449.2) and M-5/5 (1159.05) were observed, indicating the presence of the 17-mer as a major component.

Example 14 (a)

Preparation of Styrene Oxide (S)—P(V) Reagent (Compound 1-13)

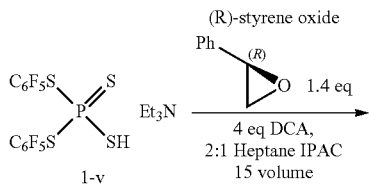

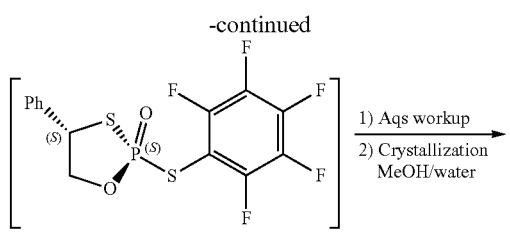

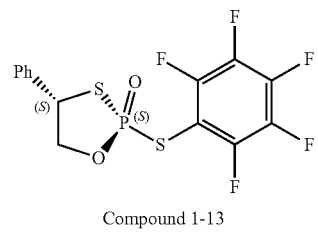

Compound 1-13

To a 2.5-L Chemglass reactor was added phosphate TEA salt (100 g, 1.0 eq), hexanes (1 L) and isopropyl acetate (500 mL). (R)-styrene oxide (28.3 g, 1.4 eq) was then added, followed by dichloroacetic acid (86.6 g, 4 eq). The resulting mixture was stirred at ambient temperature until the reaction was complete. The mixture was then washed with hexanes (200 mL) and water (400 mL). The separated organic phase was then washed with 10% aqueous $KH_2PO_4$ solution (400 mL), and passed through a $MgSO_4$ pad. The resulting filtrate was then solvent-swapped into MeOH. After the volume of batch was adjusted to 0.35 L, the batch was cooled to 0° C. and stirred until a seed bed was formed. Water (20 mL) was added into the batch, and the resulting slurry was stirred for 1 h at 0° C. before filtration. The filter cake was washed with cold isopropyl alcohol (0° C., 60 mL), and dried in vacuum. The product was isolated in 45-53% yield with 98 AP and 99 ee %.

Recrystallization: The dry cake (20 g) was dissolved in dichloromethane (80 mL) at ambient temperature. The solution was solvent-swapped into heptane, and the final batch volume was adjusted to about 60 mL. The resulting mixture was cooled to 0° C., stirred for 1 h, and filtered. The filtrate was recycled to the reactor to complete the transfer of the slurry. The cake was then washed with cold heptane (0° C., 20 mL), and dried at 50° C. under vacuum. The recovery yield was typically 90%. UHPLC retention time is 1.81 min. Chiral HPLC retention time is 14.60 min.

Example 14 (b)

Preparation of Styrene Oxide (R)—P(V) Reagent (Compound 1-14)

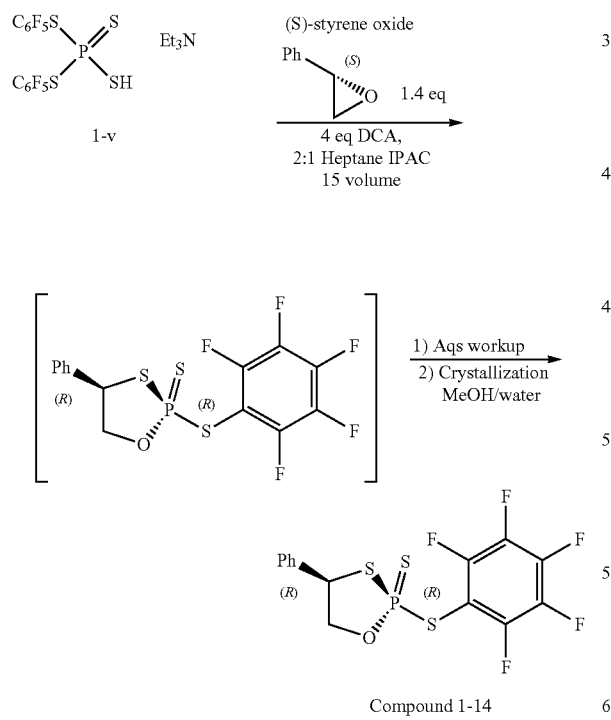

The procedure to make styrene oxide (R)—P(V) reagent (compound 1-14) is same as the procedure to make compound 1-13 except that styrene oxide in the reaction is a (S)-isomer. Chiral HPLC retention time for compound 1-14 is 12.74 min.

Diastereomers of compounds 1-13 and 1-14 were a minor product of each reaction. Chiral HPLC retention time of the diastereomer from (S)-styrene oxide is 12.09 min. Chiral HPLC retention time of the diastereomer from (R)-styrene oxide is 12.42 min.

Example 15

Preparation of Phosphodiester Products

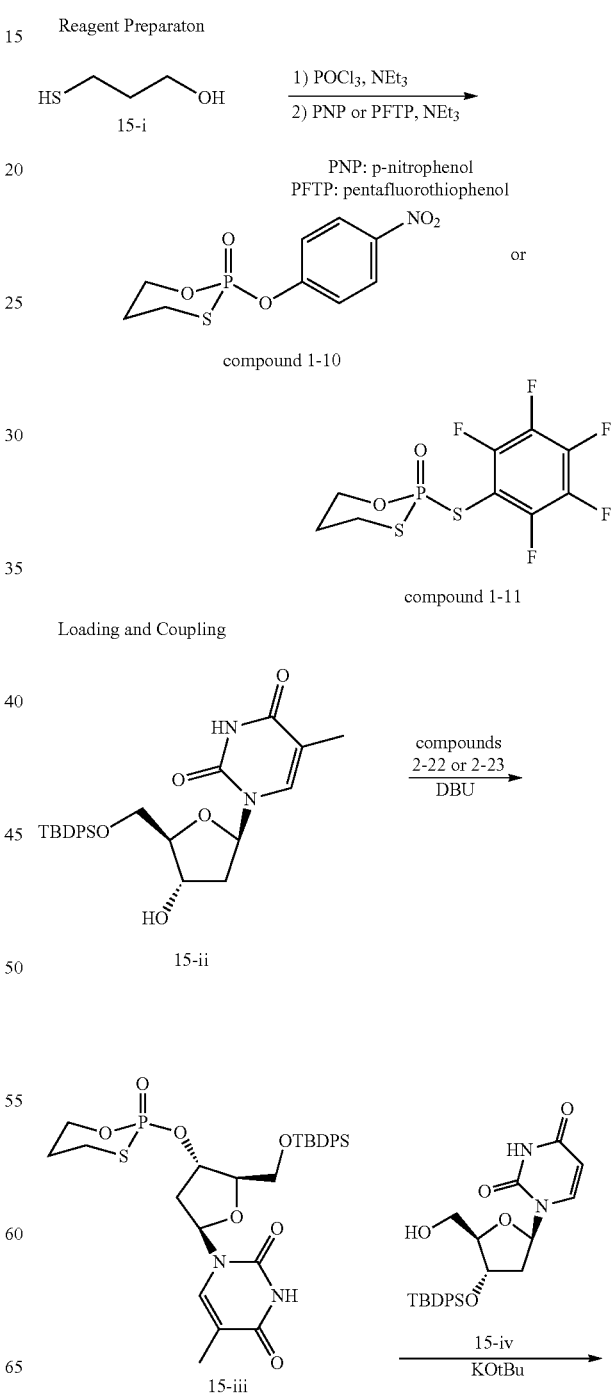

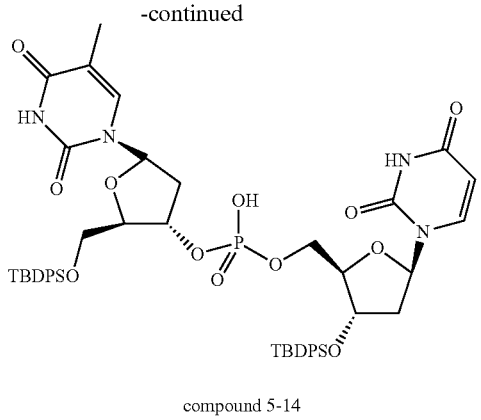

compound 5-14

In a similar fashion to the phosphorous thiosulfates, phosphodiester products can be prepared. In this case, reagents such as compounds 1-10 or 1-11, shown above, were used. A phosphorous (V) reagent containing a leaving group is loaded onto the first coupling partner (for example, a nucleoside such as 15-ii) under basic conditions. This affords a loaded compound as an inconsequential mixture of diastereomers at phosphorous (such as 15-iii). This loaded compound is then coupled with the next coupling partner under basic conditions (for example, a nucleoside such as 15-iv) to afford the coupled phosphodiester product (compound 5-14). Detailed procedures for the preparation of dinucleotides are listed below.

a. Reagent Preparation (Compound 1-10)

To a solution of phosphoryl chloride (0.173 g, 1.00 equiv., 1.15 mmol) in toluene (3.5 mL) was added 3-mercapto-1-propanol (0.100 mL, 1.15 mmol), followed by triethylamine (0.32 mL, 2.00 equiv., 2.30 mmol) at ambient temperature. The reaction mixture was stirred for 1 h, and TEA (0.16 mL, 1.0 equiv) was added, followed by 4-nitrophenol (0.160 g, 1.00 equiv., 1.15 mmol). After mixing for 16 h, the reaction mixture was filtered. The reactor was rinsed with toluene (3 mL), and the rinse was applied to the cake wash. The combined filtrates were concentrated, and the resulting residue was purified by silica gel chromatography, providing compound 1-10 as white solids (81 mg, 25%). $^1$H NMR (400 MHz, CHLOROFORM-d) δ 8.30 (d, J=8.8 Hz, 2H), 7.48 (dd, J=8.8, 1.1 Hz, 2H), 4.77-4.67 (m, 2H), 3.25-3.14 (m, 1H), 3.13-2.97 (m, 1H), 2.45-2.24 (m, 1H), 2.19-2.07 (m, 1H). LCMS m/z (M+H)+276.

b. Reagent Preparation (Compound 1-11)

To a solution of 3-mercapto-1-propanol (0.500 mL, 5.75 mmol) in toluene (15 mL) was added phosphoryl chloride (0.865 g, 1.00 equiv., 5.75 mmol), followed by TEA (1.78 mL, 2.20 equiv., 12.7 mmol) at 0° C. The reaction mixture was stirred at 0° C. for 1 h, then warmed to ambient temperature and mixed for 1 h. TEA (0.89 mL, 1.1 equiv.) was added, followed by pentafluorothiophenol (1.15 g, 1.0 equiv., 5.75 mmol). The resulting mixture was stirred for 6 h, and filtered. The filtrate was concentrated, and the resulting residue was purified by silica gel chromatography, providing compound 1-11 as white solids (0.23 g, 13%). $^1$H NMR (500 MHz, CHLOROFORM-d) δ 4.83-4.60 (m, 2H), 3.48-3.32 (m, 1H), 3.25-3.07 (m, 1H), 2.37-2.22 (m, 1H), 2.19-2.08 (m, 1H). LCMS m/z (M+H)$^+$ 337.

c. Loading with Compound 1-10

To a solution of compound 1-10 (80 mg, 1.5 equiv., 0.29 mmol) and 15-ii (85 mg, 0.18 mmol) in THF (1.7 mL) was added 1,8-diazabicyclo[5.4.0]undec-7-ene (0.08 mL, 3.1 equiv., 0.5 mmol) at ambient temperature. After stirring for 16 h, the reaction mixture was concentrated. The resulting residue was purified by silica gel chromatography, providing 15-iii as white solids (45 mg, 41%). $^1$H NMR (500 MHz, CHLOROFORM-d) δ 8.67-8.42 (m, 1H), 7.67-7.51 (m, 4H), 7.47-7.26 (m, 7H), 6.48-6.28 (m, 1H), 5.35-5.12 (m, 1H), 4.59-4.35 (m, 2H), 4.33-4.13 (m, 1H), 4.00-3.77 (m, 2H), 3.07-2.76 (m, 2H), 2.67-2.52 (m, 1H), 2.33-2.05 (m, 2H), 2.02-1.84 (m, 1H), 1.52 (d, J=16.8 Hz, 3H), 1.03 (s, 9H). LCMS m/z (M+H)+617.

d. Loading with Compound 1-11

To a solution of compound 1-11 (50 mg, 2 equiv., 0.15 mmol) and 15-ii (35 mg, 0.073 mmol) in acetonitrile (0.7 mL) was added 1,8-diazabicyclo[5.4.0]undec-7-ene (0.022 mL, 2.0 equiv., 0.15 mmol) at 0° C. After 20 min, the reaction mixture was concentrated. The resulting residue was purified by silica gel chromatography, providing 15-iii as white solids (30 mg, 66%).

e. Coupling

To a solution of 15-iii (20 mg, 0.032 mmol) and 15-iv (31 mg, 2.0 equiv., 0.065 mmol) in THF (0.6 mL) was added a solution of potassium t-butoxide in THF (1.0 M, 0.11 mL, 3.5 equiv.) at ambient temperature. After 20 min, acetic acid (10 µL, 5 equiv.) was added, and the reaction mixture was concentrated. The resulting residue was purified by silica gel chromatography, providing compound 5-14 as white solids (17 mg, 53%). LCMS m/z (M+H)$^+$ 1023.

Example 16

Synthesis of Loaded Nucleosides
1. Synthesis of 5'-O-Protected Nucleosides (General Procedure 1)

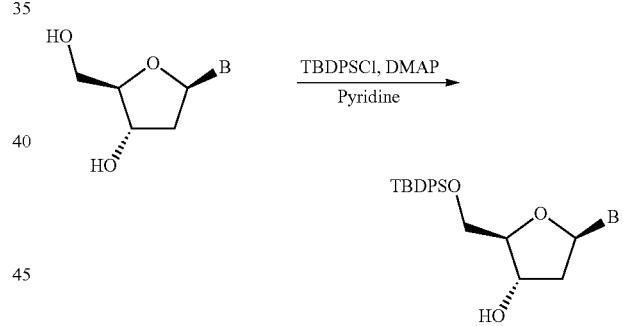

All 5'-OTBDPS nucleosides were prepared from the commercially available compounds according to the following procedures.

1.1 Intermediate 16-i

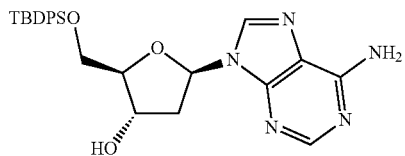

2'-Deoxyadenosine (15.0 g, 58.5 mmol, 1.0 equiv.) and imidazole (9.96 g, 146 mmol, 2.5 equiv.) were dissolved in dry pyridine (100 mL) and concentrated in vacuo. The resulting mixture was dissolved in anhydrous DMF (75 mL), TBDPSCl (16.3 mL, 61.4 mmol, 1.1 equiv.) was added, and the mixture was stirred for 2 h. The solution was concentrated in vacuo then dissolved in EtOAc (500 mL), and washed with water (2×250 mL), then brine (250 mL). The organic layer was dried over MgSO₄, filtered, and concentrated in vacuo to afford a thick oil that was purified by flash column chromatography over silica gel (0% to 5% MeOH in EtOAc) to afford the product as a white solid 16-i (18.0 g, 63%) spectral characteristics consistent with the literature (Krishnakumar, K., et al., Synlett 7, 1055-1058 (2010)).

1.2 Intermediate 16-ii

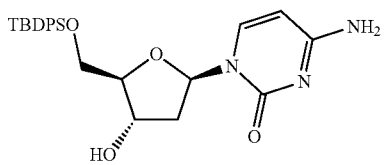

Intermediate 16-ii prepared from 2'-deoxycytidine (15.0 g) under the same protocol as intermediate 16-iv. Following completion of the reaction as assessed by TLC, the mixture was concentrated in vacuo. The crude syrup was dissolved in EtOAc (500 mL), washed with 1 N HCl (150 mL, final pH=6), washed with sodium phosphate (100 mL, 1.0 M, pH=7) buffer, then brine (200 mL). The organics were dried over MgSO₄, filtered, and concentrated to afford a thick oil. The oil was purified by flash column chromatography (0% to 10% MeOH in DCM). The isolated foam was broken down into MTBE/hexane (1:1 v/v, 200 mL) then filtered and the solid was dried at 50° C. at 20 torr until constant weight was achieved. 16-ii (20.0 g, 66%) was isolated as a white solid.

Physical State: White solid;

$^1$H NMR (600 MHz, DMSO-d$_6$): δ 7.70 (d, J=7.4 Hz, 1H), 7.64 (dq, J=6.6, 1.2 Hz, 4H), 7.52-7.41 (m, 6H), 7.17 (s, 1H), 7.13 (s, 1H), 6.18 (t, J=6.5 Hz, 1H), 5.56 (d, J=7.4 Hz, 1H), 5.29 (d, J=4.5 Hz, 1H), 4.29 (dq, J=6.0, 3.9 Hz, 1H), 3.89-3.82 (m, 1H), 3.85 (s, 1H), 3.78-3.71 (m, 1H), 2.19 (ddd, J=13.2, 6.3, 4.1 Hz, 1H), 1.99 (dt, J=13.2, 6.5 Hz, 1H), 1.01 (s, 9H); $^{13}$C NMR (151 MHz, DMSO-d$_6$): δ 165.26, 154.67, 140.49, 135.15, 134.99, 132.69, 132.38, 130.02, 129.98, 127.98, 93.83, 86.35, 84.68, 69.77, 63.82, 40.51, 26.84, 26.67, 18.81; HRMS (ESI-TOF): calcd. for C$_{25}$H$_{32}$N$_3$O$_8$Si [M+H]$^+$ 466.2156; found 466.2157.

1.3 Intermediate 16-iii

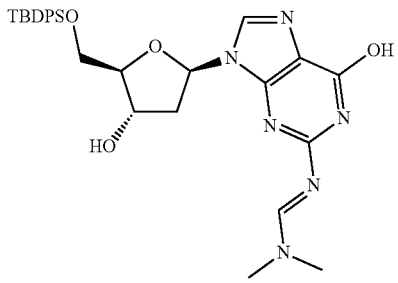

2'-Deoxyguanosine was first converted to the dimethylformyl protected compound to increase solubility in pyridine according to the procedure described in Huang, H., et al., J. Am. Chem. Soc. 133, 20357-20368 (2011). To a solution of 2'-deoxyguanosine (30.0 g, 112 mmol, 1.0 equiv.) in methanol (300 mL) was added N,N-dimethylformamide dimethyl acetal (60 mL). After stirring for 72 h, the reaction was filtered and washed with MeOH (200 mL). To a solution of the DMF protected intermediate (34.4 g, 107 mmol, 1.0 equiv.) and DMAP (2.63 g, 21.4 mmol, 0.2 equiv.) in dry pyridine (344 mL) was added TBDPSCl (32.6 mL, 123 mmol, 1.2 equiv.). After stirring for 24 h the reaction was concentrated in vacuo. The residue obtained was partitioned between EtOAc (500 mL) and HCl (1 N, 500 mL, final pH=6). The organic layer was washed with brine (500 mL), dried over Na2SO4, filtered, then concentrated. The crude oil was purified by flash column chromatography (0% to 10% MeOH in DCM). The resulting solids obtained were stirred with MTBE for 1 h, filtered then dried to constant weight. The stir/filter protocol was repeated twice. 16-iii (40.0 g, 67%) was isolated spectral characteristics consistent with the literature Hutter, D., et al., Nucleosides Nucleotides Nucleic Acids 29, 879-895 (2010).

1.4 Intermediate 16-iv

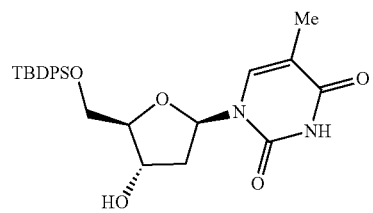

To a solution of 2'-deoxythymidine (15.0 g, 61.3 mmol. 1.0 equiv.) and DMAP (1.51 g, 12.26 mmol, 0.2 equiv.) in dry pyridine (75 mL) was added TBDPSCl (18.7 mL, 70.5 mmol, 1.2 equiv.). The mixture was stirred for 16 h, then diluted with EtOAc (200 mL) and washed with water (200 mL), ammonium chloride (saturated aqueous, 100 mL), then brine (100 mL). The organic layer was dried over MgSO₄, filtered, then concentrated in vacuo to afford a residue that was purified by flash column chromatography over silica gel (25% EtOAc in hexanes to 100% EtOAc). Residual pyridine was removed by stirring in MTBE/hexanes (1:1, v/v, 150 mL). The resulting solid was isolated by filtration and washed with MTBE (100 mL). The white solid was dried at 50° C. and 20 torr until constant weight was achieved. 16-iv (22.59 g, 77%) was isolated with spectral characteristics consistent with the literature (Nagaya, Y., et al., Nucleosides Nucleotides Nucleic Acids 35, 64-75 (2016)).

1.5 Intermediate 16-v

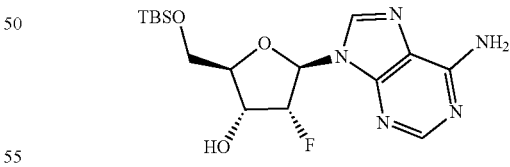

2'-Deoxy-2'-fluoroadenosine (2.10 g, 7.81 mmol, 1.0 equiv.) was dried by co-evaporation with anhydrous pyridine (20 mL×3) in vacuo then dissolved in anhydrous DMF (40 mL, 0.2 M) in a flame-dried round bottom flask. Imidazole (1.17 g, 17.2 mmol, 2.2 equiv.) was added, followed by TBSCl (1.29 g, 8.60 mmol, 1.1 equiv.). The reaction was stirred overnight at ambient temperature. The reaction was quenched on addition of water (40 mL). After stirring for 20 minutes, the solids were collected by filtration and washed with water (40 mL). After drying in vacuo overnight, 16-v (2.54 g, 85%) was isolated as a white solid with spectral characteristics consistent with the literature (Wnuk, S., et al., J. Org. Chem. 67, 8794-8797 (2002)).

2. Synthesis of Loaded Nucleosides (General Procedure 2)

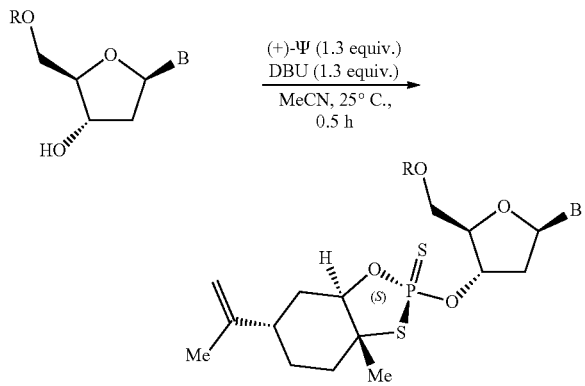

The loaded nucleosides were prepared as follows. Nucleoside (1.0 equiv.) and (+) or (−)-Ψ (1.3 equiv.) were dissolved in anhydrous acetonitrile (0.1 M) in a flame-dried round-bottom flask. DBU (1.3 equiv.) was added dropwise to the reaction mixture while stirring. Reaction progress was monitored by $^{31}$P NMR. After 30 minutes, the crude reaction mixture was filtered through a short pad of silica gel (approximately 1 inch); then the silica gel was washed with EtOAc (4×5 mL). The filtrate was washed with saturated aqueous NaHCO$_3$ (30 mL), water (30 mL), saturated aqueous KH$_2$PO$_4$ (30 mL), dried over MgSO$_4$ and the solvent was removed in vacuo. The crude product was purified by silica gel column chromatography.

(+)-Ψ refers to (2R,3aR,6S,7aR)-3a-methyl-2-((perfluorophenyl)thio)-6-(prop-1-en-2-yl)hexahydrobenzo[d][1,3,2]oxathiaphosphole 2-sulfide, shown below.

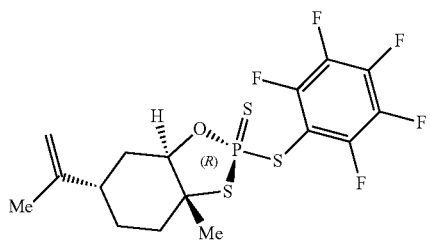

(−)-Ψ refers to (2S,3aS,6R,7aS)-3a-methyl-2-((perfluorophenyl)thio)-6-(prop-1-en-2-yl)hexahydrobenzo[d][1,3,2]oxathiaphosphole 2-sulfide, shown below.

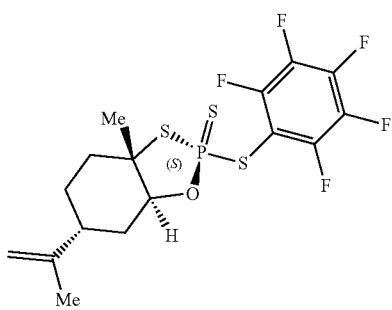

2.1. Compound 3-107

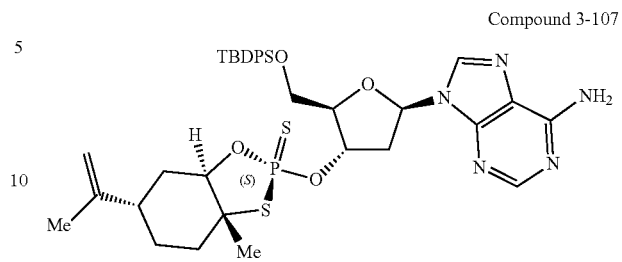

Compound 3-107

To a 250 mL flask were added nucleoside (2R,3S,5R)-5-(6-amino-9H-purin-9-yl)-2-(((tert-butyldiphenylsilyl)oxy)methyl)tetrahydrofuran-3-ol (intermediate 16-i) 4.14 g, 8.46 mmol, 1 equiv.) and the (+)-ψ reagent (4.93 g, 11.0 mmol, 1.3 equiv.) in THF (42 mL). Then, DBU (1.60 mL, 10.6 mmol, 1.3 equiv.) was added dropwise at ambient temperature. After 20 minutes, the reaction was quenched with AcOH (1.5 mL, 26 mmol, 3.1 equiv.) and stirred vigorously under air for 5 h. The crude mixture was filtered and concentrated to a paste that was purified by flash column chromatography (0% to 100% EtOAc in DCM) to afford the desired compound 3-107 as a white solid (6.01 g, 97% yield).

Physical State: White solid;

$^1$H NMR (400 MHz, Chloroform-d): δ 8.23 (s, 1H), 8.07 (s, 1H), 7.76-7.54 (m, 4H), 7.48-7.31 (m, 6H), 6.87 (br s, 2H), 6.50 (t, J=7.1 Hz, 1H), 5.70-5.59 (m, 1H), 5.04 (s, 1H), 4.89 (s, 1H), 4.48 (dt, J=12.6, 3.2 Hz, 1H), 4.41-4.33 (m, 1H), 3.98-3.89 (m, 2H), 2.88-2.73 (m, 2H), 2.59 (br s, 1H), 2.27 (br d, J=13.1 Hz, 1H), 2.17-2.07 (m, 3H), 1.97-1.80 (m, 2H), 1.78 (s, 3H), 1.71 (s, 3H), 1.07 (s, 9H);

$^{13}$C NMR (101 MHz, Chloroform-d): δ 155.4, 152.0, 149.3, 144.8, 138.5, 135.6, 135.4, 132.6, 132.2, 128.98, 128.97, 127.9, 119.1, 112.0, 86.4 (d, J=3.4 Hz), 86.0, 84.3, 79.6 (J=8.0 Hz), 65.7, 63.6, 39.6 (d, J=7.3 Hz), 38.8, 33.8, 33.7, 27.8, 27.6, 26.9, 23.4, 22.7, 21.7, 19.2;

$^{31}$P NMR (162 MHz, Chloroform-d): δ 101.0;

HRMS (ESI-TOF, m/z): HRMS (ESI) Calcd for $[C_{36}H_{46}N_5O_4PS_2Si+H]^+$ 736.2571; Found 736.2584 (1.7 ppm error).

R$_f$=0.45 (25% EtOAc in DCM); UV, KMnO$_4$.

2.2. Compound 3-108

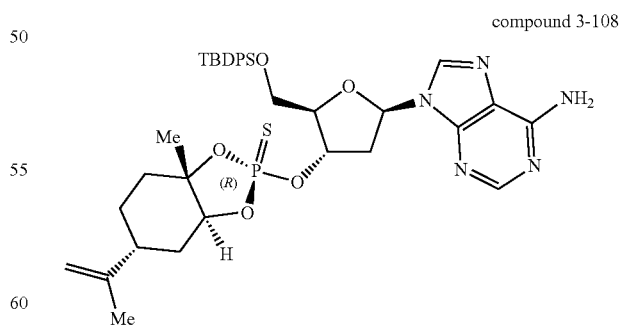

compound 3-108

To a 250 mL flask were added nucleoside (2R,3S,5R)-5-(6-amino-9H-purin-9-yl)-2-(((tert-butyldiphenylsilyl)oxy)methyl)tetrahydrofuran-3-ol (intermediate 16-i) (3.89 g, 7.95 mmol, 1 equiv.) and the (−)-ψ reagent (4.61 g, 10.3 mmol, 1.3 equiv.) in THF (40 mL). DBU (1.50 mL, 9.9 mmol, 1.3 equiv.) was then added dropwise at ambient temperature. After 20 minutes, the reaction was quenched with AcOH (1.4 mL, 24 mmol, 3.0 equiv.) and stirred vigorously under air for 5 h. The crude was filtered and concentrated to a paste that was purified by flash column chromatography (0% to 100% EtOAc in DCM) to afford the desired compound 3-108 as a white solid (5.59 g, 96% yield).

Physical State: White solid;
M.P. 181.6° C.

$^1$H NMR (400 MHz, Chloroform-d): δ δ 8.31 (s, 1H), 8.05 (s, 1H), 7.72-7.59 (m, 4H), 7.45-7.33 (m, 6H), 6.50 (dd, J=8.6, 5.6 Hz, 1H), 6.07 (s, 2H), 5.64 (br dd, J=11.4, 5.3 Hz, 1H), 5.06 (s, 1H), 4.92 (s, 1H), 4.49 (dt, J=12.5, 3.1 Hz, 1H), 4.36-4.29 (m, 1H), 3.91 (d, J=3.3 Hz, 2H), 2.87-2.70 (m, 2H), 2.60 (br s, 1H), 2.33 (br d, J=13.1 Hz, 1H), 2.19-2.08 (m, 1H), 2.02-1.83 (m, 3H), 1.83-1.69 (m, 7H), 1.07 (s, 9H);

$^{13}$C NMR (101 MHz, Chloroform-d): δ 155.5, 152.9, 149.7, 144.7, 138.3, 135.6, 135.4, 132.6, 132.3, 129.95, 129.92, 127.9, 119.8, 112.1, 85.96 (d, J=6.6 Hz), 85.95, 83.8, 79.1 (d, J=7.3 Hz), 65.8, 63.6, 39.7 (d, J=4.4 Hz), 38.8, 33.7, 33.6, 27.8, 27.6, 26.9, 23.3, 22.7, 21.7, 19.2;

$^{31}$P NMR (162 MHz, Chloroform-d): δ 101.1 (s, 1P);

HRMS (ESI-TOF, m/z): HRMS (ESI) Calcd for [C$_{36}$H$_{46}$N$_5$O$_4$PS$_2$Si+H]$^+$ 736.2571; Found 736.2581 (1.4 ppm error).

R$_f$=0.35 (25% EtOAc in DCM); UV, KMnO$_4$.

2.3. Compound 3-109

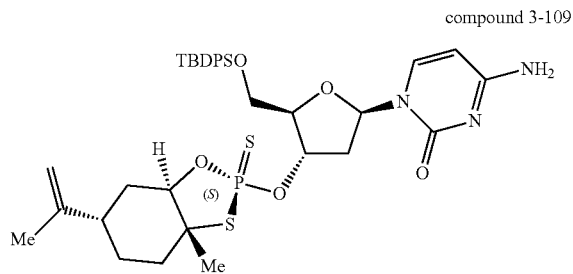

compound 3-109

To a solution of nucleoside 4-amino-1-((2R,4S,5R)-5-(((tert-butyldiphenylsilyl)oxy)methyl)-4-hydroxytetrahydrofuran-2-yl)pyrimidin-2(1H)-one (intermediate 16-ii) (3.20 g, 6.89 mmol, 1.0 equiv) and (−)-ψ reagent (4.20 g, 9.41 mmol, 1.5 equiv) and in THF (46 mL) was added DBU (1.35 mL, 8.98 mmol, 1.35 equiv) at 0° C. After 1 h, the mixture was diluted with EtOAc, DCM, and heptane (60 mL each). The mixture was then washed with K$_2$HPO$_4$ (10% aq., 65 mL then 35 mL). The organic layer was dried over MgSO$_4$, and concentrated. The resulting residue was purified by flash chromatography (0 to 10% MeOH in DCM) to afford the desired compound 3-109 as a white solid (4.3 g, 87% yield).

Physical State: White solid;
$^1$H NMR (400 MHz, Chloroform-d): δ 7.94-7.85 (m, 1H), 7.71-7.62 (m, 4H), 7.54-7.34 (m, 7H), 6.49-6.42 (m, 1H), 5.58-5.46 (m, 2H), 5.05 (s, 1H), 4.88 (s, 1H), 4.45 (dt, J=12.4, 3.2 Hz, 1H), 4.27 (br d, J=2.0 Hz, 1H), 4.04-3.92 (m, 2H), 2.74 (ddd, J=14.1, 5.6, 1.8 Hz, 1H), 2.58 (br s, 1H), 2.31-2.09 (m, 3H), 2.04-1.74 (m, 8H), 1.70 (s, 3H), 1.08 (s, 9H);

$^{13}$C NMR (101 MHz, Chloroform-d): δ 144.6, 141.4, 135.7, 135.4, 132.8, 131.9, 130.2, 130.0, 128.1, 128.0, 112.2, 94.3, 86.1, 79.1, 65.6, 63.6, 40.3, 38.8, 33.8, 27.8, 27.0, 23.4, 22.6, 21.7, 19.3;

$^{31}$P NMR (162 MHz, Chloroform-d): δ 101.4;

HRMS (ESI-TOF, m/z): HRMS (ESI) Calcd for [C$_{35}$H$_{46}$N$_3$O$_5$PS$_2$Si+H]$^+$ 712.2459; Found 712.2470 (1.6 ppm error).

R$_f$=0.52 (10% MeOH in DCM); UV, KMnO$_4$.

2.4. Compound 3-110

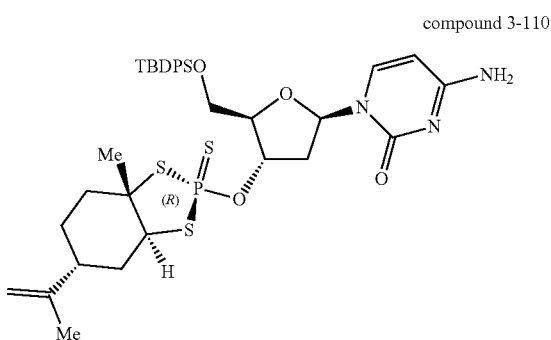

compound 3-110

To a solution of nucleoside 4-amino-1-((2R,4S,5R)-5-(((tert-butyldiphenylsilyl)oxy)methyl)-4-hydroxytetrahydrofuran-2-yl)pyrimidin-2(1H)-one (intermediate 16-ii) (3.5 g, 7.5 mmol, 1.0 equiv) and (+)-ψ reagent (4.9 g, 11 mmol, 1.5 equiv) in THF (60 mL, 20 v) was added DBU (1.52 mL, 10.1 mmol. 1.35 equiv) at 0° C. After 1 h, the mixture was diluted with EtOAc, DCM, and heptane (each 60 mL). The mixture was then washed with K$_2$HPO$_4$ (10% aq., 65 mL then 35 mL. The organic layer was dried over MgSO$_4$, and concentrated. The resulting residue was purified by flash chromatography (0 to 10% MeOH in DCM) to afford the desired compound 3-110 as a white solid (4.2 g, 82% yield).

Physical State: White solid;
$^1$H NMR (400 MHz, Chloroform-d): δ 7.93 (d, J=7.3 Hz, 1H), 7.67 (ddd, J=7.8, 3.9, 1.5 Hz, 4H), 7.53-7.34 (m, 7H), 6.45 (dd, J=7.3, 5.8 Hz, 1H), 5.60-5.33 (m, 3H), 5.08 (s, 1H), 4.92 (s, 1H), 4.47 (dt, J=12.6, 3.3 Hz, 1H), 4.23 (br d, J=2.5 Hz, 1H), 4.02-3.90 (m, 2H), 2.73 (ddd, J=14.0, 5.7, 2.5 Hz, 1H), 2.63-2.57 (m, 1H), 2.35 (br d, J=11.6 Hz, 1H), 2.28-2.10 (m, 2H), 2.10-1.95 (m, 1H), 1.94-1.86 (m, 2H), 1.85-1.77 (m, 4H), 1.71 (s, 3H), 1.08 (s, 9H);

$^{13}$C NMR (101 MHz, Chloroform-d): δ 165.1, 155.4, 144.6, 141.1, 135.7, 135.4, 132.8, 132.0, 130.1, 130.0, 128.0 (d, J=10.9 Hz, 1C), 112.2, 94.2, 85.7, 85.7 (d, J=6.4 Hz, 1C), 78.3 (d, J=7.3 Hz, 1C), 65.8, 63.4, 40.4 (d, J=4.5 Hz, 1C), 38.8, 33.7 (d, J=9.1 Hz, 1C), 27.7 (d, J=15.4 Hz, 1C), 27.0, 23.4, 22.7, 21.8, 19.2;

$^{31}$P NMR (162 MHz, Chloroform-d): δ 101.5;

HRMS (ESI-TOF, m/z): HRMS (ESI) Calcd for [C$_{35}$H$_{46}$N$_3$O$_5$PS$_2$Si+H]$^+$ 712.2459; Found 712.2473 (2.0 ppm error).

R$_f$=0.55 (10% MeOH in DCM); UV, KMnO$_4$.

2.5. Compound 3-111

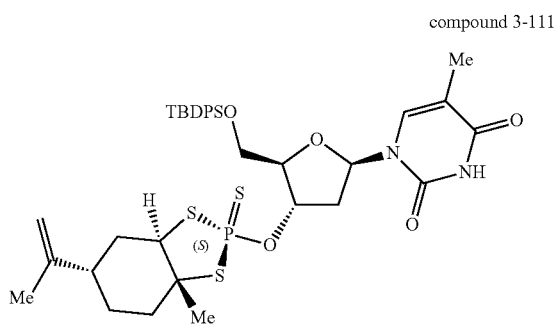

compound 3-111

A suspension of nucleoside 1-((2R,4S,5R)-5-(((tert-butyl-diphenylsilyl)oxy)methyl)-4-hydroxytetrahydrofuran-2-yl)-5-methylpyrimidine-2,4(1H,3H)-dione (intermediate 16-iv) (4.00 g, 8.32 mmol, 1.00 equiv.) and the (+)-ψ reagent (4.83 g, 10.8 mmol, 1.3 equiv.) in MeCN (83 mL) was cooled to an internal temperature of 0° C. DBU (1.63 mL, 10.8 mmol, 1.3 equiv.) was added in one portion and stirred at 0° C. for 30 min. The resulting mixture was passed through a plug of silica gel (ca. 1") and washed with ethyl acetate (82 mL). The organic layer was washed with water (42 mL) then $NaH_2PO_4$ (10 wt % aq., 42 mL). The organic layer was dried over $MgSO_4$, filtered and concentrated in vacuo to afford a yellow gel that was purified by flash column chromatography (10% to 90% EtOAc in hexanes) to afford a foam which was broken down into a powder by stirring in hexane (3×50 mL). This process was repeated three times total. The compound 3-111 was isolated as a white powder which was dried at 50° C. and 20 Torr until constant weight was reached (5.76 g, 95 wt %, remainder hexanes and EtOAc, 90% corrected yield).

Physical State: White solid;

$^1$H NMR (400 MHz, Chloroform-d): δ 8.19 (br s, 1H), 7.64-7.75 (m, 4H), 7.38-7.55 (m, 7H), 6.47 (dd, J=9.5, 5.2 Hz, 1H), 5.60 (dd, J=11.1, 6.1 Hz, 1H), 5.07 (s, 1H), 4.90 (s, 1H), 4.48 (dt, J=12.4, 3.3 Hz, 1H), 4.27 (s, 1H), 3.92-4.09 (m, 2H), 2.51-2.65 (m, 2H), 2.16 (td, J=13.3, 3.9 Hz, 1H), 1.75-2.05 (m, 4H), 1.79 (s, 3H), 1.72 (s, 3H), 1.57-1.59 (m, 4H), 1.10 (s, 9H)

$^{13}$C NMR (101 MHz, Chloroform-d): δ 163.4, 150.2, 144.6, 135.6, 135.2, 134.9, 132.8, 131.7, 130.2, 130.1, 128.1, 128.0, 112.2, 111.6, 86.0, 85.9 (d, J=2.9 Hz), 84.4, 79.6 (d, J=7.3 Hz), 65.7, 63.8, 39.2 (d, J=8.0 Hz), 38.8, 33.7, 33.6, 27.8, 27.6, 27.0, 23.4, 22.6, 21.7, 19.4, 11.9;

$^{31}$P NMR (162 MHz, Chloroform-d): δ 101.49;

HRMS (ESI-TOF, m/z): Calcd for $[C_{36}H_{47}N_2O_6PS_2Si+H]^+$ 727.2455; Found 727.2478 (3.1 ppm error).

$R_f$=0.41 (40% EtOAc in hexane); UV, $KMnO_4$.

2.6. Compound 3-112

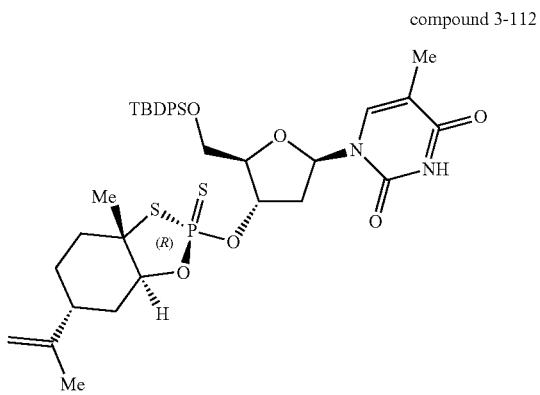

compound 3-112

A suspension of nucleoside 1-((2R,4S,5R)-5-(((tert-butyl-diphenylsilyl)oxy)methyl)-4-hydroxytetrahydrofuran-2-yl)-5-methylpyrimidine-2,4(1H,3H)-dione (intermediate 16-iv) (3.00 g, 6.24 mmol, 1.0 equiv.) and the (−)-ψ reagent (3.62 g, 8.11 mmol, 1.3 equiv.) in MeCN (62 mL) was cooled to 0° C. DBU (1.22 mL, 8.11 mmol, 1.3 equiv.) was added in one portion, stirred at 0° C. for 30 min then the mixture, then passed through a plug of silica gel (ca. 1") and washed with ethyl acetate (62 mL). The solution was washed with water (31 mL) then with $K_2HPO_4$ (10 wt % aq., 31 mL). The organic layer was dried over $MgSO_4$, filtered and concentrated in vacuo to afford a yellow gel that was purified by flash column chromatography (10% to 90% EtOAc in hexanes) to afford a foam which was broken down into a powder by concentration from heptane (3×50 mL). The compound 3-112 was isolated as a white powder which was dried at 50° C. and 20 Torr until constant weight was reached (4.46 g, 91.5 wt %, remainder heptane, 90% corrected yield).

Physical State: White solid;

$^1$H NMR (400 MHz, Chloroform-d): δ 8.22 (br s, 1H), 7.64-7.74 (m, 4H), 7.51 (d, J=1.3 Hz, 1H), 7.38-7.50 (m, 6H), 6.45 (dd, J=9.3, 5.1 Hz, 1H), 5.59 (dd, J=11.4, 5.8 Hz, 1H), 5.09 (s, 1H), 4.93 (s, 1H), 4.50 (dt, J=12.7, 3.3 Hz, 1H), 4.24 (d, J=1.5 Hz, 1H), 3.97 (d, J=2.0 Hz, 2H), 2.57-2.65 (br m, 1H), 2.57 (dd, J=14.0, 5.4 Hz, 1H), 2.27-2.38 (m, 2H), 2.14 (td, J=13.3, 3.9 Hz, 1H), 1.86-2.02 (m, 3H), 1.82 (s, 3H), 1.72-1.82 (m, 1H), 1.72 (s, 3H), 1.59 (d, J=1.0 Hz, 3H), 1.10 (s, 9H);

$^{13}$C NMR (101 MHz, Chloroform-d): δ 163.6, 150.2, 144.6, 135.6, 135.2, 134.9, 132.8, 131.7, 130.2, 130.0, 128.1, 128.0, 112.2, 111.5, 86.0, 85.8 (d, J=7.1 Hz), 84.2, 79.1 (d, J=8.1 Hz), 65.8, 63.9, 39.5 (d, J=4.0 Hz), 38.8, 33.7, 33.6, 27.8, 27.6, 27.0, 23.3, 22.6, 21.7, 19.3, 11.9;

$^{31}$P NMR (162 MHz, Chloroform-d): δ 101.67;

HRMS (ESI-TOF, m/z): HRMS (ESI) Calcd for $[C_{36}H_{47}N_2O_6PS_2Si+H]^+$ 727.2455; Found 727.2474 (2.6 ppm error).

$R_f$=0.41 (40% EtOAc in hexane); UV, $KMnO_4$.

2.7. Compound 3-113

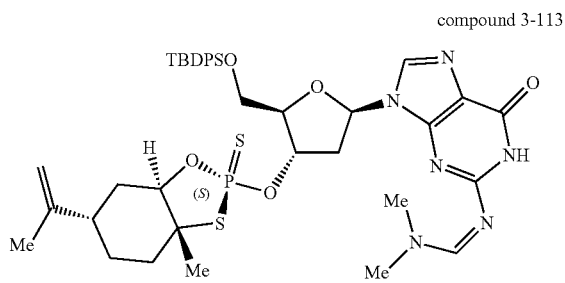
compound 3-113

To a 100 mL flask were added (E)-N'-(9-((2R,4S,5R)-5-(((tert-butyldiphenylsilyl)oxy)methyl)-4-hydroxytetrahydrofuran-2-yl)-6-hydroxy-9H-purin-2-yl)-N,N-dimethylformimidamide (intermediate 16-iii) (1.50 g, 2.60 mmol, 1.0 equiv.) and (−)-ψ (1.67 g, 3.74 mmol, 1.4 equiv.) in MeCN (27 mL). The mixture was cooled to 0° C. and DBU (0.52 mL, 3.48 mmol, 1.3 equiv.) was added dropwise; the reaction was left to stir at ambient temperature. After 1 h UPLC analysis showed complete consumption of intermediate 16-iii. The reaction mixture was diluted with EtOAc (27 mL) then washed with water (27 mL) and Na$_2$HPO$_4$ (10 wt %, 27 mL). The organic phase was dried over Na$_2$SO$_4$, filtered and the solvent was removed in vacuo. The crude residue was purified by silica gel column chromatography (100% EtOAc to 100% THF) to afford the compound 3-113 as a light yellow solid (1.96 g, 91%). Note: The isolated product contains BHT (from stabilized THF).

Physical State: White solid;
$^1$H NMR (400 MHz, Chloroform-d): δ 9.90 (br s, 1H), 8.52 (s, 1H), 7.79 (s, 1H), 7.69-7.60 (m, 4H), 7.44-7.28 (m, 6H), 6.32 (dd, J=7.7, 6.2 Hz, 1H), 5.64 (ddt, J=11.5, 6.0, 2.7 Hz, 1H), 4.99 (s, 1H), 4.87 (s, 1H), 4.47 (dt, J=12.7, 3.1 Hz, 1H), 4.28 (q, J=3.4 Hz, 1H), 3.92-3.82 (m, 2H), 3.12 (s, 3H), 3.06 (s, 3H), 2.90-2.55 (m, 4H), 2.27-2.22 (m, 1H), 2.18-2.04 (m, 1H), 2.00-1.80 (m, 3H), 1.76 (s, 3H), 1.73 (s, 3H), 1.04 (s, 9H);
$^{13}$C NMR (101 MHz, Chloroform-d): δ 158.4, 157.8, 156.8, 150.0, 145.0, 136.4, 135.5, 135.4, 132.5, 132.3, 129.9, 127.8, 127.8, 120.5, 111.8, 86.0, 85.8, 85.7, 83.4, 79.0, 78.9, 65.8, 63.5, 41.3, 39.0, 39.0, 38.7, 35.2, 33.7, 33.6, 27.7, 27.5, 26.8, 23.3, 22.6, 21.7, 19.1;
$^{31}$P NMR (162 MHz, Chloroform-d): δ 100.5;
HRMS (ESI-TOF, m/z): HRMS (ESI) Calcd for [C$_{39}$H$_{51}$N$_6$O$_5$PS$_2$Si+H]$^+$ 807.2942; Found 807.2957 (1.8 ppm error).
R$_f$=0.68 (100% THF); UV, KMnO$_4$.

2.8. Compound 3-114

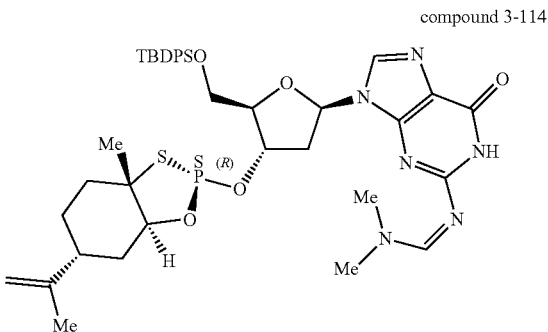
compound 3-114

To a 100 mL flask were added (E)-N'-(9-((2R,4S,5R)-5-(((tert-butyldiphenylsilyl)oxy)methyl)-4-hydroxytetrahydrofuran-2-yl)-6-hydroxy-9H-purin-2-yl)-N,N-dimethylformimidamide (intermediate 16-iii) (1.10 g, 1.96 mmol, 1.0 equiv.) and the (−)-ψ v reagent (1.14 g, 2.55 mmol, 1.4 equiv.) in MeCN (20 mL). The mixture was cooled to 0° C. and DBU (0.38 mL, 2.55 mmol, 1.3 equiv.) was added dropwise and the reaction was left to stir at ambient temperature. After 1 h UPLC analysis showed complete consumption of SI-3. The reaction mixture was diluted with EtOAc (20 mL) then washed with water (20 mL) and Na2HPO$_4$ (10 wt %, 20 mL). The organic phase was dried over Na$_2$SO$_4$, filtered, and the solvent was removed in vacuo. The crude residue was purified by silica gel column chromatography (0 to 100% THF in EtOAc) to afford the compound 3-114 as a white solid (1.20 g, 76%). Note: The isolated product contains BHT (from stabilized THF).

Physical State: White solid;
$^1$H NMR (400 MHz, Chloroform-d): δ 9.61 (br s, 1H), 8.57 (s, 1H), 7.77 (s, 1H), 7.69-7.60 (m, 4H), 7.44-7.32 (m, 6H), 6.32 (dd, J=7.7, 6.2 Hz, 1H), 5.64 (ddt, J=11.5, 6.0, 2.7 Hz, 1H), 5.00 (s, 1H), 4.88 (s, 1H), 4.48 (dt, J=12.7, 3.1 Hz, 1H), 4.27 (q, J=3.4 Hz, 1H), 3.92-3.82 (m, 2H), 3.14 (s, 3H), 3.10 (s, 3H), 2.93-2.81 (m, 1H), 2.71-2.58 (m, 2H), 2.37-2.27 (m, 1H), 2.18-2.04 (m, 1H), 2.00-1.80 (m, 4H), 1.77 (s, 3H), 1.73 (s, 3H), 1.05 (s, 9H);
$^{13}$C NMR (101 MHz, Chloroform-d): δ 158.0, 157.8, 156.8, 150.0, 145.0, 136.2, 135.6, 135.4, 132.6, 132.4, 129.9, 127.8, 127.8, 120.8, 111.8, 85.9, 85.6, 85.5, 83.2, 78.5, 78.5, 65.8, 63.5, 41.3, 39.0, 39.0, 38.8, 35.2, 33.8, 33.7, 27.7, 27.6, 26.9, 23.3, 22.7, 21.7, 19.1;
$^{31}$P NMR (162 MHz, Chloroform-d): δ 100.9;
HRMS (ESI-TOF, m/z): HRMS (ESI) Calcd for [C$_{39}$H$_{51}$N$_6$O$_5$PS$_2$Si+H]$^+$ 807.2942; Found 807.2957 (1.8 ppm error).
R$_f$=0.68 (100% THF); UV, KMnO$_4$.

2.9. Compound 3-115

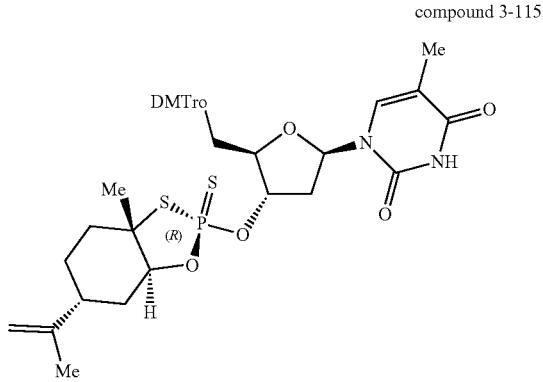
compound 3-115

Compound 3-115 was prepared according to General Procedure 2 using 5'-O-(4,4'-dimethoxytrityl)-2'-deoxythymidine (544 mg, 1.00 mmol). Purification by silica gel column chromatography (30 to 50% EtOAc in hexanes with 1% Et$_3$N) afforded compound 3-115 (459 mg, 58%).

Physical State: White solid;
$^1$H NMR (600 MHz, Acetone-d$_6$): δ 10.04 (s, 1H), 7.62 (d, J=1.5 Hz, 1H), 7.54-7.49 (m, 2H), 7.42-7.31 (m, 6H), 7.30-7.24 (m, 2H), 6.96-6.90 (m, 4H), 6.38 (dd, J=8.2, 6.1 Hz, 1H), 5.58 (ddt, J=10.8, 5.5, 2.4 Hz, 1H), 5.02 (q, J=1.5 Hz, 1H), 4.97-4.93 (m, 1H), 4.53 (dt, J=12.8, 3.4 Hz, 1H), 4.26 (q, J=3.0 Hz, 1H), 3.81 (s, 6H), 3.50 (dd, J=10.6, 3.4

Hz, 1H), 3.41 (dd, J=10.6, 3.2 Hz, 1H), 2.67 (s, 1H), 2.70-2.57 (m, 2H), 2.35 (ddd, J=13.2, 3.6, 1.8 Hz, 1H), 2.12-2.04 (m, 1H), 2.03-1.94 (m, 3H), 1.89 (ddt, J=13.9, 10.5, 5.6 Hz, 1H), 1.81 (s, 3H), 1.71 (s, 3H), 1.49 (d, J=1.2 Hz, 3H).

$^{13}$C NMR (151 MHz, Acetone): δ 164.11, 159.79, 159.77, 151.20, 146.30, 145.70, 136.45, 136.25, 136.01, 131.00, 130.99, 128.96, 128.79, 127.80, 114.08, 112.18, 111.32, 87.77, 86.78, 85.10, 85.05, 85.04, 80.01, 79.96, 66.91, 64.22, 55.55, 39.77, 39.48, 39.46, 34.47, 34.41, 28.26, 28.15, 23.93, 22.79, 22.06, 12.15.

$^{31}$P NMR (162 MHz, Acetone): δ 101.75.

HRMS (ESI-TOF, m/z): Calcd for $C_{41}H_{47}N_2O_8PS_2$ [M−DMTr+H]$^+$ 489.1277; found 489.1278.

R$_f$=0.43 (5% Acetone in DCM); UV, KMnO$_4$.

2.10. Compound 3-116

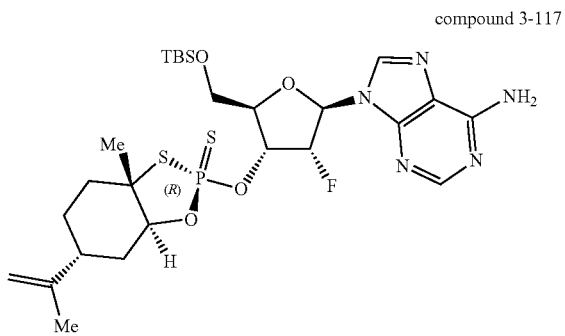

compound 3-116

Compound 3-116 prepared according to General Procedure 2 using 5'-O-(tert-butyldimethylsilyl)-2'-deoxy-2'-fluoroadenosine intermediate 16-v (1.37 g, 3.58 mmol). Crystallization of the crude reaction mixture from acetonitrile afforded compound 3-116 (1.85 g, 82%).

Physical State: White solid;

$^1$H NMR (600 MHz, Acetone-d$_6$): δ 8.22 (d, J=7.6 Hz, 2H), 6.71 (s, 2H), 6.35 (dd, J=17.8, 2.1 Hz, 1H), 5.89-5.74 (m, 2H), 5.02 (q, J=1.5 Hz, 1H), 4.97-4.93 (m, 1H), 4.59 (dt, J=12.8, 3.5 Hz, 1H), 4.33 (dt, J=6.2, 3.1 Hz, 1H), 4.06 (dd, J=11.8, 2.8 Hz, 1H), 3.90 (dd, J=11.8, 3.4 Hz, 1H), 2.86 (s, 1H), 2.65 (d, J=5.8 Hz, 1H), 2.30 (dtd, J=13.4, 3.3, 1.6 Hz, 1H), 2.12 (td, J=13.6, 4.4 Hz, 1H), 2.05-1.83 (m, 4H), 1.81-1.78 (m, 3H), 1.70 (s, 3H), 0.89 (s, 9H), 0.07 (d, J=22.5 Hz, 6H).

$^{13}$C NMR (151 MHz, Acetone-d$_6$): δ 157.23, 153.94, 150.28, 146.20, 140.03, 120.64, 112.05, 93.35, 92.10, 87.64, 87.42, 86.66, 82.85, 82.79, 73.87, 73.83, 73.78, 73.73, 67.33, 62.14, 39.79, 34.41, 34.35, 28.23, 28.13, 26.35, 23.93, 22.67, 22.09, 18.95, −5.20, −5.30.

$^{19}$F NMR (376 MHz, Acetone-d$_6$): δ −202.95.

$^{31}$P NMR (162 MHz, Acetone-d$_6$): δ 101.65.

HRMS (ESI-TOF, m/z): Calcd for $C_{26}H_{41}FN_5O_4PS_2Si$ [M+H]$^+$ 630.2164; found 630.2167;

R$_f$=0.43 (20% acetone in DCM); UV, KMnO$_4$.

2.11. Compound 3-117

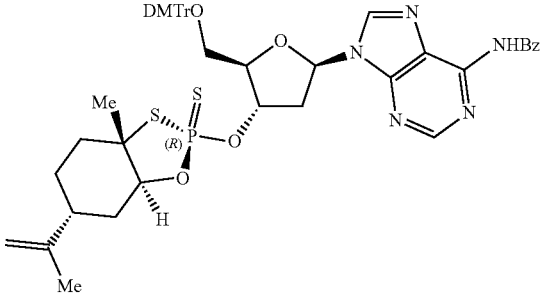

compound 3-117

Compound 3-117 was prepared according to General Procedure 2 using 5'-O-(tert-butyldimethylsilyl)-2'-deoxy-2'-fluoroadenosine intermediate 16-v (685 mg, 1.79 mmol). Crystallization of the crude reaction mixture from acetonitrile afforded compound 3-117 (933 mg, 83%).

Physical State: White solid;

$^1$H NMR (600 MHz, CDCl$_3$): δ 8.39 (s, 1H), 8.16 (s, 1H), 6.39 (dd, J=14.3, 3.7 Hz, 1H), 5.82 (s, 2H), 5.65-5.49 (m, 2H), 5.06 (q, J=1.4 Hz, 1H), 4.94-4.90 (m, 1H), 4.55 (ddd, J=12.8, 3.7, 2.5 Hz, 1H), 4.44 (h, J=2.1 Hz, 1H), 4.04 (dd, J=11.7, 2.3 Hz, 1H), 3.90 (dd, J=11.7, 2.7 Hz, 1H), 2.62 (s, 1H), 2.33 (ddt, J=13.0, 3.8, 1.7 Hz, 1H), 2.18 (td, J=13.5, 4.2 Hz, 1H), 2.04-1.86 (m, 3H), 1.74 (s, 3H), 0.95 (s, 7H), 0.14 (d, J=8.8 Hz, 7H);

$^{13}$C NMR (151 MHz, CDCl$_3$): δ 155.00, 152.90, 149.28, 144.34, 138.10, 119.43, 111.59, 91.66, 91.64, 90.35, 90.33, 85.84, 85.50, 85.29, 82.70, 82.66, 73.80, 73.75, 73.70, 73.66, 65.18, 61.27, 38.41, 33.23, 33.17, 27.33, 27.22, 25.53, 22.92, 22.23, 21.24, 17.99, −5.82, −5.86;

$^{19}$F NMR (376 MHz, CDCl$_3$): δ −204.21;

$^{31}$P NMR (162 MHz, CDCl$_3$): δ 103.12;

HRMS (ESI-TOF, m/z): Calcd for $C_{26}H_{41}FN_5O_4PS_2Si$ [M+H]$^+$ 630.2164; found 630.2165;

R$_f$=0.43 (20% acetone in DCM); UV, KMnO$_4$.

2.12. Compound 3-118 compound 3-118

Compound 3-118 was prepared according to General Procedure 2 using N$^6$-benzoyl-5'-O-(4,4'-dimethoxytrityl)-2'-deoxyadenosine (657 mg, 1.00 mmol). Purification by silica gel column chromatography (30 to 50% EtOAc in hexanes with 1% TEA) afforded compound 3-118 (461 mg, 51%).

Physical State: White solid;

$^1$H NMR (600 MHz, Acetone-d$_6$): δ 10.00 (s, 1H), 8.58 (s, 1H), 8.42 (s, 1H), 8.14 (d, J=7.4 Hz, 2H), 7.69-7.62 (m, 1H), 7.57 (t, J=7.8 Hz, 2H), 7.54-7.46 (m, 2H), 7.38-7.26 (m, 7H), 7.25-7.19 (m, 1H), 6.89-6.82 (m, 4H), 6.58 (dd, J=7.7, 6.1 Hz, 1H), 5.71 (ddt, J=11.3, 5.7, 2.7 Hz, 1H), 5.05 (q, J=1.5 Hz, 1H), 4.98 (d, J=1.8 Hz, 1H), 4.58 (dt, J=12.8, 3.4 Hz, 1H), 4.39 (td, J=5.0, 2.6 Hz, 1H), 3.79 (d, J=2.5 Hz, 6H), 3.52-3.35 (m, 3H), 2.87-2.78 (m, 1H), 2.68 (s, 1H), 2.36 (ddq, J=13.8, 3.3, 1.6 Hz, 1H), 2.12 (td, J=13.6, 4.5 Hz, 1H), 2.07-1.96 (m, 2H), 1.95-1.85 (m, 1H), 1.82 (s, 3H), 1.73 (s, 3H).

$^{13}$C NMR (151 MHz, Acetone-d$_6$): δ 159.75, 152.98, 152.70, 151.45, 146.60, 146.05, 143.56, 136.73, 135.21, 133.87, 133.35, 131.13, 131.07, 130.56, 129.54, 129.30, 129.11, 128.74, 127.72, 126.37, 114.06, 112.29, 87.41, 87.01, 85.63, 85.58, 85.56, 80.20, 80.15, 67.03, 64.30, 55.66, 39.95, 38.49, 38.47, 34.72, 34.66, 28.45, 28.34, 24.11, 22.99, 22.24.

$^{31}$P NMR (162 MHz, Acetone): δ 101.42.

HRMS (ESI-TOF, m/z): Calcd for C$_{48}$H$_{50}$N$_5$O$_7$PS$_2$ [M+H]$^+$ 904.2963; found 904.2968;

R$_f$=0.57 (5% Acetone in DCM); UV, KMnO$_4$.

2.13. Compound 3-119

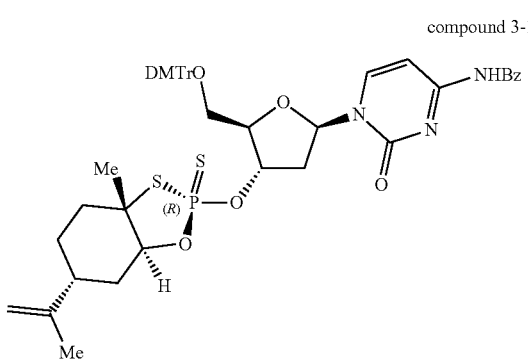

Compound 3-119 was prepared according to General Procedure 2 using N$^4$-benzoyl-5'-O-(4,4'-dimethoxytrityl)-2'-deoxycytidine (634 mg, 1.00 mmol). Purification by silica gel column chromatography (30 to 50% EtOAc in hexanes with 1% Et$_3$N) afforded 3-119 (395 mg, 45%).

Physical State: White solid;

$^1$H NMR (600 MHz, CDCl$_3$): δ 8.68 (s, 1H), 8.20 (d, J=7.5 Hz, 1H), 7.91 (d, J=7.7 Hz, 2H), 7.63 (t, J=7.5 Hz, 1H), 7.54 (t, J=7.5 Hz, 2H), 7.41 (d, J=7.2 Hz, 2H), 7.36-7.29 (m, 6H), 7.28-7.24 (m, 1H), 6.88 (dd, J=8.8, 3.5 Hz, 4H), 6.37 (t, J=6.5 Hz, 1H), 5.61-5.52 (m, 1H), 5.09 (s, 1H), 4.94 (s, 1H), 4.48 (dt, J=12.7, 3.2 Hz, 1H), 4.43-4.39 (m, 1H), 3.82 (s, 3H), 3.81 (s, 3H), 3.55 (dd, J=10.9, 3.3 Hz, 1H), 3.46 (dd, J=10.9, 2.8 Hz, 1H), 2.93 (ddd, J=14.4, 5.8, 2.8 Hz, 1H), 2.62 (d, J=6.2 Hz, 1H), 2.46-2.33 (m, 2H), 2.15 (td, J=13.5, 4.2 Hz, 1H), 2.03-1.97 (m, 1H), 1.96-1.88 (m, 2H), 1.85 (s, 3H), 1.82-1.75 (m, 1H), 1.73 (s, 3H) ppm;

$^{13}$C NMR (151 MHz, CDCl$_3$): δ 162.2, 158.8, 158.8, 144.8, 144.1, 135.3, 135.1, 133.3, 130.2, 130.1, 129.2, 128.2, 127.6, 127.3, 113.5, 113.5, 112.3, 87.3, 87.2, 86.2, 85.8, 85.7, 78.6, 78.6, 66.1, 62.8, 55.4, 55.4, 40.9, 40.9, 39.0, 33.9, 33.8, 27.9, 27.8, 25.7, 23.5, 22.9, 21.9 ppm;

$^{31}$P NMR (162 MHz, CDCl$_3$): δ 102.1 ppm;

HRMS (ESI-TOF): calcd. for C$_{47}$H$_{51}$N$_3$O$_8$PS$_2$ [M+H]$^+$ 880.2855; found 880.2878;

R$_f$=0.25 (30% EtOAc in hexanes); UV, KMnO$_4$.

2.14. Compound 3-120

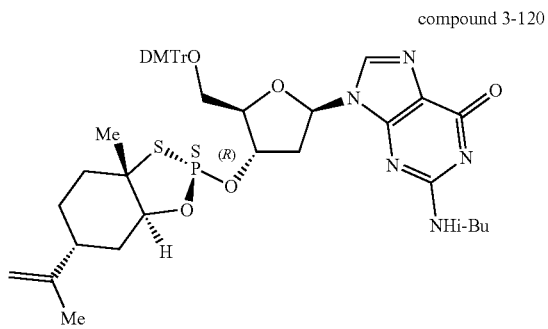

Compound 3-120 was prepared according to General Procedure 2 using N$^6$-benzoyl-5'-O-(4,4'-dimethoxytrityl)-2'-deoxyadenosine (657 mg, 1.00 mmol). Purification by silica gel column chromatography (50 to 100% EtOAc in hexanes with 0.1% TEA) afforded compound 3-120 (263 mg, 30%).

Physical State: White solid;

$^1$H NMR (600 MHz, Acetone-d$_6$): δ 10.26 (s, 1H), 7.94 (s, 1H), 7.47-7.42 (m, 2H), 7.34-7.29 (m, 4H), 7.26 (s, 1H), 7.26-7.17 (m, 2H), 6.87-6.80 (m, 4H), 6.26 (dd, J=8.2, 5.8 Hz, 1H), 5.55 (ddt, J=11.3, 5.5, 2.6 Hz, 1H), 5.00 (q, J=1.4 Hz, 1H), 4.93 (dt, J=1.9, 0.9 Hz, 1H), 4.50 (dt, J=12.8, 3.4 Hz, 1H), 4.25 (td, J=4.6, 2.5 Hz, 1H), 4.05 (q, J=7.2 Hz, 1H), 3.77 (s, 6H), 3.44 (dd, J=10.5, 5.1 Hz, 1H), 3.34 (dd, J=10.4, 4.2 Hz, 1H), 3.15 (ddd, J=14.1, 8.2, 5.9 Hz, 1H), 2.72 (ddd, J=14.1, 5.9, 2.6 Hz, 1H), 2.66 (s, 1H), 2.36-2.29 (m, 1H), 2.12-1.94 (m, 9H), 1.88 (ddt, J=15.0, 13.2, 4.9 Hz, 1H), 1.77 (dt, J=1.4, 0.7 Hz, 3H), 1.71 (s, 3H), 1.25-1.17 (m, 8H).

$^{13}$C NMR (151 MHz, Acetone): δ 180.74, 180.67, 171.03, 159.80, 159.79, 155.85, 149.55, 149.24, 146.62, 146.01, 137.95, 136.72, 136.65, 131.14, 131.08, 129.12, 128.75, 127.77, 122.46, 114.06, 112.27, 87.44, 87.12, 85.73, 85.68, 84.65, 80.05, 80.00, 67.12, 64.45, 60.68, 55.65, 39.92, 38.70, 38.67, 36.80, 36.76, 34.73, 34.67, 30.50, 30.34, 30.21, 29.85, 29.70, 28.44, 28.34, 24.07, 22.94, 22.21, 20.98, 19.50, 19.36, 14.65.

$^{31}$P NMR (162 MHz, Acetone): δ 100.84.

HRMS (ESI) m/z: calculated for C$_{45}$H$_{52}$N$_5$O$_8$PS$_2$ [M+H]$^+$ 886.3068; found 886.3066.

R$_f$=0.25 (60% EtOAc in hexanes+0.1% Et$_3$N); UV, KMnO$_4$.

2.15. Compound 3-121

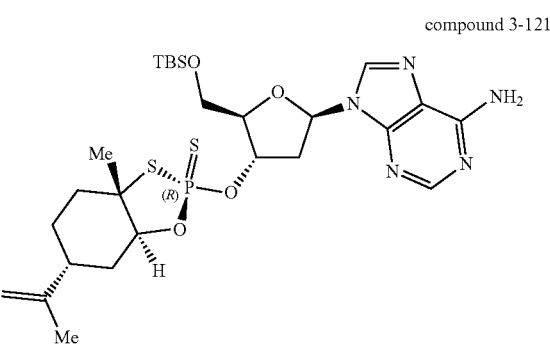

Compound 3-121 was prepared according to General Procedure 2 using 5'-O-(tert-butyldimethylsilyl)-2'-deoxyadenosine (585 mg, 1.6 mmol). Purification by flash column chromatography (70% EtOAc in hexanes) afforded compound 3-121 (628 mg, 64% yield).

Physical State: White solid;

$^1$H NMR (600 MHz, Acetone-$d_6$): δ 8.21 (d, J=7.5 Hz, 2H), 6.61 (s, 1H), 6.49-6.41 (m, 1H), 5.54 (ddt, J=10.4, 5.6, 2.2 Hz, 1H), 5.06 (q, J=1.5 Hz, 1H), 5.01-4.98 (m, 1H), 4.57, (dt, J=12.8, 3.4 Hz, 1H), 4.26 (td, J=4.5, 2.0 Hz, 1H), 3.98 (dd, J=11.1, 5.0 Hz, 1H), 3.89 (dd, J=11.2, 4.0 Hz, 1H), 3.11 (ddd, J=14.0, 8.3, 5.7 Hz, 1H), 2.74 (ddd, J=14.2, 5.9, 2.3 Hz, 1H), 2.68 (s, 1H), 2.37 (ddt, J=13.4, 3.3, 1.7 Hz, 1H), 2.13 (td, J=13.6, 4.4 Hz, 1H), 2.05-1.95 (m, 5H), 1.89 (tdd, J=14.8, 6.0, 4.5 Hz, 1H), 1.82 (s, 3H), 1.71 (s, 3H), 0.95 (s, 1H), 0.93 (s, 9H), 0.17 (d, J=2.7 Hz, 1H), 0.12 (s, 6H), 0.08 (d, J=8.0 Hz, 1H).

$^{13}$C NMR (151 MHz, Acetone): δ 157.31, 153.89, 150.76, 146.59, 139.92, 112.34, 87.03, 86.70, 85.04, 80.47, 73.55, 67.02, 64.06, 39.98, 39.35, 34.64, 28.36, 26.53, 24.12, 22.99, 22.23, 19.10, −5.04.

$^{31}$P NMR (162 MHz, Acetone): δ 100.35.

HRMS (ESI) m/z: calculated for $C_{26}H_{42}N_5O_4PS_2Si$ [M+H]$^+$ 612.2258; found 612.2258.

$R_f$=0.31 (60% EtOAc in hexanes+0.1% Et$_3$N); UV, KMnO$_4$.

2.16. Compound 3-122 compound 3-122

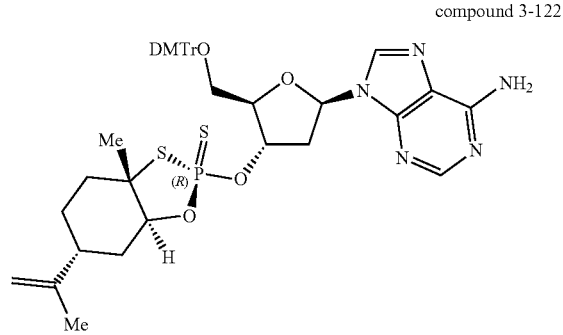

Compound 3-122 was prepared according to General Procedure 2 using 5'-O-(tert-butyldimethylsilyl)-2'-deoxyadenosine (516 mg, 0.93 mmol). Purification by flash column chromatography (20% Acetone in DCM) afforded compound 3-122 (454 mg, 58% yield).

Physical State: White solid;

$^1$H NMR (600 MHz, Acetone-$d_6$): δ 8.13 (d, J=4.4 Hz, 2H), 7.50-7.44 (m, 2H), 7.37-7.31 (m, 4H), 7.27 (t, J=7.7 Hz, 2H), 7.24-7.16 (m, 1H), 6.87-6.80 (m, 4H), 6.67 (s, 2H), 6.44 (dd, J=7.9, 6.1 Hz, 1H), 5.65 (ddt, J=11.2, 5.6, 2.6 Hz, 1H), 5.03 (q, J=1.5 Hz, 1H), 4.97-4.94 (m, 1H), 4.54 (dt, J=12.8, 3.4 Hz, 1H), 4.32 (td, J=5.0, 2.5 Hz, 1H), 3.77 (d, J=1.5 Hz, 6H), 3.47 (dd, J=10.3, 5.2 Hz, 1H), 3.39 (dd, J=10.3, 5.0 Hz, 1H), 3.32 (ddd, J=14.0, 7.9, 5.9 Hz, 1H), 2.72 (ddd, J=14.2, 6.1, 2.7 Hz, 1H), 2.66 (s, 1H), 2.34 (ddq, J=13.4, 3.1, 1.6 Hz, 1H), 2.09 (s, 1H), 2.04-1.96 (m, 3H), 1.88 (dddd, J=14.9, 13.5, 6.0, 4.5 Hz, 1H), 1.80 (s, 3H), 1.70 (s, 3H).

$^{13}$C NMR (151 MHz, Acetone-$d_6$): δ 158.73, 158.71, 156.23, 152.72, 149.65, 145.54, 145.06, 139.47, 135.74, 130.11, 130.06, 128.10, 127.70, 126.67, 119.99, 113.01, 111.27, 86.36, 85.94, 84.42, 84.36, 84.24, 79.34, 79.29, 65.97, 63.30, 54.61, 38.91, 37.48, 37.46, 33.68, 33.62, 29.72, 27.40, 27.30, 23.07, 21.95, 21.20.

$^{31}$P NMR (162 MHz, Acetone-$d_6$): δ 100.33.

HRMS (ESI) m/z: calculated for $C_{41}H_{46}N_5O_6PS_2$ [M+H]$^+$ 800.2700; found 800.2701.

$R_f$=0.29 (20% Acetone in DCM 2.17. Compound 3-128 compound 3-128

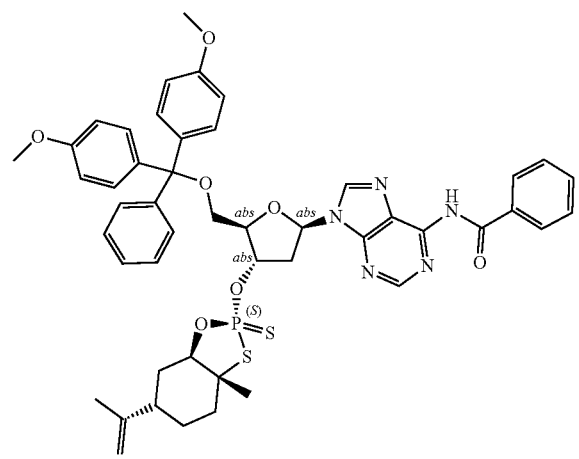

A dry 250 mL round bottom flask was charged with (2R,3aR,6S,7aR)-3a-methyl-2-((perfluorophenyl)thio)-6-(prop-1-en-2-yl)hexahydrobenzo[d][1,3,2]oxathiaphosphole 2-sulfide, (4.40 g, 9.86 mmol) and N$_6$-benzoyl-5'-O-(4,4'-dimethoxytrityl)-2'-deoxyadenosine (5.0 g, 7.60 mmol) under a stream of nitrogen. N,N-Dimethylformamide (30 mL) was added to the mixture which was allowed to stir at room temperature until it became homogeneous. The mixture was cooled to 0° C., and 1,8-diazabicyclo[5.4.0]undec-7-ene (1.5 mL, 10.03 mmol) was then added drop-wise over 1 minute. The reaction mixture was allowed to stir at 0° C. for a total of 15 minutes. The cold reaction mixture was diluted with toluene (150 mL). The mixture was transferred to a separatory funnel where it was washed twice with 1M pH 7.4 phosphate buffer solution (Aldrich P3619, 100 mL). The organics were dried using MgSO$_4$ and the mixture was filtered and the filtrate was concentrated to dryness. The residue was dissolved in ethyl acetate (<5 mL). The mixture was purified via Biotage medium pressure liquid chromatography (Silica; Isco RediSep 120 g; 70% EtOAc-Hex 1% triethylamine to 100% Ethyl acetate 1% triethylamine over 16 CV), affording 4.24 g of solid white foam. LCMS (Waters Aquity UPLC BEH C18 2.1×50 mm 1.7 mm; 2% CH3CN—H2O 0.05% TFA to 98% CH3CN—H2O 0.05% TFA over 1.5 min at 0.8 mL/min, 50° C.) (M+H)$^+$=904.5 (rf 1.66 min). 1H NMR (500 MHz, CHLOROFORM-d) δ 9.03 (s, 1H), 8.76 (s, 1H), 8.20 (s, 1H), 8.08-7.98 (m, 2H), 7.67-7.60 (m, 1H), 7.57-7.51 (m, 2H), 7.45-7.40 (m, 2H), 7.35-7.30 (m, 4H), 7.30-7.25 (m, 2H), 7.25-7.19 (m, 1H), 6.82 (d, J=9.0 Hz, 4H), 6.58 (dd, J=8.8, 5.6 Hz, 1H), 5.67 (br dd, J=11.1, 5.4 Hz, 1H), 5.06 (s, 1H), 4.92 (s, 1H), 3.79 (s, 5H), 3.56-3.38 (m, 2H), 3.11-2.98 (m, 1H), 2.83 (dd, J=13.9, 5.6 Hz, 1H), 2.62 (br s, 1H), 2.29 (br d, J=13.1 Hz, 1H), 2.17 (td, J=13.4, 3.9 Hz, 1H), 2.04-1.86 (m, 4H), 1.80 (s, 3H), 1.85-1.76 (m, 2H), 1.74 (s, 3H).

2.18. Compound 3-129 compound 3-129

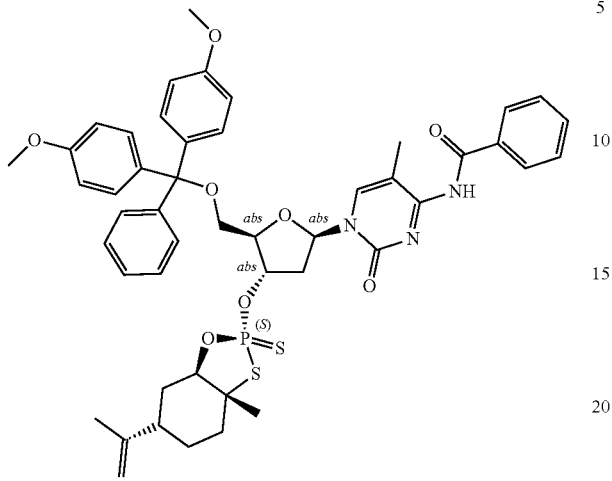

A dry 250 mL round bottom flask was charged with (2R,3aR,6S,7aR)-3a-methyl-2-((perfluorophenyl)thio)-6-(prop-1-en-2-yl)hexahydrobenzo[d][1,3,2]oxathiaphosphole 2-sulfide (4.45 g, 9.97 mmol) and 5'-O-(4,4'-dimethoxytrityl)-n4-benzoyl-5-methyl-2'-deoxycytidine (5.00 g, 7.72 mmol) under a stream of nitrogen. N,N-Dimethylformamide (4 mL) was added to the mixture which was allowed to stir at room temperature until it became homogeneous. The mixture was cooled to 0° C. 1,8-diazabicyclo[5.4.0]undec-7-ene (1.5 mL, 10.03 mmol) was then added to the mixture drop-wise. The mixture was stirred at 0° C. for 20 minutes. The cold reaction mixture was diluted to ~25 mL with toluene. The mixture was transferred to a separatory funnel where it was washed twice with 1M pH 7.4 phosphate buffer solution (Aldrich P3619). Organics were dried using $MgSO_4$. The mixture was filtered and the filtrate was concentrated to dryness. The residue was dissolved in ethyl acetate (<5 mL). The mixture was purified via Biotage medium pressure liquid chromatography (Silica; Isco RediSep 24 g; 20% EtOAc-Hex 1% triethylamine to 50% EtOAc-Hex 1% triethylamine over 16 CV). Major peak was isolated and concentrated to dryness. The resulting residue was treated with acetonitrile (50 mL). The mixture was then filtered through a 0.45 m PVDF Whatman syringe filter. The filtrate was then concentrated to dryness. 4.95 g of solid white foam was obtained. 1H NMR (500 MHz, CHLOROFORM-d) δ 13.30 (br s, 1H), 8.32 (d, J=7.5 Hz, 2H), 7.82 (s, 1H), 7.60-7.51 (m, 1H), 7.48-7.40 (m, 4H), 7.37-7.30 (m, 6H), 7.27-7.22 (m, 1H), 6.87 (d, J=8.7 Hz, 4H), 6.53 (dd, J=8.9, 5.4 Hz, 1H), 5.65 (dd, J=11.1, 6.0 Hz, 1H), 5.07 (s, 1H), 4.90 (s, 1H), 4.47 (dt, J=12.7, 3.0 Hz, 1H), 4.34 (s, 1H), 3.81 (s, 6H), 3.63-3.38 (m, 2H), 2.69 (dd, J=14.0, 5.5 Hz, 1H), 2.60 (br s, 1H), 2.52-2.33 (m, 2H), 2.25 (br d, J=11.9 Hz, 1H), 2.17 (td, J=13.5, 4.0 Hz, 1H), 2.04-1.91 (m, 2H), 1.86 (td, J=13.1, 5.9 Hz, 1H), 1.77-1.72 (m, 1H), 1.71 (s, 3H), 1.69-1.64 (m, 2H), 1.63 (s, 3H). $^{31}P$ NMR (202 MHz, CHLOROFORM-d) δ 101.4 (br d, J=10.0 Hz, 1P).

LCMS (Waters Aquity UPLC BEH C18 2.1×50 mm 1.7 mm; 2% CH3CN—H2O 0.05% TFA to 98% CH3CN—H2O 0.05% TFA over 1.5 min at 0.8 mL/min) (M+H)+=894.5 (rf 1.93 min). Data are consistent with the desired N-(1-((2R,4S,5R)-5-((bis(4-methoxyphenyl)(phenyl)methoxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-5-methyl-2-oxo-1,2-dihydropyrimidin-4-yl)benzamide (4.95 g, 5.54 mmol, 71.7% yield).

2.19. Compound 3-130 compound 3-130

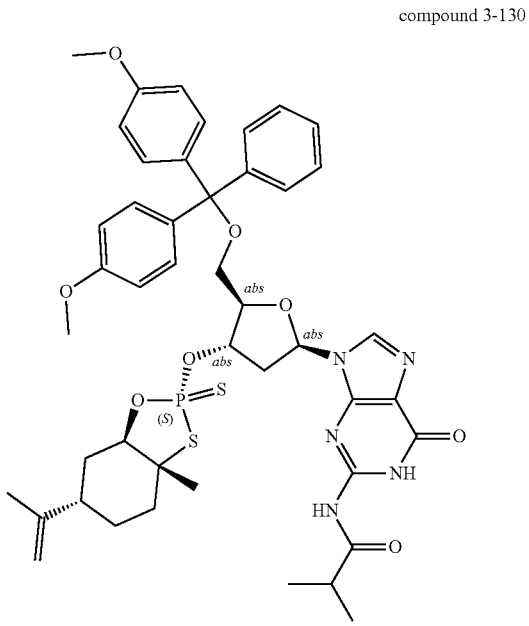

A dry 250 mL round bottom flask was charged with (2R,3aR,6S,7aR)-3a-methyl-2-((perfluorophenyl)thio)-6-(prop-1-en-2-yl)hexahydrobenzo[d][1,3,2]oxathiaphosphole 2-sulfide (5.8 g, 12.99 mmol) and N-(9-((2R,4S,5R)-5-((bis(4-methoxyphenyl)(phenyl)methoxy)methyl)-4-hydroxytetrahydrofuran-2-yl)-6-oxo-6,9-dihydro-1H-purin-2-yl)isobutyramide (8.9 g, 13.9 mmol) under a stream of nitrogen. N,N-Dimethylformamide (50 mL) was added to the mixture which was allowed to stir at room temperature until it became homogeneous. The mixture was cooled to 0° C. 1,8-diazabicyclo[5.4.0]undec-7-ene (2.081 mL, 13.91 mmol) was then added to the mixture drop-wise. The mixture was stirred at 0° C. for 10 minutes.

The cold reaction mixture was diluted with ~200 mL toluene. The mixture was transferred to a separatory funnel where it was washed twice with 1M pH 7.4 phosphate buffer solution (Aldrich P3619). Organics were dried with $Na_2SO_4$. The mixture was filtered and the filtrate was concentrated to dryness. 9.25 g. Evaporate onto celite (toluene) The mixture was purified via Biotage medium pressure liquid chromatography (Silica; Isco RediSep 120 g; 70% EtOAc-Hex 1% triethylamine to 100% Ethyl acetate 1% triethylamine over 6 CV, hold at 100% for 10 CV). Major peak was isolated. N-(9-((2R,4S,5R)-5-((bis(4-methoxyphenyl)(phenyl)methoxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-6-oxo-6,9-dihydro-1H-purin-2-yl)isobutyramide (5.8 g, 6.55 mmol, 47.1% yield). $^1H$ NMR (500 MHz, ACETONITRILE-$d_3$) δ 12.06-11.78 (m, 1H), 9.22 (br s, 1H), 7.82 (s, 1H), 7.46-7.34 (m, 2H), 7.34-7.16 (m, 8H), 6.90-6.72 (m, 4H), 6.26 (t, J=6.8 Hz, 1H), 5.54-5.42 (m, 1H), 4.99 (d, J=1.2 Hz, 1H), 4.87 (s, 1H), 4.43 (dt, J=12.7, 3.2 Hz, 1H), 4.30 (dt, J=5.8, 3.1 Hz, 1H), 4.09 (q, J=7.1 Hz, 1H), 3.76 (d, J=2.9 Hz, 6H), 3.45 (dd, J=10.5, 5.9 Hz, 1H), 3.29 (dd, J=10.4, 3.5 Hz, 1H), 3.15-

3.02 (m, 1H), 2.70-2.53 (m, 3H), 2.20 (s, 8H), 2.03-1.91 (m, 7H), 1.76 (s, 3H), 1.67 (s, 3H), 1.17 (t, J=7.2 Hz, 6H).

2.20. Compound 3-131

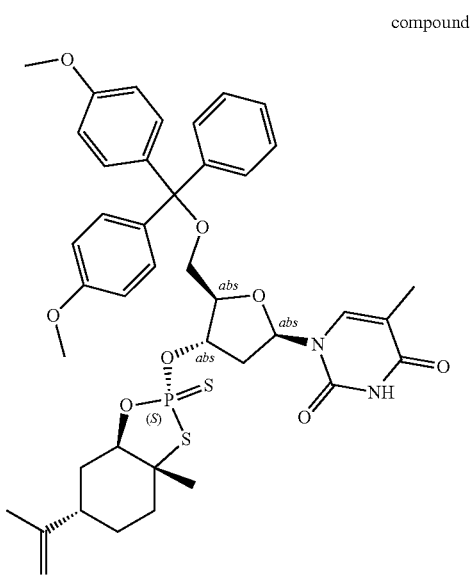

compound 3-131

A dry 250 mL round bottom flask was charged with (2R,3aR,6S,7aR)-3a-methyl-2-((perfluorophenyl)thio)-6-(prop-1-en-2-yl)hexahydrobenzo[d][1,3,2]oxathiaphosphole 2-sulfide (5.33 g, 11.94 mmol) and 1-((2R,4S,5R)-5-((bis(4-methoxyphenyl)(phenyl)methoxy)methyl)-4-hydroxytetrahydrofuran-2-yl)-5-methylpyrimidine-2,4(1H,3H)-dione (5 g, 9.18 mmol) under a stream of nitrogen. N,N-Dimethylformamide (40 mL) was added to the mixture which was allowed to stir at room temperature until it became homogeneous. The mixture was cooled to 0° C. 1,8-diazabicyclo[5.4.0]undec-7-ene (1.785 mL, 11.94 mmol) was then added to the mixture drop-wise. After 10 minutes, the cold reaction mixture was diluted with ~200 mL toluene. The mixture was transferred to a separatory funnel where it was washed twice with 1M pH 7.4 phosphate buffer solution (Aldrich P3619). Organics were dried Na$_2$SO$_4$. The mixture was filtered and the filtrate was concentrated to dryness. 9.25 g. The filtrate was evaporated onto celite (toluene) The mixture was purified via Biotage medium pressure liquid chromatography (Silica; Isco RediSep 24 g; 40% EtOAc-Hex 1% triethylamine to 100% Ethyl acetate 1% triethylamine over 16 CV). (4.3 g, 1-((2R,4S,5R)-5-((bis(4-methoxyphenyl)(phenyl)methoxy)methyl)-4-(((2S,3aR,6S,7aR)-3a-methyl-6-(prop-1-en-2-yl)-2-sulfidohexahydrobenzo[d][1,3,2]oxathiaphosphol-2-yl)oxy)tetrahydrofuran-2-yl)-5-methylpyrimidine-2,4(1H,3H)-dione (4.3 g, 59% yield). $^1$H NMR (500 MHz, ACETONITRILE-d$_3$) δ 9.25-9.00 (m, 1H), 7.55-7.42 (m, 3H), 7.39-7.30 (m, 6H), 7.30-7.23 (m, 1H), 7.01-6.78 (m, 4H), 6.27 (dd, J=8.1, 6.1 Hz, 1H), 5.55-5.42 (m, 1H), 4.98 (d, J=1.1 Hz, 1H), 4.87 (s, 1H), 4.44 (dt, J=12.7, 3.3 Hz, 1H), 4.21 (q, J=3.0 Hz, 1H), 3.79 (s, 7H), 3.51-3.28 (m, 2H), 2.62 (br s, 1H), 2.53-2.38 (m, 2H), 2.31-2.11 (m, 8H), 2.11-2.02 (m, 1H), 2.02-1.75 (m, 11H), 1.75-1.61 (m, 4H), 1.55-1.45 (m, 3H). $^{31}$P NMR (202 MHz, ACETONITRILE-d$_3$) δ 100.4 (br d, J=10.0 Hz, 1P).

Example 17

1. Synthesis of 3'-O-Protected Nucleosides (General Procedure 1)

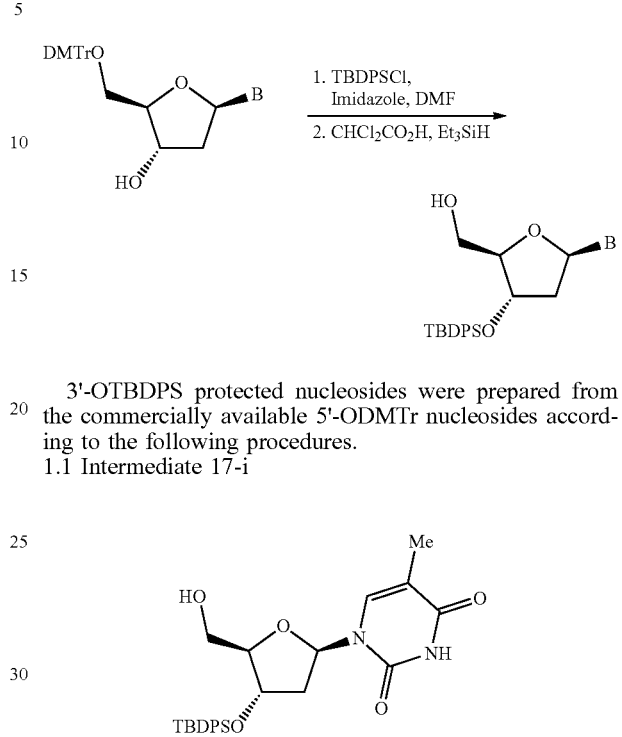

3'-OTBDPS protected nucleosides were prepared from the commercially available 5'-ODMTr nucleosides according to the following procedures.

1.1 Intermediate 17-i

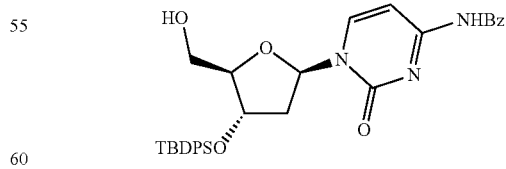

To a solution of 5'-O-(4,4'-dimethoxytrityl)thymidine (15.0 g, 27.6 mmol, 1.0 equiv.) and imidazole (3.14 g, 46.2 mmol, 2.0 equiv.) in DMF (30 mL) was added TBDPS-Cl (7.39 g, 33.1 mmol, 1.2 equiv.) at ambient temperature and stirred for 3 days. The resulting mixture was then poured into water (0.7 L), and mixed for 0.5 h. The slurry was filtered and the cake was washed with water, and then hexanes. The filter cake was dissolved in DCM. The resulting solution washed with 5% aqueous citric acid solution and dried over MgSO$_4$. To the resulting DCM stream was added dichloroacetic acid (11.4 mL) and Et$_3$SiH (18 mL). After stirring for 18 h, the mixture was quench with saturated aqueous NaHCO$_3$ and heptane. The isolated organic layer was concentrated, and the resulting residue was purified by chromatography (EtOAc/DCM). Intermediate 17-i (10.1 g, 75%) was isolated as a white solid with spectral characteristics consistent with the literature Gao, R., et al., Biochemistry 43, 6167-6181 (2004).

1.2 Intermediate 17-ii

[Structure: HO-CH2-tetrahydrofuran with N-linked cytosine bearing NHBz, and TBDPSO at 3' position]

Intermediate 17-ii was prepared analogously to Intermediate 17-i using N$_4$-benzoyl-5'-O-(4,4'-dimethoxytrityl)-2'-deoxycytidine (15.0 g, 23.7 mmol, 1.0 equiv.). SI-7 (10.3 g, 73%) was isolated as a white solid with spectral characteristics consistent with the literature Gao, R., et al., Biochemistry 43, 6167-6181 (2004).

1.3 Intermediate 17-iii

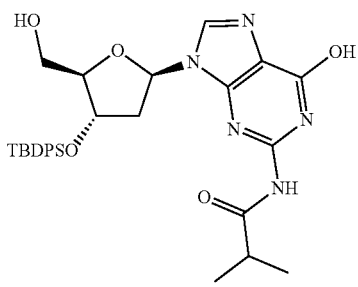

Intermediate 17-iii was prepared analogously to Intermediate 17-i using N²-isobutyryl-5'-O-(4,4'-dimethoxytrityl)-2'-deoxyguanosine (15.0 g, 23.5 mmol, 1.0 equiv.). Intermediate 17-iii (9.8 g, 75%) was isolated as a white solid with spectral characteristics consistent with the literature (Gao, R., et al., Biochemistry 43, 6167-6181 (2004)).

1.4 Intermediate 17-iv

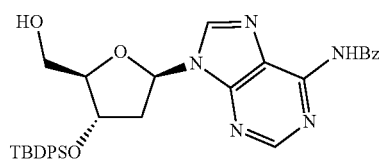

Intermediate 17-iv was prepared analogously to Intermediate 17-i using N₆-benzoyl-5'-O-(4,4'-dimethoxytrityl)-2'-deoxyadenosine (35.0 g, 53.3 mmol, 1.0 equiv.). Intermediate 17-iv (17.8 g, 56%) was isolated as a white solid with spectral characteristics consistent with the literature (Gao, R., et al., Biochemistry 43, 6167-6181 (2004)).

2. Synthesis of Dinucleotides

2.1 Compound 5-1

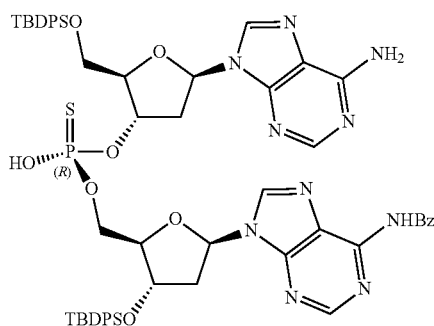

compound 5-1

To a 50 mL flask were added compound 3-107 (535 mg, 0.73 mmol, 1.0 equiv.) and nucleoside N-(9-((2R,4S,5R)-4-((tert-butyldiphenylsilyl)oxy)-5-(hydroxymethyl)tetrahydrofuran-2-yl)-9H-purin-6-yl)benzamide (intermediate 17-iv) (0.88 g, 1.5 mmol, 2.0 equiv.) in THF (5 mL). DBU (0.33 mL, 2.19 mmol, 3 equiv.) was then added dropwise and the reaction was left to stir at ambient temperature. After 10 minutes UPLC analysis showed complete consumption of compound 3-107. The reaction mixture was diluted with EtOAc (10 mL), DCM (5 mL) and 20% citric acid (5 mL). The organic phase was washed with brine (5 mL), dried over Na₂SO₄, filtered and the solvent was removed in vacuo. The crude residue was purified by silica gel column chromatography (0 to 100% MeOH in DCM) to afford the compound 5-1 as a white solid (548 mg, 65%).

Physical State: White solid;

$^1$H NMR (400 MHz, DMSO-d$_6$): δ 11.1 (br s, 1H), 8.84 (s, 1H), 8.71 (s, 1H), 8.21 (s, 1H), 8.08 (s, 1H), 8.05-8.00 (m, 2H), 7.72-7.47 (m, 12H), 7.45-7.27 (m, 11H), 6.62 (dd, J=8.5, 5.9 Hz, 1H), 6.27 (dd, J=8.5, 6.0 Hz, 1H), 5.10 (br dd, J=6.2, 3.4 Hz, 1H), 4.69 (br s, 1H), 4.19 (br d, J=16.4 Hz, 2H), 3.89 (br dd, J=11.1, 4.0 Hz, 2H), 3.80-3.66 (m, 2H), 2.82-2.65 (m, 2H), 2.48-2.23 (m, 2H), 1.06 (s, 9H), 0.93 (s, 9H);

$^{13}$C NMR (101 MHz, DMSO-d$_6$): δ 151.9, 150.1, 148.8, 142.9, 139.1, 135.1, 134.9, 134.8, 134.3, 133.3, 132.7, 132.6, 132.6, 132.4, 132.2, 129.9, 129.8, 129.6, 129.6, 128.3, 128.2, 127.7, 127.6, 127.4, 125.3, 118.9, 86.4, 85.9, 83.4, 75.1, 74.6, 64.8, 64.7, 63.9, 48.4, 40.2, 39.9, 37.3, 30.5, 26.6, 26.5, 26.4, 18.6, 18.5;

$^{31}$P NMR (162 MHz, DMSO-d$_6$): δ 53.8;

HRMS (ESI-TOF, m/z): Calcd for [C$_{59}$H$_{65}$N$_{10}$O$_8$PSSi$_2$+H]$^+$ 1161.4057; Found 1161.4094 (3.3 ppm error).

R$_f$=0.30 (10% MeOH in DCM); UV, KMnO$_4$.

2.2. Compound 5-2

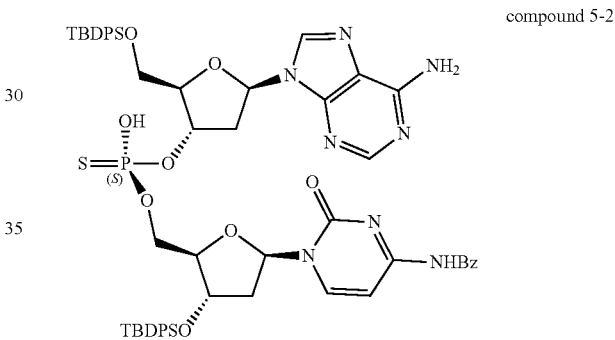

compound 5-2

To a 50 mL flask were added compound 3-108 (1.00 g, 1.36 mmol, 1.0 equiv.) and nucleoside N-(1-((2R,4S,5R)-4-((tert-butyldiphenylsilyl)oxy)-5-(hydroxymethyl)tetrahydrofuran-2-yl)-2-oxo-1,2-dihydropyrimidin-4-yl)benzamide (intermediate 17-ii) (1.55 g, 2.72 mmol, 2.0 equiv.) in THF (3 mL) and MeCN (20 mL). DBU (0.41 mL, 2.72 mmol, 2 equiv.) was then added dropwise and the reaction was left to stir at ambient temperature. After 1 hour UPLC analysis showed complete consumption of compound 3-108. The reaction mixture was diluted with EtOAc (25 mL) and 20% citric acid (25 mL). Then the organic phase was washed with brine (25 mL), dried over Na₂SO₄, filtered and the solvent was removed in vacuo. The crude residue was purified by silica gel column chromatography (0 to 35% MeOH in EtOAc) to afford the product 5-2 as a white solid (1.41 g, 91%).

Physical State: White solid;

$^1$H NMR (400 MHz, DMSO-d$_6$): δ 11.21 (br s, 1H), 8.55 (d, J=7.3 Hz, 1H), 8.22 (s, 1H), 8.09 (s, 1H), 8.00-7.95 (m, 2H), 7.63-7.54 (m, 9H), 7.53-7.26 (m, 17H), 6.38 (t, J=6.5 Hz, 1H), 6.32 (t, J=6.7 Hz, 1H), 5.18-5.11 (m, 1H), 4.48 (br d, J=4.3 Hz, 1H), 4.23-4.03 (m, 2H), 3.91-3.78 (m, 2H), 3.73 (br dd, J=11.1, 4.8 Hz, 1H), 3.68-3.52 (m, 1H), 2.89-2.78 (m, 1H), 2.57-2.50 (m, 1H), 2.28 (br dd, J=12.5, 5.4 Hz, 1H), 1.94 (ddd, J=13.3, 8.3, 5.2 Hz, 1H), 1.02 (s, 9H), 0.93 (s, 9H);

$^{13}$C NMR (101 MHz, DMSO-d$_6$): δ 167.3, 163.0, 155.3, 154.4, 151.7, 149.1, 145.5, 139.1, 136.4, 135.2, 135.2, 135.1, 135.0, 134.5, 133.2, 132.8, 132.7, 132.7, 132.5, 130.0, 129.8, 129.7, 129.2, 128.4, 128.0, 128.0, 127.8, 127.7, 127.5, 119.1, 96.7, 86.8, 86.8, 86.3, 85.9, 85.8, 83.6, 75.0, 75.0, 74.5, 64.5, 64.4, 64.1, 41.2, 38.0, 26.7, 26.6, 18.7, 18.6;

$^{31}$P NMR (162 MHz, DMSO-d$_6$): δ 54.1;

HRMS (ESI-TOF, m/z): Calcd for [C$_{58}$H$_{65}$N$_8$O$_9$PSSi$_2$+H]$^+$ 1137.3944; Found 1137.3969 (2.1 ppm error).

2.3. Compound 5-3

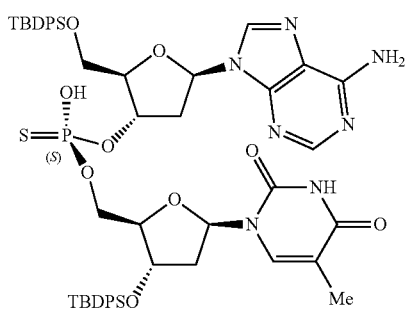

compound 5-3

To a 50 mL flask were added compound 3-108 (1.01 g, 1.37 mmol, 1.0 equiv.) and nucleoside 1-((2R,4S,5R)-4-((tert-butyldiphenylsilyl)oxy)-5-(hydroxymethyl)tetrahydrofuran-2-yl)-5-methylpyrimidine-2,4(1H,3H)-dione (Intermediate 17-i) (1.15 g, 2.39 mmol, 1.8 equiv.) in THF (10 mL). DBU (0.55 mL, 3.70 mmol, 2.7 equiv.) was then added dropwise and the reaction was left to stir at ambient temperature. After 10 minutes UPLC analysis showed complete consumption of compound 3-108. The reaction mixture was diluted with EtOAc (10 mL), DCM (5 mL), and 20% citric acid (5 mL). The organic phase was washed with brine (5 mL), dried over Na$_2$SO$_4$, filtered, and the solvent was removed in vacuo. The crude residue was purified by silica gel column chromatography (0 to 100% MeOH in DCM) to afford the compound 5-3 as a white solid (0.88 g, 61%).

Physical State: White solid;

$^1$H NMR (400 MHz, DMSO-d$_6$): δ 11.24 (s, 1H), 8.29 (s, 1H), 8.14 (s, 1H), 7.67-7.58 (m, 1H), 7.58-7.48 (m, 9H), 7.43-7.23 (m, 12H), 6.36-6.22 (m, 2H), 5.12 (br d, J=2.8 Hz, 1H), 4.48-4.33 (m, 1H), 4.09-3.90 (m, 2H), 3.81 (br dd, J=11.1, 4.3 Hz, 1H), 3.76-3.51 (m, 3H), 2.79-2.83 (m, 1H), 2.71 (d, J=15.4 Hz, 1H), 2.61 (d, J=15.4 Hz, 1H), 2.03-1.99 (m, 1H), 1.72 (s, 3H), 0.97 (s, 9H), 0.89 (s, 9H);

$^{13}$C NMR (101 MHz, DMSO-d$_6$): δ 174.5, 171.2, 163.6, 150.5, 148.5, 135.8, 135.2, 135.1, 135.0, 135.0, 134.4, 132.7, 132.6, 132.4, 130.0, 129.8, 129.8, 128.0, 127.9, 127.8, 127.7, 127.5, 119.0, 110.0, 85.7, 83.9, 83.7, 74.3, 72.4, 48.6, 42.6, 40.9, 40.8, 40.7, 40.4, 26.7, 26.6, 18.7, 18.6, 14.1, 12.1;

$^{31}$P NMR (162 MHz, DMSO-d$_6$): δ 57.0;

HRMS (ESI-TOF, m/z): Calcd for [C$_{52}$H$_{62}$N$_7$O$_9$PSSi$_2$+H]$^+$ 1048.3679; Found 1048.3705 (2.5 ppm error).

2.4. Compound 5-4

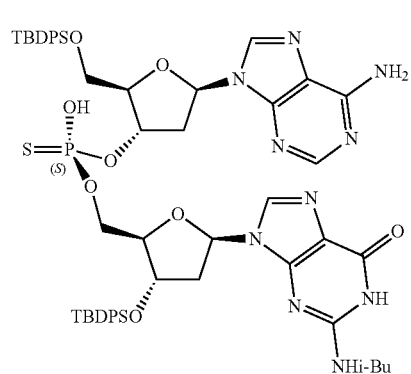

compound 5-4

To a 50 mL flask were added compound 3-108 (803 mg, 1.09 mmol, 1.0 equiv.) and nucleoside N-(9-((2R,4S,5R)-4-((tert-butyldiphenylsilyl)oxy)-5-(hydroxymethyl)tetrahydrofuran-2-yl)-6-hydroxy-9H-purin-2-yl)isobutyramide (Intermediate 17-iii) (1.24 g, 2.18 mmol, 2.0 equiv.) in THF (10 mL). DBU (0.47 mL, 3.27 mmol, 3 equiv.) was then added dropwise and the reaction was left to stir at ambient temperature. After 30 minutes UPLC analysis showed complete consumption of compound 3-108. The reaction mixture was diluted with EtOAc (20 mL) and 20% citric acid (10 mL). Then the organic phase was washed with brine (5 mL), dried over Na$_2$SO$_4$, filtered, and the solvent was removed in vacuo. The crude residue was purified by silica gel column chromatography (0 to 20% MeOH in DCM) to afford the compound 5-4 as a white solid (986 mg, 79%).

Physical State: White solid;

$^1$H NMR (400 MHz, DMSO-d$_6$): δ 12.22 (s, 1H), 12.08 (s, 1H), 8.30 (s, 1H), 8.20 (s, 1H), 8.08 (s, 1H), 7.80-7.21 (br m, 23H), 6.37 (dd, J=9.4, 5.3 Hz, 1H), 6.27 (dd, J=8.1, 6.1 Hz, 1H), 5.21-5.09 (br m, 1H), 4.75 (br d, J=4.6 Hz, 1H), 4.19-4.05 (br, 2H), 3.95-3.69 (br m, 4H), 3.08-2.93 (br m, 1H), 2.92-2.77 (m, 2H), 2.17 (br dd, J=12.6, 5.3 Hz, 1H), 1.10 (d, J=6.8 Hz, 3H), 1.07 (s, 9H), 1.05 (d, J=6.8 Hz, 3H), 0.95 (s, 9H);

$^{13}$C NMR (101 MHz, DMSO-d$_6$): δ 180.3, 155.6, 154.9, 152.0, 149.1, 148.5, 147.6, 139.1, 139.0, 135.3, 135.2, 135.1, 135.0, 133.0, 132.8, 132.7, 132.5, 130.0, 129.8, 129.7, 128.0, 127.9, 127.8, 127.7, 120.8, 119.1, 87.0, 86.9, 85.7, 85.6, 84.7, 83.5, 83.4, 75.0, 74.7, 74.6, 64.6, 64.5, 64.0, 37.7, 34.5, 26.8, 26.6, 18.9, 18.7, 18.7, 18.6;

$^{31}$P NMR (162 MHz, DMSO-d$_6$): δ 54.3;

HRMS (ESI-TOF, m/z): Calcd for [C$_{56}$H$_{67}$N$_{10}$O$_9$PSSi$_2$+H]$^+$ 1143.4162, Found 1143.4186 (2.1 ppm error).

2.5. Compound 5-5

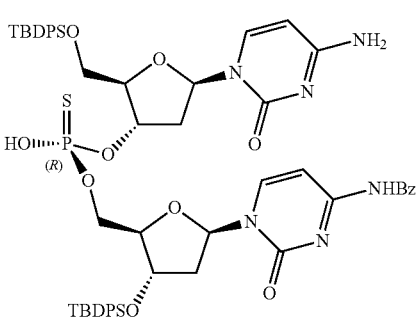

compound 5-5

To a 50 mL flask were added compound 3-109 (1.02 g, 1.43 mmol, 1.0 equiv.) and nucleoside N-(1-((2R,4S,5R)-4-((tert-butyldiphenylsilyl)oxy)-5-(hydroxymethyl)tetrahydrofuran-2-yl)-2-oxo-1,2-dihydropyrimidin-4-yl)benzamide (Intermediate ii) (1.60 g, 2.86 mmol, 2.0 equiv.) in MeCN (20 mL) and THF (5 mL). DBU (0.32 mL, 2.15 mmol, 3 equiv.) was then added dropwise and the reaction was left to stir at ambient temperature. After 1 hour UPLC analysis showed complete consumption of compound 3-109. The reaction mixture was diluted with EtOAc (25 mL) and 20% citric acid (20 mL). Then the organic phase was washed with brine (10 mL), dried over $Na_2SO_4$, filtered, and the solvent was removed in vacuo. The crude residue was purified by silica gel column chromatography (20% MeOH in DCM) to afford the product 5-5 as a white solid (1.23 g, 73%).

Physical State: White solid;

$^1$H NMR (500 MHz, DMSO-$d_6$): δ 11.20 (br s, 1H), 9.23 (br s, 1H), 8.47 (br d, J=7.5 Hz, 1H), 8.21 (br s, 1H), 7.98 (d, J=7.8 Hz, 2H), 7.90 (d, J=7.8 Hz, 1H), 7.64-7.58 (m, 9H), 7.52-7.37 (m, 14H), 7.29 (br s, 1H), 6.33 (t, J=7.0 Hz, 1H), 6.08 (t, J=6.5 Hz, 1H), 5.81 (d, J=7.8 Hz, 1H), 4.96 (br d, J=2.9 Hz, 1H), 4.52-4.45 (m, 1H), 4.16 (br s, 2H), 3.92-3.85 (m, 2H), 3.85-3.71 (m, 1H), 3.70-3.25 (m, 2H), 2.48-2.28 (m, 2H), 2.14 (dt, J=13.7, 6.7 Hz, 1H), 2.00-1.90 (m, 1H), 1.05 (s, 9H), 0.96 (s, 9H);

$^{13}$C NMR (126 MHz, DMSO-$d_6$): δ 162.9, 159.8, 148.0, 145.2, 143.0, 135.2, 135.2, 135.1, 134.9, 134.4, 133.1, 132.7, 132.7, 132.6, 132.1, 129.9, 129.1, 128.1, 127.9, 127.5, 96.4, 93.9, 86.7, 86.1, 86.3, 85.7, 74.3, 74.2, 64.5, 63.7, 41.1, 26.7, 26.6, 18.7, 18.6;

$^{31}$P NMR (202 MHz, DMSO-$d_6$): δ 54.6;

HRMS (ESI-TOF, m/z): Calcd for $[C_{57}H_{65}N_6O_{10}PSSi_2+H]^+$ 1113.3832; Found 1113.3859 (2.4 ppm error).

2.6. Compound 5-6

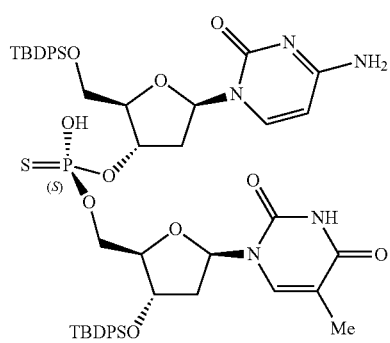

compound 5-6

To a 50 mL flask were added compound 3-110 (1.00 g, 1.40 mmol, 1.0 equiv.) and nucleoside 1-((2R,4S,5R)-4-((tert-butyldiphenylsilyl)oxy)-5-(hydroxymethyl)tetrahydrofuran-2-yl)-5-methylpyrimidine-2,4(1H,3H)-dione (Intermediate 17-i) (1.35 g, 2.80 mmol, 2.0 equiv.) in MeCN (20 mL) and THF (5 mL). DBU (0.33 mL, 2.10 mmol, 3 equiv.) was then added dropwise and the reaction was left to stir at ambient temperature. After 1 hour UPLC analysis showed complete consumption of compound 3-110. The reaction mixture was diluted with EtOAc (25 mL) and 20% citric acid (20 mL). Then the organic phase was washed with brine (10 mL), dried over $Na_2SO_4$, filtered and the solvent was removed in vacuo. The crude residue was purified by silica gel column chromatography (20% MeOH in DCM) to afford Compound 5-6 as a white solid (1.12 g, 76%).

Physical State: White solid;

$^1$H NMR (500 MHz, DMSO-$d_6$): δ 11.25 (s, 1H), 8.36 (br s, 1H), 7.84-7.71 (m, 3H), 7.63 (br t, J=6.3 Hz, 4H), 7.57 (br s, 4H), 7.48-7.36 (m, 12H), 6.36 (br t, J=7.2 Hz, 1H), 6.08 (br t, J=6.4 Hz, 1H), 5.71 (br d, J=7.3 Hz, 1H), 4.98 (br s, 1H), 4.45 (br s, 1H), 3.95 (br d, J=17.9 Hz, 2H), 3.81-3.76 (m, 1H), 3.73-3.65 (m, 2H), 3.57-3.50 (m, 2H), 2.40-2.31 (m, 1H), 2.12-2.04 (m, 1H), 2.04-1.92 (m, 2H), 1.81 (s, 3H), 1.02 (s, 9H), 0.97 (s, 9H);

$^{13}$C NMR (126 MHz, DMSO-$d_6$): δ 164.2, 162.9, 151.6, 151.0, 142.2, 136.5, 135.7, 135.6, 135.4, 133.2, 133.1, 132.6, 130.5, 130.4, 128.4, 110.6, 94.3, 86.5, 86.0, 85.7, 84.3, 75.3, 74.4, 72.9, 65.0, 64.2, 27.2, 27.1, 19.2, 19.0, 12.5;

$^{31}$P NMR (202 MHz, DMSO-$d_6$): δ 53.5;

HRMS (ESI-TOF, m/z): Calcd for $[C_{51}H_{62}N_5O_{10}PSSi_2+H]^+$ 1024.3566, Found 1024.3600 (3.3 ppm error).

2.7. Compound 5-7

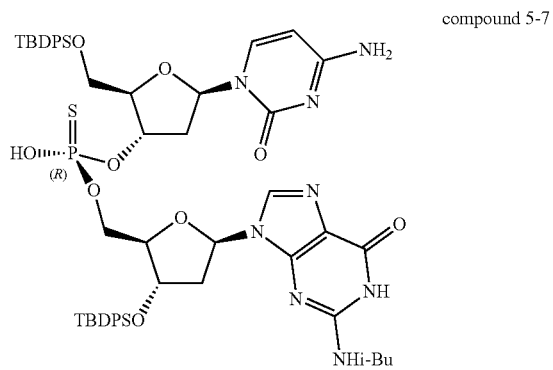

compound 5-7

A mixture of compound 3-109 (1.00 g, 1.35 mmol, 1.00 equiv.) and the nucleoside N-(9-((2R,4S,5R)-4-((tert-butyldiphenylsilyl)oxy)-5-(hydroxymethyl)tetrahydrofuran-2-yl)-6-hydroxy-9H-purin-2-yl)isobutyramide (Intermediate 17-iii) (1.55 g, 2.70 mmol, 2.0 equiv.) was dissolved in a mixture of THF (10 mL) and MeCN (20 mL), then concentrated in vacuo (3×). The residue was dissolved in a mixture of THF (10 mL) and MeCN (20 mL) and DBU (608 µL, 4.04 mmol, 3.0 equiv.) was added. The reaction mixture was stirred for 30 min, then diluted with EtOAc (20 mL) and aqueous 1 N HCl (20 mL, pH=1). The layers were separated and the aqueous layer was extracted with EtOAc (2×20 mL). The combined organic extracts were dried over sodium sulfate, filtered, and concentrated in vacuo to afford a gel. The gel was purified by flash column chromatography (5 to 20% MeOH in DCM, performed twice). The desired compound 5-7 was isolated as a gel, which was stirred in MTBE (40 mL) for 1 h to convert the product to a white powder which was isolated by filtration (1.23 g, 82%).

Physical State: White solid;

$^1$H NMR (400 MHz, DMSO-$d_6$): δ 12.31 (br s, 1H), 12.08 (br s, 1H), 9.23 (br s, 1H), 8.25 (br s, 2H), 7.90 (d, J=7.8 Hz, 1H), 7.53-7.70 (m, 9H), 7.35-7.49 (m, 13H), 6.35 (dd, J=9.5, 5.4 Hz, 1H), 6.04 (t, J=6.5 Hz, 1H), 5.80 (d, J=7.8 Hz, 1H), 4.94 (dt, J=6.0, 2.9 Hz, 1H), 4.57 (br d, J=4.5 Hz, 1H), 4.08-4.11 (m, 2H), 3.75-3.93 (m, 3H), 3.53-3.58 (m, 3H), 2.76-2.96 (m, 2H), 2.24-2.33 (m, 1H), 2.26-2.20 (m, 2H), 1.05-1.10 (m, 16H), 0.97 (s, 9H);

$^{13}$C NMR (101 MHz, DMSO-$d_6$): δ 180.4, 159.7, 154.9, 148.5, 147.86, 147.82, 143.1, 138.5, 135.25, 135.20, 135.1, 134.9, 132.74, 132.70, 132.6, 129.98, 129.94, 129.90, 127.94, 127.88, 120.6, 94.0, 86.60, 86.53, 86.13, 85.8, 84.3, 74.7, 74.2, 64.8, 63.7, 34.6, 26.7, 26.6, 18.8, 18.7, 18.6;

$^{31}$P NMR (162 MHz, DMSO-d$_6$): δ 54.78;

HRMS (ESI-TOF, m/z): Calcd for [C$_{55}$H$_{67}$N$_8$O$_{10}$PSSi$_2$+H]$^+$ 1119.4050; Found 1119.4071 (1.9 ppm error).

2.8. Compound 5-8

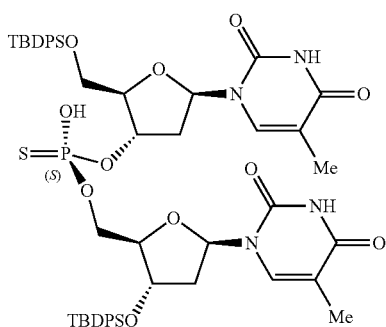

compound 5-8

To a solution of the compound 3-112 (1.00 g, 1.26 mmol, 1.0 equiv.) and nucleoside 1-((2R,4S,5R)-4-((tert-butyldiphenylsilyl)oxy)-5-(hydroxymethyl)tetrahydrofuran-2-yl)-5-methylpyrimidine-2,4(1H,3H)-dione (Intermediate 17-i) (1.17 g, 1.17 g, 2.52 mmol, 2.0 equiv.) in THF (10 mL) was added DBU (581 μL, 3.78 mmol, 3.0 equiv.). The reaction mixture was stirred for 30 min, then diluted with EtOAc (10 mL) and aqueous 1 N HCl (5 mL, pH=1). The layers were separated and the aqueous layer was extracted with EtOAc (10 mL). The combined organic extracts were dried over Na$_2$SO$_4$, filtered, then concentrated in vacuo to afford a gel. The gel was purified by flash column chromatography (0 to 10% to 30% MeOH in DCM to 30%, performed twice). The desired compound 5-8 was isolated as a gel, which was concentrated from hexanes (10 mL) to afford a white powder (926.1 mg, 72%).

Physical State: White solid;

$^1$H NMR (400 MHz, DMSO-d$_6$): δ 11.37 (s, 1H), 11.26 (s, 1H), 7.84 (s, 1H), 7.61-7.66 (m, 5H), 7.55-7.57 (m, 4H), 7.35-7.45 (m, 13H), 6.35 (dd, J=8.5, 6.2 Hz, 1H), 6.13 (dd, J=8.8, 5.6 Hz, 1H), 5.03-5.07 (m, 1H), 4.40 (m, 1H), 3.94 (br d, J=9.3 Hz, 2H), 3.65-3.76 (m, 3H), 3.41-3.53 (m, 1H), 2.24 (br dd, J=12.9, 5.1 Hz, 1H), 2.03-2.14 (m, 1H), 1.90-2.03 (m, 2H), 1.82 (s, 3H), 1.43 (s, 3H), 1.01 (s, 9H), 0.98 (s, 9H);

$^{13}$C NMR (101 MHz, DMSO-d$_6$): δ 163.8, 163.6, 150.6, 150.4, 136.1, 135.20, 135.18, 135.1, 135.0, 134.9, 132.8, 132.72, 132.68, 132.0, 130.03, 129.96, 127.96, 127.91, 110.2, 109.7, 86.2, 86.1, 85.4, 85.3, 83.9, 74.97, 74.85, 64.4, 64.2, 38.7, 26.7, 26.6, 18.8, 18.5, 12.1, 11.8;

$^{31}$P NMR (162 MHz, DMSO-d$_6$): δ 53.01;

HRMS (ESI-TOF, m/z): Calcd for [C$_{52}$H$_{63}$N$_4$O$_{11}$PSSi$_2$+H]$^+$ 1039.3563; Found 1039.3586 (2.3 ppm error).

2.9. Compound 5-9

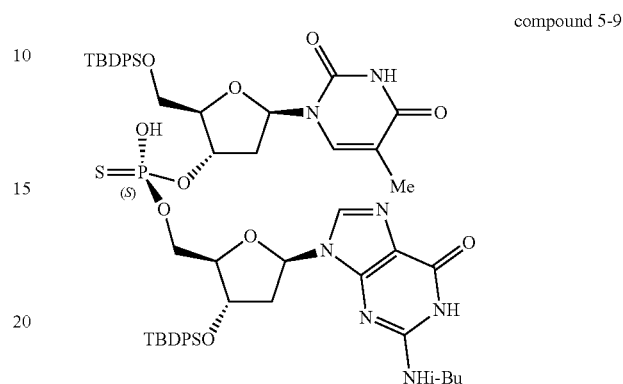

compound 5-9

To a mixture of compound 3-112 (734 mg, 1.0 equiv.) and N-(9-((2R,4S,5R)-4-((tert-butyldiphenylsilyl)oxy)-5-(hydroxymethyl)tetrahydrofuran-2-yl)-6-hydroxy-9H-purin-2-yl)isobutyramide (Intermediate 17-iii) (1.20 g, 2.1 equiv.) in THF was added DBU (0.45 mL, 3.0 equiv.). After 30 min, EtOAc (20 mL) and 20% citric acid (10 mL) were added. The phases were separated and the organic phase was washed with brine (5 mL) and dried over Na$_2$SO$_4$. The solution was filtered and the solvent was removed under vacuum. The residue was dissolved with DCM, and purified by ISCO flash chromatography (80 g silica gel column, 0 to 20% MeOH in DCM, 18 min run). The pure fractions were combined and solvents were removed to afford the desired compound 5-9 (380 mg) as white solid. Then, the impure fractions were combined, solvents were removed in vacuo and a second ISCO flash chromatography was performed using the same conditions. The desired compound 5-9 (388 mg) was obtained as white solid. In total, compound 5-9 (768 mg, 67%) was obtained.

Physical State: White solid;

$^1$H NMR (400 MHz, DMSO-d$_6$): δ 12.17 (s, 1H), 12.06 (s, 1H), 11.37 (s, 1H), 8.30 (s, 1H), 7.77-7.35 (br m, 21H), 6.35 (dd, J=9.6, 5.3 Hz, 1H), 6.13 (dd, J=8.8, 5.6 Hz, 1H), 5.16-5.01 (br m, 1H), 4.71 (br d, J=4.6 Hz, 1H), 4.12-4.04 (br m, 1H), 4.02-3.93 (br m, 1H), 3.86-3.73 (br m, 3H), 3.72-3.63 (br m, 1H), 3.02-2.89 (br m, 1H), 2.87-2.76 (br m, 1H), 2.30 (br dd, J=13.1, 6.8 Hz, 1H), 2.20-2.04 (br m, 2H), 1.44 (s, 3H), 1.12 (d, J=6.8 Hz, 3H), 1.10 (d, J=6.8 Hz, 3H), 1.06 (s, 9H), 0.99 (s, 9H);

$^{13}$C NMR (101 MHz, DMSO-d$_6$): δ 180.3, 163.6, 154.9, 150.3, 148.5, 147.6, 139.1, 135.3, 135.2, 135.1, 135.0, 134.8, 132.9, 132.8, 132.8, 132.1, 129.9, 128.0, 127.9, 120.7, 109.6, 87.0, 86.9, 85.3, 85.2, 84.6, 83.8, 75.0, 74.7, 74.6, 64.3, 64.2, 64.1, 54.9, 38.7, 38.4, 34.5, 26.8, 26.6, 18.9, 18.8, 18.7, 18.6, 11.7;

$^{31}$P NMR (162 MHz, DMSO-d$_6$): δ 54.1;

HRMS (ESI-TOF, m/z): Calcd for [C56H68N7O11PSSi2+H]+ 1134.4046, Found 1134.4080 (2.9 ppm error).

2.10. Compound 5-10

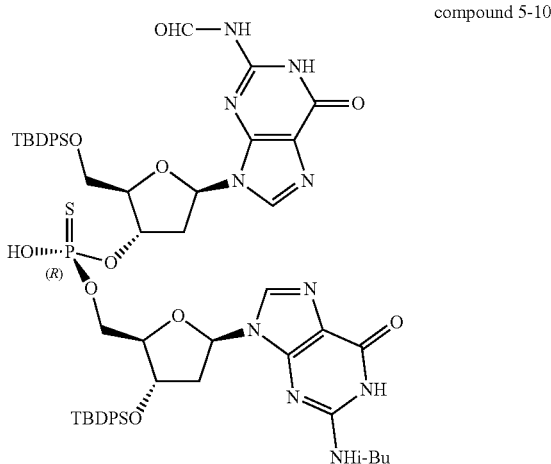

compound 5-10

To a 50 mL flask were added compound 3-113 (1.00 g, 1.24 mmol, 1.0 equiv.) and nucleoside N-(9-((2R,4S,5R)-4-((tert-butyldiphenylsilyl)oxy)-5-(hydroxymethyl)tetrahydrofuran-2-yl)-6-hydroxy-9H-purin-2-yl)isobutyramide (Intermediate 17-iii) (1.42 g, 2.48 mmol, 2.0 equiv.) in MeCN (20 mL) and THF (3 mL). DBU (0.37 mL, 2.48 mmol, 2 equiv.) was then added dropwise and the reaction was left to stir at ambient temperature. After 2 hour UPLC analysis showed complete consumption of compound 3-113. The reaction mixture was diluted with EtOAc (25 mL) and 20% citric acid (25 mL) and was allowed to stir at ambient temperature for 4 hours. The dimethylaminomethylene was converted to formamide based on HPLC-MS analysis. Then the organic phase was washed with brine (25 mL), dried over $Na_2SO_4$, filtered and the solvent was removed in vacuo. The crude residue was purified by silica gel column chromatography (0 to 60% MeOH in EtOAc) to afford the compound 5-10 as a white solid (1.27 g, 86%).

Physical State: White solid;

$^1$H NMR (400 MHz, DMSO-$d_6$): δ 12.33 (br s, 1H), 12.10 (s, 1H), 8.28 (s, 1H), 8.00 (s, 1H), 7.78-7.63 (m, 1H), 7.63-7.54 (m, 8H), 7.46-7.25 (m, 13H), 6.36 (dd, J=9.2, 5.4 Hz, 1H), 6.14 (t, J=6.6 Hz, 1H), 5.05 (br s, 1H), 4.64-4.55 (m, 1H), 4.14 (br s, 2H), 4.00-3.88 (m, 1H), 3.88-3.70 (m, 2H), 3.67-3.55 (m, 1H), 2.96-2.74 (m, 2H), 2.58-2.50 (m, 1H), 2.33-2.14 (m, 2H), 1.12-1.05 (m, 6H), 1.02 (s, 9H), 0.93 (s, 9H);

$^{13}$C NMR (101 MHz, DMSO-$d_6$): δ 6 180.5, 154.9, 148.5, 148.3, 147.8, 147.2, 139.1, 137.3, 135.2, 135.2, 135.1, 135.0, 132.8, 132.5, 130.0, 129.8, 129.7, 128.0, 127.9, 127.8, 127.7, 120.8, 120.6, 86.7, 86.6, 86.2, 86.2, 84.8, 83.3, 74.8, 74.6, 64.7, 64.3, 48.6, 37.9, 34.6, 26.8, 26.6, 18.9, 18.8, 18.6;

$^{31}$P NMR (162 MHz, DMSO-$d_6$): δ 54.2; 1

HRMS (ESI-TOF, m/z): Calcd for $[C_{57}H_{67}N_{10}O_{11}PSSi_2+H]^+$ 1187.4060; Found 1187.4085 (2.0 ppm error).

The table below lists UPLC/HPLC conditions and retention times for compounds above.

UPLC/HPLC Conditions and Retention Times

| Entry | Product | Assay Conditions | Retention time |
|---|---|---|---|
| 1 | compound 5-1 | UPLC<br>Ascentis express C18 2.7 um 2.1 × 50 mm<br>Solvent A: 0.05% TFA in MeCN:$H_2O$ (5:95)<br>Solvent B: 0.05% TFA in MeCN:$H_2O$ (95:5)<br>Gradient: Complex - 0% to 100% B over 2 min<br>Flow rate: 1 mL/min<br>PDA wavelength: 220 nm | 1.91 |
| 2 | compound 5-2 | UPLC<br>Ascentis express C18 2.6 um 2.1 × 50 mm<br>Solvent A: 0.05% TFA in MeCN:$H_2O$ (5:95)<br>Solvent B: 0.05% TFA in MeCN:$H_2O$ (95:5)<br>Gradient: Complex - 0% to 100% B over 2 min<br>Flow rate: 1 mL/min<br>PDA wavelength: 220 nm | 2.08 |

| Entry | Product | Assay Conditions | Retention time |
|---|---|---|---|
| 3 | 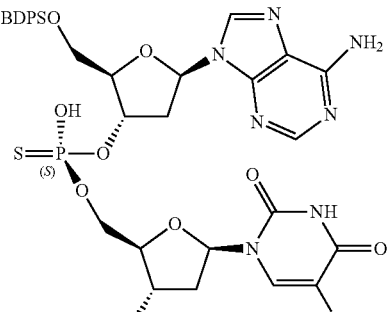compound 5-3 | UPLC<br>Ascentis express C18 2.7 um 2.1 × 50 mm<br>Solvent A: 0.05% TFA in MeCN:H$_2$O (5:95)<br>Solvent B: 0.05% TFA in MeCN:H$_2$O (95:5)<br>Gradient: Complex - 10% to 100% B over 2 min<br>Flow rate: 1 mL/min<br>PDA wavelength: 220 nm | 1.88 |
| 4 | 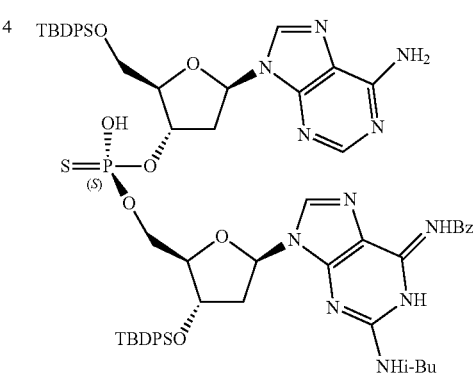compound 5-4 | UPLC<br>Ascentis express C18 2.7 um 2.1 × 50 mm<br>Solvent A: 0.01% NH$_4$OAc in MeCN:H$_2$O (5:95)<br>Solvent B: 0.01% NH$_4$OAc in MeCN:H$_2$O (95:5)<br>Gradient: Complex - 0% to 100% B over 2 min<br>Flow rate: 1 mL/min<br>PDA wavelength: 220 nm | 1.92 |
| 5 | 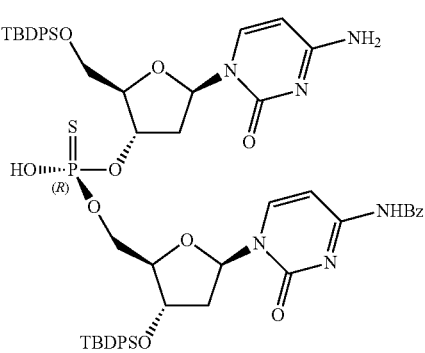compound 5-5 | UPLC<br>Thermo Accucore aQ 2.6 um 2.1 × 50 mm<br>Solvent A: 0.01% NH$_4$OAc in MeCN:H$_2$O (5:95)<br>Solvent B: 0.01% NH$_4$OAc in MeCN:H$_2$O (95:5)<br>Gradient: Complex - 10% to 100% B over 2 min<br>Flow rate: 1 mL/min<br>PDA wavelength: 220 nm | 1.49 |
| 6 | 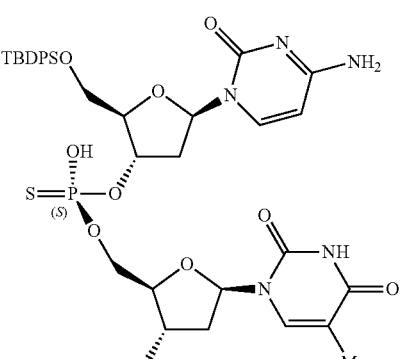compound 5-6 | UPLC<br>Ascentis express C18 2.7 um 2.1 × 50 mm<br>Solvent A: 0.01% NH$_4$OAc in MeCN:H$_2$O (5:95)<br>Solvent B: 0.01% NH$_4$OAc in MeCN:H$_2$O (95:5)<br>Gradient: Complex - 10% to 100% B over 2 min<br>Flow rate: 1 mL/min<br>PDA wavelength: 220 nm | 1.77 |

| Entry | Product | Assay Conditions | Retention time |
|---|---|---|---|
| 7 | 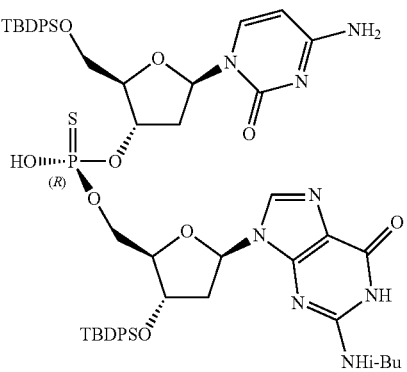 compound 5-7 | HPLC<br>Xbridge BEH Shield RP18 2.5 um 4.6 × 50 mm<br>Solvent A: 0.05% TFA in MeOH:H$_2$O (20:80)<br>Solvent B: 0.05% TFA in MeOH:ACN (20:80)<br>Gradient: Complex - 0% to 100% B over 30 min<br>Flow rate: 0.8 mL/min<br>PDA wavelength: 220 nm, 256 nm | 22.91 |
| 8 | 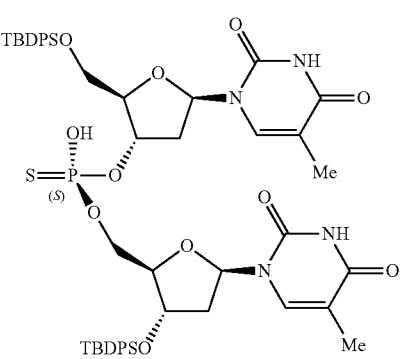 compound 5-8 | HPLC<br>Supelco Ascentis express C18 2.7 um 4.6 × 150 mm<br>Solvent A: 0.05% TFA in MeOH:H$_2$O (20:80)<br>Solvent B: 0.05% TFA in MeOH:ACN (20:80)<br>Gradient: Complex - 0% to 100% B over 30 min<br>Flow rate: 1 mL/min<br>PDA wavelength: 220 nm, 256 nm | 30.82 |
| 9 | 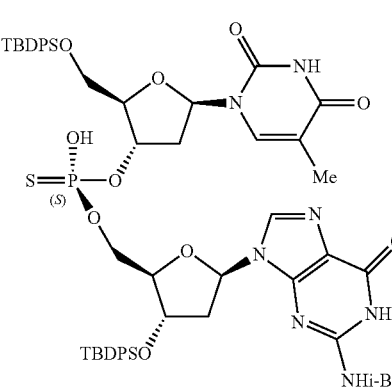 compound 5-9 | UPLC<br>Ascentis express C18 2.7 um 2.1 × 50 mm<br>Solvent A: 0.01% NH$_4$OAc in MeCN:H$_2$O (5:95)<br>Solvent B: 0.01% NH$_4$OAc in MeCN:H$_2$O (95:5)<br>Gradient: Complex - 0% to 100% B over 2 min<br>Flow rate: 1 mL/min<br>PDA wavelength: 220 nm | 2.04 |

| Entry | Product | Assay Conditions | Retention time |
|---|---|---|---|
| 10 | 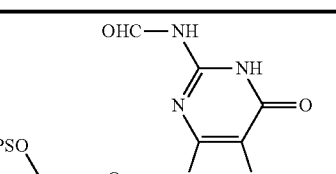compound 5-10 | UPLC<br>Agilent Poroshell EC-C18 1.9 um 2.1 × 50 mm<br>Solvent A: 0.01% NH₄OAc in MeCN:H₂O (5:95)<br>Solvent B: 0.01% NH₄OAc in MeCN:H₂O (95:5)<br>Gradient: Complex - 0% to 100% B over 2 min<br>Flow rate: 1 mL/min<br>PDA wavelength: 220 nm | 2.02 |
Example 18
Alternative Preparation of Phosphodiester Products
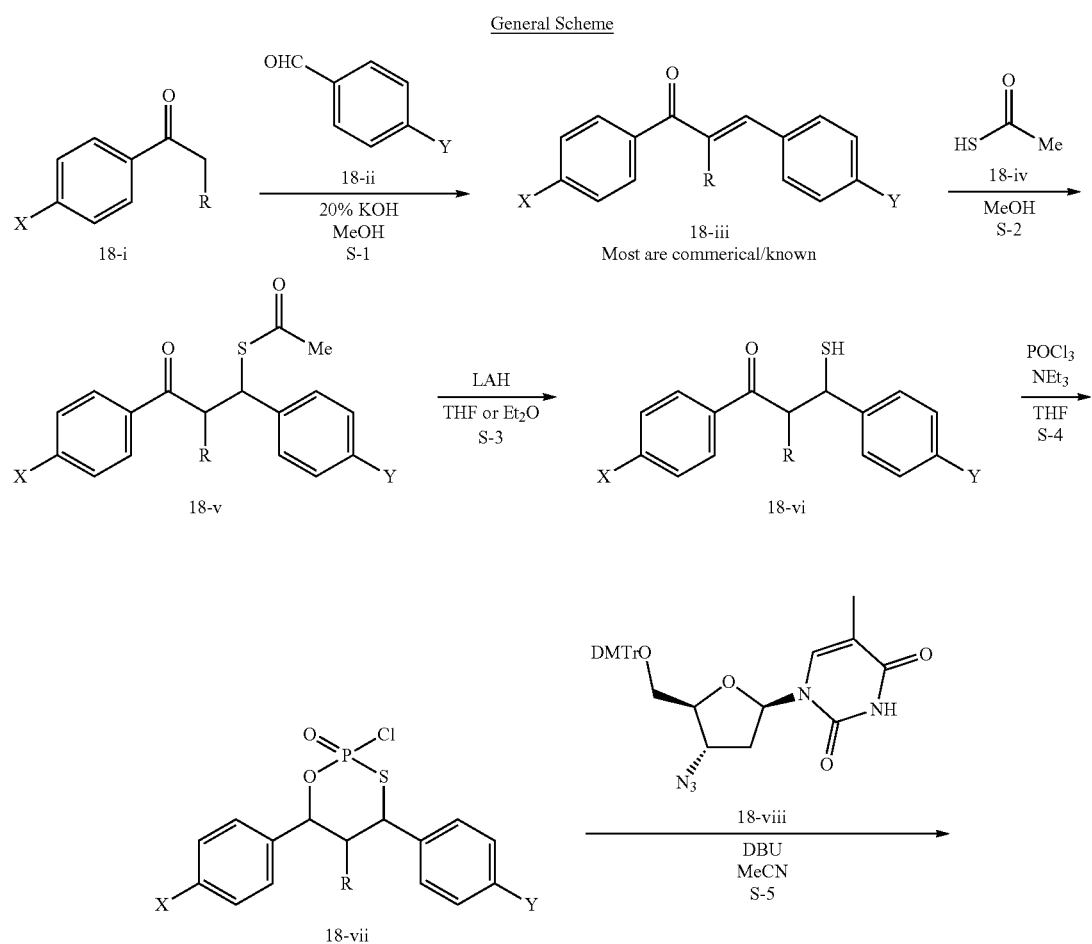

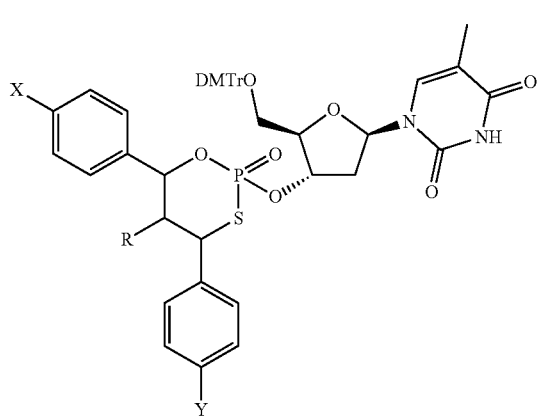

18-ix

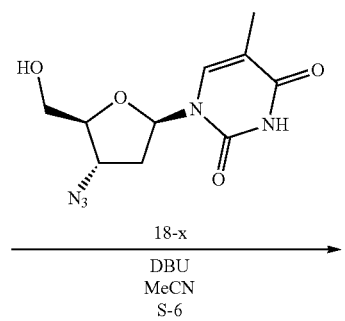

Variables of X, Y, and R are listed in the Table 8.

TABLE 8

| # | 1 | 2 | 3 | 4 | 5 | 6 | 7 | 8 |
|---|---|---|---|---|---|---|---|---|
| X= | OMe | OMe | OMe | OMe | H | H | Ph | Ph |
| Y= | H | F | OMe | Br | F | Br | H | F |
| R= | H | H | H | H | H | H | H | H |

| # | 9 | 10 | 11 | 12 | 13 | 14 | 15 | 16 | 17 |
|---|---|---|---|---|---|---|---|---|---|
| X= | Ph | Ph | H | H | H | Cl | H | Br | H |
| Y= | OMe | Br | H | Br | H | Cl | OMe | Br | Cl |
| R= | H | H | Ph | Ph | H | H | H | H | H |

The reaction yields and times are listed in Table 9

TABLE 9

| # | S-1 Yield | S-2 Yield | S-3 Yield | S-4 Yield | S-5 Yield | S-6 Time |
|---|---|---|---|---|---|---|
| 1 | 92% | 67% | 99% | 74% | 28% | 0.5-1 hr |
| 2 | 99%. | 44% | — | — | — | — |
| 3 | 31% | 61% | 96% | — | — | — |
| 4 | 89% | 67% | 98% | — | — | — |
| 5 | 63% | 42% | — | — | — | — |
| 6 | 99%. | 85% | — | — | — | — |
| 7 | 44% | 84% | — | — | — | — |
| 8 | 36% | 45% | — | — | — | — |
| 9 | 82% | 95% | — | — | — | — |
| 10 | 42% | 88% | — | — | — | — |
| 11 | — | — | — | — | — | — |
| 12 | — | — | — | — | — | — |
| 13 | N/A | 81% | 79% | 53% | 60% | 0.5-1 hr |
| 14 | N/A | 76% | 67% | 54% | 89% | 0.5-1 hr |

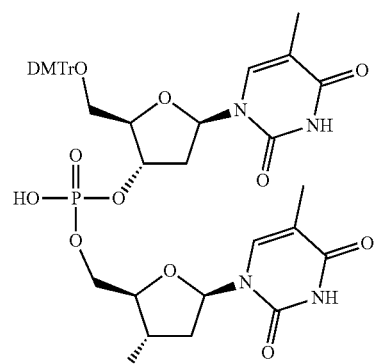

compound 5-12

TABLE 9-continued

| # | S-1 Yield | S-2 Yield | S-3 Yield | S-4 Yield | S-5 Yield | S-6 Time |
|---|---|---|---|---|---|---|
| 15 | N/A | 65% | — | — | — | — |
| 16 | 96% | 74% | — | — | — | 0.5-1 hr |
| 17 | N/A | 89% | 55% | 62% | 85% | 0.2-0.5 hr |

The detailed procedures below are for illustration, which started from chalcone (18-iii) that is commercial available.

Step 2

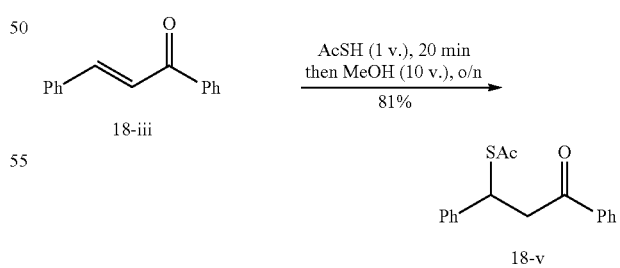

To a 1 L RBF was added chalcone (18-iii, 55 g, 0.26 mol, 1.0 equiv.) followed by thioacetic acid (55 mL, 1 v.). After 5 min, the reaction became homogeneous. After stirring for 20 minutes, the light yellow solution was diluted with methanol (550 mL, 10 v.). The product immediately precipitated and this was allowed to stir overnight. The solids were collected by filtration and dried. The product was obtained as a white solid (61 g, 81% yield). 1H NMR (400 MHz, Chloroform-d) δ 8.08-7.88 (m, 2H), 7.61-7.28 (m, 8H), 5.40-5.19 (m, 1H), 3.81-3.60 (m, 2H), 2.33 (t, J=3.0 Hz, 3H).

b. Step 3

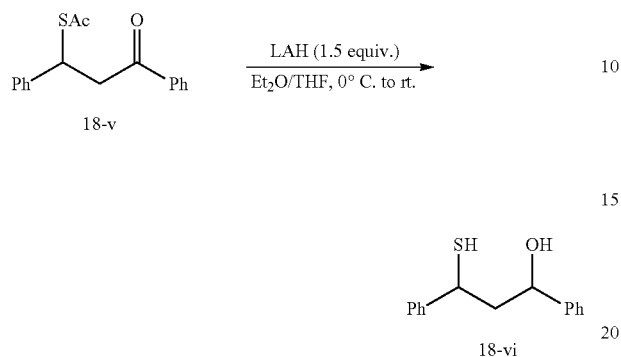

Lithium aluminum hydride (12.24 g, 1.5 equiv.) was slowly dissolved in Et$_2$O at 0° C. To this was added a solution of thioacetate (18-v, 61 g, 0.21 mol, 1.0 equiv.) in THF/Et$_2$O (200 mL, 1:1) dropwise over 1 hour at 0° C. After the addition was complete, solid LAH (1 g) was added. The reaction was stirred overnight (HPLC analysis revealed full conversion to product). The reaction was quenched via the addition of ethyl acetate dropwise (~100 mL) followed by saturated aqueous potassium sodium tartrate and lastly 1 M NaOH. This was partitioned between 1:1 ethyl acetate/hexane and additional water overnight. The organic layer was decanted and additional solvent was added and the mixing/decanting was repeated (2×1 L). The combined organics were concentrated to ~200 mL and dried over MgSO$_4$, filtered and concentrated. The product was obtained as a colorless oil (18-vi, 41 g, 79% yield).

An alternative method to make intermediate 18-vi:

A RBF was charged with thiomichael adduct (5 g) followed by THF (175 mL, 0.1 M) and cooled to 0° C. LAH (1.3 g, 2.0 equiv.) was slowly added as a solid. After warming to rt overnight, the reaction was quenched by slow addition of solid Na$_2$SO$_4$ heptahydrate. After stirring for an hour the reaction was filtered and concentrated to a clear oil. Note: this was >80% pure by NMR. Quick flash chromatography provided the mercaptopropanol as a colorless oil.

Another Alternative Method to Make Intermediate 18-vi:

To a solution of thioacetate (61 g, 0.21 mol, 1.0 equiv.) in THF (200 mL) was added Lithium aluminum hydride (12.24 g, 1.5 equiv.) was slowly at 0° C. The reaction was stirred overnight (Reaction complete within 1 hour, HPLC analysis revealed full conversion to product). The reaction was quenched via the addition of ethyl acetate dropwise (~100 mL) followed by concentrated HCl or Sulfuric acid. This was partitioned between 1:1 ethyl acetate/hexane and water. The organic phase was washed with additional HCl (1M) followed twice by water and lastly brine. The combined organics were dried over MgSO$_4$, filtered and concentrated. The product was obtained as a colorless oil (41 g, 79% yield).

$^1$H NMR (400 MHz, Chloroform-d) δ 7.49-7.20 (m, 10H), 4.96-4.48 (m, 1H), 4.21 (dtd, J=10.8, 8.7, 7.3, 3.8 Hz, 1H), 2.52-2.19 (m, 2H), 2.02 (ddd, J=15.1, 5.8, 1.8 Hz, 1H).

Procedures to Prepare an Enantiomer Enriched Intermediate 18-vi.

Procedure 1:

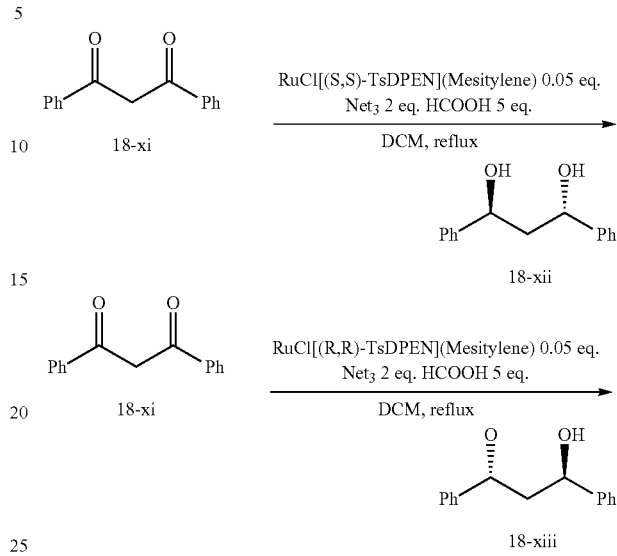

28 g 1,3-diphenyl-1,3-propanedinone was dissolved in 280 mL of DCM. To this solution was added 23.6 mL of HCOOH, 34.5 mL of TEA, and 3.89 g of Ru Catalyst. The reaction solution was refluxed for 10 h. 280 mL of hexane was added, then the mixture was stirred in ice bath for 10 min. The product was filtered and washed using 300 mL of DCM:Hexane (1:1). 19.8 g of product (18-xii or 18-xiii) was obtained after dried in vacuum overnight. $^1$H NMR (400 MHz, CHLOROFORM-d) δ7.40-7.27 (m, 10H), 5.01 (t, J=5.8 Hz, 2H), 2.25-2.18 (m, 2H).

Procedure 2:

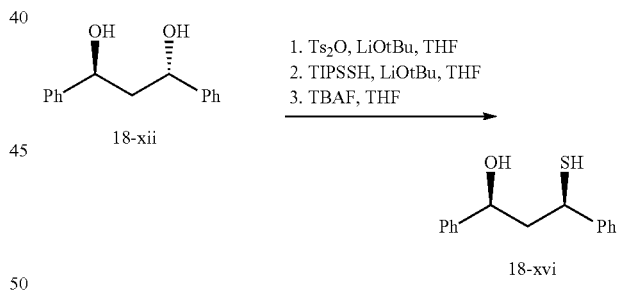

20 mmol (4.56 g) of 1,3-diphenyl-dipropanediol (18-xii) and 20 mmol of Ts$_2$O were dissolved in 100 mL of THF. Then the temperature was decreased to −78° C. After 20 mmol of 1M Li tert-BuO/THF was added, the temperature was increased to room temperature. After the temperature was decreased to −30° C., 22 mmol of TIPS (4.20 g) was added followed by another 20 mmol of 1M Li tert-BuO. The temperature was increased to room temperature again and most of THF was evaporated using Rotovap. The reaction mixture was added with 50 mL of water and extracted using 100 mL of MTBE three times. The combined MTBE phase was dried over Na$_2$SO$_4$, and the solvent was removed using Rotovap to obtain the crude TIPS-1,3-diphenyl-3-TIPS-1-dipropanediol. The crude TIPS capped diol was dissolved in 50 mL of THF. After bubbled THF solution with N$_2$, 26 mL 1M TBAF in THF was added. The reaction was run at room temperature for 1 h in a N₂ atmosphere, and then 4 mL of Acetic acid was added. The THF was removed using Rotovap and the residue was dissolved in 100 mL of MTBE and washed using 30 mL of aqueous NH₄Cl solution three times. The product was extracted from the MTBE phase using 30 mL 10% NaOH three times. The product was immediately released using concentrated HCl and extracted using MTBE (80 mL, five times). The MTBE phase was washed with 50 mL of water three times and 30 mL of brine three times, and then dried over Na₂SO₄. MTBE was removed using Rotovap, 4 g of product (18-xiv) was obtained after being dried in a vacuum. ¹H NMR (400 MHz, CHLOROFORM-d) δ7.29-7.06 (m, 10H), 4.42 (dd, J=9.1, 4.3 Hz, 1H), 4.11 (dt, J=9.1, 6.1 Hz, 1H), 2.38-2.16 (m, 2H).
Procedure 3:

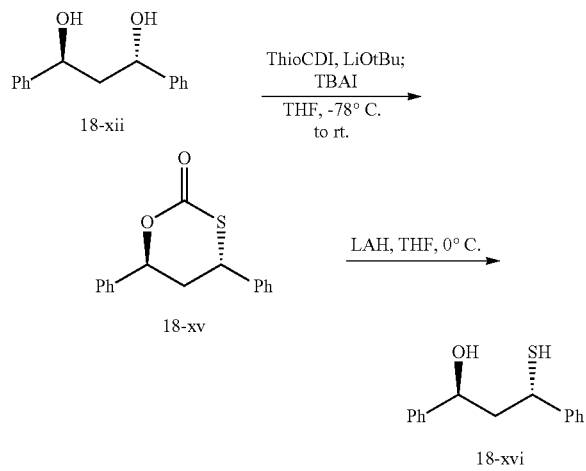

Diol protection using thiocarbonyl group and rearrangement of the thiocarbonyl protective group: After 10 mmol (2.28 g) of 1,3-diphenyl-dipropanediol (18-xii) and 11 mmol of thiocarbonyldiimidzaole dissolved in 50 mL of THF, the temperature was decreased to −78° C. Subsequently, 20 mmol of 1M Li tert-BuO/THF was added, followed by removing reaction to room temperature. The reaction mixture was diluted using 100 mL of MTBE and quenched using 50 mL of citric acid (10%). The organic layer was washed with NaHCO₃ (5%), water and brine before being dried over Na₂SO₄. After filtering the solid out, the organic solution was added with 1 equiv. of tetrabutylammonium iodide. The solution was refluxed for 2 h. The solvent was removed using Rotovap and 2 g of purified rearrangement product was obtained via a silica column (EA:Hexane=1:4).

Synthesis of
(S,S)-1,3-diphenyl-3-hydroxyl-1-propanethiol

The 2 g of purified rearrangement product was dissolved in 50 mL of THF. And then 4 equiv. LiAiH₄ was injected at 0° C. The solution was stirred for 1 h. The reaction was quenched using 10 mL of EA followed by 10 mL of water at 0° C. After the mixture was poured into a beaker containing 15 mL concentrated HCl and 100 g of ice, 100 mL of MTBE was immediately added. Subsequently, the aqueous layer was separated and extracted using 40 mL of MTBE for another three times. The combined organic layer was washed using 50 mL brine three times. After being dried over Na₂SO₄, the solid was removed via filtration and solvent was removed using Rotovap. At last, 1.2 g of (S,S)-1,3-diphenyl-3-hydroxyl-1-propanethiol (18-xvi) was obtained using Silica column (EA:Hexane=1:4).

c. Step 4

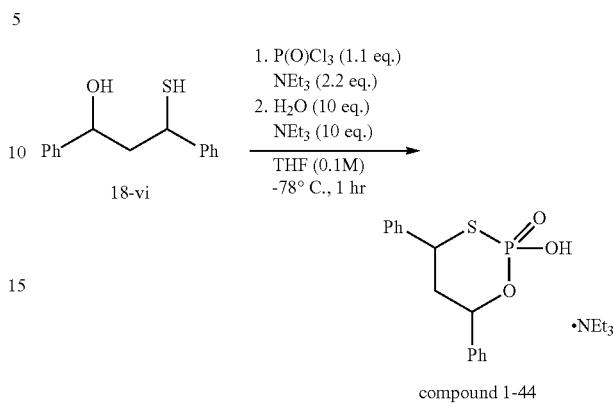

POCl₃ (0.54 mL, 1.1 equiv.) in THF (35 mL) was cooled to −78° C. A solution of mercaptopropanol (18-vi, 1.36 g, 1.0 equiv.) and Et₃N (1.68 mL, 2.2 equiv.) in THE (20 mL) was prepared and added dropwise to the POCl₃ solution at −78° C. After stirring for 1 hour at this temperate, an aliquot was analyzed by ³¹P NNR. The solution was then warmed to room temperature and Et₃N (7.7 mL, 10 equiv.) and water (1.0 mL, 10 equiv.) were added. After stirring for 10 minutes the reaction was partitioned between water and EtOAc. The organic layer was washed with water (3×) and finally brine. The aqueous layer (after saturating with brine) was back extracted multiple times with DCM (~600 mL for this scale) and the organics were pooled, dried and concentrated giving pure triethylammonium salt (1.36 g, 60% yield) as a sticky goo.

Compounds 1-45 or 1-46

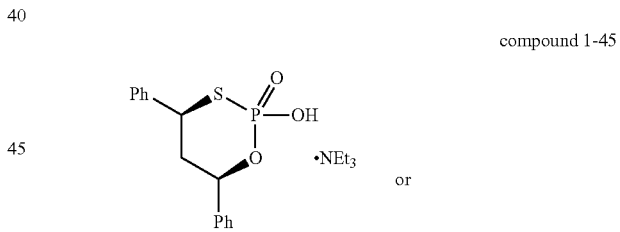

or

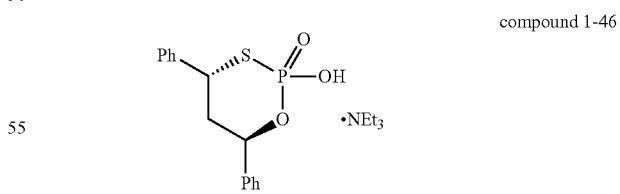

The title compounds were made by using the same chemistry as the preparation of compound 1-44. ¹H NMR (400 MHz, Chloroform-d) δ 7.57-7.50 (m, 1H), 7.41-7.13 (m, 10H), 5.56 (dq, J=7.7, 3.7 Hz, 1H), 4.65 (dt, J=11.4, 2.7 Hz, 0.5H), 4.53 (dt, J=12.6, 6.5 Hz, 0.5H), 2.98 (dq, J=10.9, 6.9, 4.9 Hz, 6H), 2.40 (tdd, J=14.3, 8.5, 5.4 Hz, 1H), 2.30-2.15 (m, 1H), 1.25 (t, J=7.3 Hz, 9H). ³¹P NMR (162 MHz, Chloroform-d) δ 13.80, 11.33.

Compounds 1-47 or 1-48

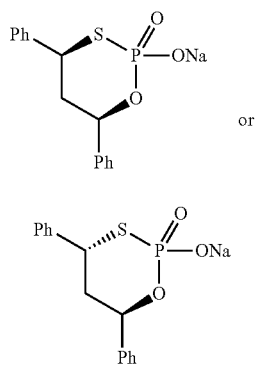

compound 1-47 or compound 1-48

¹H NMR (400 MHz, Chloroform-d) δ 7.61-7.11 (m, 10H), 5.55 (td, J=8.9, 4.5 Hz, 1H), 4.57 (ddd, J=11.3, 8.4, 5.6 Hz, 1H), 2.61-2.14 (m, 2H). ³¹P NMR (162 MHz, Methanol-d₄) δ 16.03, 12.56.

Compound 1-49

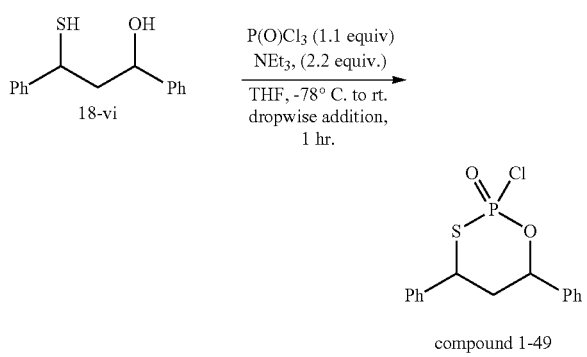

compound 1-49

To a cooled solution of POCl₃ (1.1 equiv.) in THF (0.1 M) at −78° C. was added dropwise a solution of mercaptopropanol (18-6, 1.0 equiv.) and NEt₃ (2.2 equiv.) in THF (0.1 M) over 5 min. After stirring for 1 hr, the reaction was warmed to rt and an aliquot was checked by ³¹P NMR. >90% product detected. Filtration of the precipitated salts followed by concentration afforded the product.

Compound 1-50

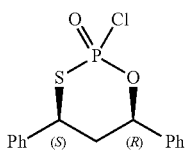

compound 1-50

The title compounds were made by using the same chemistry as preparation of compound 1-49. ¹H NMR (400 MHz, CHLOROFORM-d) 7.48-7.28 (m, 11H), 5.89 (br dd, J=11.6, 2.3 Hz, 1H), 5.08-4.96 (m, 1H), 2.81 (dt, J=15.1, 12.1 Hz, 1H), 2.53 (br d, J=15.1 Hz, 1H). ³¹P NMR (202 MHz, CHLOROFORM-d) 26.0 (s, 1P).

Compound 1-51

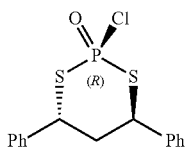

compound 1-51

The title compounds were made by using the same chemistry as preparation of compound 18-7f. ¹H NMR (400 MHz, CHLOROFORM-d) δ7.52-7.35 (m, 10H), 5.77 (td, J=8.4, 3.6 Hz, 1H), 4.93-4.86 (m, 1H), 2.97 (ddd, J=15.2, 7.2, 3.7 Hz, 1H), 2.78-2.71 (m, 1H).

General Procedures to Make Compounds 1-52 and 1-53

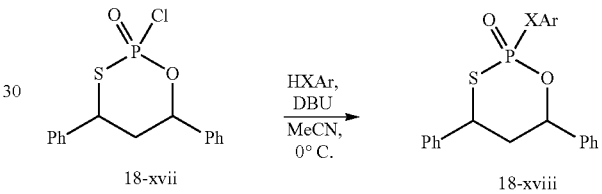

To a cooled solution of P(V)Cl (1.5 equiv.) and HXAr (1.0 equiv.) in MeCN (0.1 M) at 0° C. was added dropwise DBU (1.2 equiv.) After stirring for 1 hr, the reaction was warmed to rt. The precipitated salts were filtered and the product isolated after column chromatography.

Compound 1-52

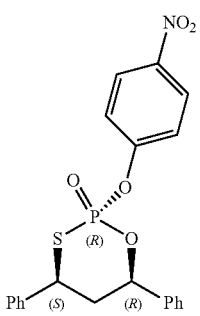

compound 1-52

¹H NMR (400 MHz, CHLOROFORM-d) δ8.37-8.29 (m, J=9.0 Hz, 2H), 7.60-7.54 (m, J=8.9 Hz, 2H), 7.50-7.33 (m, 10H), 5.75 (br d, J=11.4 Hz, 1H), 4.67 (br d, J=12.1 Hz, 1H), 2.68-2.58 (m, 1H), 2.56-2.45 (m, 1H). ³¹P NMR (202 MHz, CHLOROFORM-d) δ12.1 (s, 1P).

Compound 1-53

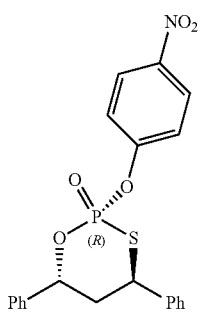

compound 1-53

¹H NMR (400 MHz, CHLOROFORM-d) δ8.34 (d, J=9.0 Hz, 1H), 8.19-8.15 (m, J=9.0 Hz, 2H), 7.49-7.37 (m, 11H), 7.11-7.07 (m, J=9.0 Hz, 2H), 5.95-5.90 (m, 1H), 4.86-4.79 (m, 1H), 2.95 (br dd, J=15.6, 5.3 Hz, 1H), 2.76 (ddd, J=15.3, 10.3, 4.5 Hz, 1H). ³¹P NMR (202 MHz, CHLOROFORM-d) δ12.5 (s, 1P).

d. Step 5

General Procedure A to Prepare Loaded Nucleosides

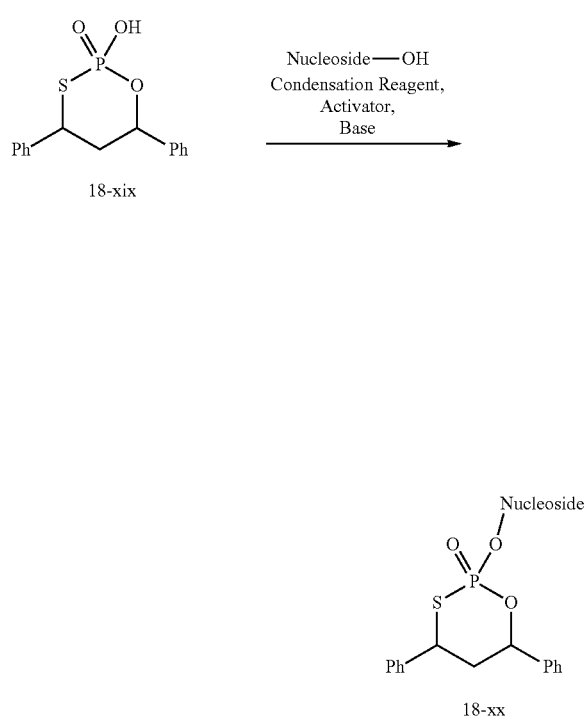

To a solution of P(V) reagent (excess) and nucleoside (1.0 equiv.) in MeCN or THF or Pyridine or DMF (0.1 M) was added Condensation Reagent, Base and Activator (excess.) The reaction proceeds sometimes with heat or at room temperature for 1-48 hours. The product is isolated after column chromatography.

Specific conditions that work the best: Triisopropylbenzene sulfonyl chloride or mesityl sulfonyl chloride as condensation reagents with N-Methyl Imidazole as base in THF at 50/60° C.

Compound 3-132

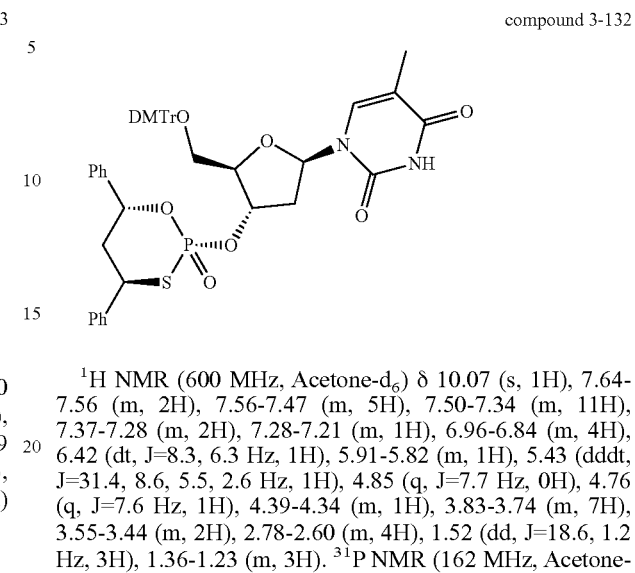

compound 3-132

¹H NMR (600 MHz, Acetone-d₆) δ 10.07 (s, 1H), 7.64-7.56 (m, 2H), 7.56-7.47 (m, 5H), 7.50-7.34 (m, 11H), 7.37-7.28 (m, 2H), 7.28-7.21 (m, 1H), 6.96-6.84 (m, 4H), 6.42 (dt, J=8.3, 6.3 Hz, 1H), 5.91-5.82 (m, 1H), 5.43 (dddt, J=31.4, 8.6, 5.5, 2.6 Hz, 1H), 4.85 (q, J=7.7 Hz, 0H), 4.76 (q, J=7.6 Hz, 1H), 4.39-4.34 (m, 1H), 3.83-3.74 (m, 7H), 3.55-3.44 (m, 2H), 2.78-2.60 (m, 4H), 1.52 (dd, J=18.6, 1.2 Hz, 3H), 1.36-1.23 (m, 3H). ³¹P NMR (162 MHz, Acetone-d₆) δ 21.08 (d, J=10.0 Hz).

General Procedure B to Prepare Loaded Nucleosides

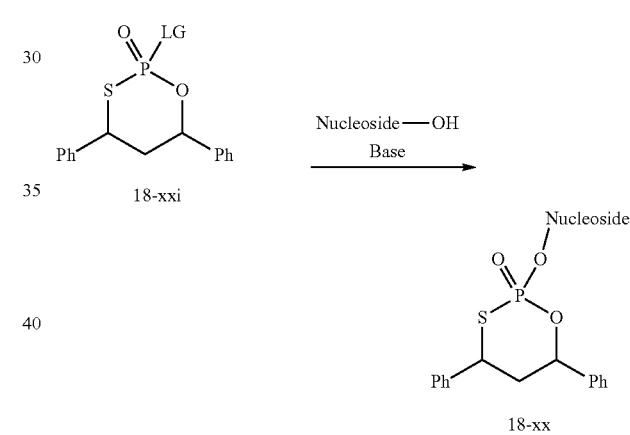

To a solution of P(V) reagent (1.3 equiv.) and nucleoside (1.0 equiv.) in MeCN (0.1 M) was added dropwise DBU (1.3 equiv.) After stirring for 0.5 hr. The product was worked up as usual and the product isolated after column chromatography.

Compound 3-133

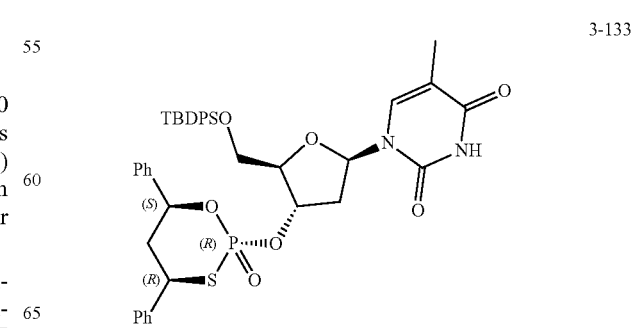

¹H NMR (400 MHz, CHLOROFORM-d) δ8.32 (s, 1H), 7.57 (br t, J=8.4 Hz, 4H), 7.38-7.23 (m, 16H), 6.42 (dd, J=9.1, 5.1 Hz, 1H), 5.67 (br d, J=11.3 Hz, 1H), 5.40 (br t, J=6.5 Hz, 1H), 4.83 (br d, J=11.9 Hz, 1H), 4.22 (br s, 1H), 3.93 (br d, J=11.6 Hz, 1H), 3.85 (br d, J=11.4 Hz, 1H), 2.59 (br dd, J=13.8, 5.0 Hz, 1H), 2.50-2.38 (m, 1H), 2.38-2.30 (m, 1H), 2.30-2.19 (m, 1H), 1.02 (s, 9H). ³¹P NMR (202 MHz, CHLOROFORM-d) δ20.5 (s, 1P)
Compound 3-134

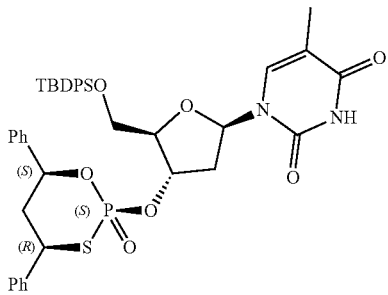

compound 3-134

¹H NMR (400 MHz, CHLOROFORM-d) δ7.66 (br d, J=7.0 Hz, 4H), 7.48-7.34 (m, 16H), 6.58 (dd, J=9.2, 5.0 Hz, 1H), 5.57 (br d, J=11.4 Hz, 1H), 5.41 (br t, J=6.7 Hz, 1H), 4.54 (br d, J=11.6 Hz, 1H), 4.45 (s, 1H), 4.08-3.99 (m, 2H), 2.85 (dd, J=13.8, 5.0 Hz, 1H), 2.64-2.46 (m, 1H), 2.45-2.29 (m, 2H), 1.16-1.06 (m, 9H). ³¹P NMR (202 MHz, CHLOROFORM-d) δ15.8 (s, 1P).
Compound 3-135

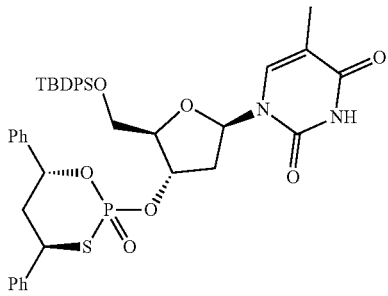

compound 3-135

¹H NMR (400 MHz, CHLOROFORM-d) δ8.09 (br s, 1H), 7.70-7.62 (m, 4H), 7.54 (br d, J=7.6 Hz, 1H), 7.50-7.35 (m, 14H), 7.27-7.22 (m, 1H), 6.38-6.28 (m, 1H), 5.79 (br s, 1H), 5.18 (br d, J=6.1 Hz, 1H), 4.76 (br d, J=19.8 Hz, 1H), 3.95 (s, 1H), 3.72-3.67 (m, 1H), 2.88-2.76 (m, 1H), 2.67 (br dd, J=9.8, 5.2 Hz, 1H), 1.12 (s, 5H), 1.09 (s, 4H). ³¹P NMR (202 MHz, CHLOROFORM-d) δ17.9 (s, 1P), 17.6 (s, 1P).
e. Step 6

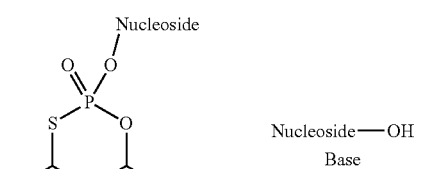

18-xxii

Nucleoside—OH
Base →

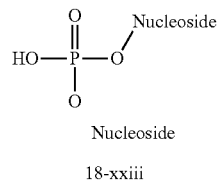

18-xxiii

To a solution of P(V) reagent (1.0 equiv.) and nucleoside (2.0 equiv.) in MeCN (0.1 M) was added dropwise DBU (3.0 equiv.) After stirring for 1 hr. The product was worked up as usual and the product isolated after column chromatography.
Compound 5-11

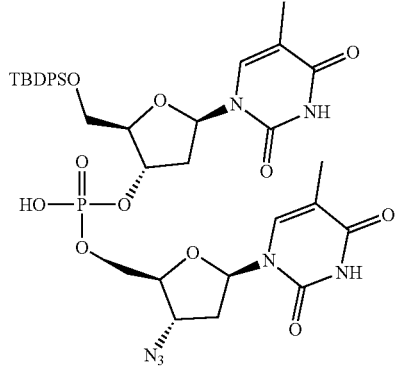

compound 5-11

³¹P NMR (202 MHz, CHLOROFORM-d) δ −1.74 (s, 1P).
Compound 5-12 compound 5-12

³¹P NMR (202 MHz, MeCN-d) 6-0.81 (s, 1P).

It is to be appreciated that the Detailed Description section, and not the Summary and Abstract sections, is intended to be used to interpret the claims. The Summary and Abstract sections may set forth one or more but not all exemplary embodiments of the present disclosure as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A stereochemically pure compound of formula IV:

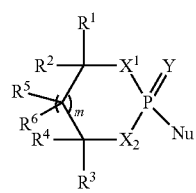

(IV)

wherein
(a) $R^1$, $R^2$, $R^3$, $R^4$, $R^5$, and $R^6$ are independently hydrogen, $CD_3$, $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups; or
(b) any two of $R^1$, $R^2$, $R^3$, $R^4$, $R^5$, and $R^6$ together with the carbons to which they are attached form a $C_4$-$C_8$ cycloalkyl group, optionally substituted with one or more, the same or different, $R^a$ groups, while the remaining $R^1$, $R^2$, $R^3$, $R^4$, $R^5$, and $R^6$ are as defined in (a);

$R^a$ is hydrogen, deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

$X^1$ is O, $X^2$ is S; or $X^1$ is S, $X^2$ is O;

Y is O, S or $NR^c$;

$R^c$ is hydrogen;

m is 0, 1 or 2, and

Nu is a nucleoside, wherein the phosphorus atom is covalently bonded to a 5'- or 3'-oxygen atom on the nucleoside sugar;

with the proviso that the compound of formula IV does not include the following compounds:

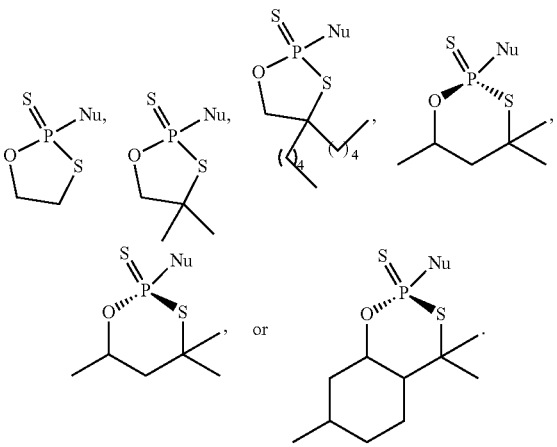

2. The compound according to claim 1, having the formula:

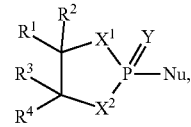

wherein $R^1$, $R^2$, $R^3$, and $R^4$, $X^1$ and $X^2$, Y, and Nu are as defined in claim 1.

3. The compound according to claim 1, having any one of formula V-Vc:

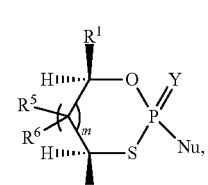

(V)

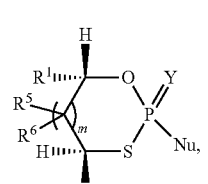

(Va)

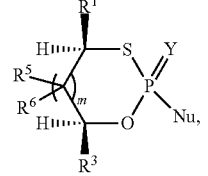

(Vb)

(Vc)

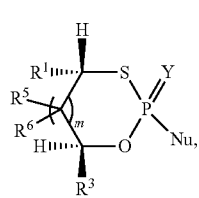

wherein (a) $R^1$, $R^3$, $R^5$ and $R^6$ are independently hydrogen, $CD_3$, $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups; or (b) any two of $R^1$, $R^3$, $R^5$, and $R^6$ together with the carbons to which they are attached form a $C_4$-$C_8$ cycloalkyl group, optionally substituted with one or more, the same or different, $R^a$ groups, while the $R^1$, $R^3$, $R^5$ and $R^6$ remaining are as defined above in (a);

$R^a$ is hydrogen, deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

Y is O, S or NR, wherein $R^c$ is hydrogen or $C_1$-$C_4$ alkyl;

m is 0, 1, or 2, and

Nu is a nucleoside, wherein the phosphorus atom is covalently bonded to a 5'- or 3'-oxygen atom on the nucleoside sugar.

4. The compound according to claim 3, having any one of formula Vd-Vg:

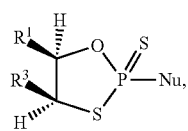

(Vd)

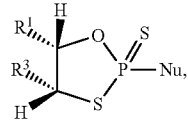

(Ve)

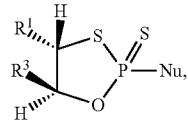

(Vf)

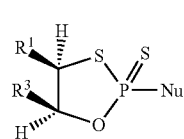

(Vg)

(a) $R^1$ and $R^3$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups; or (b) $R^1$, and $R^3$ together with the carbons to which they are attached form a $C_4$-$C_8$ cycloalkyl group, optionally substituted with one or more, the same or different, $R^a$ groups;

$R^a$ is hydrogen; deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl; and Nu is a nucleoside, wherein the phosphorus atom is covalently bonded to a 5'- or 3'-oxygen atom on the nucleoside sugar.

5. The compound of claim 1, having the formula:

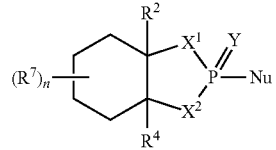

wherein $R^2$ and $R^4$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

$R^a$ is hydrogen, deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

$R^7$ is hydrogen; $CD_3$, OH, halogen, CN, $CF_3$, linear or branched $C_1$-$C_6$ alkyl; linear or branched $C_2$-$C_6$ alkenyl, or linear or branched $C_2$-$C_6$ alkynyl;

$X^1$ is O, $X^2$ is S; or $X^1$ is S, $X^2$ is O;

Y is O, S or $NR^c$;

$R^c$ is hydrogen or $C_1$-$C_4$ alkyl;

n is 0, 1, 2, 3 or 4; and

Nu is a nucleoside, wherein the phosphorus atom is covalently bonded to a 5'- or 3'-oxygen atom on the nucleoside sugar.

6. The compound of claim 4, having any one of formulae VI-VIc:

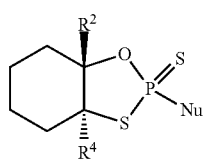

(VI)

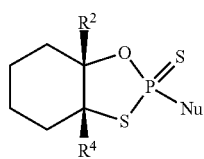

(VIa)

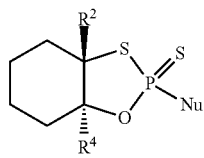

(VIb)

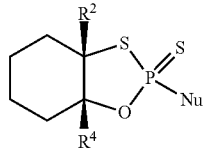

(VIc)

wherein $R^2$ and $R^4$ are independently hydrogen, $CD_3$, $CF_3$, or linear or branched $C_1$-$C_6$ alkyl, optionally substituted with one or more, the same or different, $R^a$ groups;

$R^a$ is hydrogen, deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl; and Nu is a nucleoside, wherein the phosphorus atom is covalently bonded to a 5'- or 3'-oxygen atom on the nucleoside sugar.

7. The compound according to claim 5 having the formula:

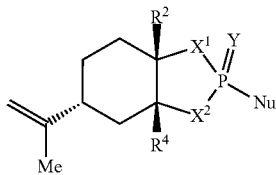

wherein $R^2$ and $R^4$ are independently hydrogen, $CD_3$, $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups;

$R^a$ is hydrogen, deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

provided that either the carbon bearing the $R^2$ group, the carbon bearing the $R^4$ group, or both, is chiral;

$X^1$ is O, $X^2$ is S; or $X^1$ is S, $X^2$ is O;

Y is O, S or $NR^c$;

$R^c$ is hydrogen or $C_1$-$C_4$ alkyl; and

Nu is a nucleoside, wherein the phosphorus atom is covalently bonded to a 5'- or 3'-oxygen atom on the nucleoside sugar.

8. The compound of claim 1, wherein the nucleoside is a natural nucleoside or a nucleoside with a modified base, a modified sugar or both modified base and modified sugar.

9. The compound of claim 8, wherein the nucleoside is a ribonucleoside.

10. The compound of claim 8, wherein the nucleoside is a deoxyribonucleoside.

11. The compound of claim 8, wherein the nucleoside is a sugar-modified nucleoside selected from the group consisting of Locked Nucleic Acid, 2'-O-alkyl-RNA, 2'-amino-DNA, 2'-fluoro-DNA, arabino nucleic acid, 2'-fluoro-ANA, hexitol nucleic acid, intercalating nucleic acid, constrained ethyl nucleoside, 2'-O-methyl nucleic acid, and 2'-O-methoxyethyl nucleic acid.

12. A method for preparing a compound of claim 1, comprising reacting a nucleoside having a hydroxy group on the 5' or 3' carbon of the nucleoside sugar, in the presence of a base with a compound of any one of formula II-IIc:

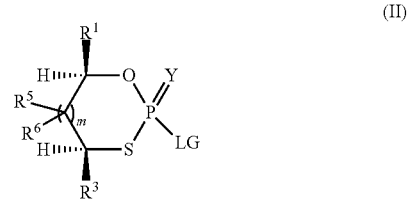

(II)

-continued

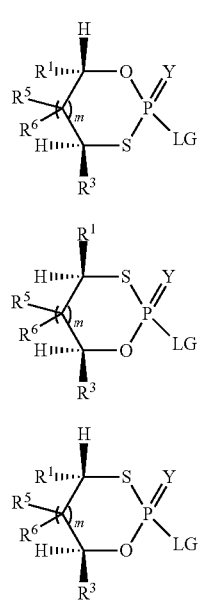

(IIa)

(IIb)

(IIc)

wherein
(a) $R^1$, $R^3$, $R^5$ and $R^6$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl, optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups; or
(b) any two of $R^1$, $R^3$, $R^5$, and $R^6$ together with the carbons to which they are attached form a $C_4$-$C_8$ cycloalkyl group, optionally substituted with one or more, the same or different, $R^a$ groups, while the remaining $R^1$, $R^3$, $R^5$, and $R^6$ are as defined in (a);
$R^a$ is hydrogen, deuterium, $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;
$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;
Y is O, S or $NR^c$, where $R^c$ is hydrogen or $C_1$-$C_4$ alkyl;
m is 0, 1 or 2, and
LG is a leaving group; selected from the group consisting of

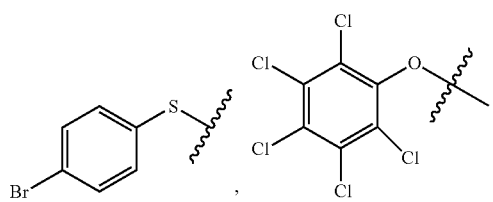

-continued

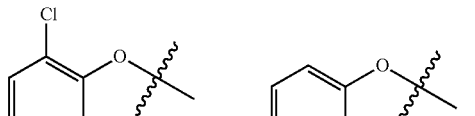

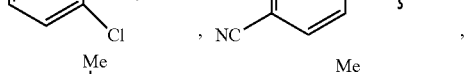

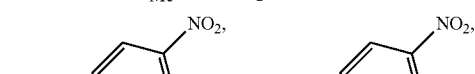

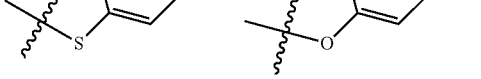

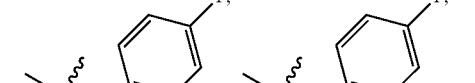

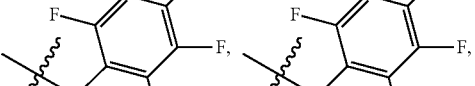

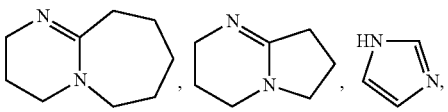

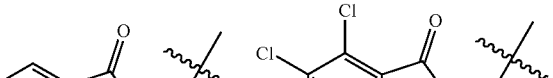

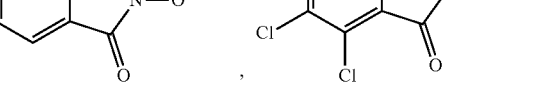

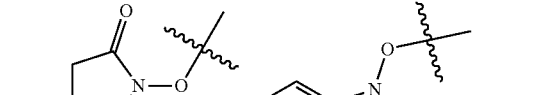

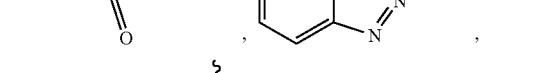

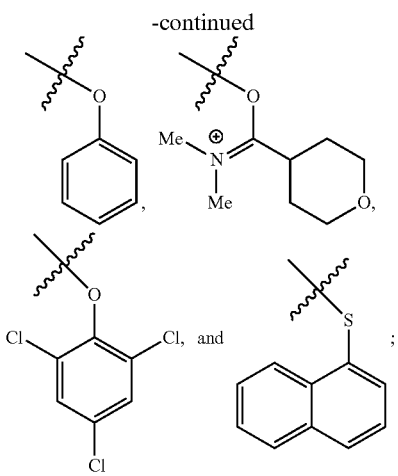

provided that either the carbon bearing the $R^1$ group, the carbon bearing the $R^3$ group, or both, is chiral;
wherein the compound of any one of formula II-IIc is at least 90% stereochemically pure.

13. The method of claim 12, wherein the base is selected from the group consisting of DBU, BTMG, TMG, LiHMDS, LiOtBu, KHMDS, KOtBu, NaHMDS, NaOtBu, DABCO, NMI, DIPEA, Pyr, 2,6-Lut, and imidazole.

14. The method of claim 12, wherein the reaction is conducted at a temperature range of from about −78° C. to about 25° C.

15. The method of claim 12, wherein the reaction is conducted for about 10 minutes to about 10 hours.

16. The method of any one of claims 12 through 15, wherein the nucleoside is a natural nucleoside or a nucleoside with a modified base, a modified sugar or both modified base and modified sugar.

17. The method of claim 16, wherein the nucleoside is a ribonucleoside.

18. The method of claim 16, wherein the nucleoside is a deoxyribonucleoside.

19. The method of claim 16, wherein the nucleoside is a sugar-modified nucleoside selected from the group consisting of Locked Nucleic Acid, 2′-O-alkyl-RNA; 2′-amino-DNA; 2′-fluoro-DNA; arabino nucleic acid; 2′-fluoro-ANA, hexitol nucleic acid, intercalating nucleic acid, constrained ethyl nucleoside, 2′-O-methyl nucleic acid, and 2′-O-methoxyethyl nucleic acid.

20. A method of making an oligonucleotide, comprising:
a) reacting the compound of formula I with a first nucleoside having a hydroxy group on the 5′ or 3′ carbon of the nucleoside sugar, in the presence of a base to form a loaded nucleoside, wherein formula I is

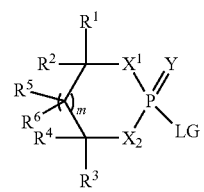

(I)

wherein
(a) $R^1$, $R^2$, $R^3$, $R^4$, $R^5$, and $R^6$ are independently hydrogen, $CD_3$ or $CF_3$, linear or branched $C_1$-$C_{20}$ alkyl, optionally substituted with one or more, the same or different, $R^a$ groups; linear or branched $C_2$-$C_{12}$ alkenyl; optionally substituted with one or more, the same or different, $R^a$ groups; linear or branched $C_2$-$C_{12}$ alkynyl, optionally substituted with one or more, the same or different, $R^a$ groups; aryl, optionally substituted with one or more, the same or different, $R^a$ groups; heteroaryl, optionally substituted with one or more, the same or different, $R^a$ groups; heterocyclyl, optionally substituted with one or more, the same or different, $R^a$ groups; or $C_3$-$C_8$ cycloalkyl, optionally substituted with one or more, the same or different, $R^a$ groups; or (b) any two of $R^1$, $R^2$, $R^3$, $R^4$, $R^5$, and $R^6$ together with the carbons to which they are attached form a $C_4$-$C_8$ cycloalkyl group, optionally substituted with one or more, the same or different, $R^a$ groups, while the remaining $R^1$, $R^2$, $R^3$, $R^4$, $R^5$, and $R^6$ are as defined in (a);

$R^a$ is hydrogen; deuterium; $CD_3$, $C_1$-$C_6$ alkyl, OH, halogen, CN, $CF_3$, O—$C_1$-$C_6$ alkyl, O-aryl, O-heteroaryl, O—$C_3$-$C_8$ cycloalkyl, O-heterocyclyl, —$NR^bR^b$, —$COOR^b$ or —$CONR^bR^b$;

$R^b$ is independently at each occurrence, the same or different, hydrogen, linear or branched $C_1$-$C_{12}$ alkyl, aryl, heteroaryl, heterocyclyl or $C_3$-$C_8$ cycloalkyl;

$X^1$ is O, $X^2$ is S; or $X^1$ is S, $X^2$ is O;
Y is O, S or $NR^c$;
m is 0, 1 or 2,
and
LG is a leaving group; selected from the group consisting of

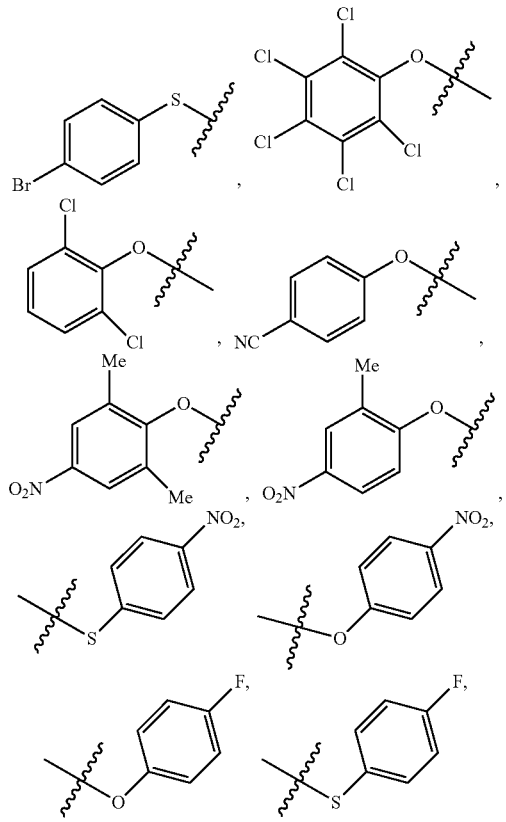

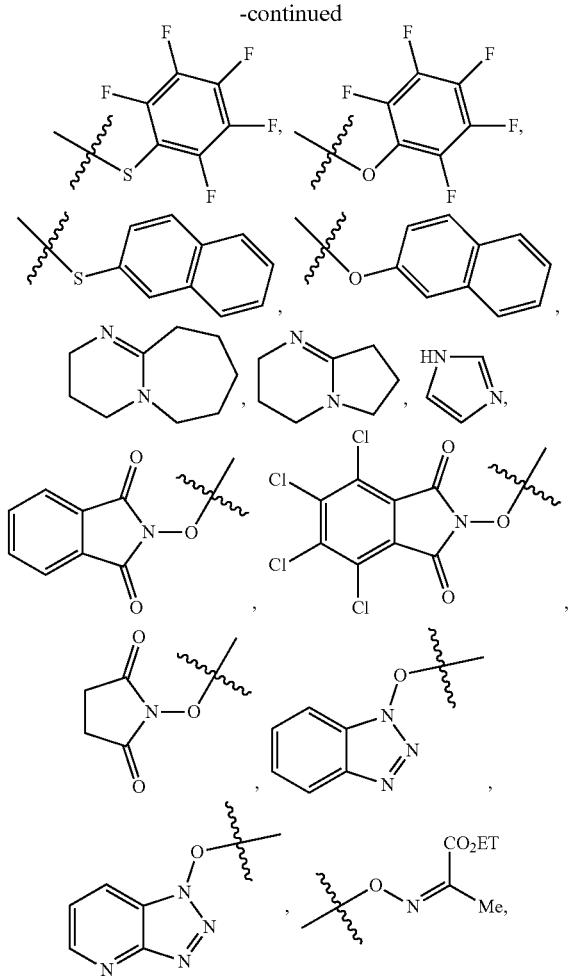
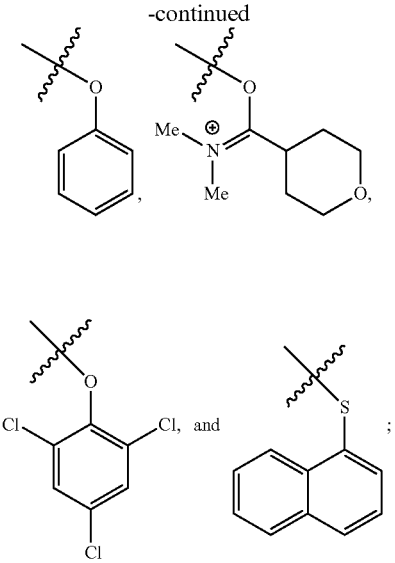

wherein the compound of any one of formulae I is at least 90% stereochemically pure;

b) reacting the loaded nucleoside formed in step (a) with a second nucleoside, thereby coupling the two nucleosides to form a dinucleotide;

c) adding a compound of formula I as defined above to the dinucleotide to form a loaded dinucleotide;

d) adding another nucleoside to the loaded dinucleotide, thereby adding an additional nucleoside to said dinucleotide; and e) repeating steps (c) and (d) one or more times to form an oligonucleotide having a desired number of nucleotides.

* * * * *

UNITED STATES PATENT AND TRADEMARK OFFICE
CERTIFICATE OF CORRECTION

PATENT NO. : 12,077,558 B2
APPLICATION NO. : 18/167772
DATED : September 3, 2024
INVENTOR(S) : Michael Anthony Schmidt et al.

It is certified that error appears in the above-identified patent and that said Letters Patent is hereby corrected as shown below:

On the Title Page

In Column 2, Line 3 of item (57) the Abstract, delete "organophosphorous" and insert -- organophosphorus --, therefor.

In the Claims

In Column 317, Claim 3, Line 40, delete "NR," and insert -- NR$^c$, --, therefor.

In Column 318, Claim 4, Line 24, delete "R$^1$, and R$^3$" and insert -- R$^1$ and R$^3$ --, therefor.

In Column 322, Claim 12, Lines 41-45, delete " 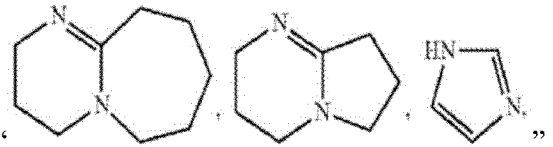 ", therefor.

In Column 323, Claim 12, Lines 2-8, delete " 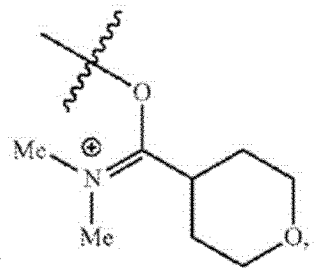 " and insert

Signed and Sealed this
Thirteenth Day of May, 2025

Coke Morgan Stewart
*Acting Director of the United States Patent and Trademark Office*

CERTIFICATE OF CORRECTION (continued)
U.S. Pat. No. 12,077,558 B2

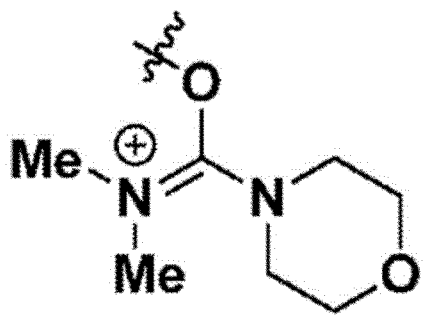 --, therefor.

In Column 325, Claim 20, Lines 12-16, delete " 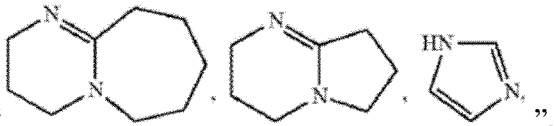 ", therefor.

In Column 326, Claim 20, Lines 2-8, delete " 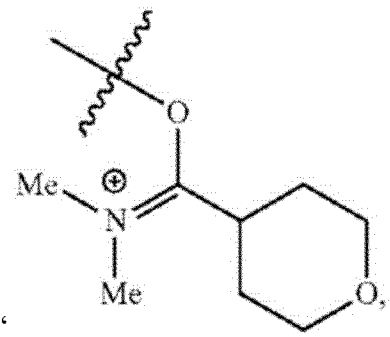 " and insert -- 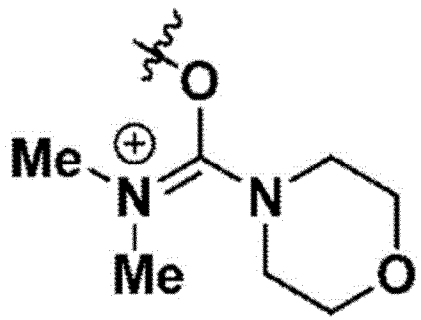 --, therefor.